US011016092B2

(12) United States Patent
McQuiston et al.

(10) Patent No.: US 11,016,092 B2
(45) Date of Patent: May 25, 2021

(54) METHODS FOR AIDING IN THE DIAGNOSIS AND DETERMINATION OF THE EXTENT OF TRAUMATIC BRAIN INJURY IN A HUMAN SUBJECT USING THE EARLY BIOMARKER UBIQUITIN CARBOXY-TERMINAL HYDROLASE L1

(71) Applicant: Abbott Laboratories, Abbott Park, IL (US)

(72) Inventors: Beth McQuiston, Abbott Park, IL (US); Justin Rogers, Abbott Park, IL (US); Saul Datwyler, Abbott Park, IL (US); Jaime Marino, Abbott Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 15/934,541

(22) Filed: Mar. 23, 2018

(65) Prior Publication Data
US 2018/0313837 A1 Nov. 1, 2018

Related U.S. Application Data

(60) Provisional application No. 62/475,662, filed on Mar. 23, 2017.

(51) Int. Cl.
*G01N 33/573* (2006.01)
*G01N 33/68* (2006.01)
*A61B 6/03* (2006.01)
*A61B 6/00* (2006.01)

(52) U.S. Cl.
CPC ............ *G01N 33/573* (2013.01); *A61B 6/032* (2013.01); *A61B 6/501* (2013.01); *C12Y 301/02015* (2013.01); *G01N 33/6896* (2013.01); *G01N 2333/916* (2013.01); *G01N 2800/28* (2013.01); *G01N 2800/50* (2013.01)

(58) Field of Classification Search
CPC ............ G01N 33/573; G01N 33/6896; G01N 2333/916; G01N 2800/28; G01N 2800/50; C12Y 301/02015
See application file for complete search history.

(56) References Cited

U.S. PATENT DOCUMENTS

| | | | |
|---|---|---|---|
| 8,492,107 | B2 | 7/2013 | Wang et al. |
| 9,265,441 | B2 | 2/2016 | Pereira et al. |
| 2003/0199000 | A1 | 10/2003 | Valkirs et al. |
| 2011/0143375 | A1 | 6/2011 | Wang et al. |
| 2014/0303041 | A1 | 10/2014 | Hayes et al. |
| 2014/0342381 | A1 | 11/2014 | Hayes et al. |
| 2015/0224499 | A1 | 8/2015 | Wang et al. |
| 2015/0268252 | A1 | 9/2015 | Svetlov et al. |
| 2018/0106800 | A1 | 4/2018 | Datwyler et al. |
| 2018/0106818 | A1 | 4/2018 | Jewell et al. |
| 2019/0302127 | A1 | 10/2019 | Lukaszewska |

FOREIGN PATENT DOCUMENTS

| | | |
|---|---|---|
| WO | WO 2005/029088 | 3/2005 |
| WO | WO 2005/106038 | 10/2005 |
| WO | WO 2005/113798 | 12/2005 |
| WO | WO 2009/100131 | 8/2009 |
| WO | WO 2010/019553 A2 | 2/2010 |
| WO | WO 2010/148391 | 12/2010 |
| WO | WO 2011/011334 A2 | 1/2011 |
| WO | WO 2011/032155 | 3/2011 |
| WO | WO 2011/160096 A2 | 12/2011 |
| WO | WO 2012/051519 | 4/2012 |
| WO | WO 2014/194329 | 12/2014 |
| WO | WO 2015/009907 | 1/2015 |
| WO | WO 2015/066211 | 5/2015 |
| WO | WO 2015/157300 | 10/2015 |
| WO | WO 2016/055148 A2 | 4/2016 |
| WO | WO 2016/166419 A1 | 10/2016 |
| WO | WO 2016/196522 A1 | 12/2016 |
| WO | WO 2018/067468 A1 | 4/2018 |
| WO | WO 2018/067474 | 4/2018 |
| WO | WO 2018/081649 A1 | 5/2018 |
| WO | WO 2018/136825 A1 | 7/2018 |
| WO | WO 2018/175942 | 9/2018 |
| WO | WO 2018/191531 | 10/2018 |
| WO | WO 2018/200823 | 11/2018 |

(Continued)

OTHER PUBLICATIONS

Agoston, Denes V. et al., "Biofluid Biomarkers of Traumatic Brain Injury" Brain Injury, 31(9):1195-1203 (Jul. 29, 2017).
Banyan BTI Brain Trauma Indicator, Publicly available Feb. 2018.
Bazarian et al., "Serum GFAP and UCH-L1 for prediction of absence of intracranial injuries on head CT (ALERT-TBI): a multicentre observational study" The Lancelot, Neurology, vol. 17, Issue 9, P782-789, Sep. 1, 2018.
Benninger et al., "Glial fibrillary acidic protein as a marker of astrocytic activation in the cerebrospinal fluid of patients with amyotrophic lateral sclerosis." *Journal of Clinical Neuroscience*, 26:75-78 (Nov. 2015).

(Continued)

*Primary Examiner* — Olga N Chernyshev
(74) *Attorney, Agent, or Firm* — Lisa L. Mueller; Casimir Jones, S.C.; Audrey L. Bartnicki

(57) ABSTRACT

Disclosed herein are methods that aid in the diagnosis and evaluation of a human subject that has sustained or may have sustained an injury to the head, such as mild or moderate to severe traumatic brain injury (TBI), using an early biomarker, ubiquitin carboxy-terminal hydrolase L1 (UCH-L1). Also disclosed here are methods that aid in determining whether a human subject that has sustained an injury or may have sustained to the head would benefit from and thus receive a head computerized tomography (CT) scan based on the levels of UCH-L1. These methods involve detecting levels and changes in levels of UCH-L1 in one or more samples taken from a human subject at time points within 24 hours after the subject has sustained or may have sustained an injury to the head.

19 Claims, 19 Drawing Sheets
Specification includes a Sequence Listing.

(56) References Cited

FOREIGN PATENT DOCUMENTS

| WO | WO 2018/218169 | 11/2018 |
|---|---|---|
| WO | WO 2018/222783 | 12/2018 |
| WO | WO 2018/222784 | 12/2018 |
| WO | WO 2019/112860 | 6/2019 |
| WO | WO 2019/113525 | 6/2019 |

OTHER PUBLICATIONS

Berger, et al., "Serum Concentrations of Ubiquitin C-Terminal Hydrolase-L1 and all-Spectrin Breakdown Product 145 kDa Correlate with Outcome after Pediatric TBI." Journal of Neurotrauma, Jan. 1, 2012; 29:162-167.
Blyth, Brian J. et al., "Elevated Serum Ubiquitin Carboxy-Terminal Hydrolase L1 is Associated with Abnormal Blood-Brain Barrier Function after Traumatic Brain Injury", *Journal of Neurotrauma.*, 28(12): 2453-2462 (Dec. 1, 2011).
Bogoslovsky T. et al., "Fluid Biomarkers of Traumatic Brain Injury and Intended Context of Use." Diagnostics (Basel). Oct. 18, 2016; 6(4). pii: E37.
Brophy, M. et al., "Biokinetic analysis of ubiquitin C-terminal hydrolase-L1 (UCH-L1) in severe traumatic brain injury patient biofluids." J Neurotrauma. Jun. 2011; 28(6):861-70.
Cai et al., "The role of cardiac troponin I in prognostication of patients with isolated severe traumatic brain injury." *J. Trauma Acute Care Surg.*, 80(3):477-483 (Mar. 2016).
Dash et al.; "Biomarkers for Diagnosis, Prognosis, and Evaluation of Treatment Efficacy for Traumatic Brain Injury." Neurotherapeutics, Jan. 2010, 7(1): 100-114.
Diaz-Arrastia, et al., "Acute biomarkers of traumatic brain injury: relationship between plasma levels of ubiquitin C-terminal hydrolase-L1 and glial fibrillary acidic protein.", *Journal of Neurotrauma*, 31:19-25 (Jan. 1, 2014).
Streeter et al., "Diagnostic Protein Biomarkers for Severe, Moderate, and Mild Traumatic Brain Injury", *Sensing Technologies for Global Health, Military Medicine, Disaster Response, and Environmental Monitoring; and Biometric Technology for Human Identification VIII*, 8029(1):1-16 (May 13, 2011).
Kiiski, H. et al., "Increased plasma UCH-L1 after aneurysmal subarachnoid hemorrhage is associated with unfavorable neurological outcome." J Neurol Sci. Feb. 15, 2016; 361:144-9.
Kiviniemi et al., "Serum levels of GFAP and EGFR in primary and recurrent high-grade gliomas: correlation to tumor volume, molecular markers, and progression-free survival." *Journal of Neuro-Oncology*, 124(2):237-245 (Jun. 2015).
Kobeissy, Firas H. et al., "Novel Differential Neuroproteomics Analysis of Traumatic Brain Injury in Rats" *Molecular & Cellular Proteomics*, 5(10):1887-1898 (Oct. 1, 2006).
Kochanek et al., "Multi-Center Pre-clinical Consortia to Enhance Translation of Therapies and Biomarkers for Traumatic Brain Injury: Operation Brain Trauma Therapy and Beyond." Frontiers in Neurology Aug. 2018, vol. 9, 13 pages.
Korley et al., "Performance Evaluation of a Multiplex Assay for Simultaneous Detection of Four Clinically Relevant Traumatic Brain Injury Biomarkers." Journal of Neurotrauma, 2015, 35:1-6.
Kou et al., "Combining Biochemical and Imaging Markers to Improve Diagnosis and Characterization of Mild Traumatic Brain Injury in the Acute Setting: Results from a Pilot Study." PLOS ONE Nov. 2013, 8(11): e80296, 14 pages.
Lecky, "Should plasma GFAP guide the management of patients with traumatic brain injury and a negative CT scan?" Lancet Neurol 2019, 2 pages.
Lee et al., "A Role of Serum-Based Neuronal and Glial Markers as Potential Predictors for Distinguishing Severity and Related Outcomes in Traumatic Brain Injury", *J. Korean Neurosurgical Society*, 58(2):93-100 (Aug. 2015).
Lippi et al., "The concentration of highly-sensitive troponin I is increased in patients with brain injury after mild head trauma." *International Journal of Cardiology*, 168(2):1617-1618 (Sep. 2013).
Liu et al., "Ubiquitin C-terminal hydrolase-L1 as a biomarker for ischemic and traumatic brain injury in rats", *Eur. J. Neurosci.*, 31(4):722-732 (Feb. 2010).
McMahon et al., "Measurement of the glial fibrillary acidic protein and its breakdown products GFAP-BDP biomarker for the detection of traumatic brain injury compared to computed tomography and magnetic resonance imaging." J Neurotrauma. Apr. 15, 2015; 32(8):527-33. (Also include in 13097/36107 IDS).
Missler et al., "Measurement of Glial Fibrillary Acidic Protein in Human Blood: Analytical Method and Preliminary Clinical Results." Clinical Chemistry, 45(1):138-141 (1999).
Mondello et al.,"Serum Concentrations of Ubiquitin C-Terminal Hydrolase-L1 and Glial Fibrillary Acidic Protein after Pediatric Traumatic Brain Injury." *Scientific Reports*, 6(28203):1-6 (Jun. 2016).
Mondello et al., "Neuronal and glial markers are differently associated with computed tomography findings and outcome in patients with severe traumatic brain injury: a case control study." Care 2011, 15: R156, 10 pages.
Mondello et al., "Clinical utility of serum levels of ubiquitin cterminal hydrolase as a biomarker for severe traumatic brain injury" Neurosurgery. Mar. 2012; 70(3): 666-675.
Nylen et al., "Increased serum-GFAP in patients with severe traumatic brain injury is related to outcome" J. Of Neurological Sciences, 240: 85-91 (2006).
Okonkwo et al., "GFAP-BDP as an acute diagnostic marker in traumatic brain injury: results from the prospective transforming research and clinical knowledge in traumatic brain injury study." J Neurotrauma. Sep. 1, 2013; 30(17):1490-7. (Also include in 13097/36107 IDS).
Papa et al., "Ubiquitin C-terminal hydrolase is a novel biomarker in humans for severe traumatic brain injury", *Crit. Care Med.*, 38(1):138-144 (Jan. 2010).
Papa et al., "Serum levels of Ubiquitin C-terminal Hydrolase (UCH-L1) distinguish mild traumatic brain injury (TBI) from trauma controls and are elevated in mild and moderate TBI patients with intracranial lesions and neurosurgical intervention", *J. Trauma Acute Care Surg.*, 72(5):1335-1344 (May 2012).
Papa et al., "Time Course and Diagnostic Accuracy of Glial and Neuronal Blood Biomarkers GFAP and UCH-L1 in a Large Cohort of Trauma Patients With and Without Mild Traumatic Brain Injury." *JAMA*, 73(5) 551-560 (Mar. 28, 2016).
Papa et al., "Elevated levels of serum glial fibrillary acidic protein breakdown products in mild and moderate traumatic brain injury are associated with intracranial lesions and neurosurgical intervention." Ann Emerg Med. Jun. 2012;59(6):471-83.
Pelinka et al., "Glial fibrillary acidic protein in serum after traumatic brain injury and multiple trauma." J Trauma. Nov. 2004; 57(5):1006-12.
Posti et al., "Glial Fibrillary Acidic Protein and Ubiquitin C-Terminal Hydrolase-L1 Are Not Specific Biomarkers for Mild CT-Negative Traumatic Brain Injury" Journal of Neurotrauma, 34(7):1427-1438 (Apr. 1, 2017).
Prieto et al., "Proteomic analysis of traumatic brain injury: the search for biomarkers." Expert Rev Proteomics. Apr. 2008; 5(2):283-91.
Puvenna et al., "Significance of ubiquitin carboxy-terminal hydrolase L1 elevations in athletes after sub-concussive head hits.", *PLOS ONE*, 9(5):e96296 (May 2014).
Ramon Diaz-Arrastia et al., "Acute Biomarkers of Traumatic Brain Injury: Relationship between Plasma Levels of Ubiquitin C-Terminal Hydrolase-L1 and Glial Fibrillary Acidic Protein", *Journal of Neurotrauma.*, 31(1): 19-25 (Jan. 1, 2014).
Rhine et al., "Are UCH-L1 and GFAP promising biomarkers for children with mild traumatic brain injury?" Brain Injury 2016, Early Online: 1-8.
Luger et al., "Glial Fibrillary Acidic Protein Serum Levels Distinguish between Intracerebral Hemorrhage and Cerebral Ischemia in the Early Phase of Stroke", *Clinical Chemistry*, 63(1):377-385 (Nov. 23, 2016).
Shahjouei et al., "The diagnostic values of UCH-L1 in traumatic brain injury: A meta analysis" Brain Injury (2017)—From email on Jun. 5 at 4:14.

(56) References Cited

OTHER PUBLICATIONS

Song et al., "Development of Digital Elisas for Ultrasensitive Measurement of Serum Glial Fibrillary Acid Protein and Ubiquitin C-Terminal Hydrolase with Clinical Utilities in Human Traumatic Brain Injury." Alzheimer's & Dementia, 13(7): P3-240 (Jul. 2017).
Strathmann et al., "Blood-based biomarkers for traumatic brain injury: evaluation of research approaches, available methods and potential utility from the clinician and clinical laboratory perspectives." Clin Biochem. Jul. 2014; 47(1011):876-88. (Also include in 13097/36107 IDS).
Takala et al., "Glial Fibrillary Acidic Protein and Ubiquitin C-Terminal Hydrolase-L1 as Outcome Predictors in Traumatic Brain Injury." World Neurosurg. Mar. 2016; 87:8-20.
Thelin et al., "Serial Sampling of Serum Protein Biomarkers for Monitoring Human Traumatic Brain injury Dynamics: A Systematic Review." Frontiers in Neurology Jul. 2017, vol. 8, Article 300, 23 pages.
Vos et al., "Glial and neuronal proteins in serum predict outcome after severe traumatic brain injury." Neurology. Apr. 27, 2004; 62(8):1303-10.
Wang et al., "An update on diagnostic and prognostic biomarkers for traumatic brain injury." Expert Review of Molecular Diagnostics, 18(2):165-180 (Jan. 2018).
Wang et al., "Proteomic identification of biomarkers of traumatic brain injury" Expert Review of Proteomics, 2(4):603-614 (Aug. 2005).
Welch et al., "Ability of Serum Glial Fibrillary Acidic Protein, Ubiquitin C-Terminal Hydrolase-L1, and S100B to Differentiate Normal and Abnormal Head Computed Tomography Findings in Patients with Suspected Mild or Moderate Traumatic Brain Injury." *Journal of Neurotrauma*, 33:203-214 (Jan. 15, 2016).
Yamauchi et al., "Ubiquitin-mediated stress response in the spinal cord after transient ischemia." Stroke. Jun. 2008; 39(6):1883-9.
Yue et al., "Association between plasma GFAP concentrations and MRI abnormalities in patients with CT-negative traumatic brain injury in the TRACK-TBI cohort: a prospective multicentre study." Lancet Neurol 2019, 9 pages.
Z. Metting et al., "Glial fibrillary acidic protein in serum after traumatic brain injury and multiple trauma", *Journal of Trauma, Williams & Wilkins*, US, 57(5):1006-1012 (Oct. 31, 2004).
Zhang et al., "Biomarkers of Traumatic Brain Injury and Their Relationship to Pathology", Laskowitz D, Grant G, editors. Translational Research in Traumatic Brain Injury, Chapter 12, Taylor and Francis Group, 2016, 12 pages.
Zoltewicz et al., "Characterization of Antibodies that Detect Human GFAP after Traumatic Brain Injury." Biomarker Insights 2012; 7:71-79.
Salim et al., "Significance of Troponin Elevation After Severe Traumatic Brain Injury." The Journal of Trauma Injury, Infection, and Critical Care 2008, 64 (1): 46-52.
Stephen et al., "The Role of Cardiac Troponin I in Prognostication of Patients with Isolated Severe Traumatic Brain Injury." J Trauma Acute Care Surg. Mar. 2016; 80(3):477-483.
International Search Report & Written Opinion dated Dec. 7, 2017 for PCT/US2017/054787, 15 pages.
International Search Report & Written Opinion dated Sep. 17, 2018 for PCT/US2018/040612, 15 pages.
International Search Report & Written Opinion dated Sep. 10, 2018 for PCT/US2018/024112, 19 pages.
International Search Report & Written Opinion dated Sep. 10, 2018 for PCT/US2018/034694, 16 pages.
International Search Report & Written Opinion dated Aug. 2, 2018 for PCT/US2018/027353, 21 pages.
International Search Report & Written Opinion dated Dec. 1, 2017 for PCT/US2017/054775, 14 pages.
International Search Report & Written Opinion dated Dec. 1, 2017 for PCT/US2018/035232, 15 pages.
International Search Report & Written Opinion dated Aug. 2, 2018 for PCT/US2018/029585, 23 pages.
International Search Report & Written Opinion dated Sep. 3, 2018 for PCT/US2018/035231, 14 pages.

METHODS FOR AIDING IN THE DIAGNOSIS AND DETERMINATION OF THE EXTENT OF TRAUMATIC BRAIN INJURY IN A HUMAN SUBJECT USING THE EARLY BIOMARKER UBIQUITIN CARBOXY-TERMINAL HYDROLASE L1

RELATED APPLICATION INFORMATION

This application claims priority to U.S. Provisional Patent Application Ser. No. 62/475,662 filed on Mar. 23, 2017, the contents of which are herein incorporated by reference in their entirety for all purposes.

TECHNICAL FIELD

The present invention relates to methods of aiding in the diagnosis and evaluation of a human subject that has sustained or may have sustained an injury to the head, such as mild or moderate to severe traumatic brain injury (TBI), by detecting changes in levels of the early biomarker ubiquitin carboxy-terminal hydrolase L1 (UCH-L1) in one or more samples (such as, for example, one or more biological samples) taken from a human subject at time points within 24 hours after the subject has sustained or may have sustained an injury to the head.

BACKGROUND

More than 5 million mild traumatic brain injuries (TBIs) occur each year in the United States alone. Currently, there is no simple, objective, accurate measurement available to help in patient assessment. In fact, much of TBI evaluation and diagnosis is based on subjective data. Unfortunately, objective measurements such as head CT and Glasgow Coma Score (GCS) are not sufficiently comprehensive or sensitive in evaluating mild TBI. Moreover, head CT is unrevealing for the vast majority of the time for mild TBI, is expensive, and exposes the patient to unnecessary radiation. Additionally, a negative head CT does not mean the patient has been cleared from having a concussion; rather, it may indicate that certain interventions, such as surgery, are not warranted. Clinicians and patients need objective, reliable information to accurately evaluate this condition to promote appropriate triage and recovery. To date, limited data have been available for the use of UCH-L1 in the acute care setting to aid in patient evaluation and management.

Mild TBI (or concussion) is much harder to objectively detect and presents an everyday challenge in emergency care units globally. Mild TBI usually causes no gross pathology, such as hemorrhage, and no abnormalities on conventional computed tomography scans of the brain, but rather rapid-onset neuronal dysfunction that resolves in a spontaneous manner over a few days to a few weeks. Approximately 15% of mild TBI patients suffer persisting cognitive dysfunction. There is an unmet need for mild TBI victims on scene, in emergency rooms and clinics, in the sports area and in military activity (e.g., combat).

SUMMARY

In one aspect, the present disclosure is directed to a method of aiding in the diagnosis and evaluation of a human subject that has sustained or may have sustained an injury to the head (or head injury). The method comprises: a) performing an assay on a biological sample taken from the subject within 24 hours after a suspected injury to the head to measure or detect a level of ubiquitin carboxy-terminal hydrolase L1 (UCH-L1) in the biological sample; and b) determining whether the subject has sustained mild or moderate to severe traumatic brain injury (TBI), wherein the subject is determined as having moderate or severe traumatic brain injury when (i) the level of UCH-L1 in the biological sample is higher than a reference level of UCH-L1 and the subject is determined as having mild traumatic brain injury when the level of UCH-L1 in the biological sample is lower than a reference level of UCH-L1; (ii) there is a statistically significant increase or decrease from the level of UCH-L1 in a biological sample taken at a first time point to the level of UCH-L1 in a biological sample taken at a second time point and the subject is determined as having mild traumatic brain injury when there is no statistically significant increase or decrease from the level of UCH-L1 in a biological sample taken at a first time point to the level of UCH-L1 in a biological sample taken at a second time point; (iii) the level of UCH-L1 decreases or increases by at least an absolute amount from the first biological sample to the second biological sample or is determined as having mild traumatic brain injury when there is no decrease or increase by at least an absolute amount in the level of UCH-L1 from the first biological sample to the second biological sample; (iv) the level of UCH-L1 decreases or increases by at least a first absolute amount from the first biological sample to the second biological sample or is determined as having mild traumatic brain injury when the level of UCH-L1 decreases or increases by at least a second absolute amount from the first biological sample to the second biological sample; or (v) the level of UCH-L1 in the biological sample is higher than a reference level of UCH-L1 or when there is a significant increase or decrease of amount X from the level of UCH-L1 in a biological sample taken at a first time point to the level of UCH-L1 in a biological sample taken at a second time point and the subject is determined as having mild traumatic brain injury when the level of UCH-L1 in the biological sample is lower than a reference level of UCH-L1 or when there is no significant increase or decrease greater than amount X from the level of UCH-L1 in a biological sample taken at a first time point to the level of UCH-L1 in a biological sample taken at a second time point.

In another aspect, the present disclosure is directed to a method of aiding in determining the extent of traumatic brain injury in a human subject who has sustained or may have sustained a suspected injury to the head (or head injury). The method comprises: a) performing an assay on at least two biological samples obtained from the subject, the first biological sample taken from the subject within 24 hours of the suspected injury and the second biological sample taken from the subject from about 3 to about 6 hours after the first biological sample is taken; b) detecting in the at least two biological samples an early biomarker of traumatic brain injury, said early biomarker consisting of ubiquitin carboxy-terminal hydrolase L1 (UCH-L1), wherein the onset of the presence of UCH-L1 appears within about 0 to about 6 hours after the suspected injury; c) determining the level of UCH-L1 in each of the first biological sample and second biological sample and determining if the level of UCH-L1 decreases or increases from the first biological sample to the second biological sample; and d) determining the extent of the traumatic brain injury in the subject based on whether the level of UCH-L1 decreases, increases, or remains the same from the first biological sample to the second biological sample.

In yet still another aspect, the present disclosure is directed to a method of aiding in the determination of whether to perform a head computerized tomography (CT) scan on a human subject that has sustained or may have sustained a suspected injury to the head (or head injury). The method comprises: a) performing an assay on at least two biological samples obtained from the subject, the first biological sample taken from the subject within 24 hours of the suspected injury and the second biological sample taken from the subject from about 3 to about 6 hours after the first biological sample is taken; b) detecting in the at least two biological samples an early biomarker of traumatic brain injury, said early biomarker consisting of ubiquitin carboxy-terminal hydrolase L1 (UCH-L1), wherein the onset of the presence of UCH-L1 appears within about 0 to about 6 hours after the suspected injury; c) determining the level of UCH-L1 in each of the first biological sample and second biological sample and determining if the level of UCH-L1 decreases or increases from the first biological sample to the second biological sample; and d) determining whether to perform a CT scan on the subject based on whether the level of UCH-L1 decreases, increases, or remains the same from the first biological sample to the second biological sample.

In yet another aspect, the present disclosure relates to a method of aiding in the diagnosis and evaluation of a human subject that has sustained or may have sustained a head injury. For example, the method can comprise:
  a) performing an assay on a sample which has been taken from the subject within 24 hours after a suspected head injury to measure or detect a level of ubiquitin carboxy-terminal hydrolase L1 (UCH-L1) in the sample; and
  b) determining whether the subject has sustained mild or moderate to severe traumatic brain injury (TBI), wherein the subject is determined as having moderate to severe traumatic brain injury when:
    (i) the level of UCH-L1 in the sample is higher than a reference level of UCH-L1 and the subject is determined as having mild traumatic brain injury when the level of UCH-L1 in the sample is lower than a reference level of UCH-L1;
    (ii) there is a statistically significant increase or decrease from the level of UCH-L1 in a sample taken at a first time point to the level of UCH-L1 in a sample taken at a second time point and the subject is determined as having mild traumatic brain injury when there is no statistically significant increase or decrease from the level of UCH-L1 in a sample taken at a first time point to the level of UCH-L1 in a sample taken at a second time point;
    (iii) the level of UCH-L1 decreases or increases by at least an absolute amount from the first sample to the second sample or is determined as having mild traumatic brain injury when there is no decrease or increase by at least an absolute amount in the level of UCH-L1 from the first sample to the second sample;
    (iv) the level of UCH-L1 decreases or increases by at least a first absolute amount from the first sample to the second sample or is determined as having mild traumatic brain injury when the level of UCH-L1 decreases or increases by at least a second absolute amount from the first sample to the second sample; or
    (v) the level of UCH-L1 in the sample is higher than a reference level of UCH-L1 or when there is a significant increase or decrease of an amount X from the level of UCH-L1 in a sample taken at a first time point to the level of UCH-L1 in a sample taken at a second time point and the subject is determined as having mild traumatic brain injury when the level of UCH-L1 in the sample is lower than a reference level of UCH-L1 or when there is no significant increase or decrease greater than amount X from the level of UCH-L1 in a sample taken at a first time point to the level of UCH-L1 in a sample taken at a second time point.

In yet another aspect, the present disclosure relates to a method of evaluating a human subject for a head injury (such as a traumatic brain injury). For example, the method can comprise:
  a) performing an assay on a sample (such as a biological sample) which has been taken from the subject within 24 hours after a suspected head injury to measure a level of ubiquitin carboxy-terminal hydrolase L1 (UCH-L1) in the sample; and
  b) determining whether the subject has sustained a mild or a moderate to severe traumatic brain injury (TBI), wherein:
    (i) the subject has sustained a moderate to severe TBI when the level of UCH-L1 in the sample is higher than a reference level of UCH-L1, and wherein the subject has sustained a mild TBI when the level of UCH-L1 in the sample is lower than a reference level of UCH-L1;
    (ii) the subject has sustained a moderate to severe TBI when there is a statistically significant increase or decrease from the level of UCH-L1 in a sample taken at a first time point to the level of UCH-L1 in a sample taken at a second time point, and wherein the subject has sustained a mild TBI when there is no statistically significant increase or decrease from the level of UCH-L1 in a sample taken at a first time point to the level of UCH-L1 in a sample taken at a second time point;
    (iii) the subject has sustained a moderate to severe TBI when the level of UCH-L1 decreases or increases by at least an absolute amount from the first sample to the second sample, and wherein the subject has sustained a mild TBI when there is no decrease or increase by at least an absolute amount in the level of UCH-L1 from the first sample to the second sample; or
    (iv) the subject has sustained a moderate to severe TBI when the level of UCH-L1 decreases or increases by at least a first absolute amount from the first sample to the second sample, and wherein the subject has sustained a mild TBI when the level of UCH-L1 decreases or increases by at least a second absolute amount from the first sample to the second sample.

In any of the above-described methods of evaluating a human subject for a head injury, the first time point can be about 0 to about 12 hours after the suspected head injury and the statistically significant increase or decrease can be selected from the group consisting of: (a) more than about 1-fold from the second time point to the first time point; (b) more than about 0.73-fold from the second time point to the first time point; or (c) more than about 0.73-fold from the second time point to the first time point and the reference level of UCH-L1 is between about 350 pg/mL and about 550 pg/mL. In some embodiments, the significant increase or decrease is more than about 1-fold from the second time point to the first time point. In some embodiments, the significant increase or decrease is more than about 0.73-fold from the second time point to the first time point. In some embodiments, the significant increase or decrease is more than about 0.73-fold from the second time point to the first time point and the reference level of UCH-L1 is between about 350 pg/mL and about 550 pg/mL.

In any of the above described methods for evaluating a human subject for a head injury, the subject may have received a Glasgow Coma Scale score before or after the assay is performed. For example, the subject may be suspected as having moderate to severe TBI based on the Glasgow Coma Scale score. Alternatively, the subject may be suspected as having mild TBI based on the Glasgow Coma Scale score. Alternatively, the subject may not have received a Glasgow Coma Scale score before the assay is performed. Additionally, the subject may have received a head CT before the assay is performed. Also, alternatively, the subject may not have received a head CT before the assay is performed. Still further, the subject may not have received a Glasgow Coma Scale or a head CT before the assay is performed. Still further, the subject may have received a Glasgow Coma Scale but not a head CT before the assay is performed. Yet further, the subject may have received a head CT but not a Glasgow Coma Scale before the assay is performed. Still further, the subject may have received a head CT and a Glasgow Coma Scale before the assay is performed.

In any of the above described methods for evaluating a human subject for a head injury, the reference level may be correlated with subjects having moderate to severe TBI (when compared to subjects having a mild TBI). Alternatively, the reference level may be correlated with subjects having mild TBI (when compared to subjects having no TBI). Still further, the reference level can indicate that the subject has a moderate to severe TBI (when compared to subjects having a mild TBI). Yet further, the reference level can indicate that the subject has a mild TBI (when compared to subject having no TBI). Still further, the reference level may be correlated with a Glasgow Coma Scale score of 13-15. It will be evident to a skilled person which reference level to select for use in the methods of the invention.

In any of the above described methods for evaluating a human subject for a head injury, the reference level can be (a) determined by an assay having a sensitivity of between at least about 85% to about 100% and a specificity of between at least about 30% to about 100%; (b) determined by an assay having a sensitivity of at least about 99% and a specificity of at least about 75%; (c) between at least about 50 pg/mL to about 12000 pg/mL; or (d) between at least about 65 pg/mL to about 9019 pg/mL. In some embodiments, the reference level can be determined by an assay having a sensitivity of between at least about 85% to about 100% and a specificity of between at least about 30% to about 100%. In some embodiments, the reference level can be determined by an assay having a sensitivity of at least about 99% and a specificity of at least about 75%. In some embodiments, the reference level can be between at least about 50 pg/mL to about 12000 pg/mL; or (d) between at least about 65 pg/mL to about 9019 pg/mL.

In any of the above described methods for evaluating a human subject for a head injury, the sample can be (a) taken within about 0 to about 6 hours after the suspected head injury and the reference level is determined by an assay having a sensitivity of about 100% and a specificity of at least about 33%; (b) taken within about 0 to about 6 hours after the suspected head injury and the reference level is determined by an assay having a sensitivity of about 100% and a specificity of about 100%; (c) taken between about 6 hours to about 12 hours after the suspected head injury and the reference level is determined by an assay having a sensitivity of about 100% and a specificity of at least about 30%; (d) taken between about 6 hours to about 12 hours after the suspected head injury and the reference level is determined by an assay having a sensitivity of about 100% and a specificity of at least about 63%; or (e) taken between about 6 hours to about 12 hours after the suspected head injury and the reference level is determined by an assay having a sensitivity of at least about 90% and a specificity of at least about 96%. In some embodiments, the sample can be taken within about 0 to about 6 hours after the suspected head injury and the reference level is determined by an assay having a sensitivity of about 100% and a specificity of at least about 33%. In some embodiments, the sample can be taken within about 0 to about 6 hours after the suspected head injury and the reference level is determined by an assay having a sensitivity of about 100% and a specificity of about 100%. In some embodiments, the sample can be taken between about 6 hours to about 12 hours after the suspected head injury and the reference level is determined by an assay having a sensitivity of about 100% and a specificity of at least about 30%. In some embodiments, the sample can be taken between about 6 hours to about 12 hours after the suspected head injury and the reference level is determined by an assay having a sensitivity of about 100% and a specificity of at least about 63%. In some embodiments, the sample can be taken between about 6 hours to about 12 hours after the suspected head injury and the reference level is determined by an assay having a sensitivity of at least about 90% and a specificity of at least about 96%.

Alternatively, the sample can be (a) taken within 0 to about 6 hours after the suspected head injury and the reference level is about 311 pg/mL; (b) taken within 0 to 6 hours after the suspected head injury and the reference level is about 9019 pg/mL; (c) taken between about 6 hours to about 12 hours after the suspected head injury and the reference level is about 98 pg/mL; (d) taken between about 6 hours to about 12 hours after the suspected head injury and the reference level is about 209 pg/mL; or (e) taken between about 6 hours to about 12 hours after the suspected head injury and the reference level is about 569 pg/mL. In some embodiments, the sample can be taken within 0 to about 6 hours after the suspected head injury and the reference level is about 311 pg/mL. In some embodiments, the sample can be taken within 0 to 6 hours after the suspected head injury and the reference level is about 9019 pg/mL. In some embodiments, the sample can be taken between about 6 hours to about 12 hours after the suspected head injury and the reference level is about 98 pg/mL. In some embodiments, the sample can be taken between about 6 hours to about 12 hours after the suspected head injury and the reference level is about 209 pg/m. In some embodiments, the sample can be taken between about 6 hours to about 12 hours after the suspected head injury and the reference level is about 569 pg/mL.

In any of the above described methods for evaluating a human subject for a head injury, the reference level may be correlated with subjects having moderate to severe TBI (when compared to subjects having a mild TBI). Alternatively, the reference level may be correlated with subjects having mild TBI (when compared to subjects having no TBI). Still further, the reference level can indicate that the subject has a moderate to severe TBI (when compared to subjects having a mild TBI). Yet further, the reference level can indicate that the subject has a mild TBI (when compared to subject having no TBI). Yet, still further, the reference level may be correlated with a Glasgow Coma Scale score of 13-15. It will be evident to a skilled person which reference level to select for use in the methods of the invention.

In any of the above-described methods for evaluating a human subject for a head injury, the absolute amount can be determined by an assay having a sensitivity of between at least about 70% to about 100% and a specificity of between at least about 30% to about 100%.

In any of the above-described methods for evaluating a human subject for ahead injury, the sample can be (a) taken within about 0 to about 6 hours after the suspected head injury and the absolute amount is determined by an assay having a sensitivity of about 100% and a specificity of about 100%; (b) taken within about 6 to about 12 hours after the suspected head injury and the absolute amount is determined by an assay having a sensitivity of at least about 70% and a specificity of at least about 92%; (c) taken within about 0 to about 10 hours after the suspected head injury and the absolute amount is determined by an assay having a sensitivity of about 100% and a specificity of at least about 36%; (d) taken within about 0 to about 11 hours after the suspected head injury and the absolute amount is determined by an assay having a sensitivity of about 100% and a specificity of at least about 32%; or (e) taken within about 0 to about 12 hours after the suspected head injury and the absolute amount is determined by an assay having a sensitivity of at least about 75% and a specificity of at least about 76%.

Yet further, in any of the above-described methods for evaluating a human subject for a head injury, the sample can be (a) taken within about 0 to about 6 hours after the suspected head injury and the absolute amount is about 2528 pg/mL; (b) taken within about 6 to about 12 hours after the suspected head injury and the absolute amount is about 129 pg/mL; (c) taken within about 6 to about 12 hours after the suspected head injury and the absolute amount is about 25 pg/mL; (d) taken within 0 to 11 hours after the suspected head injury and the absolute amount is about 25 pg/mL; or (e) taken within about 0 to about 12 hours after the suspected head injury and the absolute amount is about 129 pg/mL.

In the above-identified methods for evaluating a human subject for a head injury that the sample (or biological sample) be a whole blood sample, a serum sample or a plasma sample. Specifically, the sample (or biological sample) can be a whole blood sample. Alternatively, the sample (or biological sample) can be a serum sample. Alternatively, the sample (or biological sample) can be a plasma sample.

In the above-described methods for evaluating a human subject for a head injury that the UCH-L1 be measured or detected using an immunoassay. In one aspect, in the above described methods that the sample (or biological sample) can be a whole blood sample and that the UCH-L1 be measured or detected using an immunoassay. In yet another aspect, in the above-described methods that the sample (or biological sample) can be a serum sample and that the UCH-L1 be measured or detected using an immunoassay. In still another aspect, in the above-described methods that the sample (or biological sample) can be a plasma sample and that the UCH-L1 be measured or detected using an immunoassay.

The above-described methods for evaluating a human subject for a head injury can further comprise treating a human subject assessed as having mild or moderate to severe TBI with a treatment for TBI. As such patient being treated for TBI can also, optionally, be monitored during and after any course of treatment. Alternatively, said methods can further comprise monitoring a subject assessed as having mild or moderate TBI (such as those, who as of yet, may not be receiving any treatment).

In yet another aspect, the present disclosure relates to a method of aiding in determining the extent of traumatic brain injury in a human subject who has sustained or may have sustained a head injury. For example, the method can comprise:
 a) performing an assay on at least two samples which have been obtained from the subject, the first sample taken from the subject within 24 hours of the suspected head injury and the second sample taken from the subject from about 3 to about 6 hours after the first sample is taken;
 b) detecting in the at least two samples an early biomarker of traumatic brain injury, said early biomarker consisting of ubiquitin carboxy-terminal hydrolase L1 (UCH-L1);
 c) determining the level of UCH-L1 in each of the first sample and second sample and determining if the level of UCH-L1 decreases or increases from the first sample to the second sample; and
 d) determining the extent of the traumatic brain injury in the subject based on whether the level of UCH-L1 decreases, increases, or remains the same from the first sample to the second sample, wherein determining the extent of the traumatic brain injury comprises determining whether the subject has sustained a mild or a moderate to severe traumatic brain injury.

In the above method for aiding in determining the extent of traumatic brain injury in a human subject, the onset of the presence of UCH-L1 (such as in step b) appears within about 0 to about 6 hours after the suspected head injury.

In yet another aspect, the present disclosure relates to a method of evaluating the extent of traumatic brain injury (TBI) in a human subject. For example, the method can comprise:
 a) performing an assay to quantify ubiquitin carboxy-terminal hydrolase L1 (UCH-L1) in at least two samples obtained from the subject, the first sample taken from the subject within 24 hours of a suspected head injury and the second sample taken from the subject from about 3 to about 6 hours after the first sample is taken; and
 b) determining the extent of the TBI in the subject based on whether the level of UCH-L1 decreases, increases, or remains the same from the first sample to the second sample, wherein determining the extent of the traumatic brain injury comprises determining whether the subject has sustained a mild or a moderate to severe traumatic brain injury.

In the above-described methods for determining or evaluating the extent of the TBI, the first sample can be taken within about 0 to about 6 hours after the suspected head injury.

In the above-described methods for determining or evaluating the extent of the TBI, the subject can be determined to have moderate to severe TBI when the level of UCH-L1 increases or decreases between at least about 20 pg/mL to at least about 6100 pg/mL from the first sample to the second sample.

In the above-described methods for determining or evaluating the extent of the TBI, the first sample can be (a) taken within about 0 to about 6 hours after the suspected head injury and the level of UCH-L1 increases or decreases by at least about 2528 pg/mL; (b) taken within about 6 to about 12 hours after the suspected head injury and the level of UCH-L1 increases or decreases by at least about 129 pg/mL;

(c) taken within about 0 to about 10 hours after the suspected head injury and the level of UCH-L1 increases or decreases by at least about 25 pg/mL; (d) taken within about 0 to about 11 hours after the suspected head injury and the level of UCH-L1 increases or decreases by at least about 25 pg/mL; or (e) taken within about 0 to about 12 hours after the suspected head injury and the level of UCH-L1 increases or decreases at least about 129 pg/mL.

In the above-identified methods for determining or evaluating the extent of the TBI, the sample (or biological sample) can be a whole blood sample, a serum sample or a plasma sample. Specifically, the sample (or biological sample) can be a whole blood sample. Alternatively, the sample (or biological sample) can be a serum sample. Alternatively, the sample (or biological sample) can be a plasma sample.

In the above-described methods for determining or evaluating the extent of the TBI that the UCH-L1 be measured or detected using an immunoassay. In another aspect, in the above described methods that the sample (or biological sample) can be a whole blood sample and that the UCH-L1 be measured or detected using an immunoassay. In another aspect, in the above-described methods that the sample (or biological sample) can be a serum sample and that the UCH-L1 be measured or detected using an immunoassay. In another aspect, in the above-described methods that the sample (or biological sample) can be a plasma sample and that the UCH-L1 be measured or detected using an immunoassay.

The above-described methods for determining or evaluating the extent of the TBI, can further comprise treating a human subject assessed as having mild or moderate to severe TBI with a treatment for TBI. As such patient being treated for TBI can also, optionally, be monitored as described herein during and after any course of treatment. Alternatively, said methods can further comprise monitoring a subject assessed as having mild or moderate TBI (such as those, who as of yet, may not be receiving any treatment).

In yet another aspect, the present disclosure relates to a method of aiding in the determination of whether to perform a head computerized tomography (CT) scan on a human subject that has sustained or may have sustained a head injury. For example, the method can comprise: performing an assay to detect or measure ubiquitin carboxy-terminal hydrolase L1 (UCH-L1) in at least two samples which have been obtained from the subject, the first sample taken from the subject within 24 hours of the suspected head injury and the second sample taken from the subject from about 3 to about 6 hours after the first sample is taken;
  a) determining the level of UCH-L1 in each of the first sample and second sample and determining if the level of UCH-L1 decreases or increases from the first sample to the second sample; and
  b) determining whether to perform a CT scan on the subject based on whether the level of UCH-L1 decreases, increases, or remains the same from the first sample to the second sample, wherein:
    (i) the CT scan is performed when the level of UCH-L1 in the first sample is higher than a reference level of UCH-L1, and wherein the CT scan is not performed when the level of UCH-L1 in the first sample is lower than a reference level of UCH-L1;
    (ii) the CT scan is performed when there is a statistically significant increase or decrease in the level of UCH-L1 in the first sample to the level of UCH-L1 in the second sample, and wherein the CT scan is not performed when there is no statistically significant increase or decrease from the level of UCH-L1 in the first sample to the level of UCH-L1 in the second sample; or
    (iii) the CT scan is performed when the level of UCH-L1 decreases or increases by at least an absolute amount from the first sample to the second sample, and wherein the CT scan is not performed when there is no decrease or increase by at least an absolute amount in the level of UCH-L1 from the first sample to the second sample.

In yet another aspect, the present disclosure relates to a method of evaluating whether to perform a head computerized tomography (CT) scan on a human subject. For example, the method can comprise:
  a) performing an assay to quantify ubiquitin carboxy-terminal hydrolase L1 (UCH-L1) in at least two samples which have been obtained from the subject, the first sample taken from the subject within about 24 hours of a suspected head injury and the second sample taken from the subject from about 3 to about 6 hours after the first sample is taken; and
  b) determining whether to perform a CT scan on the subject based on whether the level of UCH-L1 decreases, increases, or remains the same from the first sample to the second sample, wherein:
    (i) the CT scan is performed when the level of UCH-L1 in the first sample is higher than a reference level of UCH-L1, and wherein the CT scan is not performed when the level of UCH-L1 in the first sample is lower than a reference level of UCH-L1;
    (ii) the CT scan is performed when there is a statistically significant increase or decrease in the level of UCH-L1 in the first sample to the level of UCH-L1 in the second sample, and wherein the CT scan is not performed when there is no statistically significant increase or decrease from the level of UCH-L1 in the first sample to the level of UCH-L1 in the second sample; or
    (iii) the CT scan is performed when the level of UCH-L1 decreases or increases by at least an absolute amount from the first sample to the second sample, and wherein the CT scan is not performed when there is no decrease or increase by at least an absolute amount in the level of UCH-L1 from the first sample to the second sample.

In the above-described methods for determining or evaluating whether to perform a head CT the first time point can be about 0 to about 12 hours after the suspected head injury and the statistically significant increase or decrease is less than about 2-fold from the first time point to the second time point; the first time point can be about 0 to about 12 hours after the suspected head injury and the statistically significant increase or decrease is less than about 1.81-fold from the first time point to the second time point; the first time point can be about 0 to about 12 hours after the suspected head injury and the statistically significant increase is more than about 0.50-fold from the second time point to the first time point; the first time point can be about 0 to about 12 hours after the suspected head injury and the statistically significant increase is more than about 0.55-fold from the second time point to the first time point; or the first time point can be about 0 to about 12 hours after the suspected head injury, the reference level of UCH-L1 is about 550 pg/mL, and the statistically significant increase is more than about 0.55-fold from the second time point to the first time point.

In the above-described methods for determining or evaluating whether to perform a head CT, the subject may be suspected of having a traumatic brain injury based on a CT scan that already was performed. For example, depending upon a subject's medical condition (such as, if the patient is unconscious), a CT scan may be conducted shortly after the subject arrives at an emergency room, trauma center, or other site in order to assess and/or evaluate whether the subject has a TBI. Such a CT scan may be performed prior to the assay being performed to confirm and determine whether or not the subject has a mild or moderate or severe TBI. After the assay is performed, one or more subsequent CT scans can be performed based on the results of the assay as part of the physician's (or other medical personnel's) management of the TBI (such as, for example, to determine whether surgical and/or pharmacological intervention may be required).

In the above-described methods for determining or evaluating whether to perform a head CT, the reference level can be correlated with positive head CT scan.

In the above-described methods for determining or evaluating whether to perform a head CT, the reference level can be (a) determined by an assay having a sensitivity of between at least about 80% to about 100% and a specificity of between at least about 30% to about 100%; (b) between at least about 50 pg/mL to about 1000 pg/mL; or (c) between at least about 86 pg/mL to about 700 pg/mL.

In the above-described methods for determining or evaluating whether to perform a head CT, the sample can be (a) taken within about 0 to about 6 hours after the suspected head injury and the reference level is determined by an assay having a sensitivity of about 100% and a specificity of at least about 37.5%; (b) taken within about 0 to about 6 hours after the suspected head injury and the reference level is determined by an assay having a sensitivity of about 100% and a specificity of at least about 75%; (c) taken between about 6 hours to about 12 hours after the suspected head injury and the reference level is determined by an assay having a sensitivity of at least about 96% and a specificity of at least about 30%; (d) taken between about 6 hours to about 12 hours after the suspected head injury and the reference level is determined by an assay having a sensitivity of at least about 86% and a specificity of at least about 35%; or (e) taken between about 0 hours to about 12 hours after the suspected head injury and the reference level is determined by an assay having a sensitivity of about 100% and a specificity of at least about 32%.

In the above-described methods for determining or evaluating whether to perform a head CT, the sample can be (a) taken within about 0 to about 6 hours after the suspected head injury and the reference level is about 370 pg/mL; (b) taken within about 0 to about 6 hours after the suspected head injury and the reference level is about 509 pg/mL; (c) taken between about 6 hours to about 12 hours after the suspected head injury and the reference level is about 96 pg/mL; (d) taken between about 6 hours to about 12 hours after the suspected head injury and the reference level is about 86 pg/mL; or (e) taken between about 6 hours to about 12 hours after the suspected head injury and the reference level is about 550 pg/mL.

In the above-described methods for determining or evaluating whether to perform a head CT, the absolute amount is correlated with positive head CT scan.

In the above-described methods for determining or evaluating whether to perform a head CT, the absolute amount can be determined by an assay having a sensitivity of between at least about 80% to about 100% and a specificity of between at least about 30% to about 100%.

In the above-described methods for determining or evaluating whether to perform a head CT, the sample can be: (a) taken within about 0 to about 10 hours after the suspected head injury and the absolute amount is determined by an assay having a sensitivity of at least about 85% and a specificity of at least about 41%; or (b) taken within about 0 to about 10 hours after the suspected head injury and the absolute amount is determined by an assay having a sensitivity of at least about 90% and a specificity of at least about 35%.

In the above-described methods for determining or evaluating whether to perform a head CT, the sample can be (a) taken within about 0 to about 10 hours after the suspected head injury and the absolute amount is about 25 pg/mL; or (b) taken within about 0 to about 10 hours after the suspected head injury and the absolute amount is about 23 pg/mL.

The above-described methods for determining or evaluating whether to perform a head CT can further comprise treating a human subject assessed as having mild or moderate to severe TBI with a treatment for TBI. As such patient being treated for TBI can also, optionally, be monitored during and after any course of treatment. Alternatively, said methods can further comprise monitoring a subject assessed as having mild or moderate TBI (such as those, who as of yet, may not be receiving any treatment).

In the above-identified methods for determining or evaluating whether to perform a head CT, the sample (or biological sample) be a whole blood sample, a serum sample or a plasma sample. Specifically, the sample (or biological sample) can be a whole blood sample. Alternatively, the sample (or biological sample) can be a serum sample. Alternatively, the sample (or biological sample) can be a plasma sample.

In above-described methods for determining or evaluating whether to perform a head CT, UCH-L1 can be measured or detected using an immunoassay. In another aspect of the above described methods, the sample (or biological sample) can be a whole blood sample and UCH-L1 can be measured or detected using an immunoassay. In another aspect in the above-described methods, the sample (or biological sample) can be a serum sample and UCH-L1 can be measured or detected using an immunoassay. In another aspect in the above-described methods, the sample (or biological sample) can be a plasma sample and UCH-L1 can be measured or detected using an immunoassay.

In any of the above-described methods, in some embodiments, the second sample be taken from the subject between about 5 hours to about 16 hours or about 3 hours to about 6 hours after the suspected head injury. More specifically, the second sample can be taken from the subject at about 3 hours, at about 4 hours, at about 5 hours, at about 6 hours, at about 7 hours, at about 8 hours, at about 9 hours, at about 10 hours, at about 11 hours, or at about 12 hours after the suspected head injury.

Any of the above-described methods can further comprise performing an assay on the samples to measure or detect a level of one or more other biomarkers that are not UCH-L1.

In any of the above-described methods, the assay can comprise:

(a) measuring or detecting a level of one or more other biomarkers in the first sample and the second sample,
(b) determining a decrease or increase in the level of the one or more other biomarkers from the first sample to the second sample, and
(c) assessing the subject as having mild TBI if there is a statistically significant decrease or increase in the level of the one or more other biomarkers from the first sample to the level of the one or more other biomarkers in the second sample.

In the above-described methods, the one or more other biomarkers is selected from the group consisting of S100β, neuron-specific enolase (NSE), glial fibrillary acidic protein (GFAP), Apo lipoprotein 1, Tau, C-reactive protein (CRP), free brain-derived neurotrophic factor (BDNF), p-Tau, total BDNF, troponin I (TnI), and a combination thereof. More specifically, the one or more other biomarkers is S100O, BDNF, or CRP.

In any of the above-described methods, the level of UCH-L1 can be measured by performing an immunoassay. For example, the level of UCH-L1 can be measured by
(a) contacting the sample, either simultaneously or sequentially, in any order with:
 (1) a capture antibody, which binds to an epitope on UCH-L1 or UCH-L1 fragment to form a capture antibody-UCH-L1 antigen complex, and
 (2) a detection antibody which includes a detectable label and binds to an epitope on UCH-L1 that is not bound by the capture antibody, to form a UCH-L1 antigen-detection antibody complex, such that a capture antibody-UCH-L1 antigen-detection antibody complex is formed, and
(b) measuring the amount or concentration of UCH-L1 in the sample based on the signal generated by the detectable label in the capture antibody-UCH-L1 antigen-detection antibody complex.

In any of the above methods, the sample can be a whole blood sample, a serum sample, a cerebrospinal fluid sample or a plasma sample. In one aspect, the sample is a whole blood sample. In another aspect, the sample is a serum sample. In yet another aspect, the sample is a plasma sample. Such a sample can be obtained in a variety of ways. For example, the sample can be obtained after the subject sustained a head injury caused by physical shaking, blunt impact by an external mechanical or other force that results in a closed or open head trauma, one or more falls, explosions or blasts or other types of blunt force trauma. Alternatively, the sample can be obtained after the subject has ingested or been exposed to a chemical, toxin or combination of a chemical and toxin. Examples of chemicals or toxins are fire, mold, asbestos, a pesticide, an insecticide, an organic solvent, a paint, a glue, a gas, an organic metal, a drug of abuse or one or more combinations thereof. Still further, the sample can be obtained from a subject that suffers from an autoimmune disease, a metabolic disorder, a brain tumor, hypoxia, a virus, meningitis, hydrocephalus or combinations thereof.

Any of the above-described methods can be carried out on any human subject without regard to factors selected from the group consisting of the human subject's clinical condition, the human subject's laboratory values, the human subject's classification as suffering from mild or moderate to severe TBI, the human subject's exhibition of low or high levels of UCH-L1, and the timing of any event wherein the human subject may have sustained head injury.

BRIEF DESCRIPTION OF THE DRAWINGS

FIG. 9A shows the box plots for the 0-6 hour group and FIG. 9B shows the box plots for the 6-12 hour group.

FIG. 10A shows the box plots for the 0-6 hour group and FIG. 10B shows the box plots for the 6-12 hour group.

FIG. 13A shows the box plots for the 0-6 hour group and FIG. 13B shows the box plots for the 6-12 hour group.

DETAILED DESCRIPTION

Figure 1:
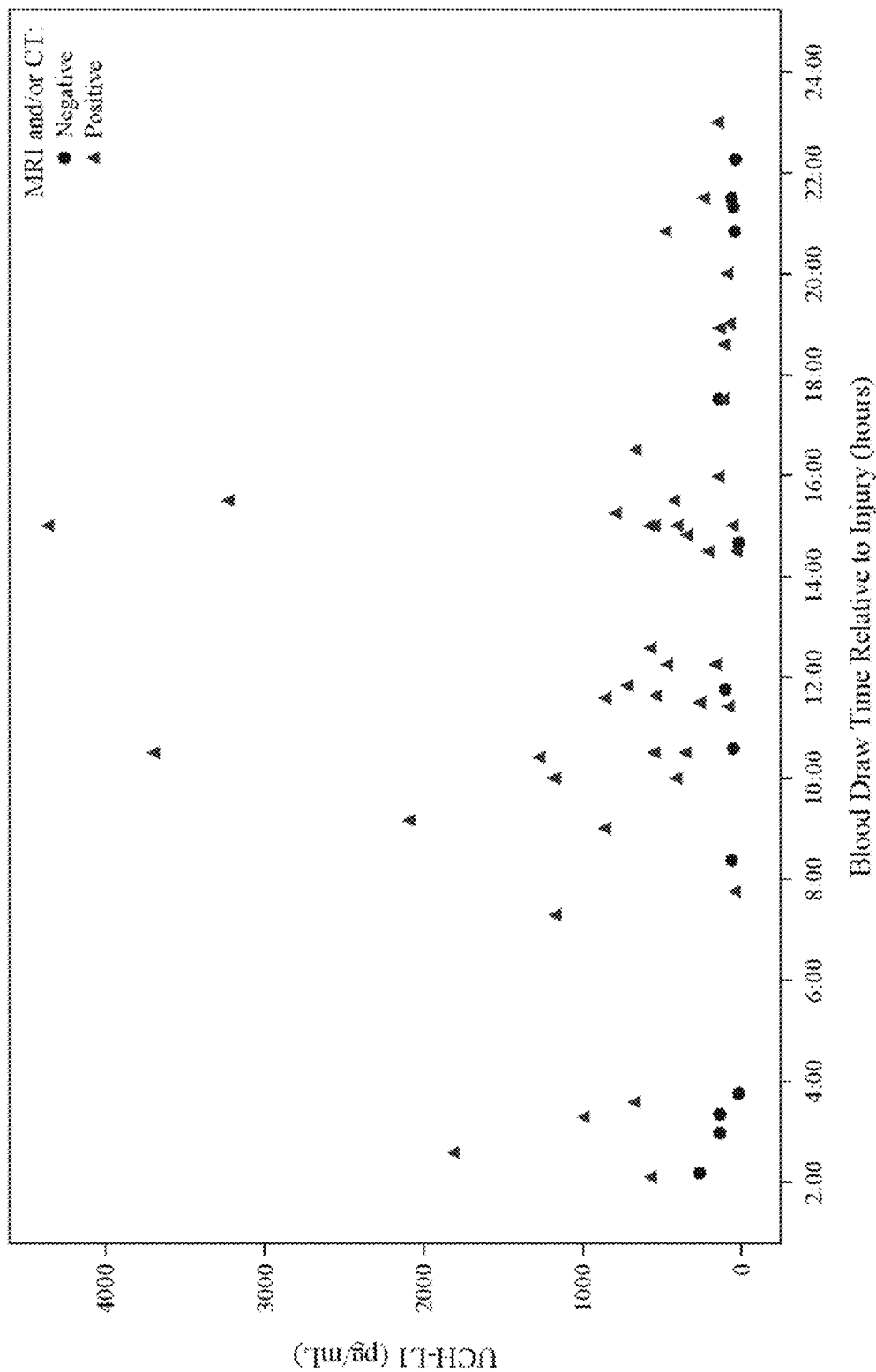
FIG. 1 shows biomarker UCH-L1 result vs. time from injury.

The present invention relates to methods that aid in the diagnosis and evaluation of a subject (such as, for example, a human subject) that has sustained an injury to the head, such as mild or moderate to severe traumatic brain injury (TBI), using an early biomarker, ubiquitin carboxy-terminal hydrolase L1 (UCH-L1). These methods involve detecting UCH-L1 levels in one or more samples (such as, for example, a biological sample) taken from the subject at different time points within 24 hours of the injury to the head or suspected injury to the head. The detection of an increase in or elevated levels of UCH-L1 that may be followed by a subsequent decrease in UCH-L1 levels within the first 24 hours after injury or suspected injury to the head provides an aid in accurately evaluating or diagnosing the subject, thus allowing for the subsequent early treatment and monitoring of patients with mild or moderate to severe traumatic brain injury. For example, subjects having a statistical significant change in UCH-L1 levels in a first sample taken within the first 6 hours, such as within 2 to 6 hours, after the injury or suspected injury compared to a second sample taken about 0.5 to 10 hours, such as 3 to 6 hours, after the first sample is taken may be identified as having moderate to severe traumatic brain injury. In another example, subjects having a UCH-L1 level higher than a reference level may also be identified as having moderate to severe traumatic brain injury. In another example, subjects having at least an increase or decrease by an absolute amount may also be identified as having moderate to severe traumatic brain injury.

The present invention also relates to methods that aid in determining whether a subject that has sustained an injury to the head would benefit from and thus receive a head computerized tomography (CT) scan based on the levels of UCH-L1. These methods involve detecting UCH-L1 levels in one or more samples taken from the subject at different time points within 24 hours of the injury to the head or suspected injury to the head. The detection of an increase in or elevated levels of UCH-L1 that may be followed by a subsequent decrease in UCH-L1 levels within the first 24 hours after injury or suspected injury to the head provides an aid in determining whether a subject should receive a head CT scan. For example, subjects having a statistical significant change in UCH-L1 levels in a first sample taken within the first 6 hours, such as within 2 to 6 hours, after the injury or suspected injury compared to a second sample taken about 0.5 to 10 hours, such as 3 to 6 hours, after the first sample is taken may be identified as likely to have a positive head CT scan and thus benefit from having a CT scan. In another example, subjects having a UCH-L1 level higher than a reference level may also be identified as likely to have a positive head CT scan and thus benefit from having a CT scan. In another example, subjects having at least an increase or decrease by an absolute amount may also be identified as likely to have a positive head CT scan (e.g., thus indicating a potential TBI) and thus benefit from having a CT scan.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Affinity matured antibody" is used herein to refer to an antibody with one or more alterations in one or more CDRs, which result in an improvement in the affinity (i.e., $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies is known in the art, including the screening of a combinatory antibody library that has been prepared using bio-display. For example, Marks et al., *BioTechnology*, 10: 779-783 (1992) describes affinity maturation by VH and VL domain shuffling. Random mutagenesis of CDR and/or framework residues is described by Barbas et al., *Proc. Nat. Acad. Sci. USA*, 91: 3809-3813 (1994); Schier et al., *Gene*, 169: 147-155 (1995); Yelton et al., *J. Immunol.*, 155: 1994-2004 (1995); Jackson et al., *J. Immunol.*, 154(7): 3310-3319 (1995); and Hawkins et al, J. Mol. Biol., 226: 889-896 (1992). Selective mutation at selective mutagenesis positions and at contact or hypermutation positions with an activity-enhancing amino acid residue is described in U.S. Pat. No. 6,914,128 B1.

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')₂ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., *Nature Biotechnology*, 25(11):1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody" (e.g., an anti-UCH-L1 antibody or a UCH-L1 antibody).

"Antibody fragment" as used herein refers to a portion of an intact antibody comprising the antigen-binding site or variable region. The portion does not include the constant heavy chain domains (i.e., CH2, CH3, or CH4, depending on the antibody isotype) of the Fc region of the intact antibody. Examples of antibody fragments include, but are not limited to, Fab fragments, Fab' fragments, Fab'-SH fragments, F(ab')₂ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

The "area under curve" or "AUC" refers to area under a ROC curve. AUC under a ROC curve is a measure of accuracy. An AUC of 1 represents a perfect test, whereas an AUC of 0.5 represents an insignificant test. A preferred AUC may be at least approximately 0.700, at least approximately 0.750, at least approximately 0.800, at least approximately 0.850, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

"Bead" and "particle" are used herein interchangeably and refer to a substantially spherical solid support. One example of a bead or particle is a microparticle. Microparticles that can be used herein can be any type known in the art. For example, the bead or particle can be a magnetic bead or magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO.Fe_2O_3$). Beads can have a solid core portion that is magnetic and is surrounded by one or more non-magnetic layers. Alternately, the magnetic portion can be a layer around a non-magnetic core. The microparticles can be of any size that would work in the methods described herein, e.g., from about 0.75 to about 5 nm, or from about 1 to about 5 nm, or from about 1 to about 3 nm.

"Binding protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (see Milstein et al., *Nature*, 305(5934): 537-540 (1983)), by chemical conjugation of two different monoclonal antibodies (see, Staerz et al., *Nature*, 314(6012): 628-631 (1985)), or by knob-into-hole or similar approaches, which introduce mutations in the Fc region (see Holliger et al., *Proc. Natl. Acad. Sci. USA*, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

"CDR" is used herein to refer to the "complementarity determining region" within an antibody variable sequence. There are three CDRs in each of the variable regions of the heavy chain and the light chain. Proceeding from the N-terminus of a heavy or light chain, these regions are denoted "CDR1", "CDR2", and "CDR3", for each of the variable regions. The term "CDR set" as used herein refers to a group of three CDRs that occur in a single variable region that binds the antigen. An antigen-binding site, therefore, may include six CDRs, comprising the CDR set from each of a heavy and a light chain variable region. A polypeptide comprising a single CDR, (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

The exact boundaries of these CDRs have been defined differently according to different systems. The system described by Kabat (Kabat et al., *Sequences of Proteins of Immunological Interest* (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, *J. Mol. Biol.*, 196: 901-917 (1987); and Chothia et al., *Nature*, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, *FASEB J.*, 9: 133-139 (1995), and MacCallum, *J. Mol. Biol.*, 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, whole blood, serum or plasma sample, in accordance with the methods described herein and other methods known in the art. Some components can be in solution or lyophilized for reconstitution for use in an assay.

"CT scan" as used herein refers to a computerized tomography (CT) scan. A CT scan combines a series of X-ray images taken from different angles and uses computer processing to create cross-sectional images, or slices, of the bones, blood vessels and soft tissues inside your body. The CT scan may use X-ray CT, positron emission tomography (PET), single-photon emission computed tomography (SPECT), computed axial tomography (CAT scan), or computer aided tomography. The CT scan may be a conventional CT scan or a spiral/helical CT scan. In a conventional CT scan, the scan is taken slice by slice and after each slice the scan stops and moves down to the next slice, e.g., from the top of the abdomen down to the pelvis. The conventional CT scan requires patients to hold their breath to avoid movement artefact. The spiral/helical CT scan is a continuous scan which is taken in a spiral fashion and is a much quicker process where the scanned images are contiguous.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g., a protein domain, said protein domain being linked by covalent or non-covalent bonds. The linkage can be based on genetic fusion according to the methods known in the art. The additional domain present in the fusion protein comprising the antibody may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g., a cytokine or growth hormone), a chemical agent, a peptide, a protein, or a drug, for example.

"Determined by an assay" is used herein to refer to the determination of a reference level or an absolute amount by any appropriate assay. The determination of a reference level or an absolute amount may, in some embodiments, be achieved by an assay of the same type as the assay that is to be applied to the sample from the subject (for example, by an immunoassay, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS)). The determination of a reference level or an absolute amount may, in some embodiments, be achieved by an assay of the same type and under the same assay conditions as the assay that is to be applied to the sample from the subject. As noted herein, this disclosure provides exemplary reference levels and absolute amounts (e.g., calculated by comparing reference levels at different time points). It is well within the ordinary skill of one in the art to adapt the disclosure herein for other assays to obtain assay-specific reference levels and absolute amounts for those other assays based on the description provided by this disclosure. For example, a set of training samples comprising samples obtained from human subjects known to have sustained an injury to the head (and more particularly, samples obtained from human subjects known to have sustained (i) mild TBI; or (ii) moderate to severe TBI and samples obtained from human subjects known not to have sustained an injury to the head (and more particularly, samples obtained from human subjects known not to have sustained any TBI) may be used to obtain assay-specific reference levels and absolute amounts. It will be understood that a reference level or absolute amount "determined by an assay" and having a recited level of "sensitivity" and/or "specificity" is used herein to refer to a reference level or absolute amount which has been determined to provide a method of the recited sensitivity and/or specificity when said reference level or absolute amount is adopted in the methods of the invention. It is well within the ordinary skill of one in the art to determine the sensitivity and specificity associated with a given reference level or absolute amount in the methods of the invention, for example by repeated statistical analysis of assay data using a plurality of different possible reference levels and absolute amounts.

"Drugs of abuse" is used herein to refer to one or more additive substances (such as a drug) taken for non-medical reasons (such as for, example, recreational and/or mind-altering effects). Excessive overindulgence, use or dependence of such drugs of abuse is often referred to as "substance abuse". Examples of drugs of abuse include alcohol, barbiturates, benzodiazepines, *cannabis*, cocaine, hallucinogens (such as ketamine, mescaline (peyote), PCP, psilocybin, DMT and/or LSD), methaqualone, opioids, amphetamines (including methamphetamines), anabolic steroids, inhalants (namely, substances which contain volatile substances that contain psychoactive properties such as, for example, nitrites, spray paints, cleaning fluids, markers, glues, etc.) and combinations thereof.

"Dual-specific antibody" is used herein to refer to a full-length antibody that can bind two different antigens (or epitopes) in each of its two binding arms (a pair of HC/LC) (see PCT publication WO 02/02773). Accordingly, a dual-specific binding protein has two identical antigen binding arms, with identical specificity and identical CDR sequences, and is bivalent for each antigen to which it binds.

"Dual variable domain" is used herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig." Such a DVD-Ig binding protein is thus tetrameric and reminiscent of an IgG molecule, but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., *Nature Biotech.*, 25: 1290-1297 (2007). A preferred example of such DVD-Ig molecules comprises a heavy chain that comprises the structural formula VD1-(X1)n-VD2-C—(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C—(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein binds at least one epitope of UCH-L1. Non-limiting examples of a DVD-Ig binding protein include a DVD-Ig binding protein that binds one or more epitopes of UCH-L1, a DVD-Ig binding protein that binds an epitope of a human UCH-L1 and an epitope of UCH-L1 of another species (for example, mouse), and a DVD-Ig binding protein that binds an epitope of a human UCH-L1 and an epitope of another target molecule.

"Dynamic range" as used herein refers to range over which an assay readout is proportional to the amount of target molecule or analyte in the sample being analyzed.

"Evaluating" and "evaluate" as used herein refers to assessing a subject with a head injury or a suspected head injury in order to obtain information pertinent to the head injury, such as the presence, absence, and/or degree of tramautic brain injury. "Evaluating" can include detecting, measuring, and/or quantifying levels of a TBI biomarker, such as UCH-L1, in a sample from a subject. "Evaluating" can also include performing various clinical assessments of a subject with a head injury or a suspected head injury, such as, but not limited to, performing a GCS assessment, a GOSE assessment, and/or imaging analysis (e.g., CT scan or MM imaging).

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"Fragment antigen-binding fragment" or "Fab fragment" as used herein refers to a fragment of an antibody that binds to antigens and that contains one antigen-binding site, one complete light chain, and part of one heavy chain. Fab is a monovalent fragment consisting of the VL, VH, CL and CH1 domains. Fab is composed of one constant and one variable domain of each of the heavy and the light chain. The variable domain contains the paratope (the antigen-binding site), comprising a set of complementarity determining regions, at the amino terminal end of the monomer. Each arm of the Y thus binds an epitope on the antigen. Fab fragments can be generated such as has been described in the art, e.g., using the enzyme papain, which can be used to cleave an immunoglobulin monomer into two Fab fragments and an Fc fragment, or can be produced by recombinant means.

"F(ab')$_2$ fragment" as used herein refers to antibodies generated by pepsin digestion of whole IgG antibodies to remove most of the Fc region while leaving intact some of the hinge region. F(ab')$_2$ fragments have two antigen-binding F(ab) portions linked together by disulfide bonds, and therefore are divalent with a molecular weight of about 110 kDa. Divalent antibody fragments (F(ab')$_2$ fragments) are smaller than whole IgG molecules and enable a better penetration into tissue thus facilitating better antigen recognition in immunohistochemistry. The use of F(ab')$_2$ fragments also avoids unspecific binding to Fc receptor on live cells or to Protein A/G. F(ab')$_2$ fragments can both bind and precipitate antigens.

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol:// vbase.mrc-cpe.cam.ac.uk/) or in the international ImMunoGeneTics® (IMGT®) immunogenetics information system (hypertext transfer protocol://imgt.cines.fr/texts/IMGTrepertoire/LocusGenes/).

"Functional antigen binding site" as used herein may mean a site on a binding protein (e.g., an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

"Glasgow Coma Scale" or "GCS" as used herein refers to a 15 point scale for estimating and categorizing the outcomes of brain injury on the basis of overall social capability or dependence on others. The test measures the motor response, verbal response and eye opening response with these values: I. Motor Response (6—Obeys commands fully; 5—Localizes to noxious stimuli; 4—Withdraws from noxious stimuli; 3—Abnormal flexion, i.e., decorticate posturing; 2—Extensor response, i.e., decerebrate posturing; and 1—No response); II. Verbal Response (5—Alert and Oriented; 4—Confused, yet coherent, speech; 3—Inappropriate words and jumbled phrases consisting of words; 2—Incomprehensible sounds; and 1—No sounds); and III. Eye Opening (4—Spontaneous eye opening; 3—Eyes open to speech; 2—Eyes open to pain; and 1—No eye opening). The final score is determined by adding the values of I+II+III. The final score can be categorized into four possible levels for survival, with a lower number indicating a more severe injury and a poorer prognosis: Mild (13-15); Moderate Disability (9-12) (Loss of consciousness greater than 30 minutes; Physical or cognitive impairments which may or may resolve: and Benefit from Rehabilitation); Severe Disability (3-8) (Coma: unconscious state. No meaningful response, no voluntary activities); and Vegetative State (Less Than 3) (Sleep wake cycles; Arousal, but no interaction with environment; No localized response to pain). Moderate brain injury is defined as a brain injury resulting in a loss of consciousness from 20 minutes to 6 hours and a Glasgow Coma Scale of 9 to 12. Severe brain injury is defined as a brain injury resulting in a loss of consciousness of greater than 6 hours and a Glasgow Coma Scale of 3 to 8.

"Glasgow Outcome Scale" as used herein refers to a global scale for functional outcome that rates patient status into one of five categories: Dead, Vegetative State, Severe Disability, Moderate Disability or Good Recovery.

"Extended Glasgow Outcome Scale" or "GOSE" as used interchangeably herein provides more detailed categorization into eight categories by subdividing the categories of severe disability, moderate disability and good recovery into a lower and upper category as shown in Table 1.

TABLE 1

| 1 | Death | D | |
|---|---|---|---|
| 2 | Vegetative state | VX | |
| 3 | Lower severe disability | SD− | Condition of unawareness with only reflex responses but with periods of spontaneous eye opening |
| 4 | Upper severe disability | SD+ | |
| 5 | Lower moderate disability | MD− | Patient who is dependent for daily support for mental or physical disability, usually a combination of both. If the patient can be left alone for more than 8 hours at home it is upper level of SD, if not then it is low level of SD. |
| 6 | Upper moderate disability | MD+ | |
| 7 | Lower good recovery | GR− | Patients have some disability such as aphasia, hemiparesis or epilepsy and/or deficits of memory or personality but are able to look after themselves. They are independent at home but dependent outside. If they are able to return to work even with special arrangement it is upper level of MD, if not then it is low level of MD. |
| 8 | Upper good recovery | GR+ | |

"Humanized antibody" is used herein to describe an antibody that comprises heavy and light chain variable region sequences from a non-human species (e.g., a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98%, or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, *From Genes to Clones* (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Injury to the head" or "head injury" as used interchangeably herein, refers to any trauma to the scalp, skull, or brain. Such injuries may include only a minor bump on the skull or may be a serious brain injury. Such injuries include primary injuries to the brain and/or secondary injuries to the brain. Primary brain injuries occur during the initial insult and result from displacement of the physical structures of the brain. More specifically, a primary brain injury is the physical damage to parenchyma (tissue, vessels) that occurs during the traumatic event, resulting in shearing and compression of the surrounding brain tissue. Secondary brain injuries occur subsequent to the primary injury and may involve an array of cellular processes. More specifically, a secondary brain injury refers to the changes that evolve over a period of time (from hours to days) after the primary brain injury. It includes an entire cascade of cellular, chemical, tissue, or blood vessel changes in the brain that contribute to further destruction of brain tissue.

An injury to the head can be either closed or open (penetrating). A closed head injury refers to a trauma to the scalp, skull or brain where there is no penetration of the skull by a striking object. An open head injury refers a trauma to the scalp, skull or brain where there is penetration of the skull by a striking object. An injury to the head may be caused by physical shaking of a person, by blunt impact by an external mechanical or other force that results in a closed or open head trauma (e.g., vehicle accident such as with an automobile, plane, train, etc.; blow to the head such as with a baseball bat, or from a firearm), a cerebral vascular accident (e.g., stroke), one or more falls (e.g., as in sports or other activities), explosions or blasts (collectively, "blast injuries") and by other types of blunt force trauma. Alternatively, an injury to the head may be caused by the ingestion and/or exposure to a chemical, toxin or a combination of a chemical and toxin. Examples of such chemicals and/or toxins include fires, molds, asbestos, pesticides and insecticides, organic solvents, paints, glues, gases (such as carbon monoxide, hydrogen sulfide, and cyanide), organic metals (such as methyl mercury, tetraethyl lead and organic tin) and/or one or more drugs of abuse. Alternatively, an injury to the head may be caused as a result of a subject suffering from an autoimmune disease, a metabolic disorder, a brain tumor, one or more viruses, meningitis, hydrocephalus, hypoxia or any combinations thereof. In some cases, it is not possible to be certain whether any such event or injury has occurred or taken place. For example, there may be no history on a patient or subject, the subject may be unable to speak, the subject may be aware of what events they were exposed to, etc. Such circumstances are described herein as the subject "may have sustained an injury to the head." In certain embodiments herein, the closed head injury does not include and specifically excludes a cerebral vascular accident, such as stroke.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromagens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as 3H, 14C, 32P, 33P, 35S, 90Y, 99Tc, 111In, 125I, 131I, 177Lu, 166Ho, and 153 Sm), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetra-chlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2nd ed., Springer Verlag, N.Y. (1997), and in Haugland, *Handbook of Fluorescent Probes and Research Chemicals* (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., *Bioorg. Med. Chem. Lett.* 16: 1324-1328 (2006); Adamczyk et al., *Bioorg. Med. Chem. Lett.* 4: 2313-2317 (2004); Adamczyk et al., *Biorg. Med. Chem. Lett.* 14: 3917-3921 (2004); and Adamczyk et al., *Org. Lett.* 5: 3779-3782 (2003)).

In one aspect, the acridinium compound is an acridinium-9-carboxamide. Methods for preparing acridinium 9-carboxamides are described in Mattingly, *J. Biolumin. Chemilumin.* 6: 107-114 (1991); Adamczyk et al., *J. Org. Chem.* 63: 5636-5639 (1998); Adamczyk et al., *Tetrahedron* 55: 10899-10914 (1999); Adamczyk et al., *Org. Lett.* 1: 779-781 (1999); Adamczyk et al., *Bioconjugate Chem.* 11: 714-724 (2000); Mattingly et al., In *Luminescence Biotechnology: Instruments and Applications*; Dyke, K. V. Ed.; CRC Press: Boca Raton, pp. 77-105 (2002); Adamczyk et al., *Org. Lett.* 5: 3779-3782 (2003); and U.S. Pat. Nos. 5,468,646, 5,543,524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., *Luminescence* 15: 245-249 (2000); Razavi et al., *Luminescence* 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Linking sequences can be used for many purposes, including in recombinant Fabs. Exemplary linking sequences include, but are not limited to: (i) Histidine (His) tags, such as a 6×His tag, which has an amino acid sequence of HHHHHH (SEQ ID NO:2), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO:3) and derivatives thereof (e.g., ADDDDK (SEQ ID NO:4), etc.); (iii) Miscellaneous sequences can be used to link or connect the light and/or heavy chain variable regions of single chain variable region fragments. Examples of other linking sequences can be found in Bird et al., *Science* 242: 423-426 (1988); Huston et al., *PNAS USA* 85: 5879-5883 (1988); and McCafferty et al., *Nature* 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

"Monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"MRI" as used herein refers to magnetic resonance imaging, which is a medical imaging technique used in radiology to form pictures of the anatomy and the physiological processes of the body in both health and disease. MRI scanners, which is based on the science of nuclear magnetic resonance (NMR), use strong magnetic fields, radio waves, and field gradients to generate images of the inside of the body.

"Multivalent binding protein" is used herein to refer to a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein that can bind two or more related or unrelated targets, including a binding protein capable of binding two or more different epitopes of the same target molecule.

"Negative predictive value" or "NPV" as used interchangeably herein refers to the probability that a subject has a negative outcome given that they have a negative test result.

"Reference level" as used herein refers to an assay cutoff value that is used to assess diagnostic, prognostic, or therapeutic efficacy and that has been linked or is associated herein with various clinical parameters (e.g., presence of disease, stage of disease, severity of disease, progression, non-progression, or improvement of disease, etc.). An "absolute amount" as used herein refers to the absolute value of a change or difference between at least two assay results taken or sampled at different time points and, which similar to a reference level, has been linked or is associated herein with various clinical parameters (e.g., presence of disease, stage of disease, severity of disease, progression, non-progression, or improvement of disease, etc.). "Absolute value" as used herein refers to the magnitude of a real number (such as, for example, the difference between two compared levels (such as levels taken at a first time point and levels taken at a second time point)) without regard to its sign, i.e., regardless of whether it is positive or negative.

This disclosure provides exemplary reference levels and absolute amounts (e.g., calculated by comparing reference levels at different time points). However, it is well-known that reference levels and absolute amounts may vary depending on the nature of the immunoassay (e.g., antibodies employed, reaction conditions, sample purity, etc.) and that assays can be compared and standardized. It further is well within the ordinary skill of one in the art to adapt the disclosure herein for other immunoassays to obtain immunoassay-specific reference levels and absolute amounts for those other immunoassays based on the description provided by this disclosure. Whereas the precise value of the reference level and absolute amount may vary between assays, the findings as described herein should be generally applicable and capable of being extrapolated to other assays. For example, the data provided herein provide greater temporal resolution of UCH-L1 levels in the context of TBI, and are not limited to single time-point assessments. Data from the present disclosure demonstrate that UCH-L1 levels vary dynamically post-injury, which can be evaluated using a variety of different assays.

"Point-of-care device" refers to a device used to provide medical diagnostic testing at or near the point-of-care (namely, outside of a laboratory), at the time and place of patient care (such as in a hospital, physician's office, urgent or other medical care facility, a patient's home, a nursing home and/or a long term care and/or hospice facility). Examples of point-of-care devices include those produced by Abbott Laboratories (Abbott Park, Ill.) (e.g., i-STAT and i-STAT Alinity, Universal Biosensors (Rowville, Australia)

(see US 2006/0134713), Axis-Shield PoC AS (Oslo, Norway) and Clinical Lab Products (Los Angeles, USA).

"Positive predictive value" or "PPV" as used interchangeably herein refers to the probability that a subject has a positive outcome given that they have a positive test result.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a reference level or control level (e.g., "low," "medium," or "high" levels), can be used. Multiple calibrators (i.e., more than one calibrator or a varying amount of calibrator(s)) can be used in conjunction to comprise a "sensitivity panel."

A "receiver operating characteristic" curve or "ROC" curve refers to a graphical plot that illustrates the performance of a binary classifier system as its discrimination threshold is varied. For example, an ROC curve can be a plot of the true positive rate against the false positive rate for the different possible cutoff points of a diagnostic test. It is created by plotting the fraction of true positives out of the positives (TPR=true positive rate) vs. the fraction of false positives out of the negatives (FPR=false positive rate), at various threshold settings. TPR is also known as sensitivity, and FPR is one minus the specificity or true negative rate. The ROC curve demonstrates the tradeoff between sensitivity and specificity (any increase in sensitivity will be accompanied by a decrease in specificity); the closer the curve follows the left-hand border and then the top border of the ROC space, the more accurate the test; the closer the curve comes to the 45-degree diagonal of the ROC space, the less accurate the test; the slope of the tangent line at a cutoff point gives the likelihood ratio (LR) for that value of the test; and the area under the curve is a measure of text accuracy.

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., *Nature Biotechnology*, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Risk assessment," "risk classification," "risk identification," or "risk stratification" of subjects (e.g., patients) as used herein refers to the evaluation of factors including biomarkers, to predict the risk of occurrence of future events including disease onset or disease progression, so that treatment decisions regarding the subject may be made on a more informed basis.

"Sample," "test sample," "specimen," "sample from a subject," "patient sample," and "biological sample" as used herein may be used interchangeably and may be a sample of blood such as whole blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. In one embodiment, the sample is a whole blood sample, plasma or a serum sample. In another embodiment, the sample is whole blood. In another embodiment, the sample is serum. In yet another embodiment, the sample is plasma. In yet other embodiments, the sample is a whole blood sample obtained from a human. In still another embodiment, the sample is a plasma sample obtained from a human. In still yet another embodiment, the sample is a serum sample obtained from a human.

A variety of cell types, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, red blood cells, platelets, interstitial fluid, cerebral spinal fluid, etc. Cell types and tissues may also include lymph fluid, cerebrospinal fluid, a fluid collected by A tissue or cell type may be provided by removing a sample of cells from a human and a non-human animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

"Sensitivity" refers to the proportion of subjects for whom the outcome is positive that are correctly identified as positive (e.g., correctly identifying those subjects with a disease or medical condition for which they are being tested). For example, this might include correctly identifying subjects as having a moderate to severe TBI from those having a mild TBI, correctly identifying subjects as having a mild TBI from those having a moderate to severe TBI, correctly identifying subjects as having a moderate to severe TBI from those having no TBI or correctly identifying subjects as having a mild TBI from those having no TBI).

"Specificity" of an assay as used herein refers to the proportion of subjects for whom the outcome is negative that are correctly identified as negative (e.g., correctly identifying those subjects who do not have a disease or medical condition for which they are being tested). For example, this might include correctly identifying subjects as not having a moderate to severe TBI from those having a mild TBI, correctly identifying subjects as not having a mild TBI from those having a moderate to severe TBI or correctly identifying subjects as not having any TBI).

"Series of calibrating compositions" refers to a plurality of compositions comprising a known concentration of UCH-L1, wherein each of the compositions differs from the other compositions in the series by the concentration of UCH-L1.

"Single molecule detection" as used herein refers to the detection and/or measurement of a single molecule of an analyte in a test sample at very low levels of concentration (such as pg/mL or femtogram/mL levels). A number of different single molecule analyzers or devices are known in the art and include nanopore and nanowell devices. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

"Solid phase" or "solid support" as used interchangeably herein, refers to any material that can be used to attach and/or attract and immobilize (1) one or more capture agents or capture specific binding partners, or (2) one or more detection agents or detection specific binding partners. The solid phase can be chosen for its intrinsic ability to attract and immobilize a capture agent. Alternatively, the solid phase can have affixed thereto a linking agent that has the ability to attract and immobilize the (1) capture agent or capture specific binding partner, or (2) detection agent or detection specific binding partner. For example, the linking agent can include a charged substance that is oppositely charged with respect to the capture agent (e.g., capture specific binding partner) or detection agent (e.g., detection specific binding partner) itself or to a charged substance conjugated to the (1) capture agent or capture specific binding partner or (2) detection agent or detection specific binding partner. In general, the linking agent can be any binding partner (preferably specific) that is immobilized on (attached to) the solid phase and that has the ability to immobilize the (1) capture agent or capture specific binding partner, or (2) detection agent or detection specific binding partner through a binding reaction. The linking agent enables the indirect binding of the capture agent to a solid phase material before the performance of the assay or during the performance of the assay. For examples, the solid phase can be plastic, derivatized plastic, magnetic, or non-magnetic metal, glass or silicon, including, for example, a test tube, microtiter well, sheet, bead, microparticle, chip, and other configurations known to those of ordinary skill in the art.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Statistically significant" as used herein refers to the likelihood that a relationship between two or more variables is caused by something other than random chance. Statistical hypothesis testing is used to determine whether the result of a data set is statistically significant. In statistical hypothesis testing, a statistical significant result is attained whenever the observed p-value of a test statistic is less than the significance level defined of the study. The p-value is the probability of obtaining results at least as extreme as those observed, given that the null hypothesis is true. Examples of statistical hypothesis analysis include Wilcoxon signed-rank test, t-test, Chi-Square or Fisher's exact test. "Significant" as used herein refers to a change that has not been determined to be statistically significant (e.g., it may not have been subject to statistical hypothesis testing).

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. In one embodiment, the subject is a human. The subject or patient may be undergoing other forms of treatment.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Traumatic Brain Injury" or "TBI" as used interchangeably herein refers to a complex injury with a broad spectrum of symptoms and disabilities. TBI is most often an acute event similar to other injuries. TBI can be classified as "mild," "moderate," or "severe." The causes of TBI are diverse and include, for example, physical shaking by a person, a car accident, injuries from firearms, cerebral vascular accidents (e.g., strokes), falls, explosions or blasts and other types of blunt force trauma. Other causes of TBI include the ingestion and/or exposure to one or more chemicals or toxins (such as fires, molds, asbestos, pesticides and insecticides, organic solvents, paints, glues, gases (such as carbon monoxide, hydrogen sulfide, and cyanide), organic metals (such as methyl mercury, tetraethyl lead and organic tin), one or more drugs of abuse or combinations thereof). Alternatively, TBI can occur in subjects suffering from an autoimmune disease, a metabolic disorder, a brain tumor, hypoxia, one or more viruses, meningitis, hydrocephalus or combinations thereof. Young adults and the elderly are the age groups at highest risk for TBI. In certain embodiments herein, traumatic brain injury or TBI does not include and specifically excludes cerebral vascular accidents such as strokes.

"Mild TBI" as used herein refers to a brain injury where loss of consciousness is brief and usually a few seconds or minutes and/or confusion and disorientation is shorter than 1 hour. Mild TBI is also referred to as a concussion, minor head trauma, minor TBI, minor brain injury, and minor head injury. While MRI and CT scans are often normal, the individual with mild TBI may have cognitive problems such as headache, difficulty thinking, memory problems, attention deficits, mood swings and frustration.

Mild TBI is the most prevalent TBI and is often missed at time of initial injury. Typically, a subject has a Glasgow Coma scale number of between 13-15 (such as 13-15 or 14-15). Fifteen percent (15%) of people with mild TBI have symptoms that last 3 months or more. Mild TBI is defined as the result of the forceful motion of the head or impact causing a brief change in mental status (confusion, disorientation or loss of memory) or loss of consciousness for less than 30 minutes. Common symptoms of mild TBI include fatigue, headaches, visual disturbances, memory loss, poor attention/concentration, sleep disturbances, dizziness/loss of balance, irritability-emotional disturbances, feelings of depression, and seizures. Other symptoms associated with mild TBI include nausea, loss of smell, sensitivity to light and sounds, mood changes, getting lost or confused, and/or slowness in thinking.

"Moderate TBI" as used herein refers to a brain injury where loss of consciousness and/or confusion and disorientation is between 1 and 24 hours and the subject has a Glasgow Coma scale number of between 9-13 (such as 9-12 or 9-13). The individual with moderate TBI have abnormal brain imaging results. "Severe TBI" as used herein refers to a brain injury where loss of consciousness is more than 24 hours and memory loss after the injury or penetrating skull injury longer than 24 hours and the subject has a Glasgow Coma scale number between 3-8. The deficits range from impairment of higher level cognitive functions to comatose states. Survivors may have limited function of arms or legs, abnormal speech or language, loss of thinking ability or emotional problems. Individuals with severe injuries can be left in long-term unresponsive states. For many people with severe TBI, long-term rehabilitation is often necessary to maximize function and independence.

Common symptoms of moderate to severe TBI include cognitive deficits including difficulties with attention, concentration, distractibility, memory, speed of processing, confusion, perseveration, impulsiveness, language processing, and/or "executive functions", not understanding the spoken word (receptive aphasia), difficulty speaking and being understood (expressive aphasia), slurred speech, speaking very fast or very slow, problems reading, problems writing, difficulties with interpretation of touch, temperature, movement, limb position and fine discrimination, the integration or patterning of sensory impressions into psychologically meaningful data, partial or total loss of vision, weakness of eye muscles and double vision (diplopia), blurred vision, problems judging distance, involuntary eye movements (nystagmus), intolerance of light (photophobia), hearing, such as decrease or loss of hearing, ringing in the ears (tinnitus), increased sensitivity to sounds, loss or diminished sense of smell (anosmia), loss or diminished sense of taste, the convulsions associated with epilepsy that can be several types and can involve disruption in consciousness, sensory perception, or motor movements, control of bowel and bladder, sleep disorders, loss of stamina, appetite changes, regulation of body temperature, menstrual difficulties, dependent behaviors, emotional ability, lack of motivation, irritability, aggression, depression, disinhibition, or denial/lack of awareness.

"Ubiquitin carboxy-terminal hydrolase L1" or "UCH-L1" as used interchangeably herein refers to a deubiquitinating enzyme encoded by the UCH-L1 gene in humans. UCH-L1, also known as ubiquitin carboxyl-terminal esterase L1 and ubiquitin thiolesterase, is a member of a gene family whose products hydrolyze small C-terminal adducts of ubiquitin to generate the ubiquitin monomer.

"UCH-L1 status" can mean either the level or amount of UCH-L1 at a point in time (such as with a single measure of UCH-L1), the level or amount of UCH-L1 associated with monitoring (such as with a repeat test on a subject to identify an increase or decrease in UCH-L1 amount), the level or amount of UCH-L1 associated with treatment for traumatic brain injury (whether a primary brain injury and/or a secondary brain injury) or combinations thereof.

"Variant" is used herein to describe a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to refer to an antigenically reactive fragment of an anti-UCH-L1 antibody that differs from the corresponding fragment of anti-UCH-L1 antibody in amino acid sequence but is still antigenically reactive and can compete with the corresponding fragment of anti-UCH-L1 antibody for binding with UCH-L1. "Variant" also can be used to describe a polypeptide or a fragment thereof that has been differentially processed, such as by proteolysis, phosphorylation, or other post-translational modification, yet retains its antigen reactivity.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. METHODS OF AIDING IN THE DIAGNOSIS AND EVALUATION OF WHETHER A HUMAN SUBJECT HAS SUSTAINED AN INJURY TO THE HEAD

The present disclosure relates, among other methods, to a method of aiding in the diagnosis and evaluation of whether a human subject has sustained or may have sustained an injury to the head. The method can aid in diagnosing and evaluating the extent of traumatic brain injury in a subject with a suspected injury to the head (e.g., determining whether the subject has mild TBI or moderate to severe TBI). As used herein, "determining whether the subject has mild traumatic brain injury or moderate to severe traumatic brain injury" refers to use of the method (e.g., with other information such as clinical assessment data) to determine that the subject is more likely than not to have mild TBI or moderate to severe TBI. The method can include obtaining a sample within 24 hours of a suspected injury to the subject, contacting the sample with an antibody for an early biomarker of traumatic brain injury, the early biomarker of traumatic brain injury consisting of ubiquitin carboxy-terminal hydrolase L1 (UCH-L1), to allow formation of a complex of the antibody and UCH-L1. In an alternative, the method can include obtaining a first sample taken at a first time point and a second sample taken at a second time point from the human subject, the first sample taken from the human subject within 24 hours of injury and the second sample taken from the human subject at a second time point after the first time point, such as about 3 hours to about 6 hours after the first sample is taken, contacting the first sample and the second sample separately with an antibody for an early biomarker of traumatic brain injury, the early biomarker of traumatic brain injury consisting of ubiquitin carboxy-terminal hydrolase L1 (UCH-L1), to allow formation of a complex of the antibody and UCH-L1. The method also includes detecting the resulting antibody-UCH-L1 complex. The early biomarker increases within about 0 to about 6 hours after the suspected injury and then decreases or increases thereafter in subjects with traumatic brain injury. In some embodiments, the onset of the presence of UCH-L1 appears within about 0, about 0.5 hours, about 1 hour, about 2 hours, about 3 hours, about 4 hours, about 5 hours, or about 6 hours after injury to the head. The sample can be a biological sample from a subject (e.g., serum or blood sample).

In some embodiments, the method includes: performing an assay on a first sample and optionally a second sample to measure or detect a level of ubiquitin carboxy-terminal hydrolase L1 (UCH-L1) in the first sample and/or second sample, wherein the first sample is taken from the subject at a first time point within 24 hours after a suspected injury to the head and the second sample is taken from the subject at a second time point after the first time point, such as about 3 hours to about 6 hours after the first time point; and determining whether the subject has sustained an injury to the head by determining the extent of the traumatic brain injury. The subject is determined as having moderate to severe traumatic brain injury when (i) the level of UCH-L1 in the first and/or second sample is higher than a reference level of UCH-L1 and the subject is determined as having mild traumatic brain injury when the level of UCH-L1 in the first and/or second sample is lower than a reference level of UCH-L1; (ii) there is a statistically significant increase or decrease from the level of UCH-L1 in the first sample to the level of UCH-L1 in the second sample and the subject is determined as having mild traumatic brain injury when there is no statistically significant increase or decrease from the level of UCH-L1 in the first sample to the level of UCH-L1 in the second sample; (iii) the level of UCH-L1 decreases or increases by at least an absolute amount from the first sample to the second sample or is determined as having mild traumatic brain injury when there is no decrease or increase by at least an absolute amount in the level of UCH-L1 from the first sample to the second sample; (iv) the level of UCH-L1 decreases or increases by at least a first absolute amount from the first sample to the second sample or is determined as having mild traumatic brain injury when the level of UCH-L1 decreases or increases by at least a second absolute amount from the first sample to the second sample; or (v) the level of UCH-L1 in the sample is higher than a reference level of UCH-L1 or when there is a significant increase or decrease of amount X from the level of UCH-L1 in a sample taken at a first time point to the level of UCH-L1 in a sample taken at a second time point and the subject is determined as having mild traumatic brain injury when the level of UCH-L1 in the sample is lower than a reference level of UCH-L1 or when there is no significant increase or decrease greater than amount X from the level of UCH-L1 in a sample taken at a first time point to the level of UCH-L1 in a sample taken at a second time point. In some embodiments, the first absolute amount and the second absolute amount can be the same. In some embodiments, the first absolute amount and the second absolute amount can be different. As used herein, "X" refers to an integer that has a value other than 0. As used herein, "determining whether the subject has mild traumatic brain injury or moderate to severe traumatic brain injury" refers to use of the method, with or without other methods, to determine that the subject is more likely than not to have mild TBI or moderate to severe TBI.

In some embodiments, the subject has received a Glasgow Coma Scale score before or after the assay is performed. In some embodiments, the subject is suspected as having moderate to severe traumatic brain injury based on the Glasgow Coma Scale score. In some embodiments, the reference level is correlated with subjects having moderate to severe traumatic brain injury. In some embodiments, the reference level is correlated with subjects having moderate to severe traumatic brain injury by analysis of corresponding samples using a corresponding assay type to identify the reference level.

Alternatively, in some embodiments, the subject may not have received a Glasgow Coma Scale score before the assay is performed. Alternatively, in some embodiments, the subject may not have received a Glasgow Coma Scale score after the assay is performed. Additionally, in other embodiments, the subject may receive a head CT before the assay is performed. Also, alternatively, in other embodiments, the subject may not have received a head CT before the assay is performed. Still further, the subject may not have received a Glasgow Coma Scale or a head CT before the assay is performed. Still in further embodiments, the subject may have received a Glasgow Coma Scale but not a head CT before the assay is performed. Yet in further embodiments, the subject may have received a head CT but not a Glasgow Coma Scale before the assay is performed. In still further embodiments, the subject may have received a head CT and a Glasgow Coma Scale before the assay is performed.

In some embodiments, the reference level is correlated with a Glasgow Coma Scale score of 3-12. In some embodiments, the subject is suspected as having mild traumatic brain injury based on the Glasgow Coma Scale score. In some embodiments, the reference level is correlated with subjects having mild traumatic brain injury. In some embodiments, the reference level is correlated with a Glasgow Coma Scale score of 13-15. In some embodiments, the reference level is correlated with subjects having mild traumatic brain injury by analysis of corresponding samples using a corresponding assay type to identify the reference level.

Generally, a reference level can also be employed as a benchmark against which to assess results obtained upon assaying a test sample for UCH-L1. Generally, in making such a comparison, the reference level is obtained by running a particular assay a sufficient number of times and under appropriate conditions such that a linkage or association of analyte presence, amount or concentration with a particular stage or endpoint of TBI or with particular indicia can be made. Typically, the reference level is obtained with assays of reference subjects (or populations of subjects). The UCH-L1 measured can include UCH-L1 fragments thereof, degradation products thereof, and/or enzymatic cleavage products thereof.

In some embodiments, the reference level is determined by an assay having a sensitivity of between at least about 85% to about 100% and a specificity of between at least about 30% to about 100%. In some embodiments, the sensitivity is at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or about 100.0%. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or about 100.0%. For example, the sensitivity is at least about 99% and the specificity is at least about 75%, the sensitivity is at least about 99% and the specificity is at least about 99%, or the sensitivity is about 100% and the specificity is about 100%. In some embodiments, is at least about 99% and the specificity is at least about 75%. In yet other embodiments, the sensitivity is at least about 99% and the specificity is at least about 99%. In still further embodiments, the sensitivity is about 100% and the specificity is about 100%.

In some embodiments, the reference level can be between at least about 50 pg/mL to about 12000 pg/mL. In some embodiments, the reference level can be between at least about 50 pg/mL to about 12000 pg/mL, between at least about 50 pg/mL to about 11000 pg/mL, between at least about 50 pg/mL to about 10000 pg/mL, between at least about 50 pg/mL to about 9500 pg/mL, between at least about 50 pg/mL to about 9000 pg/mL, between at least about 50 pg/mL to about 8500 pg/mL, between at least about 50 pg/mL to about 8000 pg/mL, between at least about 50 pg/mL to about 7500 pg/mL, between at least about 50 pg/mL to about 7000 pg/mL, between at least about 50 pg/mL to about 6500 pg/mL, between at least about 50 pg/mL to about 6000 pg/mL, between at least about 50 pg/mL to about 5500 pg/mL, between at least about 50 pg/mL to about 5000 pg/mL, between at least about 50 pg/mL to about 4500 pg/mL, between at least about 50 pg/mL to about 4000 pg/mL, between at least about 50 pg/mL to about 3500 pg/mL, between at least about 50 pg/mL to about 3000 pg/mL, between at least about 50 pg/mL to about 2500 pg/mL, between at least about 50 pg/mL to about 2000 pg/mL, between at least about 50 pg/mL to about 1500 pg/mL, between at least about 50 pg/mL to about 1000 pg/mL, between at least about 50 pg/mL to about 900 pg/mL, between at least about 50 pg/mL to about 800 pg/mL, between at least about 50 pg/mL to about 700 pg/mL, between at least about 50 pg/mL to about 600 pg/mL, between at least about 50 pg/mL to about 500 pg/mL, between at least about 100 pg/mL to about 12000 pg/mL, between at least about 100 pg/mL to about 11000 pg/mL, between at least about 100 pg/mL to about 10000 pg/mL, between at least about 100 pg/mL to about 9500 pg/mL, between at least about 100 pg/mL to about 9000 pg/mL, between at least about 100 pg/mL to about 8500 pg/mL, between at least about 100 pg/mL to about 8000 pg/mL, between at least about 100 pg/mL to about 7500 pg/mL, between at least about 100 pg/mL to about 7000 pg/mL, between at least about 100 pg/mL to about 6500 pg/mL, between at least about 100 pg/mL to about 6000 pg/mL, between at least about 100 pg/mL to about 5500 pg/mL, between at least about 100 pg/mL to about 5000 pg/mL, between at least about 100 pg/mL to about 4500 pg/mL, between at least about 100 pg/mL to about 4000 pg/mL, between at least about 100 pg/mL to about 3500 pg/mL, between at least about 100 pg/mL to about 3000 pg/mL, between at least about 100 pg/mL to about 2500 pg/mL, between at least about 100 pg/mL to about 2000 pg/mL, between at least about 100 pg/mL to about 1500 pg/mL, between at least about 100 pg/mL to about 1000 pg/mL, between at least about 100 pg/mL to about 900 pg/mL, between at least about 100 pg/mL to about 800 pg/mL, between at least about 100 pg/mL to about 700 pg/mL, between at least about 100 pg/mL to about 600 pg/mL, between at least about 100 pg/mL to about 500 pg/mL, between at least about 150 pg/mL to about 12000 pg/mL, between at least about 150 pg/mL to about 11000 pg/mL, between at least about 150 pg/mL to about 10000 pg/mL, between at least about 150 pg/mL to about 9500 pg/mL, between at least about 150 pg/mL to about 9000 pg/mL, between at least about 150 pg/mL to about 8500 pg/mL, between at least about 150 pg/mL to about 8000 pg/mL, between at least about 150 pg/mL to about 7500 pg/mL, between at least about 150 pg/mL to about 7000 pg/mL, between at least about 150 pg/mL to about 6500 pg/mL, between at least about 150 pg/mL to about 6000 pg/mL, between at least about 150 pg/mL to about 5500 pg/mL, between at least about 150 pg/mL to about 5000 pg/mL, between at least about 150 pg/mL to about 4500 pg/mL, between at least about 150 pg/mL to about 4000 pg/mL, between at least about 150 pg/mL to about 3500 pg/mL, between at least about 150 pg/mL to about 3000 pg/mL, between at least about 150 pg/mL to about 2500 pg/mL, between at least about 150 pg/mL to about 2000 pg/mL, between at least about 150 pg/mL to about 1500 pg/mL, between at least about 150 pg/mL to about 1000 pg/mL, between at least about 150 pg/mL to about 900 pg/mL, between at least about 150 pg/mL to about 800 pg/mL, between at least about 150 pg/mL to about 700 pg/mL, between at least about 150 pg/mL to about 600 pg/mL, between at least about 150 pg/mL to about 500 pg/mL, between at least about 200 pg/mL to about 12000 pg/mL, between at least about 200 pg/mL to about 11000 pg/mL, between at least about 200 pg/mL to about 10000 pg/mL, between at least about 200 pg/mL to about 9500 pg/mL, between at least about 200 pg/mL to about 9000 pg/mL, between at least about 200 pg/mL to about 8500 pg/mL, between at least about 200 pg/mL to about 8000 pg/mL, between at least about 200 pg/mL to about 7500 pg/mL, between at least about 200 pg/mL to about 7000 pg/mL, between at least about 200 pg/mL to about 6500 pg/mL, between at least about 200 pg/mL to about 6000 pg/mL, between at least about 200 pg/mL to about 5500 pg/mL, between at least about 200 pg/mL to about 5000 pg/mL, between at least about 200 pg/mL to about 4500 pg/mL, between at least about 200 pg/mL to about 4000 pg/mL, between at least about 200 pg/mL to about 3500 pg/mL, between at least about 200 pg/mL to about 3000 pg/mL, between at least about 200 pg/mL to about 2500 pg/mL, between at least about 200 pg/mL to about 2000 pg/mL, between at least about 200 pg/mL to about 1500 pg/mL, between at least about 200 pg/mL to about 1000 pg/mL, between at least about 200 pg/mL to about 900 pg/mL, between at least about 200 pg/mL to about 800 pg/mL, between at least about 200 pg/mL to about 700 pg/mL, between at least about 200 pg/mL to about 600 pg/mL, between at least about 200 pg/mL to about 500 pg/mL, between at least about 300 pg/mL to about 12000 pg/mL, between at least about 300 pg/mL to about 11000 pg/mL, between at least about 300 pg/mL to about 10000 pg/mL, between at least about 300 pg/mL to about 9500 pg/mL, between at least about 300 pg/mL to about 9000 pg/mL, between at least about 300 pg/mL to about 8500 pg/mL, between at least about 300 pg/mL to about 8000 pg/mL, between at least about 300 pg/mL to about 7500 pg/mL, between at least about 300 pg/mL to about 7000 pg/mL, between at least about 300 pg/mL to about 6500 pg/mL, between at least about 300 pg/mL to about 6000 pg/mL, between at least about 300 pg/mL to about 5500 pg/mL, between at least about 300 pg/mL to about 5000 pg/mL, between at least about 300 pg/mL to about 4500 pg/mL, between at least about 300 pg/mL to about 4000 pg/mL, between at least about 300 pg/mL to about 3500 pg/mL, between at least about 300 pg/mL to about 3000 pg/mL, between at least about 300 pg/mL to about 2500 pg/mL, between at least about 300 pg/mL to about 2000 pg/mL, between at least about 300 pg/mL to about 1500 pg/mL, between at least about 300 pg/mL to about 1000 pg/mL, between at least about 300 pg/mL to about 900 pg/mL, between at least about 300 pg/mL to about 800 pg/mL, between at least about 300 pg/mL to about 700 pg/mL, between at least about 300 pg/mL to about 600 pg/mL, between at least about 300 pg/mL to about 500 pg/mL, between at least about 400 pg/mL to about 12000 pg/mL, between at least about 400 pg/mL to about 11000 pg/mL, between at least about 400 pg/mL to about 9500 pg/mL, between at least about 400 pg/mL to about 9000 pg/mL, between at least about 400 pg/mL to about 8500 pg/mL, between at least about 400 pg/mL to about 8000 pg/mL, between at least about 400 pg/mL to about 7500 pg/mL, between at least about 400 pg/mL to about 7000 pg/mL, between at least about 400 pg/mL to about 6500 pg/mL, between at least about 400 pg/mL to about 6000 pg/mL, between at least about 400 pg/mL to about 5500 pg/mL, between at least about 400 pg/mL to about 5000 pg/mL, between at least about 400 pg/mL to about 4500 pg/mL, between at least about 400 pg/mL to about 4000 pg/mL, between at least about 400 pg/mL to about 3500 pg/mL, between at least about 400 pg/mL to about 3000 pg/mL, between at least about 400 pg/mL to about 2500 pg/mL, between at least about 400 pg/mL to about 2000 pg/mL, between at least about 400 pg/mL to about 1500 pg/mL, between at least about 400 pg/mL to about 1000 pg/mL, between at least about 400 pg/mL to about 900 pg/mL, between at least about 400 pg/mL to about 800 pg/mL, between at least about 400 pg/mL to about 700 pg/mL, between at least about 400 pg/mL to about 600 pg/mL, between at least about 400 pg/mL to about 500 pg/mL, between at least about 500 pg/mL to about 12000 pg/mL, between at least about 500 pg/mL to about 11000 pg/mL, between at least about 500 pg/mL to about 10000 pg/mL, between at least about 500 pg/mL to about 9500 pg/mL, between at least about 500 pg/mL to about 9000 pg/mL, between at least about 500 pg/mL to about 8500 pg/mL, between at least about 500 pg/mL to about 8000 pg/mL, between at least about 500 pg/mL to about 7500 pg/mL, between at least about 500 pg/mL to about 7000 pg/mL, between at least about 500 pg/mL to about 6500 pg/mL, between at least about 500 pg/mL to about 6000 pg/mL, between at least about 500 pg/mL to about 5500 pg/mL, between at least about 500 pg/mL to about 5000 pg/mL, between at least about 500 pg/mL to about 4500 pg/mL, between at least about 500 pg/mL to about 4000 pg/mL, between at least about 500 pg/mL to about 3500 pg/mL, between at least about 500 pg/mL to about 3000 pg/mL, between at least about 500 pg/mL to about 2500 pg/mL, between at least about 500 pg/mL to about 2000 pg/mL, between at least about 500 pg/mL to about 1500 pg/mL, between at least about 500 pg/mL to about 1000 pg/mL, between at least about 500 pg/mL to about 900 pg/mL, between at least about 500 pg/mL to about 800 pg/mL, between at least about 500 pg/mL to about 700 pg/mL, between at least about 500 pg/mL to about 600 pg/mL, between at least about 1000 pg/mL to about 12000 pg/mL, between at least about 1000 pg/mL to about 11000 pg/mL, between at least about 1000 pg/mL to about 10000 pg/mL, between at least about 1000 pg/mL to about 9500 pg/mL, between at least about 1000 pg/mL to about 9000 pg/mL, between at least about 1000 pg/mL to about 8500 pg/mL, between at least about 1000 pg/mL to about 8000 pg/mL, between at least about 1000 pg/mL to about 7500 pg/mL, between at least about 1000 pg/mL to about 7000 pg/mL, between at least about 1000 pg/mL to about 6500 pg/mL, between at least about 1000 pg/mL to about 6000 pg/mL, between at least about 1000 pg/mL to about 5500 pg/mL, between at least about 1000 pg/mL to about 5000 pg/mL, between at least about 1000 pg/mL to about 4500 pg/mL, between at least about 1000 pg/mL to about 4000 pg/mL, between at least about 1000 pg/mL to about 3500 pg/mL, between at least about 1000 pg/mL to about 3000 pg/mL, between at least about 1000 pg/mL to about 2500 pg/mL, between at least about 1000 pg/mL to about 2000 pg/mL, between at least about 1000 pg/mL to about 1500 pg/mL, between at least about 2000 pg/mL to about 12000 pg/mL, between at least about 2000 pg/mL to about 11000 pg/mL, between at least about 2000 pg/mL to about 10000 pg/mL, between at least about 2000 pg/mL to about 9500 pg/mL, between at least about 2000 pg/mL to about 9000 pg/mL, between at least about 2000 pg/mL to about 8500 pg/mL, between at least about 2000 pg/mL to about 8000 pg/mL, between at least about 2000 pg/mL to about 7500 pg/mL, between at least about 2000 pg/mL to about 7000 pg/mL, between at least about 2000 pg/mL to about 6500 pg/mL, between at least about 2000 pg/mL to about 6000 pg/mL, between at least about 2000 pg/mL to about 5500 pg/mL, between at least about 2000 pg/mL to about 5000 pg/mL, between at least about 2000 pg/mL to about 4500 pg/mL, between at least about 2000 pg/mL to about 4000 pg/mL, between at least about 2000 pg/mL to about 3500 pg/mL, between at least about 2000 pg/mL to about 3000 pg/mL, or between at least about 2000 pg/mL to about 2500 pg/mL. For example, the reference level can be between at least about 65 pg/mL to about 9019 pg/mL. In some embodiments, the reference level can be at least about 50 pg/mL, at least about 55 pg/mL, at least about 60 pg/mL, at least about 65 pg/mL, at least about 70 pg/mL, at least about 75 pg/mL, at least about 80 pg/mL, at least about 85 pg/mL, at least about 90 pg/mL, at least about 95 pg/mL, at least about 96 pg/mL, at least about 97 pg/mL, at least about 98 pg/mL, at least about 99 pg/mL, at least about 100 pg/mL, at least about 150 pg/mL, at least about 200 pg/mL, at least about 205 pg/mL, at least about 206 pg/mL, at least about 207 pg/mL, at least about 208 pg/mL, at least about 209 pg/mL, at least about 210 pg/mL, at least about 220 pg/mL, at least about 230 pg/mL, at least about 238 pg/mL, at least about 240 pg/mL, at least about 250 pg/mL, at least about 300 pg/mL, at least about 311 pg/mL, at least about 320 pg/mL, at least about 330 pg/mL, at least about 350 pg/mL, at least about 360 pg/mL, at least about 370 pg/mL, at least about 380 pg/mL, at least about 390 pg/mL, at least about 400 pg/mL, at least about 450 pg/mL, at least about 500 pg/mL, at least about 505 pg/mL, at least about 506 pg/mL, at least about 507 pg/mL, at least about 508 pg/mL, at least about 509 pg/mL, at least about 510 pg/mL, at least about 520 pg/mL, at least about 530 pg/mL, at least about 540 pg/mL, at least about 550 pg/mL, at least about 560 pg/mL, at least about 565 pg/mL, at least about 569 pg/mL, at least about 570 pg/mL, at least about 700 pg/mL, at least about 710 pg/mL, at least about 720 pg/mL, at least about 730 pg/mL, at least about 740 pg/mL, at least about 750 pg/mL, at least about 800 pg/mL, at least about 850 pg/mL, at least about 900 pg/mL, at least about 950 pg/mL, at least about 1000 pg/mL, at least about 1100 pg/mL, at least about 1200 pg/mL, at least about 1300 pg/mL, at least about 1400 pg/mL, at least about 1500 pg/mL, at least about 1600 pg/mL, at least about 1700 pg/mL, at least about 1800 pg/mL, at least about 1900 pg/mL, at least about 2000 pg/mL, at least about 2500 pg/mL, at least about 3000 pg/mL, at least about 3500 pg/mL, at least about 4000 pg/mL, at least about 4500 pg/mL, at least about 5000 pg/mL, at least about 5500 pg/mL, at least about 6000 pg/mL, at least about 6500 pg/mL, at least about 7000 pg/mL, at least about 7500 pg/mL, at least about 8000 pg/mL, at least about 8500 pg/mL, at least about 9000 pg/mL, at least about 9010 pg/mL, at least about 9020 pg/mL, at least about 9500 pg/mL, at least about 10000 pg/mL, at least about 11000 pg/mL, or at least about 12000 pg/mL. In some embodiments, the reference level is between at least about 50 pg/mL to about 12000 pg/mL. In other embodiments, the reference level is between at least about 65 pg/mL to about 9019 pg/mL.

In some embodiments, the first sample is taken within 24 hours after the suspected injury and the second sample is taken within about 3 hours to about 6 hours after the first sample and the reference level is determined by an assay having a particular sensitivity and specificity, as described above. For example, the first sample can be taken within about 0 hours, within about thirty minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, within about 24 hours, or more than about 24 hours after the suspected injury.

In some embodiments, the first sample is taken within about 0 to about 1 hours, within about 0 to about 2 hours, within about 0 to about 3 hours, within about 0 to about 4 hours, within about 0 to about 5 hours, within about 0 to about 6 hours, within about 0 to about 7 hours, within about 0 to about 8 hours, within about 0 to about 9 hours, within about 0 to about 10 hours, within about 0 to about 11 hours, within about 0 to about 12 hours, within about 0 to about 18 hours, within about 6 to about 12 hours, within about 12 to about 18 hours, within about 18 to about 24 hours, or greater than 24 hours after the suspected injury and the reference level is determined by an assay having a particular sensitivity and specificity, such as a sensitivity between at least about 85% and 100% and a specificity of between at least about 30% and 100%, such as a sensitivity of about 100% and a specificity of at least about 75%, a sensitivity of at least about 99% and a specificity of at least about 75%, or a sensitivity of about 100% and a specificity of about 100%.

In some embodiments, the first sample can be obtained within about 0 to about 6 hours, the reference level can be about 311 pg/mL and the assay has a sensitivity of about 100% and a specificity of at least about 33%. In some embodiments, the first sample can be obtained within about 0 to about 6 hours, the reference level can be about 509 pg/mL and the assay has a sensitivity of about 100% and a specificity of at least about 66%. In some embodiments, the first sample can be obtained within about 0 to about 6 hours, the reference level can be about 710 pg/mL and the assay has a sensitivity of about 100% and a specificity of at least about 92%. In some embodiments, the first sample can be obtained within about 0 to about 6 hours, the reference level can be about 9019 pg/mL and the assay has a sensitivity of about 100% and a specificity of about 100%.

In some embodiments, the first sample can be obtained between about 6 hours to 12 hours after the suspected injury and the reference level is between about 65 pg/mL and about 9019 pg/mL and determined by an assay having a sensitivity between at least about 85% to about 100% and a specificity between at least about 30% and about 100%. In some embodiments, the first sample is taken between about 6 hours to 12 hours after the suspected injury and the reference level is about 98 pg/mL and determined by an assay having a sensitivity of about 100% and a specificity of at least about 30%. In some embodiments, the first sample is taken between about 6 hours to 12 hours after the suspected injury and the reference level is about 209 pg/mL and determined by an assay having a sensitivity of about 100% and a specificity of at least about 63%. In some embodiments, the first sample is taken between about 6 hours to 12 hours after the suspected injury and the reference level is about 238 pg/mL and determined by an assay having a sensitivity of at least about 90% and a specificity of at least about 70%. In some embodiments, the first sample is taken between about 6 hours to 12 hours after the suspected injury and the reference level is about 569 pg/mL and determined by an assay having a sensitivity of at least about 90% and a specificity of at least about 96%.

In some embodiments, the first sample is obtained at a first time point and the second sample is obtained at second time point to determine whether the subject has a mild or moderate to severe TBI. In some embodiments, the first time point is about 0 to about 24 hours after the injury or suspected injury to the head. For example, the first time point can be between about 0 to about 24 hours, about 0 to about 20 hours, about 0 to about 18 hours, about 0 to about 16 hours, about 0 to about 14 hours, about 0 to about 12 hours, about 0 to about 10 hours, about 0 to about 8 hours, about 0 to about 6 hours, about 0 to about 4 hours, about 0 to about 2 hours, about 0 to about 1 hours, about 0 to about 1.5 hours, about 0.5 hours to about 24 hours, about 0.5 hours to about 20 hours, about 0.5 hours to about 18 hours, about 0.5 hours to about 16 hours, about 0.5 hours to about 14 hours, about 0.5 hours to about 12 hours, about 0.5 hours to about 10 hours, about 0.5 hours to about 8 hours, about 0.5 hours to about 6 hours, about 0.5 hours to about 4 hours, about 0.5 hours to about 2 hours, about 0.5 hours to about 1 hours, about 0.5 hours to about 1.5 hours, about 1 hour to about 24 hours, about 1 hour to about 20 hours, about 1 hour to about 18 hours, about 1 hour to about 16 hours, about 1 hour to about 14 hours, about 1 hour to about 12 hours, about 1 hour to about 10 hours, about 1 hour to about 8 hours, about 1 hour to about 6 hours, about 1 hour to about 4 hours, about 1 hour to about 2 hours, about 2 hours to about 24 hours, about 2 hours to about 20 hours, about 2 hours to about 18 hours, about 2 hours to about 16 hours, about 2 hours to about 14 hours, about 2 hours to about 12 hours, about 2 hours to about 10 hours, about 2 hours to about 8 hours, about 2 hours to about 6 hours, about 2 hours to about 4 hours, about 3 hours to about 24 hours, about 3 hours to about 20 hours, about 3 hours to about 18 hours, about 3 hours to about 16 hours, about 3 hours to about 14 hours, about 3 hours to about 12 hours, about 3 hours to about 10 hours, about 3 hours to about 8 hours, about 3 hours to about 6 hours, about 3 hours to about 4 hours, about 4 hours to about 24 hours, about 4 hours to about 20 hours, about 4 hours to about 18 hours, about 4 hours to about 16 hours, about 4 hours to about 14 hours, about 4 hours to about 12 hours, about 4 hours to about 10 hours, about 4 hours to about 8 hours, about 4 hours to about 6 hours, about 6 hours to about 24 hours, about 6 hours to about 20 hours, about 6 hours to about 18 hours, about 6 hours to about 16 hours, about 6 hours to about 14 hours, about 6 hours to about 12 hours, about 6 hours to about 10 hours, about 6 hours to about 8 hours, about 12 hours to about 24 hours, about 12 hours to about 20 hours, about 12 hours to about 18 hours, about 12 hours to about 16 hours, about 12 hours to about 14 hours, about 18 hours to about 24 hours, or greater than 24 hours after the suspected injury. For example, the first time point can be between about 0 hour to 6 hours, between about 6 hours to 12 hours, between about 12 hours to 18 hours, or between about 18 hours to 24 hours. In some embodiments, the first time point is between about 0 hour to 6 hours. In some embodiments, the first time point is between about 6 hours to about 12 hours. In some embodiments, the first time point is between about 12 hour to about 18 hours. In other embodiments, the first time point is between about 18 hours to about 24 hours.

In some embodiments, the second time point is about 1 hour to about 10 hours after the first time point, such as about 3 hours to about 6 hours after the first time point. In some embodiments, the second time point is about 1 hour, about 2 hours, about 3 hours, about 4 hours, about 5 hours, about 6 hours, about 7 hours, about 8 hours, about 9 hours, or about 10 hours after the first time point.

In some embodiments, the statistically significant increase or decrease is at least about 0.1-fold, at least about 0.2-fold, at least about 0.3-fold, at least about 0.4-fold, at least about 0.5-fold, at least about 0.55-fold, at least about 0.6-fold, at least about 0.7-fold, at least about 0.73-fold, at least about 0.8-fold, at least about 0.9-fold, at least about 1-fold, at least 1.5-fold, at least about 2-fold, at least about 3-fold, at least about 4-fold, at least about 5-fold, at least about 6-fold, at least about 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold from the level of UCH-L1 in the first sample taken at a first time point to the level of UCH-L1 in the second sample taken at a second time point. In some embodiments, a statistically significant decrease of at least about 0.1-fold, at least about 0.2-fold, at least about 0.3-fold, at least about 0.4-fold, at least about 0.5-fold, at least about 0.55-fold, at least about 0.6-fold, at least about 0.7-fold, at least about 0.73-fold, at least about 0.8-fold, at least about 0.9-fold, at least about 1-fold, at least 1.5-fold, at least about 2-fold, at least about 3-fold, at least about 4-fold, at least about 5-fold, at least about 6-fold, at least about 7-fold, at least about 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold from the level of UCH-L1 in the first sample taken at a first time point to the level of UCH-L1 in the second sample taken at a second time point indicates that the subject has moderate to severe traumatic brain injury. In some embodiments, a statistically significant increase of at least about 0.1-fold, at least about 0.2-fold, at least about 0.3-fold, at least about 0.4-fold, at least about 0.5-fold, at least about 0.55-fold, at least about 0.6-fold, at least about 0.7-fold, at least about 0.73-fold, at least about 0.8-fold, at least about 0.9-fold, at least about 1-fold, at least about 1.5-fold, at least about 2-fold, at least about 3-fold, at least about 4-fold, at least about 5-fold, at least about 6-fold, at least about 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold from the level of UCH-L1 in the first sample taken at a first time point to the level of UCH-L1 in the second sample taken at a second time point indicates that the subject has moderate to severe traumatic brain injury.

In some embodiments, the statistically significant increase or decrease is less than about 0.1-fold, less than about 0.2-fold, less than about 0.3-fold, less than about 0.4-fold, less than about 0.5-fold, at least about 0.55-fold, at least about 0.6-fold, at least about 0.7-fold, at least about 0.73-fold, at least about 0.8-fold, at least about 0.9-fold, less than about 1-fold, less than 1.5-fold, less than about 2-fold, less than about 3-fold, less than about 4-fold, less than about 5-fold, less than about 6-fold, less than about 7-fold, less than 8-fold, less than 9-fold, less than 10-fold, less than 11-fold, less than 12-fold, less than 13-fold, less than 14-fold, less than 15-fold, less than 16-fold, less than 17-fold, less than 18-fold, less than 19-fold, or less than 20-fold from the level of UCH-L1 in the first sample taken at a first time point to the level of UCH-L1 in the second sample taken at a second time point. In some embodiments, a statistically significant decrease of less than about 0.1-fold, less than about 0.2-fold, less than about 0.3-fold, less than about 0.4-fold, less than about 0.5-fold, at least about 0.55-fold, at least about 0.6-fold, at least about 0.7-fold, at least about 0.73-fold, at least about 0.8-fold, at least about 0.9-fold, less than about 1-fold, less than about 1.5-fold, less than about 2-fold, less than about 3-fold, less than about 4-fold, less than about 5-fold, less than about 6-fold, less than about 7-fold, less than about 8-fold, less than 9-fold, less than 10-fold, less than 11-fold, less than 12-fold, less than 13-fold, less than 14-fold, less than 15-fold, less than 16-fold, less than 17-fold, less than 18-fold, less than 19-fold, or less than 20-fold from the level of UCH-L1 in the first sample taken at a first time point to the level of UCH-L1 in the second sample taken at a second time point indicates that the subject has moderate to severe traumatic brain injury. In some embodiments, a statistically significant increase of less than about 0.1-fold, less than about 0.2-fold, less than about 0.3-fold, less than about 0.4-fold, less than about 0.5-fold, at least about 0.55-fold, at least about 0.6-fold, at least about 0.7-fold, at least about 0.73-fold, at least about 0.8-fold, at least about 0.9-fold, less than about 1-fold, less than about 1.5-fold, less than about 2-fold, less than about 3-fold, less than about 4-fold, less than about 5-fold, less than about 6-fold, less than about 7-fold, less than 8-fold, less than 9-fold, less than 10-fold, less than 11-fold, less than 12-fold, less than 13-fold, less than 14-fold, less than 15-fold, less than 16-fold, less than 17-fold, less than 18-fold, less than 19-fold, or less than 20-fold from the level of UCH-L1 in the first sample taken at a first time point to the level of UCH-L1 in the second sample taken at a second time point indicates that the subject has moderate to severe traumatic brain injury. In some embodiments, no statistically significant increase or decrease from the level of UCH-L1 in the first sample taken at a first time point to the level of UCH-L1 in the second sample taken at a second time point indicates that the subject has mild traumatic brain injury.

In some embodiments, the statistically significant increase or decrease is more than about 0.1-fold, more than about 0.2-fold, more than about 0.3-fold, more than about 0.4-fold, more than about 0.5-fold, more than about 0.55-fold, at least about 0.6-fold, at least about 0.7-fold, at least about 0.73-fold, at least about 0.8-fold, at least about 0.9-fold, more than about 1-fold, more than 1.5-fold, more than about 2-fold, more than about 3-fold, more than about 4-fold, more than about 5-fold, more than about 6-fold, more than about 7-fold, more than 8-fold, more than 9-fold, more than 10-fold, more than 11-fold, more than 12-fold, more than 13-fold, more than 14-fold, more than 15-fold, more than 16-fold, more than 17-fold, more than 18-fold, more than 19-fold, or more than 20-fold from the level of UCH-L1 in the second sample taken at a second time point to the level of UCH-L1 in the first sample taken at a first time point. In some embodiments, a statistically significant decrease of more than about 0.1-fold, more than about 0.2-fold, more than about 0.3-fold, more than about 0.4-fold, more than about 0.5-fold, more than about 0.55-fold, at least about 0.6-fold, at least about 0.7-fold, at least about 0.73-fold, at least about 0.8-fold, at least about 0.9-fold, more than about 1-fold, more than 1.5-fold, more than about 2-fold, more than about 3-fold, more than about 4-fold, more than about 5-fold, more than about 6-fold, more than about 7-fold, more than about 8-fold, more than 9-fold, more than 10-fold, more than 11-fold, more than 12-fold, more than 13-fold, more than 14-fold, more than 15-fold, more than 16-fold, more than 17-fold, more than 18-fold, more than 19-fold, or more than 20-fold from the level of UCH-L1 in the second sample taken at a second time point to the level of UCH-L1 in the first sample taken at a first time point indicates that the subject has moderate to severe traumatic brain injury. In some embodiments, a statistically significant increase of more than about 0.1-fold, more than about 0.2-fold, more than about 0.3-fold, more than about 0.4-fold, more than about 0.5-fold, more than about 0.55-fold, at least about 0.6-fold, at least about 0.7-fold, at least about 0.73-fold, at least about 0.8-fold, at least about 0.9-fold, more than about 1-fold, more than about 1.5-fold, more than about 2-fold, more than about 3-fold, more than about 4-fold, more than about 5-fold, more than about 6-fold, more than about 7-fold, more than 8-fold, more than 9-fold, more than 10-fold, more than 11-fold, more than 12-fold, more than 13-fold, more than 14-fold, more than 15-fold, more than 16-fold, more than 17-fold, more than 18-fold, more than 19-fold, or more than 20-fold from the level of UCH-L1 in the second sample taken at a second time point to the level of UCH-L1 in the first sample taken at a first time point indicates that the subject has moderate to severe traumatic brain injury. In some embodiments, no statistically significant increase or decrease from the level of UCH-L1 in the second sample taken at a second time point to the level of UCH-L1 in the first sample taken at a first time point indicates that the subject has mild traumatic brain injury.

In some embodiments, the first time point is about 0 to about 12 hours after the suspected injury and the statistically significant increase is more than about 1-fold from the second time point to the first time point. In some embodiments, the first time point is about 0 to about 12 hours after the suspected injury and the statistically significant increase is more than about 0.73-fold from the second time point to the first time point. In some embodiments, the first time point is about 0 to about 12 hours after the suspected injury, the reference level of UCH-L1 is between about 350 pg/mL and about 550 pg/mL, and the statistically significant increase is more than about 0.73-fold from the second time point to the first time point.

In some embodiments, the absolute amount can be determined by an assay having a sensitivity of between at least about 70% to about 100% and a specificity of between at least about 30% to about 100%. In some embodiments, the sensitivity is at least about 70.0%, at least about 75.0%, at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, the sensitivity is at least about 99% and the specificity is at least about 75%, the sensitivity is at least about 99% and the specificity is at least about 99%, or the sensitivity is about 100% and the specificity is about 100%.

In some embodiments, the absolute amount can be between at least about 20 pg/mL to about 6100 pg/mL. In some embodiments, the absolute amount can be between at least about 20 pg/mL to about 6100 pg/mL, between at least about 20 pg/mL to about 6000 pg/mL, between at least about 20 pg/mL to about 5500 pg/mL, between at least about 20 pg/mL to about 5000 pg/mL, between at least about 20 pg/mL to about 4500 pg/mL, between at least about 20 pg/mL to about 4000 pg/mL, between at least about 20 pg/mL to about 3500 pg/mL, between at least about 20 pg/mL to about 3000 pg/mL, between at least about 20 pg/mL to about 2500 pg/mL, between at least about 20 pg/mL to about 2000 pg/mL, between at least about 20 pg/mL to about 1500 pg/mL, between at least about 20 pg/mL to about 1000 pg/mL, between at least about 20 pg/mL to about 900 pg/mL, between at least about 20 pg/mL to about 800 pg/mL, between at least about 20 pg/mL to about 700 pg/mL, between at least about 20 pg/mL to about 600 pg/mL, between at least about 20 pg/mL to about 500 pg/mL, between at least about 20 pg/mL to about 400 pg/mL, between at least about 20 pg/mL to about 300 pg/mL, between at least about 20 pg/mL to about 200 pg/mL, between at least about 20 pg/mL to about 100 pg/mL, between at least about 20 pg/mL to about 50 pg/mL, between at least about 25 pg/mL to about 6100 pg/mL, between at least about 25 pg/mL to about 6000 pg/mL, between at least about 25 pg/mL to about 5500 pg/mL, between at least about 25 pg/mL to about 5000 pg/mL, between at least about 25 pg/mL to about 4500 pg/mL, between at least about 25 pg/mL to about 4000 pg/mL, between at least about 25 pg/mL to about 3500 pg/mL, between at least about 25 pg/mL to about 3000 pg/mL, between at least about 25 pg/mL to about 2500 pg/mL, between at least about 25 pg/mL to about 2000 pg/mL, between at least about 25 pg/mL to about 1500 pg/mL, between at least about 25 pg/mL to about 1000 pg/mL, between at least about 25 pg/mL to about 900 pg/mL, between at least about 25 pg/mL to about 800 pg/mL, between at least about 25 pg/mL to about 700 pg/mL, between at least about 25 pg/mL to about 600 pg/mL, between at least about 25 pg/mL to about 500 pg/mL, between at least about 25 pg/mL to about 400 pg/mL, between at least about 25 pg/mL to about 300 pg/mL, between at least about 25 pg/mL to about 200 pg/mL, between at least about 25 pg/mL to about 100 pg/mL, between at least about 25 pg/mL to about 50 pg/mL, between at least about 50 pg/mL to about 6100 pg/mL, between at least about 50 pg/mL to about 6000 pg/mL, between at least about 50 pg/mL to about 5500 pg/mL, between at least about 50 pg/mL to about 5000 pg/mL, between at least about 50 pg/mL to about 4500 pg/mL, between at least about 50 pg/mL to about 4000 pg/mL, between at least about 50 pg/mL to about 3500 pg/mL, between at least about 50 pg/mL to about 3000 pg/mL, between at least about 50 pg/mL to about 2500 pg/mL, between at least about 50 pg/mL to about 2000 pg/mL, between at least about 50 pg/mL to about 1500 pg/mL, between at least about 50 pg/mL to about 1000 pg/mL, between at least about 50 pg/mL to about 900 pg/mL, between at least about 50 pg/mL to about 800 pg/mL, between at least about 50 pg/mL to about 700 pg/mL, between at least about 50 pg/mL to about 600 pg/mL, between at least about 50 pg/mL to about 500 pg/mL, between at least about 50 pg/mL to about 400 pg/mL, between at least about 50 pg/mL to about 300 pg/mL, between at least about 50 pg/mL to about 200 pg/mL, between at least about 50 pg/mL to about 100 pg/mL, between at least about 100 pg/mL to about 6100 pg/mL, between at least about 100 pg/mL to about 6000 pg/mL, between at least about 100 pg/mL to about 5500 pg/mL, between at least about 100 pg/mL to about 5000 pg/mL, between at least about 100 pg/mL to about 4500 pg/mL, between at least about 100 pg/mL to about 4000 pg/mL, between at least about 100 pg/mL to about 3500 pg/mL, between at least about 100 pg/mL to about 3000 pg/mL, between at least about 100 pg/mL to about 2500 pg/mL, between at least about 100 pg/mL to about 2000 pg/mL, between at least about 100 pg/mL to about 1500 pg/mL, between at least about 100 pg/mL to about 1000 pg/mL, between at least about 100 pg/mL to about 900 pg/mL, between at least about 100 pg/mL to about 800 pg/mL, between at least about 100 pg/mL to about 700 pg/mL, between at least about 100 pg/mL to about 600 pg/mL, between at least about 100 pg/mL to about 500 pg/mL, between at least about 100 pg/mL to about 400 pg/mL, between at least about 100 pg/mL to about 300 pg/mL, between at least about 100 pg/mL to about 200 pg/mL, between at least about 129 pg/mL to about 6100 pg/mL, between at least about 129 pg/mL to about 6000 pg/mL, between at least about 129 pg/mL to about 5500 pg/mL, between at least about 129 pg/mL to about 5000 pg/mL, between at least about 129 pg/mL to about 4500 pg/mL, between at least about 129 pg/mL to about 4000 pg/mL, between at least about 129 pg/mL to about 3500 pg/mL, between at least about 129 pg/mL to about 3000 pg/mL, between at least about 129 pg/mL to about 2500 pg/mL, between at least about 129 pg/mL to about 2000 pg/mL, between at least about 129 pg/mL to about 1500 pg/mL, between at least about 129 pg/mL to about 1000 pg/mL, between at least about 129 pg/mL to about 900 pg/mL, between at least about 129 pg/mL to about 800 pg/mL, between at least about 129 pg/mL to about 700 pg/mL, between at least about 129 pg/mL to about 600 pg/mL, between at least about 129 pg/mL to about 500 pg/mL, between at least about 129 pg/mL to about 400 pg/mL, between at least about 129 pg/mL to about 300 pg/mL, between at least about 129 pg/mL to about 200 pg/mL, between at least about 200 pg/mL to about 6100 pg/mL, between at least about 200 pg/mL to about 6000 pg/mL, between at least about 200 pg/mL to about 5500 pg/mL, between at least about 200 pg/mL to about 5000 pg/mL, between at least about 200 pg/mL to about 4500 pg/mL, between at least about 200 pg/mL to about 4000 pg/mL, between at least about 200 pg/mL to about 3500 pg/mL, between at least about 200 pg/mL to about 3000 pg/mL, between at least about 200 pg/mL to about 2500 pg/mL, between at least about 200 pg/mL to about 2000 pg/mL, between at least about 200 pg/mL to about 1500 pg/mL, between at least about 200 pg/mL to about 1000 pg/mL, between at least about 200 pg/mL to about 900 pg/mL, between at least about 200 pg/mL to about 800 pg/mL, between at least about 200 pg/mL to about 700 pg/mL, between at least about 200 pg/mL to about 600 pg/mL, between at least about 200 pg/mL to about 500 pg/mL, between at least about 200 pg/mL to about 400 pg/mL, between at least about 200 pg/mL to about 300 pg/mL, between at least about 300 pg/mL to about 6100 pg/mL, between at least about 300 pg/mL to about 6000 pg/mL, between at least about 300 pg/mL to about 5500 pg/mL, between at least about 300 pg/mL to about 5000 pg/mL, between at least about 300 pg/mL to about 4500 pg/mL, between at least about 300 pg/mL to about 4000 pg/mL, between at least about 300 pg/mL to about 3500 pg/mL, between at least about 300 pg/mL to about 3000 pg/mL, between at least about 300 pg/mL to about 2500 pg/mL, between at least about 300 pg/mL to about 2000 pg/mL, between at least about 300 pg/mL to about 1500 pg/mL, between at least about 300 pg/mL to about 1000 pg/mL, between at least about 300 pg/mL to about 900 pg/mL, between at least about 300 pg/mL to about 800 pg/mL, between at least about 300 pg/mL to about 700 pg/mL, between at least about 300 pg/mL to about 600 pg/mL, between at least about 300 pg/mL to about 500 pg/mL, between at least about 300 pg/mL to about 400 pg/mL, between at least about 400 pg/mL to about 6100 pg/mL, between at least about 400 pg/mL to about 6000 pg/mL, between at least about 400 pg/mL to about 5500 pg/mL, between at least about 400 pg/mL to about 5000 pg/mL, between at least about 400 pg/mL to about 4500 pg/mL, between at least about 400 pg/mL to about 4000 pg/mL, between at least about 400 pg/mL to about 3500 pg/mL, between at least about 400 pg/mL to about 3000 pg/mL, between at least about 400 pg/mL to about 2500 pg/mL, between at least about 400 pg/mL to about 2000 pg/mL, between at least about 400 pg/mL to about 1500 pg/mL, between at least about 400 pg/mL to about 1000 pg/mL, between at least about 400 pg/mL to about 900 pg/mL, between at least about 400 pg/mL to about 800 pg/mL, between at least about 400 pg/mL to about 700 pg/mL, between at least about 400 pg/mL to about 600 pg/mL, between at least about 400 pg/mL to about 500 pg/mL, between at least about 500 pg/mL to about 6100 pg/mL, between at least about 500 pg/mL to about 6000 pg/mL, between at least about 500 pg/mL to about 5500 pg/mL, between at least about 500 pg/mL to about 5000 pg/mL, between at least about 500 pg/mL to about 4500 pg/mL, between at least about 500 pg/mL to about 4000 pg/mL, between at least about 500 pg/mL to about 3500 pg/mL, between at least about 500 pg/mL to about 3000 pg/mL, between at least about 500 pg/mL to about 2500 pg/mL, between at least about 500 pg/mL to about 2000 pg/mL, between at least about 500 pg/mL to about 1500 pg/mL, between at least about 500 pg/mL to about 1000 pg/mL, between at least about 500 pg/mL to about 900 pg/mL, between at least about 500 pg/mL to about 800 pg/mL, between at least about 500 pg/mL to about 700 pg/mL, or between at least about 500 pg/mL to about 600 pg/mL. In some embodiments, the absolute amount can be at least about 20 pg/mL, at least about 21 pg/mL, at least about 22 pg/mL, at least about 23 pg/mL, at least about 24 pg/mL, at least about 25 pg/mL, at least about 26 pg/mL, at least about 27 pg/mL, at least about 28 pg/mL, at least about 29 pg/mL, at least about 30 pg/mL, at least about 35 pg/mL, at least about 40 pg/mL, at least about 45 pg/mL, at least about 50 pg/mL, at least about 55 pg/mL, at least about 60 pg/mL, at least about 65 pg/mL, at least about 70 pg/mL, at least about 75 pg/mL, at least about 80 pg/mL, at least about 85 pg/mL, at least about 90 pg/mL, at least about 95 pg/mL, at least about 100 pg/mL, at least about 110 pg/mL, at least about 120 pg/mL, at least about 129 pg/mL, at least about 130 pg/mL, at least about 140 pg/mL, at least about 150 pg/mL, at least about 200 pg/mL, at least about 250 pg/mL, at least about 300 pg/mL, at least about 350 pg/mL, at least about 400 pg/mL, at least about 450 pg/mL, at least about 500 pg/mL, at least about 550 pg/mL, at least about 600 pg/mL, at least about 700 pg/mL, at least about 800 pg/mL, at least about 900 pg/mL, at least about 1000 pg/mL, at least about 1500 pg/mL, at least about 2000 pg/mL, at least about 2500 pg/mL, at least about 2528 pg/mL, at least about 3000 pg/mL, at least about 4000 pg/mL, at least about 5000 pg/mL, at least about 6000 pg/mL, or at least about 6100 pg/mL.

In some embodiments, the first sample can be obtained within about 0 to about 6 hours and the reference level can be about 2528 pg/mL determined by an assay having a sensitivity of about 100% and a specificity of about 100%. In some embodiments, the first sample can be obtained within about 0 to about 6 hours and the reference level can be about 129 pg/mL determined by an assay having a sensitivity of at least about 70% and a specificity of at least about 92%. In some embodiments, the first sample can be obtained within about 0 to about 10 hours and the reference level can be about 25 pg/mL determined by an assay having a sensitivity of about 100% and a specificity of at least about 36%. In some embodiments, the first sample can be obtained within about 0 to about 11 hours and the reference level can be about 25 pg/mL determined by an assay having a sensitivity of about 100% and a specificity of at least about 32%. In some embodiments, the first sample can be obtained within about 0 to about 12 hours and the reference level can be about 129 pg/mL determined by an assay having a sensitivity of at least about 75% and a specificity of at least about 76%.

In some embodiments, the method further includes treating a human subject assessed as having moderate to severe traumatic brain injury with a traumatic brain injury treatment, as described below. In some embodiments, the method further includes monitoring a human subject assessed as having mild traumatic brain injury, as described below.

The nature of the assay employed in the methods described herein is not critical and the test can be any assay known in the art such as, for example, immunoassays, clinical chemistry assays, single molecule detection assays, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in a clinical chemistry format such as would be known by one of ordinary skill in the art. Such assays are described in further detail herein in Sections 9-11. It is known in the art that the values (e.g., reference levels, cutoffs, thresholds, specificities, sensitivities, concentrations of calibrators and/or controls etc.) used in an assay that employs specific sample type (e.g., such as an immunoassay that utilizes serum or a point-of-care device that employs whole blood) can be extrapolated to other assay formats using known techniques in the art, such as assay standardization. For example, one way in which assay standardization can be performed is by applying a factor to the calibrator employed in the assay to make the sample concentration read higher or lower to get a slope that aligns with the comparator method. Other methods of standardizing results obtained on one assay to another assay are well known and have been described in the literature (See, for example, David Wild, Immunoassay Handbook, 4$^{th}$ edition, chapter 3.5, pages 315-322, the contents of which are herein incorporated by reference).

3. METHODS OF AIDING IN DETERMINING THE EXTENT OF TRAUMATIC BRAIN INJURY IN A HUMAN SUBJECT WHO MAY HAVE SUSTAINED AN INJURY TO THE HEAD

The present disclosure relates to a method of aiding in determining the extent of traumatic brain injury in a human subject with a suspected injury to the head (e.g., determining whether the subject has mild traumatic brain injury or moderate to severe traumatic brain injury). As used herein, "determining the extent of traumatic brain injury in a human subject" refers to use of the method, with or without other methods, to determine that the subject is more likely than not to have mild TBI or moderate to severe TBI. The method includes performing an assay on at least two samples obtained from the subject and detecting in the at least two samples an early biomarker of traumatic brain injury. The first sample is taken from the human subject within 24 hours of injury and the second sample is taken from the human subject about 3 to about 6 hours after the first sample is taken. The early biomarker is ubiquitin carboxy-terminal hydrolase L1 (UCH-L1). The UCH-L1 appears within about 2 to about 24 hours after the onset of injury to the head. The onset of the presence of UCH-L1 appears within about 0 to about 6 hours after the onset of the suspected injury. Levels of UCH-L1 are determined for each of the first sample and second sample. The level of UCH-L1 is determined to decrease or increase. The extent of the traumatic brain injury is determined in the subject based on whether the level of UCH-L1 decreases, increases, or remains the same from the first sample to the second sample. The early biomarker increases within about 0 to about 6 hours after the suspected injury and then decreases or increases thereafter in subjects with traumatic brain injury. In some embodiments, the onset of the presence of UCH-L1 appears within about 0, about 0.5 hours, about 1 hour, about 2 hours, about 3 hours, about 4 hours, about 5 hours, or about 6 hours after injury to the head. The samples can be biological samples.

The method includes performing an assay on at least two samples obtained from the subject. The first sample is taken from the subject within 24 hours of the suspected injury and the second sample is taken from the subject from about 3 to about 6 hours after the first sample is taken. The method includes detecting in the at least two samples an early biomarker of traumatic brain injury, said early biomarker consisting of ubiquitin carboxy-terminal hydrolase L1 (UCH-L1), wherein the onset of the presence of UCH-L1 appears within about 0 to about 6 hours after the suspected injury; determining the level of UCH-L1 in each of the first sample and second sample and determining if the level of UCH-L1 decreases or increases from the first sample to the second sample; and determining the extent of the traumatic brain injury in the subject based on whether the level of UCH-L1 decreases, increases, or remains the same from the first sample to the second sample.

In some embodiments, the first sample is taken from the subject at a first time point within 24 hours of the suspected injury and the second sample is taken from the subject at a second time point after the first time point and the subject is determined to have mild or mild to severe traumatic brain injury when the level of UCH-L1 decreases from the first sample to the second sample. In some embodiments, the UCH-L1 decreases at least about 5% from the increased levels. For example, the UCH-L1 levels may decrease about 5%, about 10%, about 20%, about 30%, about 40%, about 50%, about 60%, about 70%, about 80%, about 90%, about 100%, about 200%, about 300%, about 400%, about 500%, about 600%, about 700%, about 800%, about 900%, or about 1000% from the increased levels. In some embodiments, the UCH-L1 decreases at least about 0.1-fold, at least about 0.2-fold, at least about 0.3-fold, at least about 0.4-fold, at least about 0.5-fold, at least about 0.55-fold, at least about 0.6-fold, at least about 0.7-fold, at least about 0.73-fold, at least about 0.8-fold, at least about 0.9-fold, at least about 1-fold, at least about 1.5-fold, at least about 2-fold, at least about 3-fold, at least about 4-fold, at least about 5-fold, at least about 6-fold, at least about 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold from the increased levels. In some embodiments, the UCH-L1 decreases less than about 0.1-fold, less than about 0.2-fold, less than about 0.3-fold, less than about 0.4-fold, less than about 0.5-fold, less than about 0.55-fold, at least about 0.6-fold, at least about 0.7-fold, at least about 0.73-fold, at least about 0.8-fold, at least about 0.9-fold, less than about 1-fold, less than about 1.5-fold, less than about 2-fold, less than about 3-fold, less than about 4-fold, less than about 5-fold, less than about 6-fold, less than about 7-fold, less than 8-fold, less than 9-fold, less than 10-fold, less than 11-fold, less than 12-fold, less than 13-fold, less than 14-fold, less than 15-fold, less than 16-fold, less than 17-fold, less than 18-fold, less than 19-fold, or less than 20-fold from the increased levels.

In some embodiments, the first time point is about 0 to about 12 hours after the suspected injury and the statistically significant increase is more than about 1-fold from the second time point to the first time point. In some embodiments, the first time point is about 0 to about 12 hours after the suspected injury and the statistically significant increase is more than about 0.73-fold from the second time point to the first time point. In some embodiments, the first time point is about 0 to about 12 hours after the suspected injury, the reference level of UCH-L1 is between about 350 pg/mL and about 550 pg/mL, and the statistically significant increase is more than about 0.73-fold from the second time point to the first time point.

In some embodiments, the subject is assessed as having mild or mild to severe traumatic brain injury when the levels of UCH-L1 in the first sample changes (i.e., increases or decreases) compared to the levels of UCH-L1 in the second sample from at least about 20 pg/mL to at least about 6100 pg/mL. In some embodiments, the change (i.e., an increase or a decrease) in UCH-L1 levels can be from at least about 20 pg/mL to about 6100 pg/mL, at least about 25 pg/mL to about 6100 pg/mL, at least about 30 pg/mL to about 6100 pg/mL, at least about 40 pg/mL to about 6100 pg/mL, at least about 50 pg/mL to about 6100 pg/mL, at least about 100 pg/mL to about 6100 pg/mL, at least about 129 pg/mL to about 6100 pg/mL, at least about 200 pg/mL to about 6100 pg/mL, at least about 300 pg/mL to about 6100 pg/mL, at least about 400 pg/mL to about 6100 pg/mL, at least about 500 pg/mL to about 6100 pg/mL, at least about 600 pg/mL to about 6100 pg/mL, at least about 700 pg/mL to about 6100 pg/mL, at least about 800 pg/mL to about 6100 pg/mL, at least about 900 pg/mL to about 6100 pg/mL, at least about 1000 pg/mL to about 6100 pg/mL, at least about 2000 pg/mL to about 6100 pg/mL, at least about 3000 pg/mL to about 6100 pg/mL, at least about 4000 pg/mL to about 6100 pg/mL, at least about 5000 pg/mL to about 6100 pg/mL, at least about 20 pg/mL to about 4000 pg/mL, at least about 25 pg/mL to about 4000 pg/mL, at least about 30 pg/mL to about 4000 pg/mL, at least about 40 pg/mL to about 4000 pg/mL, at least about 50 pg/mL to about 4000 pg/mL, at least about 100 pg/mL to about 4000 pg/mL, at least about 129 pg/mL to about 4000 pg/mL, at least about 200 pg/mL to about 4000 pg/mL, at least about 300 pg/mL to about 4000 pg/mL, at least about 400 pg/mL to about 4000 pg/mL, at least about 500 pg/mL to about 4000 pg/mL, at least about 600 pg/mL to about 4000 pg/mL, at least about 700 pg/mL to about 4000 pg/mL, at least about 800 pg/mL to about 4000 pg/mL, at least about 900 pg/mL to about 4000 pg/mL, at least about 1000 pg/mL to about 4000 pg/mL, at least about 2000 pg/mL to about 4000 pg/mL, at least about 3000 pg/mL to about 4000 pg/mL, at least about 20 pg/mL to about 2500 pg/mL, at least about 25 pg/mL to about 2500 pg/mL, at least about 30 pg/mL to about 2500 pg/mL, at least about 40 pg/mL to about 2500 pg/mL, at least about 50 pg/mL to about 2500 pg/mL, at least about 100 pg/mL to about 2500 pg/mL, at least about 129 pg/mL to about 2500 pg/mL, at least about 200 pg/mL to about 2500 pg/mL, at least about 300 pg/mL to about 2500 pg/mL, at least about 400 pg/mL to about 2500 pg/mL, at least about 500 pg/mL to about 2500 pg/mL, at least about 600 pg/mL to about 2500 pg/mL, at least about 700 pg/mL to about 2500 pg/mL, at least about 800 pg/mL to about 2500 pg/mL, at least about 900 pg/mL to about 2500 pg/mL, at least about 1000 pg/mL to about 2500 pg/mL, at least about 2000 pg/mL to about 2500 pg/mL, at least about 20 pg/mL to about 1000 pg/mL, at least about 25 pg/mL to about 1000 pg/mL, at least about 30 pg/mL to about 1000 pg/mL, at least about 40 pg/mL to about 1000 pg/mL, at least about 50 pg/mL to about 1000 pg/mL, at least about 100 pg/mL to about 1000 pg/mL, at least about 129 pg/mL to about 1000 pg/mL, at least about 200 pg/mL to about 1000 pg/mL, at least about 300 pg/mL to about 1000 pg/mL, at least about 400 pg/mL to about 1000 pg/mL, at least about 500 pg/mL to about 1000 pg/mL, at least about 600 pg/mL to about 1000 pg/mL, at least about 700 pg/mL to about 1000 pg/mL, at least about 800 pg/mL to about 1000 pg/mL, at least about 900 pg/mL to about 1000 pg/mL, at least about 20 pg/mL to about 500 pg/mL, at least about 25 pg/mL to about 500 pg/mL, at least about 30 pg/mL to about 500 pg/mL, at least about 40 pg/mL to about 500 pg/mL, at least about 50 pg/mL to about 500 pg/mL, at least about 100 pg/mL to about 500 pg/mL, at least about 129 pg/mL to about 500 pg/mL, at least about 200 pg/mL to about 500 pg/mL, at least about 300 pg/mL to about 500 pg/mL, at least about 400 pg/mL to about 500 pg/mL, at least about 20 pg/mL to about 100 pg/mL, at least about 25 pg/mL to about 100 pg/mL, at least about 30 pg/mL to about 100 pg/mL, at least about 40 pg/mL to about 100 pg/mL, at least about 50 pg/mL to about 100 pg/mL, at least about 20 pg/mL to about 50 pg/mL, at least about 25 pg/mL to about 50 pg/mL, at least about 30 pg/mL to about 50 pg/mL, or at least about 40 pg/mL to about 50 pg/mL.

For example, the change (i.e., the increase or decrease) can be at least about 20 pg/mL, at least about 25 pg/mL, at least about 30 pg/mL, at least about 40 pg/mL, at least about 50 pg/mL, at least about 60 pg/mL, at least about 70 pg/mL, at least about 80 pg/mL, at least about 90 pg/mL, at least about 100 pg/mL, at least about 129 pg/mL, at least about 200 pg/mL, at least about 300 pg/mL, at least about 400 pg/mL, at least about 500 pg/mL, at least about 600 pg/mL, at least about 700 pg/mL, at least about 800 pg/mL, at least about 900 pg/mL, at least about 1000 pg/mL, at least about 1500 pg/mL, at least about 2000 pg/mL, at least about 2528 pg/mL, at least about 2500 pg/mL, at least about 3000 pg/mL, at least about 3500 pg/mL, at least about 4000 pg/mL, at least about 4500 pg/mL, at least about 5000 pg/mL, at least about 5500 pg/mL, at least about 6000 pg/mL, or at least about 6100 pg/mL.

In some embodiments, the first sample is taken within 24 hours after the suspected injury. For example, the first sample can be taken within about 0 hours, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, within about 24 hours, or more than about 24 hours after the suspected injury. In some embodiments, the first sample is taken within about 0 to about 1 hours, within about 0 to about 2 hours, within about 0 to about 3 hours, within about 0 to about 4 hours, within about 0 to about 5 hours, within about 0 to about 6 hours, within about 0 to about 7 hours, within about 0 to about 8 hours, within about 0 to about 9 hours, within about 0 to about 10 hours, within about 0 to about 11 hours, within about 0 to about 12 hours, within about 0 to about 18 hours, within about 6 to about 12 hours, within about 12 to about 18 hours, within about 18 to about 24 hours, or greater than 24 hours after the suspected injury.

In some embodiments, the second sample is obtained within about 1 hour to about 10 hours after the first sample is obtained, such as about 3 hours to about 6 hours after the first sample is obtained. In some embodiments, the second sample is obtained within about 1 hour, about 2 hours, about 3 hours, about 4 hours, about 5 hours, about 6 hours, about 7 hours, about 8 hours, about 9 hours, or about 10 hours after the first sample is obtained.

In some embodiments, the first sample is taken within 0 to about 6 hours after the suspected injury and the subject is determined to have moderate to severe traumatic brain injury when the level of UCH-L1 increases or decreases between at least about 20 pg/mL to at least about 6100 pg/mL from the first sample to the second sample.

In some embodiments, the first sample can be obtained within about 0 to about 6 hours and the increase or decrease in UCH-L1 levels is at least about 2528 pg/mL. In some embodiments, the first sample can be obtained within about 0 to about 6 hours and the increase or decrease in UCH-L1 levels is at least about 129 pg/mL. In some embodiments, the first sample can be obtained within about 0 to about 10 hours and the increase or decrease in UCH-L1 levels is at least about 25 pg/mL. In some embodiments, the first sample can be obtained within about 0 to about 11 hours and the increase or decrease in UCH-L1 levels is at least about 25 pg/mL. In some embodiments, the first sample can be obtained within about 0 to about 12 hours and the increase or decrease in UCH-L1 levels is at least about 129 pg/mL.

In some embodiments, a subject can be considered as suffering from moderate to severe traumatic brain injury when the amount of UCH-L1-antibody complex detected increases to an elevated amount (e.g., about 100 pg/mL to about 1000 pg/mL) in one or more first samples taken from the subject within about 0 to about 6 hours after injury or suspected injury to the head. In some embodiments, the UCH-L1 levels may increase within about 0 to about 6 hours, about 0.5 hours to about 6 hours, about 1 hour to about 6 hours, about 1.5 hours to about 6 hours, about 2 hours to about 6 hours, about 2.5 hours to about 6 hours, about 3 hours to about 6 hours, about 4 hours to about 6 hours, about 5 hours to about 6 hours, about 0 to about 5 hours, about 0.5 hours to about 5 hours, about 1 hour to about 5 hours, about 1.5 hours to about 5 hours, about 2 hours to about 5 hours, about 2.5 hours to about 5 hours, about 3 hours to about 5 hours, about 4 hours to about 5 hours, about 0 to about 4 hours, about 0.5 hours to about 4 hours, about 1 hour to about 4 hours, about 1.5 hours to about 4 hours, about 2 hours to about 4 hours, about 2.5 hours to about 4 hours, about 3 hours to about 4 hours, about 0 to about 3 hours, about 0.5 hours to about 3 hours, about 1 hour to about 3 hours, about 1.5 hours to about 3 hours, about 2 hours to about 3 hours, about 2.5 hours to about 3 hours, about 0 to about 2.5 hours, about 0.5 hours to about 2.5 hours, about 1 hour to about 2.5 hours, about 1.5 hours to about 2.5 hours, about 2 hours to about 2.5 hours, about 0 to about 2 hours, about 0.5 hours to about 2 hours, about 1 hour to about 2 hours, or about 1.5 hours to about 2 hours after injury to the head. In some embodiments, UCH-L1 levels may increase within about 0, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, or about 6 hours after injury to the head.

In some embodiments, UCH-L1 levels can increase to an elevated amount after injury or suspected injury to the head. The elevated amount of UCH-L1 can be between at least about 20 pg/mL to at least about 25000 pg/mL. For example, the elevated amount of UCH-L1 can be between at least about 20 pg/mL to at least about 25000 pg/mL, at least about 50 pg/mL to at least about 25000 pg/mL, at least about 100 pg/mL to at least about 25000 pg/mL, at least about 200 pg/mL to at least about 25000 pg/mL, at least about 300 pg/mL to at least about 25000 pg/mL, at least about 400 pg/mL to at least about 25000 pg/mL, at least about 500 pg/mL to at least about 25000 pg/mL, at least about 1000 pg/mL to at least about 25000 pg/mL, at least about 2000 pg/mL to at least about 25000 pg/mL, least about 3000 pg/mL to at least about 25000 pg/mL, least about 4000 pg/mL to at least about 25000 pg/mL, least about 5000 pg/mL to at least about 25000 pg/mL, at least about 20 pg/mL to at least about 15000 pg/mL, at least about 50 pg/mL to at least about 15000 pg/mL, at least about 100 pg/mL to at least about 15000 pg/mL, at least about 200 pg/mL to at least about 15000 pg/mL, at least about 300 pg/mL to at least about 15000 pg/mL, at least about 400 pg/mL to at least about 15000 pg/mL, at least about 500 pg/mL to at least about 15000 pg/mL, at least about 1000 pg/mL to at least about 15000 pg/mL, at least about 2000 pg/mL to at least about 15000 pg/mL, least about 3000 pg/mL to at least about 15000 pg/mL, least about 4000 pg/mL to at least about 15000 pg/mL, least about 5000 pg/mL to at least about 15000 pg/mL, at least about 10000 pg/mL to at least about 15000 pg/mL, at least about 20 pg/mL to at least about 10000 pg/mL, at least about 50 pg/mL to at least about 10000 pg/mL, at least about 100 pg/mL to at least about 10000 pg/mL, at least about 200 pg/mL to at least about 10000 pg/mL, at least about 300 pg/mL to at least about 10000 pg/mL, at least about 400 pg/mL to at least about 10000 pg/mL, at least about 500 pg/mL to at least about 10000 pg/mL, at least about 1000 pg/mL to at least about 10000 pg/mL, at least about 2000 pg/mL to at least about 10000 pg/mL, least about 3000 pg/mL to at least about 10000 pg/mL, at least about 4000 pg/mL to at least about 10000 pg/mL, least about 5000 pg/mL to at least about 10000 pg/mL, at least about 20 pg/mL to at least about 5000 pg/mL, at least about 50 pg/mL to at least about 5000 pg/mL, at least about 100 pg/mL to at least about 5000 pg/mL, at least about 200 pg/mL to at least about 5000 pg/mL, at least about 300 pg/mL to at least about 5000 pg/mL, at least about 400 pg/mL to at least about 5000 pg/mL, at least about 500 pg/mL to at least about 5000 pg/mL, at least about 1000 pg/mL to at least about 5000 pg/mL, at least about 2000 pg/mL to at least about 5000 pg/mL, least about 3000 pg/mL to at least about 5000 pg/mL, at least about 4000 pg/mL to at least about 5000 pg/mL, at least about 20 pg/mL to at least about 1000 pg/mL, at least about 50 pg/mL to at least about 1000 pg/mL, at least about 100 pg/mL to at least about 1000 pg/mL, at least about 200 pg/mL to at least about 1000 pg/mL, at least about 300 pg/mL to at least about 1000 pg/mL, at least about 400 pg/mL to at least about 1000 pg/mL, or at least about 500 pg/mL to at least about 1000 pg/mL. In some embodiments, the elevated amount of UCH-L1 can be at least about 100 pg/mL, at least about 200 pg/mL, at least about 300 pg/mL, at least about 400 pg/mL, at least about 500 pg/mL, at least about 600 pg/mL, at least about 700 pg/mL, at least about 800 pg/mL, at least about 900 pg/mL, at least about 1000 pg/mL, at least about 21000 pg/mL, at least about 3000 pg/mL, at least about 4000 pg/mL, at least about 5000 pg/mL, at least about 10000 pg/mL, or at least about 15000 pg/mL.

In some embodiments, the method further includes treating a subject assessed as having moderate to severe traumatic brain injury with a traumatic brain injury treatment, as described below. In some embodiments, the method further includes monitoring the subject assessed as having mild traumatic brain injury, as described below.

The nature of the assay employed in the methods described herein is not critical, and the test can be any assay known in the art such as, for example, immunoassays, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in clinical chemistry format such as would be known by one of ordinary skill in the art. Such assays are described in further detail herein in Sections 9-11.

4. METHODS FOR EVALUATING WHETHER TO PERFORM A CT SCAN ON A HUMAN SUBJECT WHO HAS SUSTAINED AN INJURY TO THE HEAD

The present disclosure relates to a method, among other methods, of aiding in the determination or evaluation of whether to perform a computerized tomography (CT) scan on a human subject who has sustained or may have sustained a suspected injury to the head. As used herein, "determination of whether to perform a CT scan on a human subject" refers to use of the method, with or without other methods, to determine that the subject is more likely than not to have a positive head CT scan. Specifically, such a method can comprise the steps of: (a) performing an assay on at least two samples obtained from the subject, the first sample taken from the subject within 24 hours of the suspected injury and the second sample taken from the subject from about 3 to about 6 hours after the first sample is taken; (b) detecting in the at least two samples an early biomarker of traumatic brain injury, said early biomarker consisting of ubiquitin carboxy-terminal hydrolase L1 (UCH-L1), wherein the onset of the presence of UCH-L1 appears within about 0 to about 6 hours after the suspected injury; (c) determining the level of UCH-L1 in each of the first sample and second sample and determining if the level of UCH-L1 decreases or increases from the first sample to the second sample; and (d) determining whether to perform a CT scan on the subject based on whether the level of UCH-L1 decreases, increases, or remains the same from the first sample to the second sample. In some embodiments, a CT scan is performed on the subject when the level of UCH-L1 in the first sample or the second sample is higher than a reference level of UCH-L1. In some embodiments, a CT scan is not performed on the subject when the level of UCH-L1 in the in the first sample or the second sample is lower than a reference level of UCH-L1. In some embodiments, a CT scan is performed on the subject when there is a statistically significant increase or decrease from the level of UCH-L1 in the first sample to the level of UCH-L1 in the second sample. In some embodiments, a CT scan is not performed on the subject when there is no statistically significant increase or decrease from the level of UCH-L1 in the first sample to the level of UCH-L1 in the second sample. In some embodiments, a CT scan is performed on the subject when the level of UCH-L1 decreases or increases by at least an absolute amount from the first sample to the second sample. In some embodiments, a CT scan is not performed on the subject when there is no decrease or increase by at least an absolute amount in the level of UCH-L1 from the first sample to the second sample. In some embodiments, a CT scan is performed on the subject when the level of UCH-L1 in the first sample is higher than a reference level of UCH-L1 or when there is a statistically significant increase or decrease from the level of UCH-L1 in the first sample to the level of UCH-L1 in the second sample. In some embodiments, a CT scan is not performed on the subject when the level of UCH-L1 in the first sample is lower than a reference level of UCH-L1 or when there is no statistically significant increase or decrease from the level of UCH-L1 in the first sample to the level of UCH-L1 in the second sample. The samples can be biological samples.

In some embodiments, the subject has received a CT scan before or after the assay is performed. In some embodiments, the subject is suspected as having a traumatic brain injury based on the CT scan. In some embodiments, the reference level is correlated with positive head CT scan.

Generally, a reference level can be employed as a benchmark against which to assess results obtained upon assaying a test sample for UCH-L1. Generally, in making such a comparison, the reference level is obtained by running a particular assay a sufficient number of times and under appropriate conditions such that a linkage or association of analyte presence, amount or concentration with a particular stage or endpoint of TBI or with particular indicia can be made. Typically, the reference level is obtained with assays of reference subjects (or populations of subjects). The UCH-L1 measured can include UCH-L1 fragments thereof, degradation products thereof, and/or enzymatic cleavage products thereof.

In some embodiments, the reference level is determined by an assay having a sensitivity of between at least about 80% to about 100% and a specificity of between at least about 30% to about 100%. In some embodiments, the sensitivity is at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, the sensitivity is at least about 99% and the specificity is at least about 75%, the sensitivity is at least about 99% and the specificity is at least about 99%, or the sensitivity is about 100% and the specificity is about 100%

In some embodiments, the reference level can be between at least about 50 pg/mL to about 1000 pg/mL. In some embodiments, the reference level can be between at least about 50 pg/mL to about 1000 pg/mL, between at least about 50 pg/mL to about 900 pg/mL, between at least about 50 pg/mL to about 800 pg/mL, between at least about 50 pg/mL to about 750 pg/mL, between at least about 50 pg/mL to about 700 pg/mL, between at least about 50 pg/mL to about 600 pg/mL, between at least about 50 pg/mL to about 500 pg/mL, between at least about 50 pg/mL to about 400 pg/mL, between at least about 50 pg/mL to about 300 pg/mL, between at least about 50 pg/mL to about 200 pg/mL, between at least about 100 pg/mL to about 1000 pg/mL, between at least about 100 pg/mL to about 900 pg/mL, between at least about 100 pg/mL to about 800 pg/mL, between at least about 100 pg/mL to about 750 pg/mL, between at least about 100 pg/mL to about 700 pg/mL, between at least about 100 pg/mL to about 600 pg/mL, between at least about 100 pg/mL to about 500 pg/mL, between at least about 100 pg/mL to about 400 pg/mL, between at least about 100 pg/mL to about 300 pg/mL, between at least about 100 pg/mL to about 200 pg/mL, between at least about 150 pg/mL to about 1000 pg/mL, between at least about 150 pg/mL to about 900 pg/mL, between at least about 150 pg/mL to about 800 pg/mL, between at least about 150 pg/mL to about 750 pg/mL, between at least about 150 pg/mL to about 700 pg/mL, between at least about 150 pg/mL to about 600 pg/mL, between at least about 150 pg/mL to about 500 pg/mL, between at least about 150 pg/mL to about 400 pg/mL, between at least about 150 pg/mL to about 300 pg/mL, between at least about 150 pg/mL to about 200 pg/mL, between at least about 200 pg/mL to about 1000 pg/mL, between at least about 200 pg/mL to about 900 pg/mL, between at least about 200 pg/mL to about 800 pg/mL, between at least about 200 pg/mL to about 750 pg/mL, between at least about 200 pg/mL to about 700 pg/mL, between at least about 200 pg/mL to about 600 pg/mL, between at least about 200 pg/mL to about 500 pg/mL, between at least about 200 pg/mL to about 400 pg/mL, between at least about 200 pg/mL to about 300 pg/mL, between at least about 300 pg/mL to about 1000 pg/mL, between at least about 300 pg/mL to about 900 pg/mL, between at least about 300 pg/mL to about 800 pg/mL, between at least about 300 pg/mL to about 750 pg/mL, between at least about 300 pg/mL to about 700 pg/mL, between at least about 300 pg/mL to about 600 pg/mL, between at least about 300 pg/mL to about 500 pg/mL, between at least about 300 pg/mL to about 400 pg/mL, between at least about 400 pg/mL to about 1000 pg/mL, between at least about 400 pg/mL to about 900 pg/mL, between at least about 400 pg/mL to about 800 pg/mL, between at least about 400 pg/mL to about 750 pg/mL, between at least about 400 pg/mL to about 700 pg/mL, between at least about 400 pg/mL to about 600 pg/mL, between at least about 400 pg/mL to about 500 pg/mL, between at least about 500 pg/mL to about 1000 pg/mL, between at least about 500 pg/mL to about 900 pg/mL, between at least about 500 pg/mL to about 800 pg/mL, between at least about 500 pg/mL to about 750 pg/mL, between at least about 500 pg/mL to about 700 pg/mL, or between at least about 500 pg/mL to about 600 pg/mL. For example, the reference level can be at least about 50 pg/mL, 55 pg/mL, 60 pg/mL, 65 pg/mL, 70 pg/mL, 75 pg/mL, 80 pg/mL, 85 pg/mL, 90 pg/mL, 95 pg/mL, 96 pg/mL, 97 pg/mL, 98 pg/mL, 98 pg/mL, 100 pg/mL, 150 pg/mL, 200 pg/mL, 250 pg/mL, 300 pg/mL, 350 pg/mL, 370 pg/mL, 400 pg/mL, 450 pg/mL, 500 pg/mL, 509 pg/mL 550 pg/mL, 600 pg/mL, 700 pg/mL, 800 pg/mL, 900 pg/mL, or 1000 pg/mL.

In some embodiments, the first sample is taken within 24 hours after the suspected injury. For example, the first sample can be taken within about 0 hours, within about 30 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, within about 24 hours, or more than about 24 hours after the suspected injury. In some embodiments, the first sample is taken within about 0 to about 6 hours, within about 6 to about 12 hours, within about 12 to about 18 hours, within about 18 to about 24 hours, or greater than about 24 hours after the suspected injury.

In some embodiments, the second sample is obtained within about 1 hour to about 10 hours after the first sample is obtained, such as about 3 hours to about 6 hours after the first sample is obtained. In some embodiments, the second sample is obtained within about 1 hour, about 2 hours, about 3 hours, about 4 hours, about 5 hours, about 6 hours, about 7 hours, about 8 hours, about 9 hours, or about 10 hours after the first sample is obtained.

In some embodiments, the first sample is taken within 24 hours after the suspected injury and the reference level is determined by an assay having a particular sensitivity and specificity, as described above. In some embodiments, the sample is taken within about 0 to about 6 hours, within about 0 to about 7 hours, within about 0 to about 8 hours, within about 0 to about 9 hours, within about 0 to about 10 hours, within about 0 to about 11 hours, within about 0 to about 12 hours, within about 6 to about 12 hours, within about 12 to about 18 hours, within about 18 to about 24 hours, or greater than 24 hours after the suspected injury and the reference level is determined by an assay having a particular sensitivity and specificity, such as a sensitivity of about 100% and a specificity of at least about 75%, a sensitivity of at least about 99% and a specificity of at least about 75%, or a sensitivity of about 100% and a specificity of about 100%.

In some embodiments, the first sample can be obtained between about 0 hours to 6 hours after the suspected injury and the reference level is at least about 370 pg/mL and determined by an assay having a sensitivity of about 100% and a specificity of at least about 37.5%. In some embodiments, the first sample is taken between about 0 hours to 6 hours after the suspected injury and the reference level is about 509 pg/mL and determined by an assay having a sensitivity of about 100% and a specificity of at least about 75%. In some embodiments, the first sample is taken between about 6 hours to 12 hours after the suspected injury and the reference level is about 96 pg/mL and determined by an assay having a sensitivity of at least about 96% and a specificity of at least about 30%. In some embodiments, the first sample is taken between about 6 hours to 12 hours after the suspected injury and the reference level is about 86 pg/mL and determined by an assay having a sensitivity of at least about 86% and a specificity of at least about 35%.

In some embodiments, the absolute amount can be determined by an assay having a sensitivity of between at least about 80% to about 100% and a specificity of between at least about 30% to about 100%. In some embodiments, the sensitivity is at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, the sensitivity can be at least about 99% and the specificity can be at least about 75%, the sensitivity can be at least about 99% and the specificity can be at least about 99%, or the sensitivity can be about 100% and the specificity can be about 100%.

In some embodiments, the absolute amount can be between at least about 20 pg/mL to about 6100 pg/mL. In some embodiments, the absolute amount can be between at least about 20 pg/mL to about 6100 pg/mL, between at least about 20 pg/mL to about 6000 pg/mL, between at least about 20 pg/mL to about 5500 pg/mL, between at least about 20 pg/mL to about 5000 pg/mL, between at least about 20 pg/mL to about 4500 pg/mL, between at least about 20 pg/mL to about 4000 pg/mL, between at least about 20 pg/mL to about 3500 pg/mL, between at least about 20 pg/mL to about 3000 pg/mL, between at least about 20 pg/mL to about 2500 pg/mL, between at least about 20 pg/mL to about 2000 pg/mL, between at least about 20 pg/mL to about 1500 pg/mL, between at least about 20 pg/mL to about 1000 pg/mL, between at least about 20 pg/mL to about 900 pg/mL, between at least about 20 pg/mL to about 800 pg/mL, between at least about 20 pg/mL to about 700 pg/mL, between at least about 20 pg/mL to about 600 pg/mL, between at least about 20 pg/mL to about 500 pg/mL, between at least about 20 pg/mL to about 400 pg/mL, between at least about 20 pg/mL to about 300 pg/mL, between at least about 20 pg/mL to about 200 pg/mL, between at least about 20 pg/mL to about 100 pg/mL, between at least about 20 pg/mL to about 50 pg/mL, between at least about 25 pg/mL to about 6100 pg/mL, between at least about 25 pg/mL to about 6000 pg/mL, between at least about 25 pg/mL to about 5500 pg/mL, between at least about 25 pg/mL to about 5000 pg/mL, between at least about 25 pg/mL to about 4500 pg/mL, between at least about 25 pg/mL to about 4000 pg/mL, between at least about 25 pg/mL to about 3500 pg/mL, between at least about 25 pg/mL to about 3000 pg/mL, between at least about 25 pg/mL to about 2500 pg/mL, between at least about 25 pg/mL to about 2000 pg/mL, between at least about 25 pg/mL to about 1500 pg/mL, between at least about 25 pg/mL to about 1000 pg/mL, between at least about 25 pg/mL to about 900 pg/mL, between at least about 25 pg/mL to about 800 pg/mL, between at least about 25 pg/mL to about 700 pg/mL, between at least about 25 pg/mL to about 600 pg/mL, between at least about 25 pg/mL to about 500 pg/mL, between at least about 25 pg/mL to about 400 pg/mL, between at least about 25 pg/mL to about 300 pg/mL, between at least about 25 pg/mL to about 200 pg/mL, between at least about 25 pg/mL to about 100 pg/mL, between at least about 25 pg/mL to about 50 pg/mL, between at least about 50 pg/mL to about 6100 pg/mL, between at least about 50 pg/mL to about 6000 pg/mL, between at least about 50 pg/mL to about 5500 pg/mL, between at least about 50 pg/mL to about 5000 pg/mL, between at least about 50 pg/mL to about 4500 pg/mL, between at least about 50 pg/mL to about 4000 pg/mL, between at least about 50 pg/mL to about 3500 pg/mL, between at least about 50 pg/mL to about 3000 pg/mL, between at least about 50 pg/mL to about 2500 pg/mL, between at least about 50 pg/mL to about 2000 pg/mL, between at least about 50 pg/mL to about 1500 pg/mL, between at least about 50 pg/mL to about 1000 pg/mL, between at least about 50 pg/mL to about 900 pg/mL, between at least about 50 pg/mL to about 800 pg/mL, between at least about 50 pg/mL to about 700 pg/mL, between at least about 50 pg/mL to about 600 pg/mL, between at least about 50 pg/mL to about 500 pg/mL, between at least about 50 pg/mL to about 400 pg/mL, between at least about 50 pg/mL to about 300 pg/mL, between at least about 50 pg/mL to about 200 pg/mL, between at least about 50 pg/mL to about 100 pg/mL, between at least about 100 pg/mL to about 6100 pg/mL, between at least about 100 pg/mL to about 6000 pg/mL, between at least about 100 pg/mL to about 5500 pg/mL, between at least about 100 pg/mL to about 5000 pg/mL, between at least about 100 pg/mL to about 4500 pg/mL, between at least about 100 pg/mL to about 4000 pg/mL, between at least about 100 pg/mL to about 3500 pg/mL, between at least about 100 pg/mL to about 3000 pg/mL, between at least about 100 pg/mL to about 2500 pg/mL, between at least about 100 pg/mL to about 2000 pg/mL, between at least about 100 pg/mL to about 1500 pg/mL, between at least about 100 pg/mL to about 1000 pg/mL, between at least about 100 pg/mL to about 900 pg/mL, between at least about 100 pg/mL to about 800 pg/mL, between at least about 100 pg/mL to about 700 pg/mL, between at least about 100 pg/mL to about 600 pg/mL, between at least about 100 pg/mL to about 500 pg/mL, between at least about 100 pg/mL to about 400 pg/mL, between at least about 100 pg/mL to about 300 pg/mL, between at least about 100 pg/mL to about 200 pg/mL, between at least about 129 pg/mL to about 6100 pg/mL, between at least about 129 pg/mL to about 6000 pg/mL, between at least about 129 pg/mL to about 5500 pg/mL, between at least about 129 pg/mL to about 5000 pg/mL, between at least about 129 pg/mL to about 4500 pg/mL, between at least about 129 pg/mL to about 4000 pg/mL, between at least about 129 pg/mL to about 3500 pg/mL, between at least about 129 pg/mL to about 3000 pg/mL, between at least about 129 pg/mL to about 2500 pg/mL, between at least about 129 pg/mL to about 2000 pg/mL, between at least about 129 pg/mL to about 1500 pg/mL, between at least about 129 pg/mL to about 1000 pg/mL, between at least about 129 pg/mL to about 900 pg/mL, between at least about 129 pg/mL to about 800 pg/mL, between at least about 129 pg/mL to about 700 pg/mL, between at least about 129 pg/mL to about 600 pg/mL, between at least about 129 pg/mL to about 500 pg/mL, between at least about 129 pg/mL to about 400 pg/mL, between at least about 129 pg/mL to about 300 pg/mL, between at least about 129 pg/mL to about 200 pg/mL, between at least about 200 pg/mL to about 6100 pg/mL, between at least about 200 pg/mL to about 6000 pg/mL, between at least about 200 pg/mL to about 5500 pg/mL, between at least about 200 pg/mL to about 5000 pg/mL, between at least about 200 pg/mL to about 4500 pg/mL, between at least about 200 pg/mL to about 4000 pg/mL, between at least about 200 pg/mL to about 3500 pg/mL, between at least about 200 pg/mL to about 3000 pg/mL, between at least about 200 pg/mL to about 2500 pg/mL, between at least about 200 pg/mL to about 2000 pg/mL, between at least about 200 pg/mL to about 1500 pg/mL, between at least about 200 pg/mL to about 1000 pg/mL, between at least about 200 pg/mL to about 900 pg/mL, between at least about 200 pg/mL to about 800 pg/mL, between at least about 200 pg/mL to about 700 pg/mL, between at least about 200 pg/mL to about 600 pg/mL, between at least about 200 pg/mL to about 500 pg/mL, between at least about 200 pg/mL to about 400 pg/mL, between at least about 200 pg/mL to about 300 pg/mL, between at least about 300 pg/mL to about 6100 pg/mL, between at least about 300 pg/mL to about 6000 pg/mL, between at least about 300 pg/mL to about 5500 pg/mL, between at least about 300 pg/mL to about 5000 pg/mL, between at least about 300 pg/mL to about 4500 pg/mL, between at least about 300 pg/mL to about 4000 pg/mL, between at least about 300 pg/mL to about 3500 pg/mL, between at least about 300 pg/mL to about 3000 pg/mL, between at least about 300 pg/mL to about 2500 pg/mL, between at least about 300 pg/mL to about 2000 pg/mL, between at least about 300 pg/mL to about 1500 pg/mL, between at least about 300 pg/mL to about 1000 pg/mL, between at least about 300 pg/mL to about 900 pg/mL, between at least about 300 pg/mL to about 800 pg/mL, between at least about 300 pg/mL to about 700 pg/mL, between at least about 300 pg/mL to about 600 pg/mL, between at least about 300 pg/mL to about 500 pg/mL, between at least about 300 pg/mL to about 400 pg/mL, between at least about 400 pg/mL to about 6100 pg/mL, between at least about 400 pg/mL to about 6000 pg/mL, between at least about 400 pg/mL to about 5500 pg/mL, between at least about 400 pg/mL to about 5000 pg/mL, between at least about 400 pg/mL to about 4500 pg/mL, between at least about 400 pg/mL to about 4000 pg/mL, between at least about 400 pg/mL to about 3500 pg/mL, between at least about 400 pg/mL to about 3000 pg/mL, between at least about 400 pg/mL to about 2500 pg/mL, between at least about 400 pg/mL to about 2000 pg/mL, between at least about 400 pg/mL to about 1500 pg/mL, between at least about 400 pg/mL to about 1000 pg/mL, between at least about 400 pg/mL to about 900 pg/mL, between at least about 400 pg/mL to about 800 pg/mL, between at least about 400 pg/mL to about 700 pg/mL, between at least about 400 pg/mL to about 600 pg/mL, between at least about 400 pg/mL to about 500 pg/mL, between at least about 500 pg/mL to about 6100 pg/mL, between at least about 500 pg/mL to about 6000 pg/mL, between at least about 500 pg/mL to about 5500 pg/mL, between at least about 500 pg/mL to about 5000 pg/mL, between at least about 500 pg/mL to about 4500 pg/mL, between at least about 500 pg/mL to about 4000 pg/mL, between at least about 500 pg/mL to about 3500 pg/mL, between at least about 500 pg/mL to about 3000 pg/mL, between at least about 500 pg/mL to about 2500 pg/mL, between at least about 500 pg/mL to about 2000 pg/mL, between at least about 500 pg/mL to about 1500 pg/mL, between at least about 500 pg/mL to about 1000 pg/mL, between at least about 500 pg/mL to about 900 pg/mL, between at least about 500 pg/mL to about 800 pg/mL, between at least about 500 pg/mL to about 700 pg/mL, or between at least about 500 pg/mL to about 600 pg/mL. In some embodiments, the absolute amount can be at least about 20 pg/mL, at least about 21 pg/mL, at least about 22 pg/mL, at least about 23 pg/mL, at least about 24 pg/mL, at least about 25 pg/mL, at least about 26 pg/mL, at least about 27 pg/mL, at least about 28 pg/mL, at least about 29 pg/mL, at least about 30 pg/mL, at least about 35 pg/mL, at least about 40 pg/mL, at least about 45 pg/mL, at least about 50 pg/mL, at least about 55 pg/mL, at least about 60 pg/mL, at least about 65 pg/mL, at least about 70 pg/mL, at least about 75 pg/mL, at least about 80 pg/mL, at least about 85 pg/mL, at least about 90 pg/mL, at least about 95 pg/mL, at least about 100 pg/mL, at least about 110 pg/mL, at least about 120 pg/mL, at least about 129 pg/mL, at least about 130 pg/mL, at least about 140 pg/mL, at least about 150 pg/mL, at least about 200 pg/mL, at least about 250 pg/mL, at least about 300 pg/mL, at least about 350 pg/mL, at least about 400 pg/mL, at least about 450 pg/mL, at least about 500 pg/mL, at least about 550 pg/mL, at least about 600 pg/mL, at least about 700 pg/mL, at least about 800 pg/mL, at least about 900 pg/mL, at least about 1000 pg/mL, at least about 1500 pg/mL, at least about 2000 pg/mL, at least about 2500 pg/mL, at least about 2528 pg/mL, at least about 3000 pg/mL, at least about 4000 pg/mL, at least about 5000 pg/mL, at least about 6000 pg/mL, or at least about 6100 pg/mL.

In some embodiments, the sample is taken within 0 to 10 hours after the suspected injury and the absolute amount, such as about 25 pg/mL, is determined by an assay having a sensitivity of at least about 85% and a specificity of at least about 41%. In some embodiments, the sample is taken within 0 to 10 hours after the suspected injury and the absolute amount is about 25 pg/mL. In some embodiments, the sample is taken within 0 to 10 hours after the suspected injury and the absolute amount, such as about 23 pg/mL, is determined by an assay having a sensitivity of at least about 90% and a specificity of at least about 35%. In some embodiments, the sample is taken within 0 to 10 hours after the suspected injury and the absolute amount is about 23 pg/mL.

In some embodiments, a CT scan is performed on the subject when there is a statistically significant increase or decrease from the level of UCH-L1 in the first sample taken at a first time point to the level of UCH-L1 in the second sample taken at a second point. In some embodiments, a CT scan is not performed on the subject when there is no statistically significant increase or decrease from the level of UCH-L1 in the first sample to the level of UCH-L1 in the second sample taken at a second time point. In some embodiments, the statistically significant increase or decrease is more than about 0.1-fold, more than about 0.2-fold, more than about 0.3-fold, more than about 0.4-fold, more than about 0.5-fold, more than about 0.55-fold, more than about 0.6-fold, more than about 0.7-fold, more than about 0.73-fold, more than about 0.8-fold, more than about 0.9-fold, more than about 1-fold, more than 1.5-fold, more than 1.81-fold, more than about 2-fold, more than about 3-fold, more than about 4-fold, more than about 5-fold, more than about 6-fold, more than about 7-fold, more than 8-fold, more than 9-fold, more than 10-fold, more than 11-fold, more than 12-fold, more than 13-fold, more than 14-fold, more than 15-fold, more than 16-fold, more than 17-fold, more than 18-fold, more than 19-fold, or more than 20-fold from the level of UCH-L1 in the first sample taken at a first time point to the level of UCH-L1 in the second sample taken at a second time point. In some embodiments, a statistically significant decrease of more than about 0.1-fold, more than about 0.2-fold, more than about 0.3-fold, more than about 0.4-fold, more than about 0.5-fold, more than about 0.55-fold, more than about 0.6-fold, more than about 0.7-fold, more than about 0.73-fold, more than about 0.8-fold, more than about 0.9-fold, more than about 1-fold, more than 1.5-fold, more than 1.81-fold, more than about 2-fold, more than about 3-fold, more than about 4-fold, more than about 5-fold, more than about 6-fold, more than 7-fold, more than about 8-fold, more than 9-fold, more than 10-fold, more than 11-fold, more than 12-fold, more than 13-fold, more than 14-fold, more than 15-fold, more than 16-fold, more than 17-fold, more than 18-fold, more than 19-fold, or more than 20-fold from the level of UCH-L1 in the first sample taken at a first time point to the level of UCH-L1 in the second sample taken at a second time point indicates that the subject should have a CT scan performed. In some embodiments, a statistically significant increase of more than about 0.1-fold, more than about 0.2-fold, more than about 0.3-fold, more than about 0.4-fold, more than about 0.5-fold, more than about 0.55-fold, more than about 0.6-fold, more than about 0.7-fold, more than about 0.73-fold, more than about 0.8-fold, more than about 0.9-fold, more than about 1-fold, more than about 1.5-fold, more than 1.81-fold, more than about 2-fold, more than about 3-fold, more than about 4-fold, more than about 5-fold, more than about 6-fold, more than about 7-fold, more than about 8-fold, more than 9-fold, more than 10-fold, more than 11-fold, more than 12-fold, more than 13-fold, more than 14-fold, more than 15-fold, more than 16-fold, more than 17-fold, more than 18-fold, more than 19-fold, or more than 20-fold from the level of UCH-L1 in the first sample taken at a first time point to the level of UCH-L1 in the second sample taken at a second time point indicates that the subject should have a CT scan performed.

In some embodiments, the statistically significant increase or decrease is less than about 0.1-fold, less than about 0.2-fold, less than about 0.3-fold, less than about 0.4-fold, less than about 0.5-fold, at least about 0.55-fold, at least about 0.6-fold, at least about 0.7-fold, at least about 0.73-fold, at least about 0.8-fold, at least about 0.9-fold, less than about 1-fold, less than 1.5-fold, less than 1.81-fold, less than about 2-fold, less than about 3-fold, less than about 4-fold, less than about 5-fold, less than about 6-fold, less than about 7-fold, less than 8-fold, less than 9-fold, less than 10-fold, less than 11-fold, less than 12-fold, less than 13-fold, less than 14-fold, less than 15-fold, less than 16-fold, less than 17-fold, less than 18-fold, less than 19-fold, or less than 20-fold from the level of UCH-L1 in the first sample taken at a first time point to the level of UCH-L1 in the second sample taken at a second time point. In some embodiments, a statistically significant decrease of less than about 0.1-fold, less than about 0.2-fold, less than about 0.3-fold, less than about 0.4-fold, less than about 0.5-fold, at least about 0.55-fold, at least about 0.6-fold, at least about 0.7-fold, at least about 0.73-fold, at least about 0.8-fold, at least about 0.9-fold, less than about 1-fold, less than 1.5-fold, less than 1.81-fold, less than about 2-fold, less than about 3-fold, less than about 4-fold, less than about 5-fold, less than about 6-fold, less than about 7-fold, less than 8-fold, less than 9-fold, less than 10-fold, less than 11-fold, less than 12-fold, less than 13-fold, less than 14-fold, less than 15-fold, less than 16-fold, less than 17-fold, less than 18-fold, less than 19-fold, or less than 20-fold from the level of UCH-L1 in the first sample taken at a first time point to the level of UCH-L1 in the second sample taken at a second time point indicates that the subject should have a CT scan performed. In some embodiments, a statistically significant increase of less than about 0.1-fold, less than about 0.2-fold, less than about 0.3-fold, less than about 0.4-fold, less than about 0.5-fold, at least about 0.55-fold, at least about 0.6-fold, at least about 0.7-fold, at least about 0.73-fold, at least about 0.8-fold, at least about 0.9-fold, less than about 1-fold, less than 1.5-fold, less than 1.81-fold, less than about 2-fold, less than about 3-fold, less than about 4-fold, less than about 5-fold, less than about 6-fold, less than about 7-fold, less than 8-fold, less than 9-fold, less than 10-fold, less than 11-fold, less than 12-fold, less than 13-fold, less than 14-fold, less than 15-fold, less than 16-fold, less than 17-fold, less than 18-fold, less than 19-fold, or less than 20-fold from the level of UCH-L1 in the first sample taken at a first time point to the level of UCH-L1 in the second sample taken at a second time point indicates that the subject should have a CT scan performed. In some embodiments, no statistically significant increase or decrease from the level of UCH-L1 in the first sample taken at a first time point to the level of UCH-L1 in the second sample taken at a second time point indicates that the subject does not need a CT scan performed.

In some embodiments, the first time point is about 0 to about 12 hours after the suspected injury and the statistically significant increase or decrease is less than about 2-fold from the first time point to the second time point. In some embodiments, the first time point is about 0 to about 12 hours after the suspected injury and the statistically significant increase or decrease is less than about 1.81-fold from the first time point to the second time point. In some embodiments, the first time point is about 0 to about 12 hours after the suspected injury and the statistically significant increase is more than about 0.50-fold from the second time point to the first time point. In some embodiments, the first time point is about 0 to about 12 hours after the suspected injury and the statistically significant increase is more than about 0.55-fold from the second time point to the first time point.

In some embodiments, the method further includes treating the subject with a traumatic brain injury treatment and/or monitoring the subject, as described below.

The nature of the assay employed in the methods described herein is not critical and the test can be any assay known in the art such as, for example, immunoassays, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in clinical chemistry format such as would be known by one of ordinary skill in the art. Such assays are described in further detail herein in Sections 9-11.

5. METHOD OF PREDICTING IF A HUMAN SUBJECT SUSPECTED OF HAVING A HEAD INJURY WILL HAVE A POSITIVE OR NEGATIVE HEAD CT SCAN

The present disclosure relates, among other methods, to a method of predicting or aiding in the prediction of whether a human subject suspected of having an injury to the head will have a positive or negative head CT scan. As used herein, "prediction of whether to perform a CT scan on a human subject" refers to use of the method, with or without other methods, to predict that the subject is more likely than not to have a positive head CT scan. The method includes: (a) performing an assay on a first sample and optionally a second sample to measure or detect a level of ubiquitin carboxy-terminal hydrolase L1 (UCH-L1) in the sample, wherein the first sample is taken from the subject at a first time point within 24 hours after a suspected injury to the head and the second sample is taken from the subject at a second time point after the first time point, such as about 3 hours to about 6 hours after the first time point; (b) detecting in the first and/or second sample an early biomarker of traumatic brain injury, said early biomarker consisting of ubiquitin carboxy-terminal hydrolase L1 (UCH-L1); and (c) determining whether the subject will have a positive or negative head CT scan based on the UCH-L1 levels. The subject is (i) determined as likely having a positive head CT scan when the level of UCH-L1 in the first and/or second sample is higher than a reference level of UCH-L1 and the subject is determined as likely having a negative head CT scan when the level of UCH-L1 in the first and/or second sample is lower than a reference level of UCH-L1; (ii) determined as likely having a positive head CT scan when there is a statistically significant increase or decrease from the level of UCH-L1 in the first sample to the level of UCH-L1 in the second sample and the subject is determined likely having a negative head CT scan when there is no statistically significant increase or decrease from the level of UCH-L1 in the first sample to the level of UCH-L1 in the second sample; (iii) determined as likely having a positive head CT scan when the level of UCH-L1 decreases or increases by at least an absolute amount from the first sample to the second sample and the subject is determined likely having a negative head CT scan when there is no decrease or increase by at least an absolute amount in the level of UCH-L1 from the first sample to the second sample; or (iv) determined as likely having a positive head CT scan when the level of UCH-L1 in the first sample is higher than a reference level of UCH-L1 or when there is a statistically significant increase or decrease from the level of UCH-L1 in the first sample to the level of UCH-L1 in the second sample and the subject is determined likely having a negative head CT scan when the level of UCH-L1 in the first sample is lower than a reference level of UCH-L1 or when there is no statistically significant increase or decrease from the level of UCH-L1 in the first sample to the level of UCH-L1 in the second sample. The samples can be biological samples.

In some embodiments, the first and/or second sample is taken from the subject between about 2 hours to about 12 hours after the suspected injury. For example, the first and/or second sample is take between about 2 hours to about 12 hours, about 2 hours to about 10 hours, about 2 hours to about 8 hours, about 2 hours to about 6 hours, about 2 hours to about 4 hours, about 4 hours to about 12 hours, about 4 hours to about 10 hours, about 4 hours to about 8 hours, about 4 hours to about 6 hours, about 6 hours to about 12 hours, about 6 hours to about 10 hours, or about 6 hours to about 8 hours after injury to the head. In some embodiments, the first and/or second sample is taken at about 2 hours, about 3 hours, about 4 hours, about 5 hours, about 6 hours, about 7 hours, about 8 hours, about 9 hours, about 10 hours, about 11 hours, or about 12 hours after injury.

In some embodiments, the subject is assessed as having likely having a positive head CT scan when the level of UCH-L1 in the first and/or second sample is greater than or equal to about 100 pg/mL or 300 pg/mL, and the subject is assessed as not having any traumatic brain injury when the level of UCH-L1 in the first and/or second sample is less than about 100 pg/mL or 300 pg/mL. In some embodiments, the subject is determined as likely having a positive head CT scan when the level of UCH-L1 in the first and/or second sample is greater than or equal to about 50 pg/mL, about 100 pg/mL, about 150 pg/mL, about 200 pg/mL, about 250 pg/mL, about 300 pg/mL, about 350 pg/mL, about 400 pg/mL, about 450 pg/mL, or about 500 pg/mL. In some embodiments, the subject is determined likely having a negative head CT scan when the level of UCH-L1 in the first and/or second sample is less than about 50 pg/mL, about 100 pg/mL, about 150 pg/mL, about 200 pg/mL, about 250 pg/mL, about 300 pg/mL, about 350 pg/mL, about 400 pg/mL, about 450 pg/mL, or about 500 pg/mL.

In some embodiments, the reference level can be determined by an assay having a sensitivity of between at least about 80% to about 100% and a specificity of between at least about 30% to about 100%. In some embodiments, the sensitivity is at least about 80.0%, at least about 85.0%, at least about 87.5%, at least about 90.0%, at least about 95.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. In some embodiments, the specificity is at least about 30.0%, at least about 31.0%, at least about 32.0%, at least about 33.0%, at least about 34.0%, at least about 35.0%, at least about 36.0%, at least about 37.0%, at least about 38.0%, at least about 39.0%, at least about 40.0%, at least about 45.0%, at least about 50.0%, at least about 55.0%, at least about 60.0%, at least about 65.0%, at least about 70.0%, at least about 75.0%, at least about 80.0%, at least about 85.0%, at least about 90.0%, at least about 91.0%, at least about 92.0%, at least about 93.0%, at least about 94.0%, at least about 95.0%, at least about 96.0%, at least about 97.0%, at least about 98.0%, at least about 99.0%, at least about 99.1%, at least about 99.2%, at least about 99.3%, at least about 99.4%, at least about 99.5%, at least about 99.6%, at least about 99.7%, at least about 99.8%, at least about 99.9%, or at least about 100.0%. For example, the sensitivity is at least about 99% and the specificity is at least about 75%, the sensitivity is at least about 99% and the specificity is at least about 99%, or the sensitivity is about 100% and the specificity is about 100%

In some embodiments, the reference level can be between at least about 50 pg/mL to about 1000 pg/mL. In some embodiments, the reference level can be between at least about 50 pg/mL to about 1000 pg/mL, between at least about 50 pg/mL to about 900 pg/mL, between at least about 50 pg/mL to about 800 pg/mL, between at least about 50 pg/mL to about 750 pg/mL, between at least about 50 pg/mL to about 700 pg/mL, between at least about 50 pg/mL to about 600 pg/mL, between at least about 50 pg/mL to about 500 pg/mL, between at least about 50 pg/mL to about 400 pg/mL, between at least about 50 pg/mL to about 300 pg/mL, between at least about 50 pg/mL to about 200 pg/mL, between at least about 100 pg/mL to about 1000 pg/mL, between at least about 100 pg/mL to about 900 pg/mL, between at least about 100 pg/mL to about 800 pg/mL, between at least about 100 pg/mL to about 750 pg/mL, between at least about 100 pg/mL to about 700 pg/mL, between at least about 100 pg/mL to about 600 pg/mL, between at least about 100 pg/mL to about 500 pg/mL, between at least about 100 pg/mL to about 400 pg/mL, between at least about 100 pg/mL to about 300 pg/mL, between at least about 100 pg/mL to about 200 pg/mL, between at least about 150 pg/mL to about 1000 pg/mL, between at least about 150 pg/mL to about 900 pg/mL, between at least about 150 pg/mL to about 800 pg/mL, between at least about 150 pg/mL to about 750 pg/mL, between at least about 150 pg/mL to about 700 pg/mL, between at least about 150 pg/mL to about 600 pg/mL, between at least about 150 pg/mL to about 500 pg/mL, between at least about 150 pg/mL to about 400 pg/mL, between at least about 150 pg/mL to about 300 pg/mL, between at least about 150 pg/mL to about 200 pg/mL, between at least about 200 pg/mL to about 1000 pg/mL, between at least about 200 pg/mL to about 900 pg/mL, between at least about 200 pg/mL to about 800 pg/mL, between at least about 200 pg/mL to about 750 pg/mL, between at least about 200 pg/mL to about 700 pg/mL, between at least about 200 pg/mL to about 600 pg/mL, between at least about 200 pg/mL to about 500 pg/mL, between at least about 200 pg/mL to about 400 pg/mL, between at least about 200 pg/mL to about 300 pg/mL, between at least about 300 pg/mL to about 1000 pg/mL, between at least about 300 pg/mL to about 900 pg/mL, between at least about 300 pg/mL to about 800 pg/mL, between at least about 300 pg/mL to about 750 pg/mL, between at least about 300 pg/mL to about 700 pg/mL, between at least about 300 pg/mL to about 600 pg/mL, between at least about 300 pg/mL to about 500 pg/mL, between at least about 300 pg/mL to about 400 pg/mL, between at least about 400 pg/mL to about 1000 pg/mL, between at least about 400 pg/mL to about 900 pg/mL, between at least about 400 pg/mL to about 800 pg/mL, between at least about 400 pg/mL to about 750 pg/mL, between at least about 400 pg/mL to about 700 pg/mL, between at least about 400 pg/mL to about 600 pg/mL, between at least about 400 pg/mL to about 500 pg/mL, between at least about 500 pg/mL to about 1000 pg/mL, between at least about 500 pg/mL to about 900 pg/mL, between at least about 500 pg/mL to about 800 pg/mL, between at least about 500 pg/mL to about 750 pg/mL, between at least about 500 pg/mL to about 700 pg/mL, or between at least about 500 pg/mL to about 600 pg/mL. For example, the reference level can be at least about 50 pg/mL, 55 pg/mL, 60 pg/mL, 65 pg/mL, 70 pg/mL, 75 pg/mL, 80 pg/mL, 85 pg/mL, 90 pg/mL, 95 pg/mL, 96 pg/mL, 97 pg/mL, 98 pg/mL, 98 pg/mL, 100 pg/mL, 150 pg/mL, 200 pg/mL, 250 pg/mL, 300 pg/mL, 350 pg/mL, 370 pg/mL, 400 pg/mL, 450 pg/mL, 500 pg/mL, 509 pg/mL 550 pg/mL, 600 pg/mL, 700 pg/mL, 800 pg/mL, 900 pg/mL, or 1000 pg/mL.

In some embodiments, a first sample is obtained at a first time point within 24 hours of the suspected injury and a second sample is obtained at second time point, or optionally a third time point or fourth time point, after the first time point to determine whether the subject will have a positive or negative head CT scan. In some embodiments, the first time point is about 0 to about 24 hours after the injury or suspected injury to the head. For example, the first time point can be between about 0 to about 24 hours, about 0 to about 20 hours, about 0 to about 18 hours, about 0 to about 16 hours, about 0 to about 14 hours, about 0 to about 12 hours, about 0 to about 10 hours, about 0 to about 8 hours, about 0 to about 6 hours, about 0 to about 4 hours, about 0 to about 2 hours, about 0 to about 1 hours, about 0 to about 1.5 hours, about 0.5 hours to about 24 hours, about 0.5 hours to about 20 hours, about 0.5 hours to about 18 hours, about 0.5 hours to about 16 hours, about 0.5 hours to about 14 hours, about 0.5 hours to about 12 hours, about 0.5 hours to about 10 hours, about 0.5 hours to about 8 hours, about 0.5 hours to about 6 hours, about 0.5 hours to about 4 hours, about 0.5 hours to about 2 hours, about 0.5 hours to about 1 hours, about 0.5 hours to about 1.5 hours, about 1 hour to about 24 hours, about 1 hour to about 20 hours, about 1 hour to about 18 hours, about 1 hour to about 16 hours, about 1 hour to about 14 hours, about 1 hour to about 12 hours, about 1 hour to about 10 hours, about 1 hour to about 8 hours, about 1 hour to about 6 hours, about 1 hour to about 4 hours, about 1 hour to about 2 hours, about 2 hours to about 24 hours, about 2 hours to about 20 hours, about 2 hours to about 18 hours, about 2 hours to about 16 hours, about 2 hours to about 14 hours, about 2 hours to about 12 hours, about 2 hours to about 10 hours, about 2 hours to about 8 hours, about 2 hours to about 6 hours, about 2 hours to about 4 hours, about 3 hours to about 24 hours, about 3 hours to about 20 hours, about 3 hours to about 18 hours, about 3 hours to about 16 hours, about 3 hours to about 14 hours, about 3 hours to about 12 hours, about 3 hours to about 10 hours, about 3 hours to about 8 hours, about 3 hours to about 6 hours, about 3 hours to about 4 hours, about 4 hours to about 24 hours, about 4 hours to about 20 hours, about 4 hours to about 18 hours, about 4 hours to about 16 hours, about 4 hours to about 14 hours, about 4 hours to about 12 hours, about 4 hours to about 10 hours, about 4 hours to about 8 hours, about 4 hours to about 6 hours, about 6 hours to about 24 hours, about 6 hours to about 20 hours, about 6 hours to about 18 hours, about 6 hours to about 16 hours, about 6 hours to about 14 hours, about 6 hours to about 12 hours, about 6 hours to about 10 hours, about 6 hours to about 8 hours, about 12 hours to about 24 hours, about 12 hours to about 20 hours, about 12 hours to about 18 hours, about 12 hours to about 16 hours, about 12 hours to about 14 hours, about 18 hours to about 24 hours, or greater than 24 hours after the suspected injury. For example, the first time point can be between about 0 hour to 6 hours, between about 6 hours to 12 hours, between about 12 hours to 18 hours, or between about 18 hours to 24 hours.

In some embodiments, the second time point, or optionally a third time point or fourth time point, is about 1 hour to about 10 hours after the first time point, such as about 3 hours to about 6 hours after the first time point. In some embodiments, the second time point is about 1 hour, about 2 hours, about 3 hours, about 4 hours, about 5 hours, about 6 hours, about 7 hours, about 8 hours, about 9 hours, or about 10 hours after the first time point.

In some embodiments, the statistically significant increase or decrease is at least about 1-fold, at least about 1.5-fold, at least about 2-fold, at least about 3-fold, at least about 4-fold, at least about 5-fold, at least about 6-fold, at least about 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold from the level of UCH-L1 in the first sample taken at a first time point to the level of UCH-L1 in the second sample taken at a second time point, or optionally a third time point or fourth time point. In some embodiments, a statistically significant decrease of at least about 1-fold, at least about 1.5-fold, at least about 2-fold, at least about 3-fold, at least about 4-fold, at least about 5-fold, at least about 6-fold, at least about 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold from the level of UCH-L1 in the first sample taken at a first time point to the level of UCH-L1 in the second sample taken at a second time point, or optionally a third time point or fourth time point, indicates that the subject will have a positive head CT scan. In some embodiments, a statistically significant increase of at least about 1-fold, at least about 1.5-fold, at least about 2-fold, at least about 3-fold, at least about 4-fold, at least about 5-fold, at least about 6-fold, at least about 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold from the level of UCH-L1 in the first sample taken at a first time point to the level of UCH-L1 in the second sample taken at a second time point, or optionally a third time point or fourth time point, indicates that the subject will have a positive head CT scan. In some embodiments, no statistically significant increase or decrease from the level of UCH-L1 in the first sample taken at a first time point to the level of UCH-L1 in the second sample taken at a second time point, or optionally a third time point or fourth time point, indicates that the subject will have a negative head CT scan.

In some embodiments, the statistically significant increase or decrease is more than about 0.1-fold, more than about 0.2-fold, more than about 0.3-fold, more than about 0.4-fold, more than about 0.5-fold, more than about 0.55-fold, more than about 0.6-fold, more than about 0.7-fold, more than about 0.73-fold, more than about 0.8-fold, more than about 0.9-fold, more than about 1-fold, more than 1.5-fold, more than 1.81-fold, more than about 2-fold, more than about 3-fold, more than about 4-fold, more than about 5-fold, more than about 6-fold, more than about 7-fold, more than 8-fold, more than 9-fold, more than 10-fold, more than 11-fold, more than 12-fold, more than 13-fold, more than 14-fold, more than 15-fold, more than 16-fold, more than 17-fold, more than 18-fold, more than 19-fold, or more than 20-fold from the level of UCH-L1 in the second sample taken at a second time point to the level of UCH-L1 in the first sample taken at a first time point, or optionally a third time point or fourth time point. In some embodiments, a statistically significant decrease of more than about 0.1-fold, more than about 0.2-fold, more than about 0.3-fold, more than about 0.4-fold, more than about 0.5-fold, more than about 0.55-fold, more than about 0.6-fold, more than about 0.7-fold, more than about 0.73-fold, more than about 0.8-fold, more than about 0.9-fold, more than about 1-fold, more than 1.5-fold, more than 1.81-fold, more than about 2-fold, more than about 3-fold, more than about 4-fold, more than about 5-fold, more than about 6-fold, more than about 7-fold, more than 8-fold, more than 9-fold, more than 10-fold, more than 11-fold, more than 12-fold, more than 13-fold, more than 14-fold, more than 15-fold, more than 16-fold, more than 17-fold, more than 18-fold, more than 19-fold, or more than 20-fold from the level of UCH-L1 in the second sample taken at a second time point to the level of UCH-L1 in the first sample taken at a first time point, or optionally a third time point or fourth time point, indicates that the subject will likely have a positive head CT scan. In some embodiments, a statistically significant increase of more than about 0.1-fold, more than about 0.2-fold, more than about 0.3-fold, more than about 0.4-fold, more than about 0.5-fold, more than about 0.55-fold, more than about 0.6-fold, more than about 0.7-fold, more than about 0.73-fold, more than about 0.8-fold, more than about 0.9-fold, more than about 1-fold, more than 1.5-fold, more than 1.81-fold, more than about 2-fold, more than about 3-fold, more than about 4-fold, more than about 5-fold, more than about 6-fold, more than about 7-fold, more than 8-fold, more than 9-fold, more than 10-fold, more than 11-fold, more than 12-fold, more than 13-fold, more than 14-fold, more than 15-fold, more than 16-fold, more than 17-fold, more than 18-fold, more than 19-fold, or more than 20-fold from the level of UCH-L1 in the second sample taken at a second time point to the level of UCH-L1 in the first sample taken at a first time point, or optionally a third time point or fourth time point, indicates that the subject will likely have a positive head CT scan. In some embodiments, no statistically significant increase or decrease from the level of UCH-L1 in the second sample taken at a second time point to the level of UCH-L1 in the first sample taken at a first time point, or optionally a third time point or fourth time point, indicates that the subject will likely have a negative head CT scan.

In some embodiments, the statistically significant increase or decrease is less than about 0.1-fold, less than about 0.2-fold, less than about 0.3-fold, less than about 0.4-fold, less than about 0.5-fold, at least about 0.55-fold, at least about 0.6-fold, at least about 0.7-fold, at least about 0.73-fold, at least about 0.8-fold, at least about 0.9-fold, less than about 1-fold, less than 1.5-fold, less than 1.81-fold, less than about 2-fold, less than about 3-fold, less than about 4-fold, less than about 5-fold, less than about 6-fold, less than about 7-fold, less than 8-fold, less than 9-fold, less than 10-fold, less than 11-fold, less than 12-fold, less than 13-fold, less than 14-fold, less than 15-fold, less than 16-fold, less than 17-fold, less than 18-fold, less than 19-fold, or less than 20-fold from the level of UCH-L1 in the first sample taken at a first time point to the level of UCH-L1 in the second sample taken at a second time point. In some embodiments, a statistically significant decrease of less than about 0.1-fold, less than about 0.2-fold, less than about 0.3-fold, less than about 0.4-fold, less than about 0.5-fold, at least about 0.55-fold, at least about 0.6-fold, at least about 0.7-fold, at least about 0.73-fold, at least about 0.8-fold, at least about 0.9-fold, less than about 1-fold, less than 1.5-fold, less than 1.81-fold, less than about 2-fold, less than about 3-fold, less than about 4-fold, less than about 5-fold, less than about 6-fold, less than about 7-fold, less than about 8-fold, less than 9-fold, less than 10-fold, less than 11-fold, less than 12-fold, less than 13-fold, less than 14-fold, less than 15-fold, less than 16-fold, less than 17-fold, less than 18-fold, less than 19-fold, or less than 20-fold from the level of UCH-L1 in the first sample taken at a first time point to the level of UCH-L1 in the second sample taken at a second time point indicates that the subject will likely have a positive CT scan. In some embodiments, a statistically significant increase of less than about 0.1-fold, less than about 0.2-fold, less than about 0.3-fold, less than about 0.4-fold, less than about 0.5-fold, at least about 0.55-fold, at least about 0.6-fold, at least about 0.7-fold, at least about 0.73-fold, at least about 0.8-fold, at least about 0.9-fold, less than about 1-fold, less than about 1.5-fold, less than 1.81-fold, less than about 2-fold, less than about 3-fold, less than about 4-fold, less than about 5-fold, less than about 6-fold, less than about 7-fold, less than 8-fold, less than 9-fold, less than 10-fold, less than 11-fold, less than 12-fold, less than 13-fold, less than 14-fold, less than 15-fold, less than 16-fold, less than 17-fold, less than 18-fold, less than 19-fold, or less than 20-fold from the level of UCH-L1 in the first sample taken at a first time point to the level of UCH-L1 in the second sample taken at a second time point indicates that the subject will likely have a positive head CT scan. In some embodiments, no statistically significant increase or decrease from the level of UCH-L1 in the first sample taken at a first time point to the level of UCH-L1 in the second sample taken at a second time point indicates that the subject will likely have a negative head CT scan.

In some embodiments, the first time point is about 0 to about 12 hours after the suspected injury and the statistically significant increase or decrease is less than about 2-fold from the first time point to the second time point. In some embodiments, the first time point is about 0 to about 12 hours after the suspected injury and the statistically significant increase or decrease is less than about 1.81-fold from the first time point to the second time point. In some embodiments, the first time point is about 0 to about 12 hours after the suspected injury and the statistically significant increase is more than about 0.50-fold from the second time point to the first time point. In some embodiments, the first time point is about 0 to about 12 hours after the suspected injury and the statistically significant increase is more than about 0.55-fold from the second time point to the first time point.

In some embodiments, the subject is assessed as likely having a positive head CT scan when the level of UCH-L1 decreases or increases by at least an absolute amount from the first sample to the second sample. In some embodiments, the absolute amount is between at least about 20 pg/mL to about 6100 pg/mL. In some embodiments, the absolute amount can be between at least about 20 pg/mL to about 6100 pg/mL, between at least about 20 pg/mL to about 6000 pg/mL, between at least about 20 pg/mL to about 5500 pg/mL, between at least about 20 pg/mL to about 5000 pg/mL, between at least about 20 pg/mL to about 4500 pg/mL, between at least about 20 pg/mL to about 4000 pg/mL, between at least about 20 pg/mL to about 3500 pg/mL, between at least about 20 pg/mL to about 3000 pg/mL, between at least about 20 pg/mL to about 2500 pg/mL, between at least about 20 pg/mL to about 2000 pg/mL, between at least about 20 pg/mL to about 1500 pg/mL, between at least about 20 pg/mL to about 1000 pg/mL, between at least about 20 pg/mL to about 900 pg/mL, between at least about 20 pg/mL to about 800 pg/mL, between at least about 20 pg/mL to about 700 pg/mL, between at least about 20 pg/mL to about 600 pg/mL, between at least about 20 pg/mL to about 500 pg/mL, between at least about 20 pg/mL to about 400 pg/mL, between at least about 20 pg/mL to about 300 pg/mL, between at least about 20 pg/mL to about 200 pg/mL, between at least about 20 pg/mL to about 100 pg/mL, between at least about 20 pg/mL to about 50 pg/mL, between at least about 25 pg/mL to about 6100 pg/mL, between at least about 25 pg/mL to about 6000 pg/mL, between at least about 25 pg/mL to about 5500 pg/mL, between at least about 25 pg/mL to about 5000 pg/mL, between at least about 25 pg/mL to about 4500 pg/mL, between at least about 25 pg/mL to about 4000 pg/mL, between at least about 25 pg/mL to about 3500 pg/mL, between at least about 25 pg/mL to about 3000 pg/mL, between at least about 25 pg/mL to about 2500 pg/mL, between at least about 25 pg/mL to about 2000 pg/mL, between at least about 25 pg/mL to about 1500 pg/mL, between at least about 25 pg/mL to about 1000 pg/mL, between at least about 25 pg/mL to about 900 pg/mL, between at least about 25 pg/mL to about 800 pg/mL, between at least about 25 pg/mL to about 700 pg/mL, between at least about 25 pg/mL to about 600 pg/mL, between at least about 25 pg/mL to about 500 pg/mL, between at least about 25 pg/mL to about 400 pg/mL, between at least about 25 pg/mL to about 300 pg/mL, between at least about 25 pg/mL to about 200 pg/mL, between at least about 25 pg/mL to about 100 pg/mL, between at least about 25 pg/mL to about 50 pg/mL, between at least about 50 pg/mL to about 6100 pg/mL, between at least about 50 pg/mL to about 6000 pg/mL, between at least about 50 pg/mL to about 5500 pg/mL, between at least about 50 pg/mL to about 5000 pg/mL, between at least about 50 pg/mL to about 4500 pg/mL, between at least about 50 pg/mL to about 4000 pg/mL, between at least about 50 pg/mL to about 3500 pg/mL, between at least about 50 pg/mL to about 3000 pg/mL, between at least about 50 pg/mL to about 2500 pg/mL, between at least about 50 pg/mL to about 2000 pg/mL, between at least about 50 pg/mL to about 1500 pg/mL, between at least about 50 pg/mL to about 1000 pg/mL, between at least about 50 pg/mL to about 900 pg/mL, between at least about 50 pg/mL to about 800 pg/mL, between at least about 50 pg/mL to about 700 pg/mL, between at least about 50 pg/mL to about 600 pg/mL, between at least about 50 pg/mL to about 500 pg/mL, between at least about 50 pg/mL to about 400 pg/mL, between at least about 50 pg/mL to about 300 pg/mL, between at least about 50 pg/mL to about 200 pg/mL, between at least about 50 pg/mL to about 100 pg/mL, between at least about 100 pg/mL to about 6100 pg/mL, between at least about 100 pg/mL to about 6000 pg/mL, between at least about 100 pg/mL to about 5500 pg/mL, between at least about 100 pg/mL to about 5000 pg/mL, between at least about 100 pg/mL to about 4500 pg/mL, between at least about 100 pg/mL to about 4000 pg/mL, between at least about 100 pg/mL to about 3500 pg/mL, between at least about 100 pg/mL to about 3000 pg/mL, between at least about 100 pg/mL to about 2500 pg/mL, between at least about 100 pg/mL to about 2000 pg/mL, between at least about 100 pg/mL to about 1500 pg/mL, between at least about 100 pg/mL to about 1000 pg/mL, between at least about 100 pg/mL to about 900 pg/mL, between at least about 100 pg/mL to about 800 pg/mL, between at least about 100 pg/mL to about 700 pg/mL, between at least about 100 pg/mL to about 600 pg/mL, between at least about 100 pg/mL to about 500 pg/mL, between at least about 100 pg/mL to about 400 pg/mL, between at least about 100 pg/mL to about 300 pg/mL, between at least about 100 pg/mL to about 200 pg/mL, between at least about 129 pg/mL to about 6100 pg/mL, between at least about 129 pg/mL to about 6000 pg/mL, between at least about 129 pg/mL to about 5500 pg/mL, between at least about 129 pg/mL to about 5000 pg/mL, between at least about 129 pg/mL to about 4500 pg/mL, between at least about 129 pg/mL to about 4000 pg/mL, between at least about 129 pg/mL to about 3500 pg/mL, between at least about 129 pg/mL to about 3000 pg/mL, between at least about 129 pg/mL to about 2500 pg/mL, between at least about 129 pg/mL to about 2000 pg/mL, between at least about 129 pg/mL to about 1500 pg/mL, between at least about 129 pg/mL to about 1000 pg/mL, between at least about 129 pg/mL to about 900 pg/mL, between at least about 129 pg/mL to about 800 pg/mL, between at least about 129 pg/mL to about 700 pg/mL, between at least about 129 pg/mL to about 600 pg/mL, between at least about 129 pg/mL to about 500 pg/mL, between at least about 129 pg/mL to about 400 pg/mL, between at least about 129 pg/mL to about 300 pg/mL, between at least about 129 pg/mL to about 200 pg/mL, between at least about 200 pg/mL to about 6100 pg/mL, between at least about 200 pg/mL to about 6000 pg/mL, between at least about 200 pg/mL to about 5500 pg/mL, between at least about 200 pg/mL to about 5000 pg/mL, between at least about 200 pg/mL to about 4500 pg/mL, between at least about 200 pg/mL to about 4000 pg/mL, between at least about 200 pg/mL to about 3500 pg/mL, between at least about 200 pg/mL to about 3000 pg/mL, between at least about 200 pg/mL to about 2500 pg/mL, between at least about 200 pg/mL to about 2000 pg/mL, between at least about 200 pg/mL to about 1500 pg/mL, between at least about 200 pg/mL to about 1000 pg/mL, between at least about 200 pg/mL to about 900 pg/mL, between at least about 200 pg/mL to about 800 pg/mL, between at least about 200 pg/mL to about 700 pg/mL, between at least about 200 pg/mL to about 600 pg/mL, between at least about 200 pg/mL to about 500 pg/mL, between at least about 200 pg/mL to about 400 pg/mL, between at least about 200 pg/mL to about 300 pg/mL, between at least about 300 pg/mL to about 6100 pg/mL, between at least about 300 pg/mL to about 6000 pg/mL, between at least about 300 pg/mL to about 5500 pg/mL, between at least about 300 pg/mL to about 5000 pg/mL, between at least about 300 pg/mL to about 4500 pg/mL, between at least about 300 pg/mL to about 4000 pg/mL, between at least about 300 pg/mL to about 3500 pg/mL, between at least about 300 pg/mL to about 3000 pg/mL, between at least about 300 pg/mL to about 2500 pg/mL, between at least about 300 pg/mL to about 2000 pg/mL, between at least about 300 pg/mL to about 1500 pg/mL, between at least about 300 pg/mL to about 1000 pg/mL, between at least about 300 pg/mL to about 900 pg/mL, between at least about 300 pg/mL to about 800 pg/mL, between at least about 300 pg/mL to about 700 pg/mL, between at least about 300 pg/mL to about 600 pg/mL, between at least about 300 pg/mL to about 500 pg/mL, between at least about 300 pg/mL to about 400 pg/mL, between at least about 400 pg/mL to about 6100 pg/mL, between at least about 400 pg/mL to about 6000 pg/mL, between at least about 400 pg/mL to about 5500 pg/mL, between at least about 400 pg/mL to about 5000 pg/mL, between at least about 400 pg/mL to about 4500 pg/mL, between at least about 400 pg/mL to about 4000 pg/mL, between at least about 400 pg/mL to about 3500 pg/mL, between at least about 400 pg/mL to about 3000 pg/mL, between at least about 400 pg/mL to about 2500 pg/mL, between at least about 400 pg/mL to about 2000 pg/mL, between at least about 400 pg/mL to about 1500 pg/mL, between at least about 400 pg/mL to about 1000 pg/mL, between at least about 400 pg/mL to about 900 pg/mL, between at least about 400 pg/mL to about 800 pg/mL, between at least about 400 pg/mL to about 700 pg/mL, between at least about 400 pg/mL to about 600 pg/mL, between at least about 400 pg/mL to about 500 pg/mL, between at least about 500 pg/mL to about 6100 pg/mL, between at least about 500 pg/mL to about 6000 pg/mL, between at least about 500 pg/mL to about 5500 pg/mL, between at least about 500 pg/mL to about 5000 pg/mL, between at least about 500 pg/mL to about 4500 pg/mL, between at least about 500 pg/mL to about 4000 pg/mL, between at least about 500 pg/mL to about 3500 pg/mL, between at least about 500 pg/mL to about 3000 pg/mL, between at least about 500 pg/mL to about 2500 pg/mL, between at least about 500 pg/mL to about 2000 pg/mL, between at least about 500 pg/mL to about 1500 pg/mL, between at least about 500 pg/mL to about 1000 pg/mL, between at least about 500 pg/mL to about 900 pg/mL, between at least about 500 pg/mL to about 800 pg/mL, between at least about 500 pg/mL to about 700 pg/mL, or between at least about 500 pg/mL to about 600 pg/mL. In some embodiments, the absolute amount can be at least about 20 pg/mL, at least about 21 pg/mL, at least about 22 pg/mL, at least about 23 pg/mL, at least about 24 pg/mL, at least about 25 pg/mL, at least about 26 pg/mL, at least about 27 pg/mL, at least about 28 pg/mL, at least about 29 pg/mL, at least about 30 pg/mL, at least about 35 pg/mL, at least about 40 pg/mL, at least about 45 pg/mL, at least about 50 pg/mL, at least about 55 pg/mL, at least about 60 pg/mL, at least about 65 pg/mL, at least about 70 pg/mL, at least about 75 pg/mL, at least about 80 pg/mL, at least about 85 pg/mL, at least about 90 pg/mL, at least about 95 pg/mL, at least about 100 pg/mL, at least about 110 pg/mL, at least about 120 pg/mL, at least about 129 pg/mL, at least about 130 pg/mL, at least about 140 pg/mL, at least about 150 pg/mL, at least about 200 pg/mL, at least about 250 pg/mL, at least about 300 pg/mL, at least about 350 pg/mL, at least about 400 pg/mL, at least about 450 pg/mL, at least about 500 pg/mL, at least about 550 pg/mL, at least about 600 pg/mL, at least about 700 pg/mL, at least about 800 pg/mL, at least about 900 pg/mL, at least about 1000 pg/mL, at least about 1500 pg/mL, at least about 2000 pg/mL, at least about 2500 pg/mL, at least about 2528 pg/mL, at least about 3000 pg/mL, at least about 4000 pg/mL, at least about 5000 pg/mL, at least about 6000 pg/mL, or at least about 6100 pg/mL.

In some embodiments, the sample is taken within 0 to 10 hours after the suspected injury and the absolute amount, such as about 25 pg/mL, is determined by an assay having a sensitivity of at least about 85% and a specificity of at least about 41%. In some embodiments, the sample is taken within 0 to 10 hours after the suspected injury and the absolute amount is about 25 pg/mL. In some embodiments, the sample is taken within 0 to 10 hours after the suspected injury and the absolute amount, such as about 23 pg/mL, is determined by an assay having a sensitivity of at least about 90% and a specificity of at least about 35%. In some embodiments, the sample is taken within 0 to 10 hours after the suspected injury and the absolute amount is about 23 pg/mL.

The nature of the assay employed in the methods described herein is not critical and the test can be any assay known in the art such as, for example, immunoassays, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in clinical chemistry format such as would be known by one of ordinary skill in the art. Such assays are described in further detail herein in Sections 9-11.

6. METHODS OF AIDING IN THE EARLY DETECTION OF MILD OR MODERATE TO SEVERE TRAUMATIC BRAIN INJURY IN A HUMAN SUBJECT WHO HAS SUSTAINED AN INJURY TO THE HEAD

The present disclosure relates to a method of aiding in the early detection of traumatic brain injury in a human subject who has sustained or may have sustained an injury to the head. The method can aid in early detection of traumatic brain injury in a human subject who has sustained or may have sustained an injury to the head (e.g., determining whether the subject has traumatic brain injury). As used herein, "determining whether the subject has traumatic brain injury" refers to use of the method (e.g., with other information such as clinical assessment data) to determine that the subject is more likely than not to have TBI. The method includes performing an assay on samples from the human subject to measure or detect a level of ubiquitin carboxy-terminal hydrolase L1 (UCH-L1) in a first sample and a second sample. The first sample is taken from the human subject within 24 hours after an injury to the head, and the second sample is taken from the human subject after about 3 hours to about 6 hours after the first sample is taken. A decrease or decline in the level of UCH-L1 from the first sample to the second sample is determined and the subject is assessed as having mild or moderate to severe traumatic brain injury if there is a statistically significant decrease in the level of UCH-L1 from the first sample to the level of UCH-L1 in the second sample. The samples can be biolocal samples.

In some embodiments, the statistically significant decrease comprises a decrease or decline in UCH-L1 levels of at least 5% lower than the UCH-L1 levels in the first sample. In some embodiments, the statistically significant decrease comprises a decrease or decline in UCH-L1 levels, wherein the UCH-L1 level in the second sample is about 5% to about 1000% lower than the UCH-L1 level in the first sample. For example, the UCH-L1 levels may be at least about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 60%, about 70%, about 80%, about 90%, about 100%, about 200%, about 300%, about 400%, about 500%, about 600%, about 700%, about 800%, about 900%, or about 1000% lower than the UCH-L1 levels in the first sample. In some embodiments, the UCH-L1 levels may be at least about 1-fold, at least about 1.5-fold, at least about 2-fold, at least about 3-fold, at least about 4-fold, at least about 5-fold, at least about 6-fold, at least about 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold or at least 20-fold lower than the UCH-L1 levels in the first sample.

In some embodiments, the statistically significant decrease comprises a decrease or decline in UCH-L1 levels, wherein the level of UCH-L1 in the second sample is from at least about 20 pg/mL to at least about 6100 pg/mL lower than the level of UCH-L1 in the first sample.

Optionally, the method further comprises comparing the concentration or amount of UCH-L1 as determined in step (b), for example, with a reference level. Further, optionally the method comprises treating the subject with one or more pharmaceutical compositions for a period of time if the comparison shows that the concentration or amount of UCH-L1 as determined in step (b), for example, is unfavorably altered with respect to the reference level.

In particular, with respect to a reference level as employed for monitoring disease progression and/or treatment or for determining the risk of a subject of developing mild or moderate to severe traumatic brain injury, the amount or concentration of UCH-L1 or UCH-L1 fragment may be "unchanged," "favorable" (or "favorably altered"), or "unfavorable" (or "unfavorably altered"). "Elevated" or "increased" refers to an amount or a concentration in a test sample that is higher or greater than a typical or normal level or range (e.g., reference level), or is higher or greater than another reference level or range (e.g., earlier or baseline sample). The term "lowered" or "reduced" refers to an amount or a concentration in a test sample that is lower or less than a typical or normal level or range (e.g., reference level), or is lower or less than another reference level or range (e.g., earlier or baseline sample). The term "altered" refers to an amount or a concentration in a sample that is altered (increased or decreased) over a typical or normal level or range (e.g., reference level), or over another reference level or range (e.g., earlier or baseline sample).

The typical or normal level or range for UCH-L1 is defined in accordance with standard practice. A so-called altered level or alteration can be considered to have occurred when there is any net change as compared to the typical or normal level or range, or reference level or range that cannot be explained by experimental error or sample variation. Thus, the level measured in a particular sample will be compared with the level or range of levels determined in similar samples from a so-called normal subject. In this context, a "normal subject" is an individual with no detectable disease or disorder, and a "normal" (sometimes termed "control") patient or population is/are one(s) that exhibit(s) no detectable disease or disorder, respectively, for example. An "apparently normal subject" is a normal subject (namely, an individual with no detectable disease or disorder) in which UCH-L1 has not been or is being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level. Thus, inter alia, the disclosure provides a method of screening for a subject having, or at risk of having, mild or moderate to severe traumatic brain injury.

Generally, a reference level can also be employed as a benchmark against which to assess results obtained upon assaying a test sample for UCH-L1. Generally, in making such a comparison, the reference level is obtained by running a particular assay a sufficient number of times and under appropriate conditions such that a linkage or association of analyte presence, amount or concentration with a particular stage or endpoint of TBI or with particular indicia can be made. Typically, the reference level is obtained with assays of reference subjects (or populations of subjects). The UCH-L1 measured can include UCH-L1 fragments thereof, degradation products thereof, and/or enzymatic cleavage products thereof.

The reference level in this method can be the level of UCH-L1 in a patient having mild or moderate to severe traumatic brain injury. In some embodiments, levels higher than or equal to 5 pg/mL, 10 pg/mL, 20 pg/mL, 30 pg/mL, 40 pg/mL, 50 pg/mL, 60 pg/mL, 70 pg/mL, 80 pg/mL, 90 pg/mL, 100 pg/mL, 500 pg/mL, 1000 pg/mL, 5000 pg/mL, 10000 pg/mL, or 50000 pg/mL in serum of UCH-L1 identify the subject as having mild or moderate to severe traumatic brain injury. Optionally, in some cases, levels higher than or equal to 100000 pg/mL, 500000 pg/mL, 1000000 pg/mL, 150000 pg/mL, 200000 pg/mL, or 500000 pg/mL in serum of UCH-L1 identify the subject as having mild or moderate to severe traumatic brain injury.

In some embodiments, the method further includes treating the human subject who was determined to have a CT scan with a traumatic brain injury treatment, as described below. In some embodiments, the method further includes monitoring, as described below, the human subject who was determined to have a CT scan.

The nature of the assay employed in the methods described herein is not critical and the test can be any assay known in the art such as, for example, immunoassays, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in clinical chemistry format such as would be known by one of ordinary skill in the art. Such assays are described in further detail herein in Sections 9-11.

7. COMBINATIONS OF UCH-L1 WITH OTHER BIOMARKERS

In some embodiments, the method further includes performing an assay on the samples to measure or detect a level of one or more other biomarkers. The assay may be an assay to measure or the levels of the one or more other biomarkers in a sample, such as immunoassay, mass spectrometry, etc. Also, the assay can be employed in clinical chemistry format such as would be known by one of ordinary skill in the art. In some embodiments, the assay includes: measuring or detecting a level of one or more other biomarkers in the first sample and the second sample, determining an increase and/or decrease or rise or decline in the level of the one or more other biomarkers from the first sample to the second sample, and assessing the human subject as having mild or moderate to severe traumatic brain injury if there is a statistically significant increase or decrease in the level of the one or more other biomarkers from the first sample to the level of the one or more other biomarkers in the second sample.

The present invention contemplates that the combination of UCH-L1 with one or more biomarkers or immunoassays specific for disease may provide a greater discrimination between healthy controls and individuals with disease compared to measuring UCH-L1 alone. For example, measuring a panel of UCH-L1 and additional traumatic brain injury biomarkers may provide a greater discrimination between healthy controls and individuals with disease compared to a panel of UCH-L1 alone. The combination of UCH-L1 with at least one or more biomarkers may provide greater discrimination between healthy controls and individuals who have mild or moderate to severe traumatic brain injury. Examples of the one or more biomarkers include Glial fibrillary acidic protein (GFAP), S100 calcium-binding protein B (S100β), neuron-specific enolase (NSE), crystallin B chain (CRYAB), brain lipid binding protein (BLBP), aldolase C (ALDOC), astrocytic phosphoprotein 15 (PEA15), glutamine synthetase (GS), Apo lipoprotein 1, Tau, C-reactive protein (CRP), free brain-derived neurotrophic factor (BDNF), p-Tau, total BDNF, troponin I (TnI), and a combination thereof. In some embodiments, the one or more other biomarkers is S100β, CRP, Apo lipoprotein 1, or crystallin B chain (CRYAB).

8. TREATMENT AND MONITORING OF SUBJECTS SUFFERING FROM TRAUMATIC BRAIN INJURY

The subject identified or assessed in the methods described above as having traumatic brain injury, such as mild traumatic brain injury or moderate to severe traumatic brain injury, may be treated or monitored. In some embodiments, the method further includes treating a human subject assessed as having traumatic brain injury with a traumatic brain injury treatment, such as any treatments known in the art. For example, treatment of traumatic brain injury can take a variety of forms depending on the severity of the injury to the head. For example, for subjects suffering from mild TBI, the treatment may include one or more of rest, abstaining for physical activities, such as sports, avoiding light or wearing sunglasses when out in the light, medication for relief of a headache or migraine, anti-nausea medication, etc. Treatment for patients suffering from severe TBI might include administration of one or more appropriate medications (such as, for example, diuretics, anti-convulsant medications, medications to sedate and put an individual in a drug-induced coma, or other pharmaceutical or biopharmaceutical medications (either known or developed in the future for treatment of TBI), one or more surgical procedures (such as, for example, removal of a hematoma, repairing a skull fracture, decompressive craniectomy, etc.) and one or more therapies (such as, for example one or more rehabilitation, cognitive behavioral therapy, anger management, counseling psychology, etc.). In some embodiments, the method further includes monitoring a human subject assessed as having traumatic brain injury (e.g., mild or moderate to severe traumatic). In some embodiments, a subject identified as having traumatic brain injury, such as mild traumatic brain injury or severe traumatic brain injury, may be monitored with CT scan or MM.

9. METHODS FOR MEASURING THE LEVEL OF UCH-L1

In the methods described above, UCH-L1 levels can be measured by any means, such as antibody dependent methods, such as immunoassays, protein immunoprecipitation, immunoelectrophoresis, chemical analysis, SDS-PAGE and Western blot analysis, or protein immunostaining, electrophoresis analysis, a protein assay, a competitive binding assay, a functional protein assay, or chromatography or spectrometry methods, such as high-performance liquid chromatography (HPLC) or liquid chromatography-mass spectrometry (LC/MS). Also, the assay can be employed in clinical chemistry format such as would be known by one of ordinary skill in the art.

In some embodiments, measuring the level of UCH-L1 includes contacting the sample with a first specific binding member and second specific binding member. In some embodiments the first specific binding member is a capture antibody and the second specific binding member is a detection antibody. In some embodiments, measuring the level of UCH-L1 includes contacting the sample, either simultaneously or sequentially, in any order: (1) a capture antibody, which binds to an epitope on UCH-L1 or UCH-L1 fragment to form a capture antibody-UCH-L1 antigen complex, and (2) a detection antibody which includes a detectable label and binds to an epitope on UCH-L1 that is not bound by the capture antibody, to form a UCH-L1 antigen-detection antibody complex, such that a capture antibody-UCH-L1 antigen-detection antibody complex is formed, and measuring the amount or concentration of UCH-L1 in the sample based on the signal generated by the detectable label in the capture antibody-UCH-L1 antigen-detection antibody complex.

In some embodiments, the first specific binding member is immobilized on a solid support. In some embodiments, the second specific binding member is immobilized on a solid support. In some embodiments, the first specific binding member is a UCH-L1 antibody as described below.

In some embodiments, the sample is diluted or undiluted. The sample can be from about 1 to about 25 microliters, about 1 to about 24 microliters, about 1 to about 23 microliters, about 1 to about 22 microliters, about 1 to about 21 microliters, about 1 to about 20 microliters, about 1 to about 18 microliters, about 1 to about 17 microliters, about 1 to about 16 microliters, about 15 microliters or about 1 microliter, about 2 microliters, about 3 microliters, about 4 microliters, about 5 microliters, about 6 microliters, about 7 microliters, about 8 microliters, about 9 microliters, about 10 microliters, about 11 microliters, about 12 microliters, about 13 microliters, about 14 microliters, about 15 microliters, about 16 microliters, about 17 microliters, about 18 microliters, about 19 microliters, about 20 microliters, about 21 microliters, about 22 microliters, about 23 microliters, about 24 microliters or about 25 microliters. In some embodiments, the sample is from about 1 to about 150 microliters or less or from about 1 to about 25 microliters or less.

Some instruments (such as, for example the Abbott Laboratories instrument ARCHITECT®, and other core laboratory instruments) other than a point-of-care device may be capable of measuring levels of UCH-L1 in a sample higher or greater than 25,000 pg/mL.

Other methods of detection include the use of or can be adapted for use on a nanopore device or nanowell device. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety

10. UCH-L1 ANTIBODIES

The methods described herein may use an isolated antibody that specifically binds to ubiquitin carboxy-terminal hydrolase L1 ("UCH-L1") (or fragments thereof), referred to as "UCH-L1 antibody." The UCH-L1 antibodies can be used to assess the UCH-L1 status as a measure of traumatic brain injury, detect the presence of UCH-L1 in a sample, quantify the amount of UCH-L1 present in a sample, or detect the presence of and quantify the amount of UCH-L1 in a sample. As used throughout the present disclosure, the terms "measuring," "detecting," and "quantifying," and any derivatives thereof, can be used interchangeably to describe the methods disclosed herein for assessing levels UCH-L1 levels in a sample.

a. Ubiquitin Carboxy-Terminal Hydrolase L1 (UCH-L1)

Ubiquitin carboxy-terminal hydrolase L1 ("UCH-L1"), which is also known as "ubiquitin C-terminal hydrolase," is a deubiquitinating enzyme. UCH-L1 is a member of a gene family whose products hydrolyze small C-terminal adducts of ubiquitin to generate the ubiquitin monomer. Expression of UCH-L1 is highly specific to neurons and to cells of the diffuse neuroendocrine system and their tumors. It is abundantly present in all neurons (accounts for 1-2% of total brain protein), expressed specifically in neurons and testis/ovary. The catalytic triad of UCH-L1 contains a cysteine at position 90, an aspartate at position 176, and a histidine at position 161 that are responsible for its hydrolase activity.

Human UCH-L1 may have the following amino acid sequence:

```
(SEQ ID NO: 1)
MQLKPMEINPEMLNKVLSRLGVAGQWRFVDVLGLEEESLGSVPAPACALL

LLFPLTAQHENFRKKQIEELKGQEVSPKVYFMKQTIGNSCGTIGLIHAVA

NNQDKLGFEDGSVLKQFLSETEKMSPEDRAKCFEKNEAIQAAHDAVAQEG

QCRVDDKVNFHFILFNNVDGHLYELDGRMPFPVNHGASSEDTLLKDAAKV

CREFTEREQGEVRFSAVALCKAA.
```

The human UCH-L1 may be a fragment or variant of SEQ ID NO: 1. The fragment of UCH-L1 may be between 5 and 225 amino acids, between 10 and 225 amino acids, between 50 and 225 amino acids, between 60 and 225 amino acids, between 65 and 225 amino acids, between 100 and 225 amino acids, between 150 and 225 amino acids, between 100 and 175 amino acids, or between 175 and 225 amino acids in length. The fragment may comprise a contiguous number of amino acids from SEQ ID NO: 1.

b. UCH-L1-Recognizing Antibody

The antibody is an antibody that binds to UCH-L1, a fragment thereof, an epitope of UCH-L1, or a variant thereof. The antibody may be a fragment of the anti-UCH-L1 antibody or a variant or a derivative thereof. The antibody may be a polyclonal or monoclonal antibody. The antibody may be a chimeric antibody, a single chain antibody, an affinity matured antibody, a human antibody, a humanized antibody, a fully human antibody or an antibody fragment, such as a Fab fragment, or a mixture thereof. Antibody fragments or derivatives may comprise F(ab')$_2$, Fv or scFv fragments. The antibody derivatives can be produced by peptidomimetics. Further, techniques described for the production of single chain antibodies can be adapted to produce single chain antibodies.

The anti-UCH-L1 antibodies may be a chimeric anti-UCH-L1 or humanized anti-UCH-L1 antibody. In one embodiment, both the humanized antibody and chimeric antibody are monovalent. In one embodiment, both the humanized antibody and chimeric antibody comprise a single Fab region linked to an Fc region.

Human antibodies may be derived from phage-display technology or from transgenic mice that express human immunoglobulin genes. The human antibody may be generated as a result of a human in vivo immune response and isolated. See, for example, Funaro et al., *BMC Biotechnology*, 2008(8):85. Therefore, the antibody may be a product of the human and not animal repertoire. Because it is of human origin, the risks of reactivity against self-antigens may be minimized. Alternatively, standard yeast display libraries and display technologies may be used to select and isolate human anti-UCH-L1 antibodies. For example, libraries of naïve human single chain variable fragments (scFv) may be used to select human anti-UCH-L1 antibodies. Transgenic animals may be used to express human antibodies.

Humanized antibodies may be antibody molecules from non-human species antibody that binds the desired antigen having one or more complementarity determining regions (CDRs) from the non-human species and framework regions from a human immunoglobulin molecule.

The antibody is distinguishable from known antibodies in that it possesses different biological function(s) than those known in the art.

(1) Epitope

The antibody may immunospecifically bind to UCH-L1 (SEQ ID NO: 1), a fragment thereof, or a variant thereof. The antibody may immunospecifically recognize and bind at least three amino acids, at least four amino acids, at least five amino acids, at least six amino acids, at least seven amino acids, at least eight amino acids, at least nine amino acids, or at least ten amino acids within an epitope region. The antibody may immunospecifically recognize and bind to an epitope that has at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids of an epitope region.

c. Antibody Preparation/Production

Antibodies may be prepared by any of a variety of techniques, including those well known to those skilled in the art. In general, antibodies can be produced by cell culture techniques, including the generation of monoclonal antibodies via conventional techniques, or via transfection of antibody genes, heavy chains, and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies include Chinese Hamster Ovary (CHO cells) (including dhfr-CHO cells, described in Urlaub and Chasin, *Proc. Natl. Acad. Sci. USA*, 77: 4216-4220

(1980)), used with a DHFR selectable marker, e.g., as described in Kaufman and Sharp, *J. Mol. Biol.*, 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies. In addition, bifunctional antibodies may be produced in which one heavy and one light chain are an antibody (i.e., binds human UCH-L1) and the other heavy and light chain are specific for an antigen other than human UCH-L1 by crosslinking an antibody to a second antibody by standard chemical crosslinking methods.

In a preferred system for recombinant expression of an antibody, or antigen-binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the method of synthesizing a recombinant antibody may be by culturing a host cell in a suitable culture medium until a recombinant antibody is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with UCH-L1 or a fragment and/or variant thereof. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes electrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) *Microbiol. Immunol.* 41:901-907; Sandhu et al. (1996) *Crit. Rev. Biotechnol.* 16:95-118; Eren et al. (1998) *Immunol.* 93:154-161) that are capable of producing a repertoire of human antibodies, as known in the art and/or as described herein. Such techniques, include, but are not limited to, ribosome display (Hanes et al. (1997) *Proc. Natl. Acad. Sci. USA,* 94:4937-4942; Hanes et al. (1998) *Proc. Natl. Acad. Sci. USA,* 95:14130-14135); single cell antibody producing technologies (e.g., selected lymphocyte antibody method ("SLAM") (U.S. Pat. No. 5,627,052, Wen et al. (1987) *J. Immunol.* 17:887-892; Babcook et al. (1996) *Proc. Natl. Acad. Sci. USA* 93:7843-7848); gel microdroplet and flow cytometry (Powell et al. (1990)

Biotechnol. 8:333-337; One Cell Systems, (Cambridge, Mass.).; Gray et al. (1995) J. Imm. Meth. 182:155-163; Kenny et al. (1995) Bio/Technol. 13:787-790); B-cell selection (Steenbakkers et al. (1994) *Molec. Biol. Reports* 19:125-134 (1994)).

An affinity matured antibody may be produced by any one of a number of procedures that are known in the art. For example, see Marks et al., *BioTechnology,* 10: 779-783 (1992) describes affinity maturation by VH and VL domain shuffling. Random mutagenesis of CDR and/or framework residues is described by Barbas et al., *Proc. Nat. Acad. Sci. USA,* 91: 3809-3813 (1994); Schier et al., Gene, 169: 147-155 (1995); Yelton et a, *J. Immunol.*, 155: 1994-2004 (1995); Jackson et al., *J. Immunol.*, 154(7): 3310-3319 (1995); Hawkins et al, *J. Mol. Biol.*, 226: 889-896 (1992). Selective mutation at selective mutagenesis positions and at contact or hypermutation positions with an activity enhancing amino acid residue is described in U.S. Pat. No. 6,914,128 B1.

Antibody variants can also be prepared using delivering a polynucleotide encoding an antibody to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide to provide transgenic plants and cultured plant cells (e.g., but not limited to tobacco, maize, and duckweed) that produce such antibodies, specified portions or variants in the plant parts or in cells cultured therefrom. For example, Cramer et al. (1999) *Curr. Top. Microbiol. Immunol.* 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., *Adv. Exp. Med. Biol.* (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) *Plant Mol. Biol.* 38:101-109 and reference cited therein. Thus, antibodies can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) *Proc. Natl. Acad. Sci. USA* 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al., (1995) *Protein Eng.* 8(10):1057-1062. Briefly, these antibodies comprise a pair of tandem Fd segments (VH-CH1-VH-CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (131I), yttrium-90 (90Y), bismuth-212 (212Bi), bismuth-213 (213Bi), technetium-99m (99mTc), rhenium-186 (186Re), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, *pseudomonas* exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus* restrictus), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

Antibody production via the use of hybridoma technology, the selected lymphocyte antibody method (SLAM), transgenic animals, and recombinant antibody libraries is described in more detail below.

(1) Anti-UCH-L1 Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: *A Laboratory Manual*, second edition, (Cold Spring Harbor Laboratory Press, Cold Spring Harbor, 1988); Hammerling, et al., In *Monoclonal Antibodies and T-Cell Hybridomas*, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods of generating monoclonal antibodies as well as antibodies produced by the method may comprise culturing a hybridoma cell secreting an antibody of the invention wherein, preferably, the hybridoma is generated by fusing splenocytes isolated from an animal, e.g., a rat or a mouse, immunized with UCH-L1 with myeloma cells and then screening the hybridomas resulting from the fusion for hybridoma clones that secrete an antibody able to bind a polypeptide of the invention. Briefly, rats can be immunized with a UCH-L1 antigen. In a preferred embodiment, the UCH-L1 antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with a UCH-L1 antigen, antibodies and/or antibody-producing cells may be obtained from the animal. An anti-UCH-L1 antibody-containing serum is obtained from the animal by bleeding or sacrificing the animal. The serum may be used as it is obtained from the animal, an immunoglobulin fraction may be obtained from the serum, or the anti-UCH-L1 antibodies may be purified from the serum. Serum or immunoglobulins obtained in this manner are polyclonal, thus having a heterogeneous array of properties.

Once an immune response is detected, e.g., antibodies specific for the antigen UCH-L1 are detected in the rat serum, the rat spleen is harvested and splenocytes isolated. The splenocytes are then fused by well-known techniques to any suitable myeloma cells, for example, cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding UCH-L1. Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using UCH-L1, or a portion thereof, or a cell expressing UCH-L1. In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504.

Anti-UCH-L1 antibody-producing hybridomas are selected, cloned, and further screened for desirable characteristics, including robust hybridoma growth, high antibody production, and desirable antibody characteristics. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are rat hybridomas. In another embodiment, hybridomas are produced in a non-human, non-rat species such as mice, sheep, pigs, goats, cattle, or horses. In yet another preferred embodiment, the hybridomas are human hybridomas, in which a human non-secretory myeloma is fused with a human cell expressing an anti-UCH-L1 antibody.

Antibody fragments that recognize specific epitopes may be generated by known techniques. For example, Fab and F(ab')$_2$ fragments of the invention may be produced by proteolytic cleavage of immunoglobulin molecules, using enzymes such as papain (to produce two identical Fab fragments) or pepsin (to produce an F(ab')$_2$ fragment). A F(ab')$_2$ fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, an F(ab')$_2$ fragment is still capable of crosslinking antigen molecules like the parent IgG molecule.

(2) Anti-UCH-L1 Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., Proc. Natl. Acad. Sci. USA, 93: 7843-7848 (1996). In this method, single cells secreting antibodies of interest, e.g., lymphocytes derived from any one of the immunized animals are screened using an antigen-specific hemolytic plaque assay, wherein the antigen UCH-L1, a subunit of UCH-L1, or a fragment thereof, is coupled to sheep red blood cells using a linker, such as biotin, and used to identify single cells that secrete antibodies with specificity for UCH-L1. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example, by panning the transfected cells to isolate cells expressing antibodies to UCH-L1. The amplified immunoglobulin sequences further can be manipulated in vitro, such as by in vitro affinity maturation method. See, for example, PCT Publication No. WO 97/29131 and PCT Publication No. WO 00/56772.

(3) Anti-UCH-L1 Monoclonal Antibodies Using Transgenic Animals

In another embodiment of the invention, antibodies are produced by immunizing a non-human animal comprising some, or all, of the human immunoglobulin locus with a UCH-L1 antigen. In an embodiment, the non-human animal is a XENOMOUSE® transgenic mouse, an engineered mouse strain that comprises large fragments of the human immunoglobulin loci and is deficient in mouse antibody production. See, e.g., Green et al., *Nature Genetics,* 7: 13-21 (1994) and U.S. Pat. Nos. 5,916,771; 5,939,598; 5,985,615; 5,998,209; 6,075,181; 6,091,001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See Mendez et al., *Nature Genetics,* 15: 146-156 (1997), Green and Jakobovits, *J. Exp. Med.,* 188: 483-495 (1998), the disclosures of which are hereby incorporated by reference.

(4) Anti-UCH-L1 Monoclonal Antibodies Using Recombinant Antibody Libraries

In vitro methods also can be used to make the antibodies of the invention, wherein an antibody library is screened to identify an antibody having the desired UCH-L1-binding specificity. Methods for such screening of recombinant antibody libraries are well known in the art and include methods described in, for example, U.S. Pat. No. 5,223,409 (Ladner et al.); PCT Publication No. WO 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., Bio/Technology, 9: 1369-1372 (1991); Hay et al., *Hum. Antibod. Hybridomas,* 3: 81-85 (1992); Huse et al., *Science,* 246: 1275-1281 (1989); McCafferty et al., *Nature,* 348: 552-554 (1990); Griffiths et al., *EMBO J.,* 12: 725-734 (1993); Hawkins et al., J. Mol. Biol., 226: 889-896 (1992); Clackson et al., Nature, 352: 624-628 (1991); Gram et al., *Proc. Natl. Acad. Sci. USA,* 89: 3576-3580 (1992); Garrard et al., *Bio/Technology,* 9: 1373-1377 (1991); Hoogenboom et al., Nucl. Acids Res., 19: 4133-4137 (1991); Barbas et al., *Proc. Natl. Acad. Sci. USA,* 88: 7978-7982 (1991); U.S. Patent Application Publication No. 2003/0186374; and PCT Publication No. WO 97/29131, the contents of each of which are incorporated herein by reference.

The recombinant antibody library may be from a subject immunized with UCH-L1, or a portion of UCH-L1. Alternatively, the recombinant antibody library may be from a naive subject, i.e., one who has not been immunized with UCH-L1, such as a human antibody library from a human subject who has not been immunized with human UCH-L1. Antibodies of the invention are selected by screening the recombinant antibody library with the peptide comprising human UCH-L1 to thereby select those antibodies that recognize UCH-L1. Methods for conducting such screening and selection are well known in the art, such as described in the references in the preceding paragraph. To select antibodies of the invention having particular binding affinities for UCH-L1, such as those that dissociate from human UCH-L1 with a particular $K_{off}$ rate constant, the art-known method of surface plasmon resonance can be used to select antibodies having the desired $K_{off}$ rate constant. To select antibodies of the invention having a particular neutralizing activity for hUCH-L1, such as those with a particular $IC_{50}$, standard methods known in the art for assessing the inhibition of UCH-L1 activity may be used.

In one aspect, the invention pertains to an isolated antibody, or an antigen-binding portion thereof, that binds human UCH-L1. Optionally, the antibody is a neutralizing antibody. In various embodiments, the antibody is a recombinant antibody or a monoclonal antibody.

For example, antibodies can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies include those disclosed in Brinkmann et al., *J. Immunol. Methods,* 182: 41-50 (1995); Ames et al., *J. Immunol. Methods,* 184:177-186 (1995); Kettleborough et al., *Eur. J. Immunol.,* 24: 952-958 (1994); Persic et al., Gene, 187: 9-18 (1997); Burton et al., Advances in *Immunology,* 57: 191-280 (1994); PCT Publication No. WO 92/01047; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')$_2$ fragments can also be employed using methods known in the art such as those disclosed in PCT publication No. WO 92/22324; Mullinax et al., *BioTechniques,* 12(6): 864-869 (1992); Sawai et al., *Am. J. Reprod. Immunol.,* 34: 26-34 (1995); and Better et al., *Science,* 240: 1041-1043 (1988). Examples of techniques which can be used to produce single-chain Fvs and antibodies include those described in U.S. Pat. Nos. 4,946,778 and 5,258,498; Huston et al., Methods in Enzymology, 203: 46-88 (1991); Shu et al., *Proc. Natl. Acad. Sci. USA,* 90: 7995-7999 (1993); and Skerra et al., *Science,* 240: 1038-1041 (1988).

Alternative to screening of recombinant antibody libraries by phage display, other methodologies known in the art for screening large combinatorial libraries can be applied to the identification of antibodies of the invention. One type of alternative expression system is one in which the recombinant antibody library is expressed as RNA-protein fusions, as described in PCT Publication No. WO 98/31700 (Szostak and Roberts), and in Roberts and Szostak, *Proc. Natl. Acad. Sci. USA,* 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence (s), or by other methods for affinity maturation in vitro of recombinant antibodies, as described above. A preferred example of this methodology is PROfusion display technology.

In another approach, the antibodies can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies include those disclosed in U.S. Pat. No. 6,699,658 (Wittrup et al.) incorporated herein by reference.

d. Production of Recombinant UCH-L1 Antibodies

Antibodies may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, *Proc. Natl. Acad. Sci. USA*, 77: 4216-4220 (1980), used with a DHFR selectable marker, e.g., as described in Kaufman and Sharp, *J. Mol. Biol.*, 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds human UCH-L1) and the other heavy and light chain are specific for an antigen other than human UCH-L1 by cross-linking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

(1) Humanized Antibody

The humanized antibody may be an antibody or a variant, derivative, analog or portion thereof which immunospecifically binds to an antigen of interest and which comprises a framework (FR) region having substantially the amino acid sequence of a human antibody and a complementary determining region (CDR) having substantially the amino acid sequence of a non-human antibody. The humanized antibody may be from a non-human species antibody that binds the desired antigen having one or more complementarity determining regions (CDRs) from the non-human species and framework regions from a human immunoglobulin molecule.

As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG 1, IgG2, IgG3, and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, *From Genes to Clones* (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816, 567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present invention can be performed using any known method, such as but not limited to those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The humanized antibody may retain high affinity for UCH-L1 and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for UCH-L1, is achieved. In general, the hypervariable region residues may be directly and most substantially involved in influencing antigen binding.

As an alternative to humanization, human antibodies (also referred to herein as "fully human antibodies") can be generated. For example, it is possible to isolate human antibodies from libraries via PROfusion and/or yeast related technologies. It is also possible to produce transgenic animals (e.g., mice that are capable, upon immunization, of producing a full repertoire of human antibodies in the absence of endogenous immunoglobulin production. For example, the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. The humanized or fully human antibodies may be prepared according to the methods described in U.S. Pat. Nos. 5,770,429; 5,833,985; 5,837,243; 5,922,845; 6,017,517; 6,096,311; 6,111,166; 6,270,765; 6,303,755; 6,365,116; 6,410,690; 6,682,928; and 6,984,720, the contents each of which are herein incorporated by reference.

e. Anti-UCH-L1 Antibodies

Anti-UCH-L1 antibodies may be generated using the techniques described above as well as using routine techniques known in the art. In some embodiments, the anti-UCH-L1 antibody may be an unconjugated UCH-L1 antibody, such as UCH-L1 antibodies available from United State Biological (Catalog Number: 031320), Cell Signaling Technology (Catalog Number: 3524), Sigma-Aldrich (Catalog Number: HPA005993), Santa Cruz Biotechnology, Inc. (Catalog Numbers: sc-58593 or sc-58594), R&D Systems (Catalog Number: MAB6007), Novus Biologicals (Catalog Number: NB600-1160), Biorbyt (Catalog Number: orb33715), Enzo Life Sciences, Inc. (Catalog Number: ADI-905-520-1), Bio-Rad (Catalog Number: VMA00004), BioVision (Catalog Number: 6130-50), Abcam (Catalog Numbers: ab75275 or ab104938), Invitrogen Antibodies (Catalog Numbers: 480012), ThermoFisher Scientific (Catalog Numbers: MA1-7-16079, MA5-17235, MA1-90008, or MA1-83428), EMD Millipore (Catalog Number: MABN48), or Sino Biological Inc. (Catalog Number: 50690-R011). The anti-UCH-L1 antibody may be conjugated to a fluorophore, such as conjugated UCH-L1 antibodies available from BioVision (Catalog Number: 6960-25) or Aviva Systems Biology (Cat. Nos. OAAF01904-FITC).

11. VARIATIONS ON METHODS

The disclosed methods of determining the presence or amount of analyte of interest (UCH-L1) present in a sample may be as described herein. The methods may also be adapted in view of other methods for analyzing analytes. Examples of well-known variations include, but are not limited to, immunoassay, such as sandwich immunoassay (e.g., monoclonal-monoclonal sandwich immunoassays, monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, etc.

a. Immunoassay

The analyte of interest, and/or peptides of fragments thereof (e.g., UCH-L1, and/or peptides or fragments thereof, i.e., UCH-L1 fragments), may be analyzed using UCH-L1 antibodies in an immunoassay. The presence or amount of analyte (e.g., UCH-L1) can be determined using antibodies and detecting specific binding to the analyte (e.g., UCH-L1). For example, the antibody, or antibody fragment thereof, may specifically bind to the analyte (e.g., UCH-L1). If desired, one or more of the antibodies can be used in combination with one or more commercially available monoclonal/polyclonal antibodies. Such antibodies are available from companies such as R&D Systems, Inc. (Minneapolis, Minn.) and Enzo Life Sciences International, Inc. (Plymouth Meeting, Pa.).

The presence or amount of analyte (e.g., UCH-L1) present in a body sample may be readily determined using an immunoassay, such as sandwich immunoassay (e.g., monoclonal-monoclonal sandwich immunoassays, monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)). An example of a point-of-care device that can be used is i-STAT® (Abbott, Laboratories, Abbott Park, Ill.). Other methods that can be used include a chemiluminescent microparticle immunoassay, in particular one employing the ARCHITECT® automated analyzer (Abbott Laboratories, Abbott Park, Ill.), as an example. Other methods include, for example, mass spectrometry, and immunohistochemistry (e.g., with sections from tissue biopsies), using anti-analyte (e.g., anti-UCH-L1) antibodies (monoclonal, polyclonal, chimeric, humanized, human, etc.) or antibody fragments thereof against analyte (e.g., UCH-L1). Other methods of detection include those described in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Specific immunological binding of the antibody to the analyte (e.g., UCH-L1) can be detected via direct labels, such as fluorescent or luminescent tags, metals and radionuclides attached to the antibody or via indirect labels, such as alkaline phosphatase or horseradish peroxidase.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

A homogeneous format may be used. For example, after the test sample is obtained from a subject, a mixture is prepared. The mixture contains the test sample being assessed for analyte (e.g., UCH-L1), a first specific binding partner, and a second specific binding partner. The order in which the test sample, the first specific binding partner, and the second specific binding partner are added to form the mixture is not critical. The test sample is simultaneously contacted with the first specific binding partner and the second specific binding partner. In some embodiments, the first specific binding partner and any UCH-L1 contained in the test sample may form a first specific binding partner-analyte (e.g., UCH-L1)-antigen complex and the second specific binding partner may form a first specific binding partner-analyte of interest (e.g., UCH-L1)-second specific binding partner complex. In some embodiments, the second specific binding partner and any UCH-L1 contained in the test sample may form a second specific binding partner-analyte (e.g., UCH-L1)-antigen complex and the first specific binding partner may form a first specific binding partner-analyte of interest (e.g., UCH-L1)-second specific binding partner complex. The first specific binding partner may be an anti-analyte antibody (e.g., anti-UCH-L1 antibody that binds to an epitope having an amino acid sequence comprising at least three contiguous (3) amino acids of SEQ ID NO: 1). The second specific binding partner may be an anti-analyte antibody (e.g., anti-UCH-L1 antibody that binds to an epitope having an amino acid sequence comprising at least three contiguous (3) amino acids of SEQ ID NO: 1). Moreover, the second specific binding partner is labeled with or contains a detectable label as described above.

A heterogeneous format may be used. For example, after the test sample is obtained from a subject, a first mixture is prepared. The mixture contains the test sample being assessed for analyte (e.g., UCH-L1) and a first specific binding partner, wherein the first specific binding partner and any UCH-L1 contained in the test sample form a first specific binding partner-analyte (e.g., UCH-L1)-antigen complex. The first specific binding partner may be an anti-analyte antibody (e.g., anti-UCH-L1 antibody that binds to an epitope having an amino acid sequence comprising at least three contiguous (3) amino acids of SEQ ID NO: 1). The order in which the test sample and the first specific binding partner are added to form the mixture is not critical.

The first specific binding partner may be immobilized on a solid phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc, and a chip. In those embodiments where the solid phase is a bead, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO.Fe_2O_3$). Beads can have a solid core portion that is magnetic and is surrounded by one or more non-magnetic layers. Alternately, the magnetic portion can be a layer around a non-magnetic core. The solid support on which the first specific binding member is immobilized may be stored in dry form or in a liquid. The magnetic beads may be subjected to a magnetic field prior to or after contacting with the sample with a magnetic bead on which the first specific binding member is immobilized.

After the mixture containing the first specific binding partner-analyte (e.g., UCH-L1) antigen complex is formed, any unbound analyte (e.g., UCH-L1) is removed from the complex using any technique known in the art. For example, the unbound analyte (e.g., UCH-L1) can be removed by washing. Desirably, however, the first specific binding partner is present in excess of any analyte (e.g., UCH-L1) present in the test sample, such that all analyte (e.g., UCH-L1) that is present in the test sample is bound by the first specific binding partner.

After any unbound analyte (e.g., UCH-L1) is removed, a second specific binding partner is added to the mixture to form a first specific binding partner-analyte of interest (e.g., UCH-L1)-second specific binding partner complex. The second specific binding partner may be an anti-analyte antibody (e.g., anti-UCH-L1 antibody that binds to an epitope having an amino acid sequence comprising at least three contiguous (3) amino acids of SEQ ID NO: 1). Moreover, the second specific binding partner is labeled with or contains a detectable label as described above.

The use of immobilized antibodies or antibody fragments thereof may be incorporated into the immunoassay. The antibodies may be immobilized onto a variety of supports, such as magnetic or chromatographic matrix particles (such as a magnetic bead), latex particles or modified surface latex particles, polymer or polymer film, plastic or plastic film, planar substrate, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

(1) Sandwich Immunoassay

A sandwich immunoassay measures the amount of antigen between two layers of antibodies (i.e., at least one capture antibody) and a detection antibody (i.e., at least one detection antibody). The capture antibody and the detection antibody bind to different epitopes on the antigen, e.g., analyte of interest such as UCH-L1. Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte (e.g., UCH-L1) in a test sample. More specifically, the at least two antibodies bind to certain epitopes of analyte (e.g., UCH-L1) forming an immune complex which is referred to as a "sandwich". One or more antibodies can be used to capture the analyte (e.g., UCH-L1) in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, the binding of an antibody to its epitope desirably is not diminished by the binding of any other antibody in the assay to its respective epitope. Antibodies are selected so that the one or more first antibodies brought into contact with a test sample suspected of containing analyte (e.g., UCH-L1) do not bind to all or part of an epitope recognized by the second or subsequent antibodies, thereby interfering with the ability of the one or more second detection antibodies to bind to the analyte (e.g., UCH-L1).

The antibodies may be used as a first antibody in said immunoassay. The antibody immunospecifically binds to epitopes on analyte (e.g., UCH-L1). In addition to the antibodies of the present invention, said immunoassay may comprise a second antibody that immunospecifically binds to epitopes that are not recognized or bound by the first antibody.

A test sample suspected of containing analyte (e.g., UCH-L1) can be contacted with at least one first capture antibody (or antibodies) and at least one second detection antibodies either simultaneously or sequentially. In the sandwich assay format, a test sample suspected of containing analyte (e.g., UCH-L1) is first brought into contact with the at least one first capture antibody that specifically binds to a particular epitope under conditions which allow the formation of a first antibody-analyte (e.g., UCH-L1) antigen complex. If more than one capture antibody is used, a first multiple capture antibody-UCH-L1 antigen complex is formed. In a sandwich assay, the antibodies, preferably, the at least one capture antibody, are used in molar excess amounts of the maximum amount of analyte (e.g., UCH-L1) expected in the test sample. For example, from about 5 µg/ml to about 1 mg/ml of antibody per ml of microparticle coating buffer may be used.

i. Anti-UCH-L1 Capture Antibody

Optionally, prior to contacting the test sample with the at least one first capture antibody, the at least one first capture antibody can be bound to a solid support which facilitates the separation the first antibody-analyte (e.g., UCH-L1) complex from the test sample. Any solid support known in the art can be used, including but not limited to, solid supports made out of polymeric materials in the forms of wells, tubes, or beads (such as a microparticle). The antibody (or antibodies) can be bound to the solid support by adsorption, by covalent bonding using a chemical coupling agent or by other means known in the art, provided that such binding does not interfere with the ability of the antibody to bind analyte (e.g., UCH-L1). Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing analyte (e.g., UCH-L1) is incubated in order to allow for the formation of a first capture antibody (or multiple antibody)-analyte (e.g., UCH-L1) complex. The incubation can be carried out at a pH of from about 4.5 to about 10.0, at a temperature of from about 2° C. to about 45° C., and for a period from at least about one (1) minute to about eighteen (18) hours, from about 2-6 minutes, from about 7-12 minutes, from about 5-15 minutes, or from about 3-4 minutes.

ii. Detection Antibody

After formation of the first/multiple capture antibody-analyte (e.g., UCH-L1) complex, the complex is then contacted with at least one second detection antibody (under conditions that allow for the formation of a first/multiple antibody-analyte (e.g., UCH-L1) antigen-second antibody complex). In some embodiments, the test sample is contacted with the detection antibody simultaneously with the capture antibody. If the first antibody-analyte (e.g., UCH-L1) complex is contacted with more than one detection antibody, then a first/multiple capture antibody-analyte (e.g., UCH-L1)-multiple antibody detection complex is formed. As with first antibody, when the at least second (and subsequent) antibody is brought into contact with the first antibody-analyte (e.g., UCH-L1) complex, a period of incubation under conditions similar to those described above is required for the formation of the first/multiple antibody-analyte (e.g., UCH-L1)-second/multiple antibody complex.

Preferably, at least one second antibody contains a detectable label. The detectable label can be bound to the at least one second antibody prior to, simultaneously with or after the formation of the first/multiple antibody-analyte (e.g., UCH-L1)-second/multiple antibody complex. Any detectable label known in the art can be used.

Chemiluminescent assays can be performed in accordance with the methods described in Adamczyk et al., *Anal. Chim. Acta* 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-UCH-L1 antigen complexes form. Alternatively, if a second specific binding partner is used and the second specific binding partner is detectably labeled with an acridinium compound, detectably labeled first specific binding partner-analyte (e.g., UCH-L1)-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of UCH-L1 is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample. Other labels other than chemiluminescent labels can be employed. For instance, enzymatic labels (including but not limited to alkaline phosphatase) can be employed.

The chemiluminescent signal, or other signal, that is generated can be detected using routine techniques known to those skilled in the art. Based on the intensity of the signal generated, the amount of analyte of interest (e.g., UCH-L1) in the sample can be quantified. Specifically, the amount of analyte (e.g., UCH-L1) in the sample is proportional to the intensity of the signal generated. The amount of analyte (e.g., UCH-L1) present can be quantified by comparing the amount of light generated to a standard curve for analyte (e.g., UCH-L1) or by comparison to a reference standard. The standard curve can be generated using serial dilutions or solutions of known concentrations of analyte (e.g., UCH-L1) by mass spectroscopy, gravimetric methods, and other techniques known in the art.

(2) Forward Competitive Inhibition Assay

In a forward competitive format, an aliquot of labeled analyte of interest (e.g., analyte (e.g., UCH-L1) having a fluorescent label, a tag attached with a cleavable linker, etc.) of a known concentration is used to compete with analyte of interest (e.g., UCH-L1) in a test sample for binding to analyte of interest antibody (e.g., UCH-L1 antibody).

In a forward competition assay, an immobilized specific binding partner (such as an antibody) can either be sequentially or simultaneously contacted with the test sample and a labeled analyte of interest, analyte of interest fragment or analyte of interest variant thereof. The analyte of interest peptide, analyte of interest fragment or analyte of interest variant can be labeled with any detectable label, including a detectable label comprised of tag attached with a cleavable linker. In this assay, the antibody can be immobilized on to a solid support. Alternatively, the antibody can be coupled to an antibody, such as an antispecies antibody, that has been immobilized on a solid support, such as a microparticle or planar substrate.

The labeled analyte of interest, the test sample and the antibody are incubated under conditions similar to those described above in connection with the sandwich assay format. Two different species of antibody-analyte of interest complexes may then be generated. Specifically, one of the antibody-analyte of interest complexes generated contains a detectable label (e.g., a fluorescent label, etc.) while the other antibody-analyte of interest complex does not contain a detectable label. The antibody-analyte of interest complex can be, but does not have to be, separated from the remainder of the test sample prior to quantification of the detectable label. Regardless of whether the antibody-analyte of interest complex is separated from the remainder of the test sample, the amount of detectable label in the antibody-analyte of interest complex is then quantified. The concentration of analyte of interest (such as membrane-associated analyte of interest, soluble analyte of interest, fragments of soluble analyte of interest, variants of analyte of interest (membrane-associated or soluble analyte of interest) or any combinations thereof) in the test sample can then be determined, e.g., as described above.

(3) Reverse Competitive Inhibition Assay

In a reverse competition assay, an immobilized analyte of interest (e.g., UCH-L1) can either be sequentially or simultaneously contacted with a test sample and at least one labeled antibody.

The analyte of interest can be bound to a solid support, such as the solid supports discussed above in connection with the sandwich assay format.

The immobilized analyte of interest, test sample and at least one labeled antibody are incubated under conditions similar to those described above in connection with the sandwich assay format. Two different species analyte of interest-antibody complexes are then generated. Specifically, one of the analyte of interest-antibody complexes generated is immobilized and contains a detectable label (e.g., a fluorescent label, etc.) while the other analyte of interest-antibody complex is not immobilized and contains a detectable label. The non-immobilized analyte of interest-antibody complex and the remainder of the test sample are removed from the presence of the immobilized analyte of interest-antibody complex through techniques known in the art, such as washing. Once the non-immobilized analyte of interest antibody complex is removed, the amount of detectable label in the immobilized analyte of interest-antibody complex is then quantified following cleavage of the tag. The concentration of analyte of interest in the test sample can then be determined by comparing the quantity of detectable label as described above.

(4) One-Step Immunoassay or "Capture on the Fly" Assay

In a capture on the fly immunoassay, a solid substrate is pre-coated with an immobilization agent. The capture agent, the analyte (e.g., UCH-L1) and the detection agent are added to the solid substrate together, followed by a wash step prior to detection. The capture agent can bind the analyte (e.g., UCH-L1) and comprises a ligand for an immobilization agent. The capture agent and the detection agents may be antibodies or any other moiety capable of capture or detection as described herein or known in the art. The ligand may comprise a peptide tag and an immobilization agent may comprise an anti-peptide tag antibody. Alternately, the ligand and the immobilization agent may be any pair of agents capable of binding together so as to be employed for a capture on the fly assay (e.g., specific binding pair, and others such as are known in the art). More than one analyte may be measured. In some embodiments, the solid substrate may be coated with an antigen and the analyte to be analyzed is an antibody.

In certain other embodiments, in a one-step immunoassay or "capture on the fly", a solid support (such as a microparticle) pre-coated with an immobilization agent (such as biotin, streptavidin, etc.) and at least a first specific binding member and a second specific binding member (which function as capture and detection reagents, respectively) are used. The first specific binding member comprises a ligand for the immobilization agent (for example, if the immobilization agent on the solid support is streptavidin, the ligand on the first specific binding member may be biotin) and also binds to the analyte of interest (e.g., UCH-L1). The second specific binding member comprises a detectable label and binds to an analyte of interest (e.g., UCH-L1). The solid support and the first and second specific binding members may be added to a test sample (either sequentially or simultaneously). The ligand on the first specific binding member binds to the immobilization agent on the solid support to form a solid support/first specific binding member complex. Any analyte of interest present in the sample binds to the solid support/first specific binding member complex to form a solid support/first specific binding member/analyte complex. The second specific binding member binds to the solid support/first specific binding member/analyte complex and the detectable label is detected. An optional wash step may be employed before the detection. In certain embodiments, in a one-step assay more than one analyte may be measured. In certain other embodiments, more than two specific binding members can be employed. In certain other embodiments, multiple detectable labels can be added. In certain other embodiments, multiple analytes of interest can be detected, or their amounts, levels or concentrations, measured, determined or assessed.

The use of a capture on the fly assay can be done in a variety of formats as described herein, and known in the art. For example the format can be a sandwich assay such as described above, but alternately can be a competition assay, can employ a single specific binding member, or use other variations such as are known.

12. OTHER FACTORS

The methods of diagnosing, prognosticating, and/or assessing, as described above, can further include using other factors for the diagnosis, prognostication, and assessment. In some embodiments, traumatic brain injury may be diagnosed using the Glasgow Coma Scale or the Extended Glasgow Outcome Scale (GOSE). Other tests, scales or indices can also be used either alone or in combination with the Glasgow Coma Scale. An example is the Ranchos Los Amigos Scale. The Ranchos Los Amigos Scale measures the levels of awareness, cognition, behavior and interaction with the environment. The Ranchos Los Amigos Scale includes: Level I: No Response; Level II: Generalized Response; Level III: Localized Response; Level IV: Confused-agitated; Level V: Confused-inappropriate; Level VI: Confused-appropriate; Level VII: Automatic-appropriate; and Level VIII: Purposeful-appropriate.

13. SAMPLES

In some embodiments, the sample is obtained after the human subject sustained an injury to the head caused by physical shaking, blunt impact by an external mechanical or other force that results in a closed or open head trauma, one or more falls, explosions or blasts or other types of blunt force trauma. In some embodiments, the sample is obtained after the human subject has ingested or been exposed to a chemical, toxin or combination of a chemical and toxin. Examples of such chemicals and/or toxins include, fires, molds, asbestos, pesticides and insecticides, organic solvents, paints, glues, gases (such as carbon monoxide, hydrogen sulfide, and cyanide), organic metals (such as methyl mercury, tetraethyl lead and organic tin) and/or one or more drugs of abuse. In some embodiments, the sample is obtained from a human subject that suffers from an autoimmune disease, a metabolic disorder, a brain tumor, hypoxia, one or more viruses, meningitis, hydrocephalus or combinations thereof.

In yet another embodiment, the methods described herein use samples that also can be used to determine whether or not a subject has or is at risk of developing mild traumatic brain injury by determining the levels of UCH-L1 in a subject using the anti-UCH-L1 antibodies described below, or antibody fragments thereof. Thus, in particular embodiments, the disclosure also provides a method for determining whether a subject having, or at risk for, traumatic brain injuries, discussed herein and known in the art, is a candidate for therapy or treatment. Generally, the subject is at least one who: (i) has experienced an injury to the head; (ii) ingested and/or been exposed to one or more chemicals and/or toxins; (iii) suffers from an autoimmune disease, a metabolic disorder, a brain tumor, hypoxia, one or more viruses, meningitis, hydrocephalus or suffers from any combinations thereof; or (iv) any combinations of (i)-(iii); or, who has actually been diagnosed as having, or being at risk for TBI (such as, for example, subjects suffering from an autoimmune disease, a metabolic disorder, a brain tumor, hypoxia, one or more viruses, meningitis, hydrocephalus or combinations thereof), and/or who demonstrates an unfavorable (i.e., clinically undesirable) concentration or amount of UCH-L1 or UCH-L1 fragment, as described herein.

a. Test Sample or Biological Sample

As used herein, "sample", "test sample", "biological sample" refer to fluid sample containing or suspected of containing UCH-L1. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing UCH-L1 may be assayed directly. In a particular example, the source of UCH-L1 is a human bodily substance (e.g., bodily fluid, blood such as whole blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis.

A wide range of volumes of the fluid sample may be analyzed. In a few exemplary embodiments, the sample volume may be about 0.5 nL, about 1 nL, about 3 nL, about 0.01 µL, about 0.1 µL, about 1 µL, about 5 µL, about 10 µL, about 100 µL, about 1 mL, about 5 mL, about 10 mL, or the like. In some cases, the volume of the fluid sample is between about 0.01 µL and about 10 mL, between about 0.01 µL and about 1 mL, between about 0.01 µL and about 100 µL, or between about 0.1 µL and about 10 µL.

In some cases, the fluid sample may be diluted prior to use in an assay. For example, in embodiments where the source of UCH-L1 is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use. In other cases, the fluid sample is not diluted prior to use in an assay.

In some cases, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source of UCH-L1 is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

b. Controls

It may be desirable to include a control sample. The control sample may be analyzed concurrently with the sample from the subject as described above. The results obtained from the subject sample can be compared to the results obtained from the control sample. Standard curves may be provided, with which assay results for the sample may be compared. Such standard curves present levels of marker as a function of assay units, i.e., fluorescent signal intensity, if a fluorescent label is used. Using samples taken from multiple donors, standard curves can be provided for reference levels of the UCH-L1 in normal healthy tissue, as well as for "at-risk" levels of the UCH-L1 in tissue taken from donors, who may have one or more of the characteristics set forth above.

Thus, in view of the above, a method for determining the presence, amount, or concentration of UCH-L1 in a test sample is provided. The method comprises assaying the test sample for UCH-L1 by an immunoassay, for example, employing at least one capture antibody that binds to an epitope on UCH-L1 and at least one detection antibody that binds to an epitope on UCH-L1 which is different from the epitope for the capture antibody and optionally includes a detectable label, and comprising comparing a signal generated by the detectable label as a direct or indirect indication of the presence, amount or concentration of UCH-L1 in the test sample to a signal generated as a direct or indirect indication of the presence, amount or concentration of UCH-L1 in a calibrator. The calibrator is optionally, and is preferably, part of a series of calibrators in which each of the calibrators differs from the other calibrators in the series by the concentration of UCH-L1.

14. KIT

Provided herein is a kit, which may be used for assaying or assessing a test sample for UCH-L1 or UCH-L1 fragment. The kit comprises at least one component for assaying the test sample for UCH-L1 instructions for assaying the test sample for UCH-L1. For example, the kit can comprise instructions for assaying the test sample for UCH-L1 by immunoassay, e.g., chemiluminescent microparticle immunoassay. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The at least one component may include at least one composition comprising one or more isolated antibodies or antibody fragments thereof that specifically bind to UCH-L1. The antibody may be a UCH-L1 capture antibody and/or a UCH-L1 detection antibody.

Alternatively or additionally, the kit can comprise a calibrator or control, e.g., purified, and optionally lyophilized, UCH-L1, and/or at least one container (e.g., tube, microtiter plates or strips, which can be already coated with an anti-UCH-L1 monoclonal antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve.

The kit may further comprise reference standards for quantifying UCH-L1. The reference standards may be employed to establish standard curves for interpolation and/or extrapolation of UCH-L1 concentrations. The reference standards may include a high UCH-L1 concentration level, for example, about 100000 pg/mL, about 125000 pg/mL, about 150000 pg/mL, about 175000 pg/mL, about 200000 pg/mL, about 225000 pg/mL, about 250000 pg/mL, about 275000 pg/mL, or about 300000 pg/mL; a medium UCH-L1 concentration level, for example, about 25000 pg/mL, about 40000 pg/mL, about 45000 pg/mL, about 50000 pg/mL, about 55000 pg/mL, about 60000 pg/mL, about 75000 pg/mL or about 100000 pg/mL; and/or a low UCH-L1 concentration level, for example, about 1 pg/mL, about 5 pg/mL, about 10 pg/mL, about 12.5 pg/mL, about 15 pg/mL, about 20 pg/mL, about 25 pg/mL, about 30 pg/mL, about 35 pg/mL, about 40 pg/mL, about 45 pg/mL, about 50 pg/mL, about 55 pg/mL, about 60 pg/mL, about 65 pg/mL, about 70 pg/mL, about 75 pg/mL, about 80 pg/mL, about 85 pg/mL, about 90 pg/mL, about 95 pg/mL, or about 100 pg/mL.

Any antibodies, which are provided in the kit, such as recombinant antibodies specific for UCH-L1, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes (e.g., UCH-L1) or reagents for detecting the analyte (e.g., UCH-L1). The antibodies, calibrators, and/or controls can be provided in separate containers or pre-dispensed into an appropriate assay format, for example, into microtiter plates, Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays, The kit can also optionally include other reagents required to conduct a diagnostic assay or facilitate quality control evaluations, such as buffers, salts, enzymes, enzyme cofactors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine, whole blood, plasma, or serum sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc, or chip.

If desired, the kit can further comprise one or more components, alone or in further combination with instructions, for assaying the test sample for another analyte, which can be a biomarker, such as a biomarker of traumatic brain injury or disorder.

a. Adaptation of Kit and Method

The kit (or components thereof), as well as the method for assessing or determining the concentration of UCH-L1 in a test sample by an immunoassay as described herein, can be adapted for use in a variety of automated and semi-automated systems (including those wherein the solid phase comprises a microparticle), as described, e.g., U.S. Pat. No. 5,063,081, U.S. Patent Application Publication Nos. 2003/0170881, 2004/0018577, 2005/0054078, and 2006/0160164 and as commercially marketed e.g., by Abbott Laboratories (Abbott Park, Ill.) as Abbott Point of Care (i-STAT® or i-STAT Alinity, Abbott Laboratories) as well as those described in U.S. Pat. Nos. 5,089,424 and 5,006,309, and as commercially marketed, e.g., by Abbott Laboratories (Abbott Park, Ill.) as ARCHITECT® or the series of Abbott Alinity devices.

Some of the differences between an automated or semi-automated system as compared to a non-automated system (e.g., ELISA) include the substrate to which the first specific binding partner (e.g., analyte antibody or capture antibody) is attached (which can affect sandwich formation and analyte reactivity), and the length and timing of the capture, detection, and/or any optional wash steps. Whereas a non-automated format such as an ELISA may require a relatively longer incubation time with sample and capture reagent (e.g., about 2 hours), an automated or semi-automated format (e.g., ARCHITECT® and any successor platform, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT® and any successor platform) may have a relatively shorter incubation time (e.g., approximately 4 minutes for the ARCHITECT® and any successor platform).

Other platforms available from Abbott Laboratories include, but are not limited to, immunoassay analyzers including AxSYM®, IMx® (see, e.g., U.S. Pat. No. 5,294,404, which is hereby incorporated by reference in its entirety), PRISM®, EIA (bead), and Quantum™ II (dual-wavelength analyzer system), as well as other platforms. Additionally, the assays, kits, and kit components can be employed in other formats, for example, on electrochemical or other hand-held or point-of-care assay systems. As mentioned previously, the present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Patent App. Publication Nos. 2003/0170881, 2004/0018577, 2005/0054078, and 2006/0160164, which are incorporated in their entireties by reference for their teachings regarding same.

In particular, with regard to the adaptation of an assay to the i-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an i-STAT® cartridge with a fluidics format suitable for immunoassay. On a portion of the silicon chip, there is a specific binding partner for UCH-L1, such as one or more UCH-L1 antibodies (one or more monoclonal/polyclonal antibody or a fragment thereof, a variant thereof, or a fragment of a variant thereof that can bind UCH-L1) or one or more anti-UCH-L1 DVD-Igs (or a fragment thereof, a variant thereof, or a fragment of a variant thereof that can bind UCH-L1), either of which can be detectably labeled. Within the fluid pouch of the cartridge is an aqueous reagent that includes p-aminophenol phosphate.

In operation, a sample from a subject suspected of suffering from TBI is added to the holding chamber of the test cartridge, and the cartridge is inserted into the i-STAT® reader. A pump element within the cartridge pushes the sample into a conduit containing the chip. The sample is brought into contact with the sensors allowing the enzyme conjugate to dissolve into the sample. The sample is oscillated across the sensors to promote formation of the sandwich of approximately 2-12 minutes. In the penultimate step of the assay, the sample is pushed into a waste chamber and wash fluid, containing a substrate for the alkaline phosphatase enzyme, is used to wash excess enzyme conjugate and sample off the sensor chip. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of UCH-L1 in the sample by means of an embedded algorithm and factory-determined calibration curve.

The methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an i-STAT® cartridge format, using a nucleic acid sequence linked to the signal antibody as a signal amplifier. Adaptation of a cartridge for multiplex use, such as used for i-Stat, has been described in the patent literature, such as for example, U.S. Pat. No. 6,438,498, the contents of which are herein incorporated by reference.

The methods and kits as described herein may also involve single molecule counting. In certain embodiments, a method for analyte analysis may involve assessing an analyte present in a sample. In certain embodiments, the assessing may be used for determining presence of and/or concentration of an analyte in a sample. In certain embodiments, the method may also be used for determining presence of and/or concentration of a plurality of different analytes present in a sample.

Any device known in the art that allows for the detection of a single molecule of one or more analytes of interest can be used in the systems described herein. For example, the device can be a microfluidics device, digital microfluidics device (DMF), a surface acoustic wave based microfluidic device (SAW), an integrated DMF and analyte detection device, an integrated SAW and analyte detection device, or robotics-based assay processing unit. Examples of other devices that can be used include the Quanterix fully automated immunoassay instrument SIMOA™, (Lexington, Mass.), Singulex's single molecule counting (SMC™) technology (Alameda, Calif., see for example, U.S. Pat. No. 9,239,284, the contents of which are herein incorporated by reference), etc.

While certain embodiments herein are advantageous when employed to assess disease, such as traumatic brain injury, the assays and kits also optionally can be employed to assess UCH-L1 in other diseases, disorders, and conditions as appropriate.

The method of assay also can be used to identify a compound that ameliorates diseases, such as traumatic brain injury. For example, a cell that expresses UCH-L1 can be contacted with a candidate compound. The level of expression of UCH-L1 in the cell contacted with the compound can be compared to that in a control cell using the method of assay described herein.

The present invention has multiple aspects, illustrated by the following non-limiting examples.

15. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present invention has multiple aspects, illustrated by the following non-limiting examples.

Example 1 i-STAT® UCH-L1 Assay

The i-STAT® UCH-L1 assay was used in a TBI patient population study. Monoclonal antibody pairs, such as Antibody A as a capture monoclonal antibody and Antibody B and C as a detection monoclonal antibody, were used. Antibody A is an exemplary anti-UCH-L1 antibody that was internally developed at Abbott Laboratories (Abbott Park, Ill.). Antibody B and C recognize different epitopes of UCH-L1 and enhance the detection of antigen in the sample that were developed by Banyan Biomarkers (Alachua, Fla.). Other antibodies that were internally developed at Abbott Laboratories (Abbott Park, Ill.) also show or are expected to show similar enhancement of signal when used together as capture antibodies or detection antibodies, in various combinations. The UCH-L1 assay design was evaluated against key performance attributes. The cartridge configuration was Antibody Configuration: Antibody A (Capture Antibody)/ Antibody B+C (Detection Antibody); Reagent conditions: 0.8% solids, 125 µg/mL Fab Alkaline Phosphatase cluster conjugate; and Sample Inlet Print: UCH-L1 standard. The assay time was 10-15 min (with 7-12 min sample capture time).

Example 2

TBI Population Study (TRACK-TBI)

The Transforming Research and Clinical Knowledge in Traumatic Brain Injury (TRACK-TBI) study is a large and complex project. Its institutional and public-private partnership is comprised of over 11 clinical sites, 7 Cores, for a total of nearly 50 collaborating institutions, corporations, and philanthropy. An earlier TRACK-TBI Pilot study, based on clinical data from three clinical sites, helped refine TBI Common Data Elements and created a prototype of the TBI Information Commons for the TRACK-TBI study.

Subject Groups:

A total of 2,700 to 3000 TBI patients were enrolled evenly across 3 clinical groups, differentiated by clinical care path: 1. Patients evaluated in the Emergency Department and discharged (ED); 2. Patients admitted to the hospital, but not to ICU (ADM); and 3. Patients admitted to the ICU (ICU). An additional 100 patients per clinical group (n=300) with extracranial trauma but no TBI were enrolled as controls for a total enrollment of 3000 patients. This stratification plan facilitated comparative effectiveness research (CER) analysis and was not constrained by traditional differentiation into "Mild/Moderate/Severe" TBI. Data collection was dependent on the clinical care path (ED, ADM, ICU) and requirements of each aim. Patients in each group were stratified into 3 cohorts that define the extent of data to be collected.

The controls were adult orthopedic trauma patients who met the following criteria: 1. An Abbreviated Injury Score of <4 (not life threatening) for their extremity and/or pelvis injury and/or rib fracture; 2. Met the same inclusion and exclusion criteria as the TBI subjects except that the criterion of having undergone a CT or MM in the ED for suspected head injury did not apply. TBI was ruled out for the current injury by interviewing potential controls about loss of consciousness (LOC), disturbance of consciousness, and posttraumatic amnesia (PTA)/RA; 3. Each site was provided a plan for the number of controls to target according to age and gender distributions derived from the TBI Cohort; and 4. Controls were enrolled into the CA-MM cohort for follow-up and drop to comprehensive assessment (CA) at 2-weeks if unable to complete the MM visit.

Subject Eligibility:

Adult patients were enrolled of all ages presenting to the Emergency Department (ED) with a history of acute TBI as per American Congress of Rehabilitation Medicine (ACRM) Criteria, in which the patient had sustained a traumatically induced physiological disruption of brain function, as manifested by ≥one of the following: any period of loss of consciousness (LOC); any loss of memory for events (e.g., amnesia) immediately before or after the accident; any alteration of mental state at the time of the accident (feeling dazed, disoriented, and/or confused); and/or focal neurologic deficits that may or may not be permanent. Traumatically induced included the head being struck, the head striking an object, or the brain undergoing an acceleration/ deceleration movement (e.g., whiplash) without direct external trauma to the head.

The Inclusion/Exclusion Criteria used is shown in Table 2.

TABLE 2

| Criterion | Data Source | Comments |
| --- | --- | --- |
| Inclusion Criteria | | |
| 1. Age 0-100 | Chart | |
| 2. Documented/verified TBI (ACRM Criteria) | Chart, Interview | |
| 3. Injury occurred <24 hours ago | Chart, Interview | |
| 4. Acute brain CT for clinical care | Chart | Subject must have brain CT scan |
| 5. Visual acuity/hearing adequate for testing | Chart, Interview | |
| 6. Fluency in English or Spanish | Chart, Interview | Test battery or personnel availability |
| 7. Ability to provide informed consent | Interview | |
| Exclusion Criteria | | |
| 1. Significant polytrauma that would interfere with follow-up and outcome assessment | Chart | Significant body trauma may confound TBI outcomes testing. |
| 2. Prisoners or patients in custody | Chart, Interview | |
| 3. Pregnancy in female subjects | Chart, Interview | |
| 4. Patients on psychiatric hold (e.g., 5150, 5250) | Chart | |
| 5. Major debilitating baseline mental health disorders (e.g., schizophrenia or bipolar disorder) that would interfere with follow-up and the validity of outcome assessment | Chart, Interview | Debilitating psychiatric disorders can significantly impact the reliability of follow up and/or pose difficulties in attributing to index TBI. |
| 6. Major debilitating neurological disease (e.g., stroke, CVA, dementia, | Chart, Interview | Documented debilitating baseline cognitive impairment will confound |

TABLE 2-continued

| Criterion | Data Source | Comments |
|---|---|---|
| tumor) impairing baseline awareness cognition or validity of follow-up and outcome assessment | | outcome assessment in addition to not being fully consentable. |
| 7. Significant history of pre-existing conditions that would interfere with follow-up and outcome assessment (e.g., substance abuse, alcoholism, HIV/AIDS, major transmittable diseases that may interfere with consent, end-stage cancers, learning disabilities, developmental disorders) | Chart, Interview | |
| 8. Contraindications to MRI (for CA + MRI cohort) | MRI Screening | |
| 9. Low likelihood of follow-up (e.g., participant or family indicating low interest, residence in another state or country, homelessness or lack of reliable contacts) | Interview | |
| 10. Current participant in an interventional trial (e.g., drug, device, behavioral) | Chart, Interview | Exception to co-enrollment exclusion is made for sites participating in Resuscitation Outcomes Consortium Prehospital Tranexamic Acid for TBI Study. |
| 11. Penetrating TBI | Chart | |
| 12. Spinal cord injury with ASIA score of C or worse | Chart | |

For each of the 3 clinical groups (i.e., ED, ADM, and ICU), the subjects were further placed into one of three different assessment cohorts: Brief Assessment (BA Cohort), Compressive Assessment (CA) Cohort, or Comprehensive Assessment+MM (CA+MRI) Cohort. See Table 3 for Milestone plan with 80% follow up rate.

TABLE 3

| (Add) | Year 1 | | | Year 2 | | | Year 3 | | | Year 4 | Total |
|---|---|---|---|---|---|---|---|---|---|---|---|
| Group | CA + MRI | CA | N | CA + MRI | CA | N | CA | BA | N | BA | N |
| ED | 150 | 87 | 237 | 50 | 58 | 108 | 155 | 100 | 255 | 300 | 900 |
| ADM | 150 | 87 | 237 | 50 | 58 | 108 | 155 | 100 | 255 | 300 | 900 |
| ICU | 150 | 87 | 237 | 50 | 58 | 108 | 155 | 100 | 255 | 300 | 900 |
| Controls | 0 | 99 | 99 | 0 | 66 | 66 | 135 | 0 | 135 | 0 | 300 |
| Totals | 450 | 360 | 810 | 150 | 240 | 390 | 600 | 300 | 900 | 900 | 3000 |

The Brief Assessment (BA) Cohort included 1200 total subjects, with 400 subjects each for ED, ADM, and ICU Groups. The following data was gathered for the BA Cohort: demographic and full clinical course data; blood draw for serum, plasma, DNA and RNA on Day 1 (<24 hours of injury); repeat blood draw for serum within 3-6 hours of the Day 1 baseline collection (optional for sites to include this component); clinical brain CT scan from Day 1 acquired as part of hospital course; and outcome data collected via structured telephone interview at 2 weeks, 3, 6, and 12 months using NIH TBI-CDEs v.2.0 Core outcome measures as published on the NINDS CDE website.

The Compressive Assessment (CA) Cohort included 1200 total subjects, with 300 subjects+100 controls each for ED, ADM, and ICU Groups. The following data was gathered for the CA Cohort: demographic and full clinical course data; high density daily clinical data for ADM and ICU Groups; blood draw for serum, plasma, RNA, and DNA on Day 1 (<24 hours of injury); repeat blood draw for serum within 3-6 hours of the Day 1 baseline collection (optional for sites to include this component); blood draw for serum, plasma and RNA of Day 3 (48-72 hours) and 5 (96-120 hours) for ADM and ICU; collection of cerebrospinal fluid on days 1 through 5 (optional for sites to include this component); all clinical brain CT scans acquired as part of hospital course; blood draw for serum, plasma and RNA at 2 weeks and 6 months; and outcome data collected via structured in-person interview at 2 weeks, 6, and 12 months and at 3 months via structured telephone interview using NIH TBI-CDEs v.2.0 Core, Basic and Supplemental outcome measures.

The Comprehensive Assessment+MRI (CA+MRI) Cohort included 600 total subjects, with 200 each for ED, ADM, and ICU Groups. The following data was gathered for the CA+MRI Cohort: demographic and full clinical course data; high density daily clinical data for ADM and ICU Groups; blood draw for serum, plasma, RNA, and DNA on Day 1 (<24 hours of injury); repeat blood draw for serum within 3-6 hours of the Day 1 baseline collection (optional for sites to include this component); blood draw for serum, plasma, and RNA on Day 3 (48-72 hours) and 5 (96-120 hours) for ADM and ICU; collection of cerebrospinal fluid on days 1 through 5 (optional for sites to include this component); all clinical head CT scans acquired as part of hospital course; blood draw for serum, plasma and RNA at 2 weeks and 6 months; 3T research MRI acquired at 2 weeks and 6 months; and outcome data collected via structured in-person interview at 2 weeks, 6, and 12 months and at 3 month via structured telephone interview using NIH TBI-CDEs v.2.0 Core, Basic, and Supplemental outcome measures.

Upon enrollment, data collection began in the hospital. For CA+MRI patients, the 2-week MRI was completed at 14 days ±4 days from the date of injury. Corresponding 2-week outcomes were completed ±3 days of the 2-week MM. For CA and BA patients, 2-week outcomes were completed ±4 days of 14 days from the date of injury. Outcomes at 3 months were completed ±7 days of 90 days from the date of injury. For CA+MRI patients, MRIs at 6 months were completed ±14 days of 180 days from the date of injury, with corresponding 6-month outcomes ±14 days of the 6-month MM. For CA and BA patients, 6-month outcomes were completed ±14 days of 180 days from the date of injury. BTACT should be completed with ±7 days of Outcomes (but not on the same day and no greater than 201 days from injury). Outcomes at 12 months were completed ±30 days of 360 days from the date of injury.

UCH-L1 was measured in a subset of 59 TRACK TBI patients in the i-STAT assay format (Table 4).

TABLE 4

Subject Characteristics by CT Scan and MRI Result

| Subject Characteristics | Total (n = 59) | CT or MRI Positive* (n = 46, 77.97%) | CT and MRI Negative* (n = 13, 22.03%) | P value |
|---|---|---|---|---|
| Age | 46.0 [24.0 to 60.0] | 45.5 [23.0 to 60.0] | 50.0 [39.0 to 57.0] | 0.7419 |
| Sex | | | | |
| Male | 50/59 (85%) | 39/46 (85%) | 11/13 (85%) | 1.000 |
| Female | 9/59 (15%) | 7/46 (15%) | 2/13 (15%) | |
| Race/Ethnicity | | | | |
| African-American or African | 6/58 (10%) | 4/45 (9%) | 2/13 (15%) | 0.2398 |
| Caucasian | 48/58 (83%) | 39/45 (87%) | 9/13 (69%) | |
| Hispanic | 4/58 (7%) | 2/45 (4%) | 2/13 (15%) | |
| TBI History | | | | |
| Yes, with No LOC | 9/56 (16%) | 3/43 (7%) | 6/13 (46%) | 0.0037 |
| Yes, with LOC | 8/56 (14%) | 6/43 (14%) | 2/13 (15%) | |
| No Prior TBI | 39/56 (70%) | 34/43 (79%) | 5/13 (38%) | |
| ED Presentation Loss of Conciousness | | | | |
| No | 6/58 (10%) | 2/45 (4%) | 4/13 (31%) | 0.0227 |
| Yes | 47/58 (81%) | 38/45 (84%) | 9/13 (69%) | |
| Unknown | 5/58 (9%) | 5/45 (11%) | | |
| Glasgow Coma Scale | 15.0 [3.0 to 15.0] | 14.0 [3.0 to 15.0] | 15.0 [15.0 to 15.0] | 0.0162 |
| Glasgow Coma Scale Classification | | | | |
| Severe (3-8) | 16/59 (27%) | 16/46 (35%) | | 0.0177 |
| Moderate (9-12) | 3/59 (5%) | 3/46 (7%) | | |
| Mild (13-15) | 40/59 (68%) | 27/46 (59%) | 13/13 (100%) | |
| Mechanism of Injury | | | | |
| Motor Vehicle (driver/passenger) | 10/59 (17%) | 9/46 (20%) | 1/13 (8%) | 0.2975 |
| Motorcycle/ATV/golf cart (driver/passenger) | 5/59 (8%) | 3/46 (7%) | 2/13 (15%) | |
| Individual struck by any type of vehicle | 3/59 (5%) | 2/46 (4%) | 1/13 (8%) | |
| Fall from a moving object (bike/skateboard/horse/etc.) | 3/59 (5%) | 3/46 (7%) | | |
| Fall from stationary object (roof/latter/etc.) | 27/59 (46%) | 20/46 (43%) | 7/13 (54%) | |
| Assault | 10/59 (17%) | 9/46 (20%) | 1/13 (8%) | |
| Struck on head by object, not assault (tree/etc.) | 1/59 (2%) | | 1/13 (8%) | |
| Alcohol Level (g/dL) | 0.1 [0.0 to 0.2] | 0.1 [0.0 to 0.2] | 0.0 [0.0 to 0.0] | 0.1588 |
| Drug Screen | | | | |
| Negative | 51/59 (86%) | 41/46 (89%) | 10/13 (77%) | 0.3567 |
| Positive | 8/59 (14%) | 5/46 (11%) | 3/13 (23%) | |
| Biomarker Results | | | | |
| Collection Time Since Injury (Minutes) | 771.0 (+/−339.8) | 779.4 (+/−296.8) | 743.0 (+/−468.7) | 0.7383 |
| UCH-L$_1$ (pg/mL) | 345.5 [102.8 to 718.3] | 514.0 [167.2 to 859.8] | 62.4 [44.5 to 136.8] | <0.001 |
| Prognostic Scores | | | | |
| Glasgow Outcome Scale (3 months) | 6.0 [5.0 to 7.0] | 5.5 [4.0 to 7.0] | 7.0 [7.0 to 7.0] | 0.0130 |

TABLE 4-continued

Subject Characteristics by CT Scan and MRI Result

| Subject Characteristics | Total (n = 59) | CT or MRI Positive* (n = 46, 77.97%) | CT and MRI Negative* (n = 13, 22.03%) | P value |
|---|---|---|---|---|
| Glasgow Outcome Scale (6 months) | 6.0 [5.0 to 7.0] | 6.0 [4.0 to 7.0] | 7.0 [5.5 to 7.5] | 0.1941 |
| Glasgow Outcome Scale (12 months) | 7.0 [5.0 to 8.0] | 6.5 [5.0 to 8.0] | 7.0 [6.6 to 8.0] | 0.4412 |
| Rivermead Questionnaire First 3 Items (6 months) | 0.0 [0.0 to 2.0] | 0.0 [0.0 to 2.5] | 0.0 [0.0 to 2.0] | 0.8378 |
| Rivermead Questionnaire Last 13 Items (6 months) | 9.0 [4.0 to 15.0] | 8.5 [4.0 to 15.0] | 13.0 [0.0 to 27.0] | 0.5449 |
| WAIS-III Processing Speed Index (6 months) | 30.0 [5.0 to 55.0] | 30.0 [5.0 to 50.0] | 43.0 [18.0 to 77.0] | 0.3235 |
| Satisfaction with Life Scale (6 months) | 21.5 (+/−6.2) | 21.7 (+/−5.7) | 20.4 (+/−8.5) | 0.6205 |
| Functional Independence Measure (6 months) | 126.0 [125.0 to 126.0] | 126.0 [124.0 to 126.0] | 126.0 [126.0 to 126.0] | 0.2958 |

*24 subjects received an MRI
Continuous variables are presented as median [25-75% Inter Quartile Range] and compared using Wilcoxon rank sum test or Mean (+/−SD) and compared using a t-test based on the distribution of the data.
Categorical variables are presented as number/total (percent) and compared using Chi-Square or Fisher's exact test.

In addition to a blood draw within 24 hours of brain injury, each patient had an extensive medical evaluation including head CT, neuropsychiatric testing, Glasgow Coma Score (GCS), and many patients also had a follow up MRI within 2 weeks of injury. Following a meticulous standardized blood draw protocol and processing, plasma samples were aliquotted for storage at −80° C., later thawed and tested. Each sample was run in duplicate with the listed results being an average of the two runs. FIG. 1 shows that UCH-L1 levels correlated with injury throughout the first 24 hours after injury (range approximately 2-23 hours). Table 4 shows that ethanol (ETOH) levels did not correlate with biomarker levels (Pearson Correlation=0.023, p-value=0.89) as ETOH consumption is frequently related to TBI, in particular severe TBI.

Table 5 shows the possible outcomes of TBI patients using a UCH-L1 reference level confirmed by CT scan.

TABLE 5

| | TBI Affection (head CT positive) | Not TBI affection (head CT negative) | |
|---|---|---|---|
| >reference level | True Positive (TP) | False Positives (FP) | Total Positives ($T_{POSITIVE}$) |
| <reference level | False Negatives (FN) | True Negatives (TN) | Total Negatives ($T_{NEGATIVE}$) |

TABLE 5-continued

| TBI Affection (head CT positive) | Not TBI affection (head CT negative) |
|---|---|
| Total TBI Affections ($T_{TBI}$) | Total Not TBI ($T_{NOT\ TBI}$) |

Sensitivity was determined by the test: $TP/T_{TBI}$ and specificity was determined by the test: $TN/T_{NOT\ TBI}$. PPV was determined by $TP/T_{POSITIVE}$. NPV was determined by $TN/T_{NEGATIVE}$. Accuracy was determined by $(TP+TN)/T_{ALL\ SUBJECTS}$.

Table 6 shows the results of using UCH-L1 cut-off levels of 100 pg/mL and 300 pg/mL compared to imaging results. Using these UCH-L1 cutoff values, a subject that has sustained or may have sustained a head injury can be evaluated for the presence or absence of a tramautic brain injury. For example, the methods of the present disclosure can determine that a subject with UCH-L1 levels of at least 100 pg/mL will have a greater than 86% probability of having sustained a traumatic brain injury based on imaging result. Additionally, the methods of the present disclosure can determine that a subject with UCH-L1 levels of at least 300 pg/mL will have a greater than 96% probability of having sustained a tramautic brain injury based on imaging result.

TABLE 6

Biomarker Cut-offs (Reference Levels) for UCH-L1 Compared to Imaging Results

| Imaging Method | UCH-L1 Reference Level (pg/mL) | Imaging Method | Biomarker Positive | Biomarker Negative | Sensitivity (95% CI) | Specificity (95% CI) | PPV (95% CI) | NPV (95% CI) |
|---|---|---|---|---|---|---|---|---|
| CT | 100 | Positive | 39 (A) | 6 (B) | 88.64% (39/44) (75.44%, 96.21%) | 60.00% (9/15) (32.29%, 83.66%) | 86.67% (39/45) (73.21%, 94.95%) | 64.29% (9/14) (35.14%, 87.24%) |
| | | Negative | 5 (C) | 9 (D) | | | | |
| MRI or CT | 100 | Positive | 40 (A) | 5 (B) | 86.96% (40/46) (73.74%, 95.06%) | 61.54% (8/13) (31.58%, 86.14%) | 88.89% (40/45) (75.95%, 96.29%) | 57.14% (8/14) (28.86%, 82.34%) |
| | | Negative | 6 (C) | 8 (D) | | | | |

TABLE 6-continued

Biomarker Cut-offs (Reference Levels) for UCH-L1 Compared to Imaging Results

| Imaging Method | UCH-L1 Reference Level (pg/mL) | Imaging Method | Biomarker Positive | Biomarker Negative | Sensitivity (95% CI) | Specificity (95% CI) | PPV (95% CI) | NPV (95% CI) |
|---|---|---|---|---|---|---|---|---|
| CT | 300 | Positive | 30 (A) | 1 (B) | 68.18% (30/44) (52.42%, 81.39%) | 93.33% (14/15) (68.05%, 99.83%) | 96.77% (30/31) (83.30%, 99.92%) | 50.00% (14/28) (30.65%, 69.35%) |
|  |  | Negative | 14 (C) | 14 (D) |  |  |  |  |
| MRI or CT | 300 | Positive | 31 (A) | 0 (B) | 67.39% (31/46) (51.98%, 80.47%) | 100.00% (13/13) (75.29%, 100.00%) | 100.00% (31/31) (88.78%, 100.00%) | 46.43% (13/28) (27.51%, 66.13%) |
|  |  | Negative | 15 (C) | 13 (D) |  |  |  |  |

Sensitivity = A/(A + C) times 100
Specificity = D/(B + D) times 100
PPV = A/(A + B) times 100
NPV = D/(C + D) times 100
*Note: In the above table, "Biomarker Cutoff" and Biomarker Reference Level are used interchangeably herein.

Using a reference level of 300 pg/mL for the UCH-L1 assay in this sample size population, the biomarker results were highly predictive of the Extended Glasgow Outcome Score (GOSE) at 3 months (p-value=0.0082). UCH-L1 levels correlated with injury throughout the first 24 hours after injury (range approximately 2-23 hours). This time of appearance to disappearance of markers exceeds initial expectations of this assay. This data demonstrates superior sensitivity/specificity and range of the UCH-L1 assay in predicting need for head CT/MRI patients with TBI.

Figure 2:
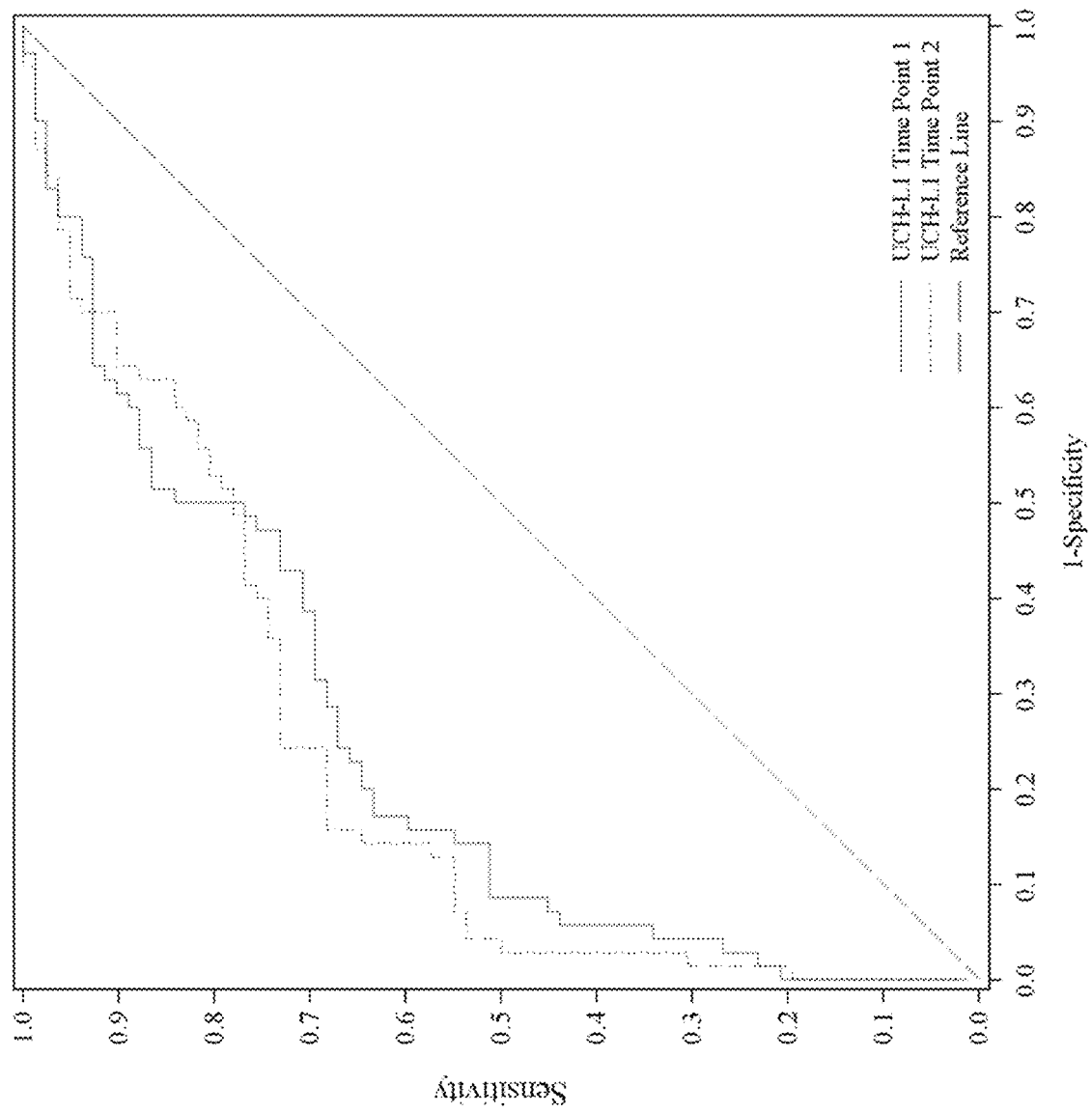
FIG. 2 shows a receiver operating characteristic (ROC) analysis of UCH-L1 levels correlated with CT by time point.
Figure 3:
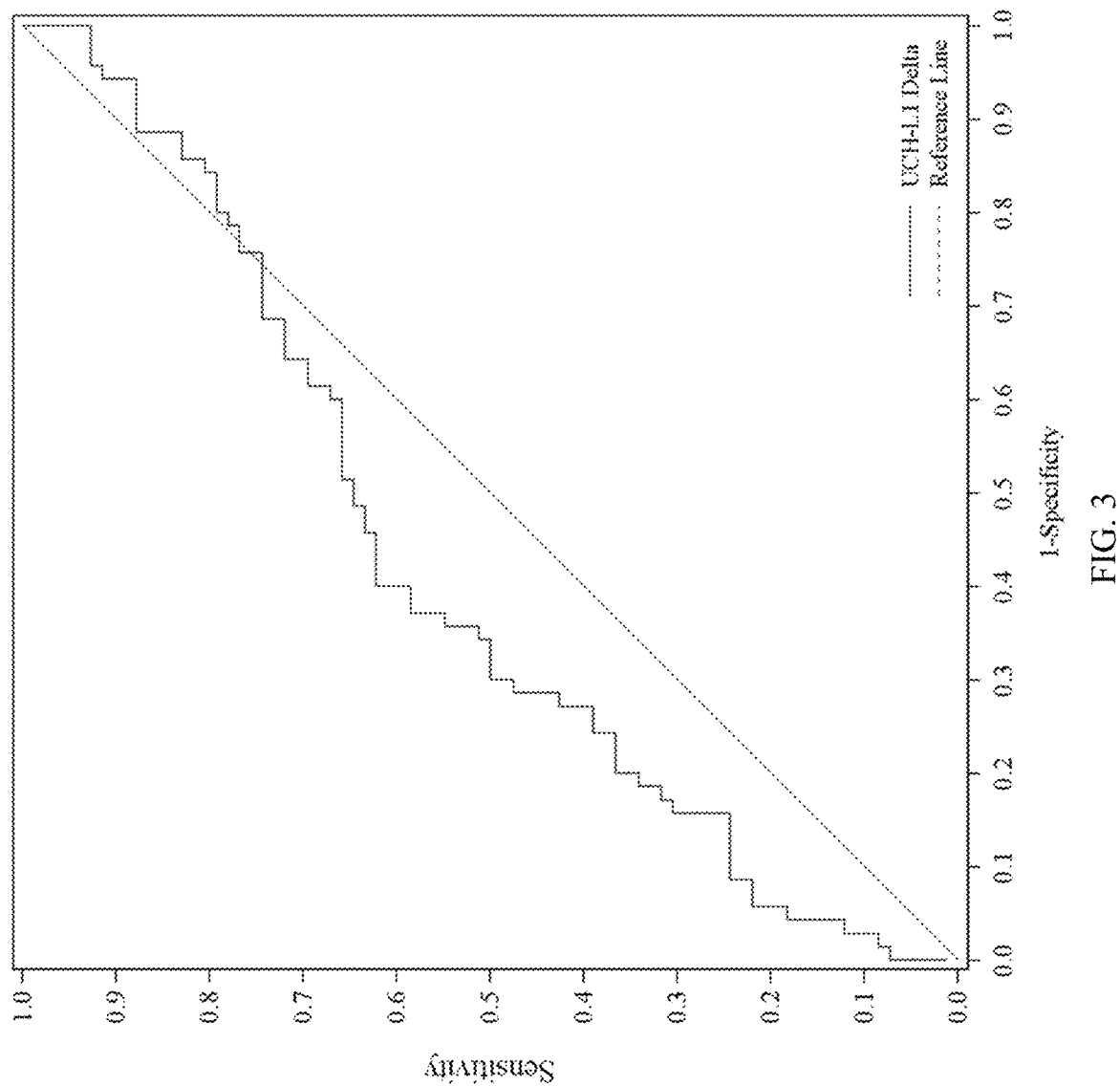
FIG. 3 shows receiver operating characteristic (ROC) analysis of change in UCH-L1 levels at time point 2 compared to time point 1 ("delta" (i.e., time point 2-time point 1)) correlated with CT.
Figure 4:
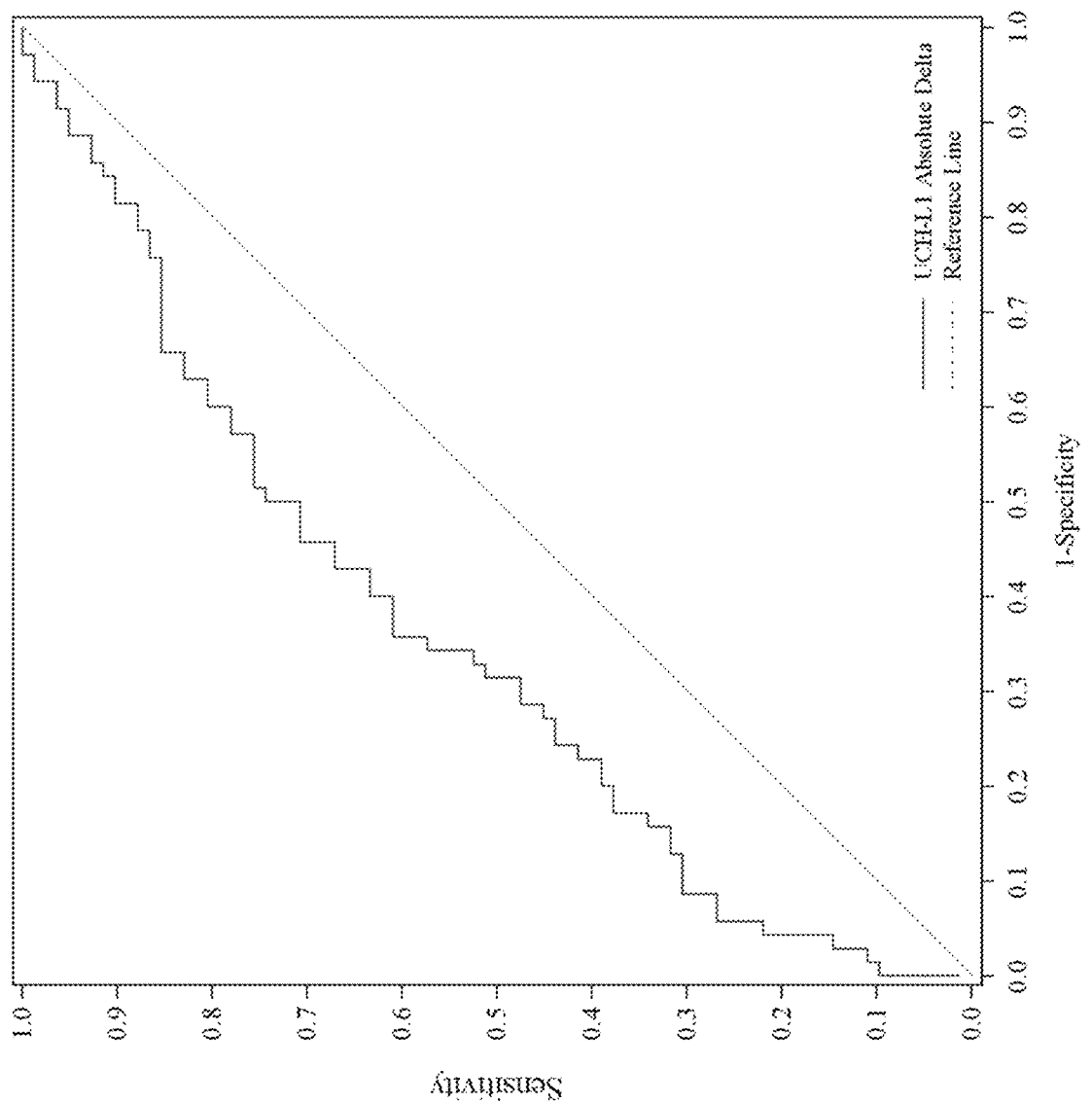
FIG. 4 shows receiver operating characteristic (ROC) analysis of absolute amount ("absolute delta") of UCH-L1 results (i.e., the absolute difference between UCH-L1 levels at Time Point 2 and UCH-L1 levels at Time Point 1) correlated with CT.

FIGS. 2 and 3 show receiver operating characteristic (ROC) analysis of UCH-L1 and CT scan results for all of the subjects by Time Point (FIG. 2) and by change in UCH-L1 levels at Time Point 2 compared to Time Point 1 (FIG. 3). FIG. 4 shows the receiver operating characteristic (ROC) analysis of UCH-L1 levels and CT scan results for all of the subjects by the absolute amount ("absolute delta") (i.e., change between the UCH-L1 levels in the first time point ("Time Point 1") to the UCH-L1 levels in the second time point ("Time Point 2")).

Figure 5:
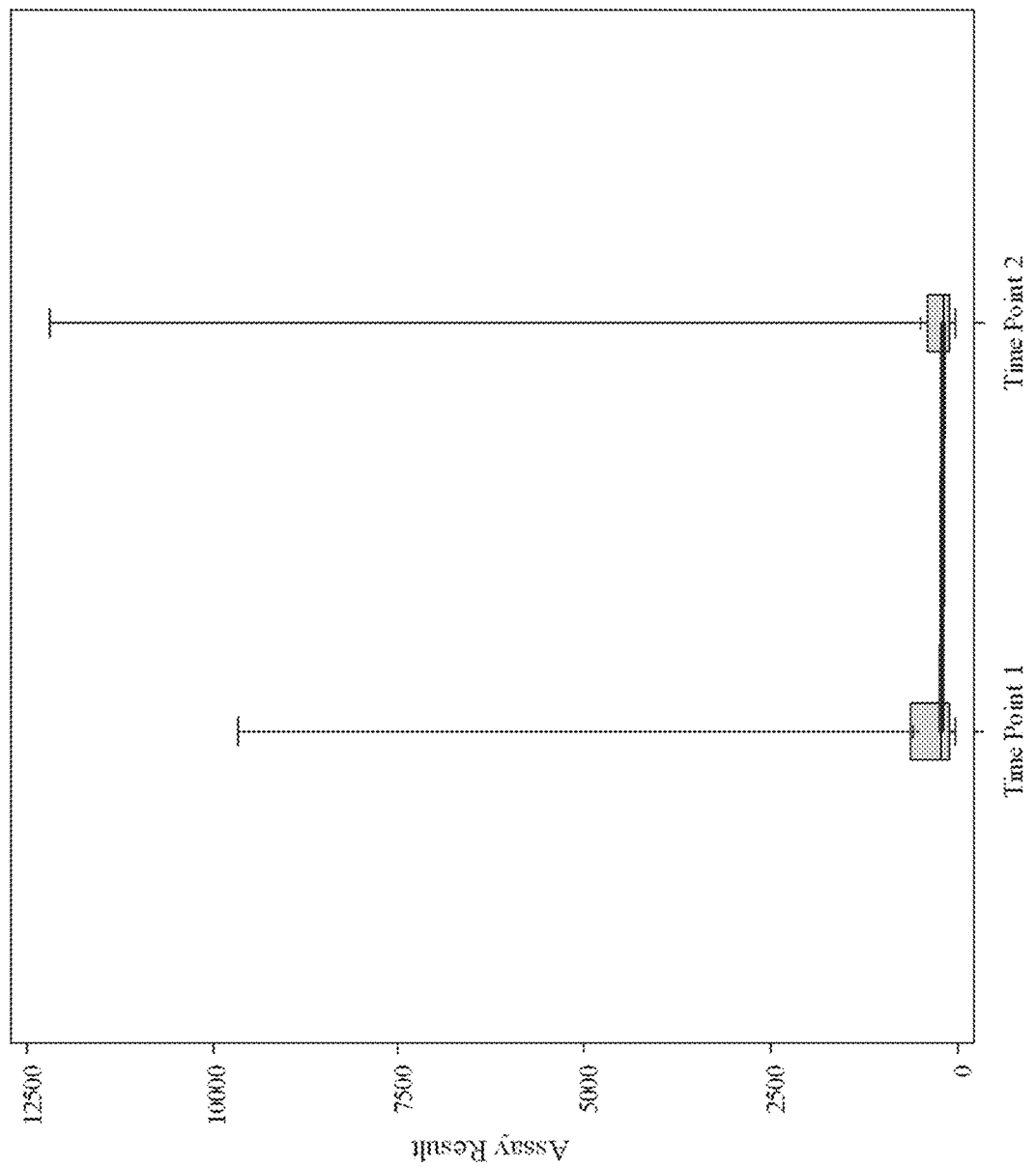
FIG. 5 shows a box plot of UCH-L1 assay results by time point.
Figure 6:
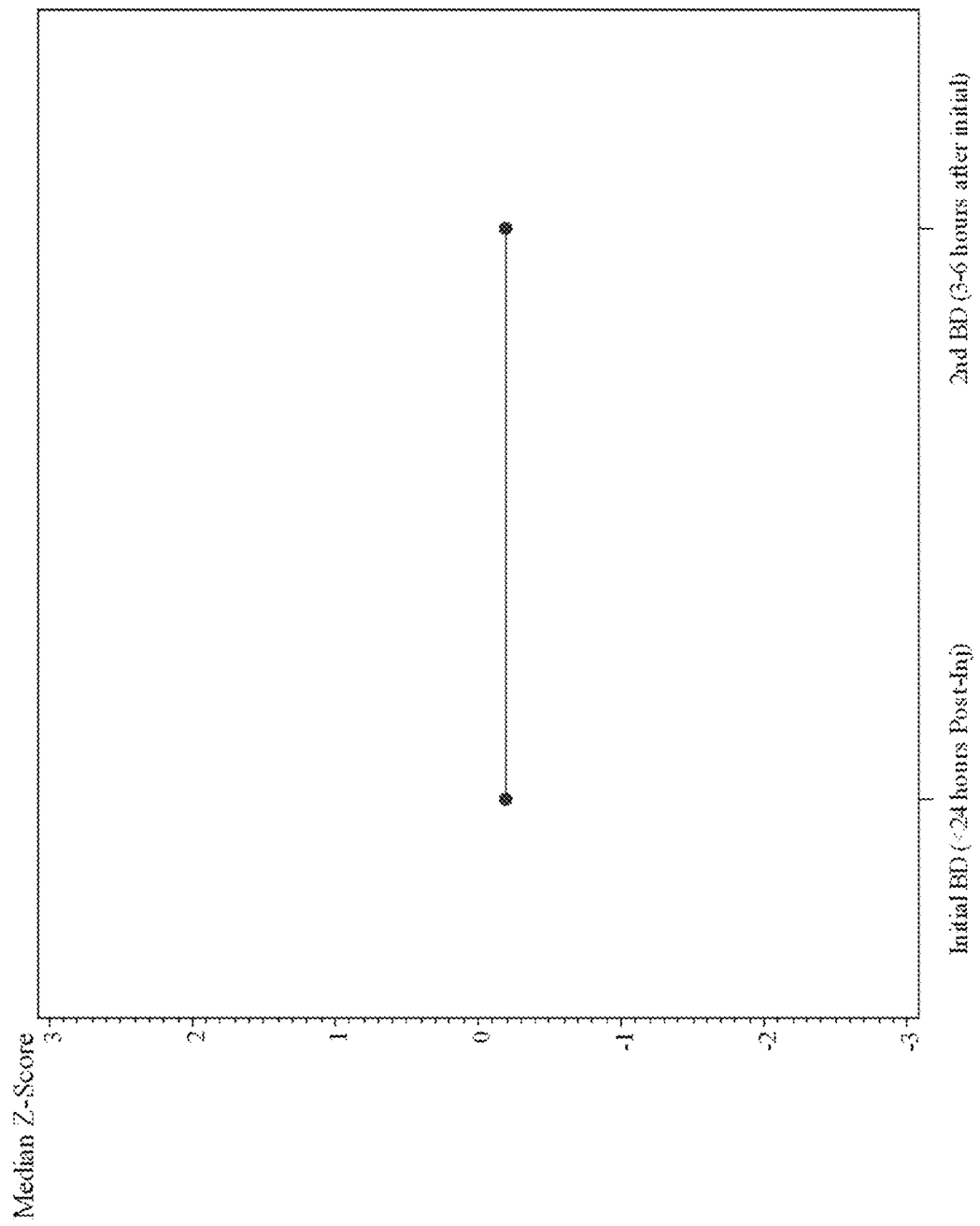
FIG. 6 shows assay kinetics median Z-score of testing results by time point.

Table 7 shows the analysis of TRACK data in a sample size of 191 patients, specifically, the analysis of the change between Time Point 2 and Time Point 1 in UCH-L1 levels. The Time Point 1 sample was taken within 24 hours from injury and Time Point 2 sample was taken about 3-6 hours after the Time Point 1 sample was taken. UCH-L1 appears to have a significant change from Time Point 1 to Time Point 2 (n=191, median delta (i.e., change from Time Point 1 to Time Point 2)=−38 pg/mL, Wilcoxon Signed-Rank Test p-value <0.0001). See also FIGS. 5 and 6. FIG. 5 shows a box and whisker plot indicating the UCH-L1 levels determined in all of the patients of the study at Time Point 1 and Time Point 2. FIG. 6 shows the assay kinetics median Z-score of testing results by time point. These data were simply analyses comparing the time points, and are not based on CT, MRI or GCS +/−.

TABLE 7

| Assay | Sample Size (n) | Median Delta | Minimum Delta | Maximum Delta | Wilcoxon Signed-Rank Statistic | P value |
|---|---|---|---|---|---|---|
| UCH-L1 | 191 | −38 | −6070 | 2528 | −5398.5 | <0.0001 |

The TRACK data from the 191 samples was further analyzed based on when the Time Point 1 sample was taken, e.g., 0 to about 6 hours after injury ("0-6 hour group"), about 6 to about 12 hours after injury ("6-12 hour group") and correlated with head CT scan results and/or GCS scores. The UCH-L1 levels in the Time Point 1 and Time Point 2 samples were compared to the positive or negative head CT scan results and/or GCS scores indicating mild or moderate/severe TBI. As this analysis was based on the time of when the Time Point 1 sample was taken, the number of subjects per group was small. See Table 8.

TABLE 8

|  |  | Time Range (hours)* | | | | | Total # of Subjects |
|---|---|---|---|---|---|---|---|
|  |  | 0-6 | 6-12 | 12-18 | 18-24 | >24 |  |
| CT Scan | Positive | 6 | 21 | 33 | 31 | 4 | 95 |
|  | Negative | 8 | 17 | 25 | 25 | 0 | 75 |
| GCS Score | Mild | 12 | 27 | 45 | 41 | 1 | 126 |
|  | Moderate/Severe | 2 | 10 | 15 | 15 | 2 | 44 |

*time of first sample taken from time of injury

Figure 7B:
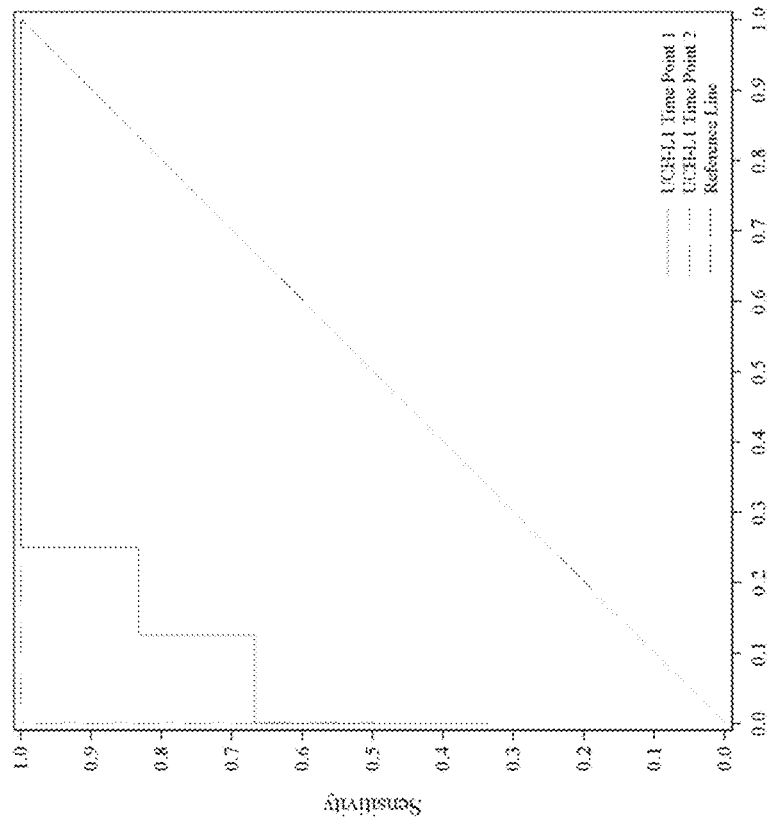
FIG. 7B shows ROC curve of UCH-L1 assay results at Time Point 1 and Time Point 2 correlated with positive vs. negative CT scan results.
Figure 7A:
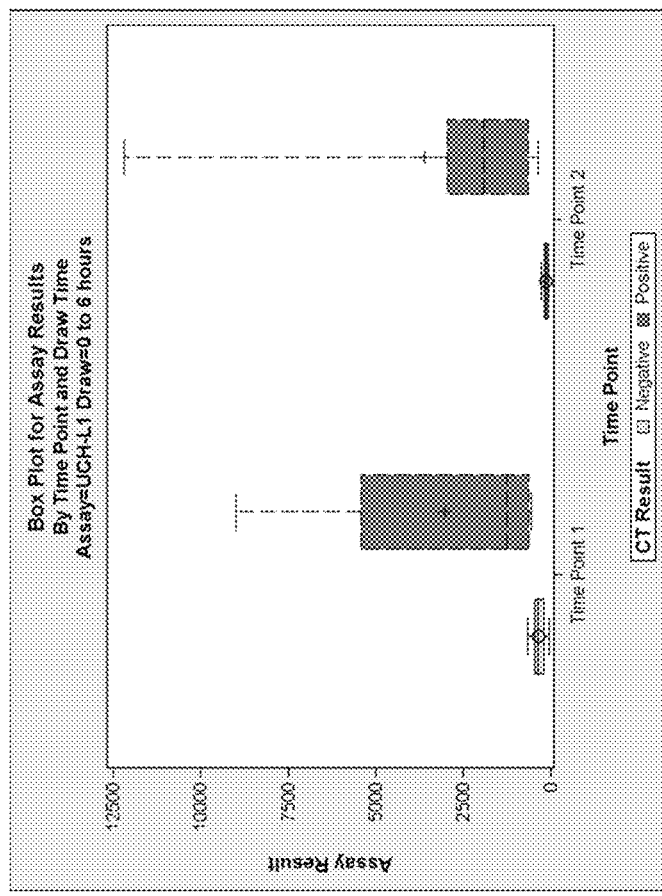
FIG. 7A shows box plot of UCH-L1 assay results at Time Point 1 (taken within 0 to 6 hours after head injury) and Time Point 2 (taken 3 to 6 hours after the sample of Time Point 1) correlated with positive vs. negative CT scan results.
Figure 8B:
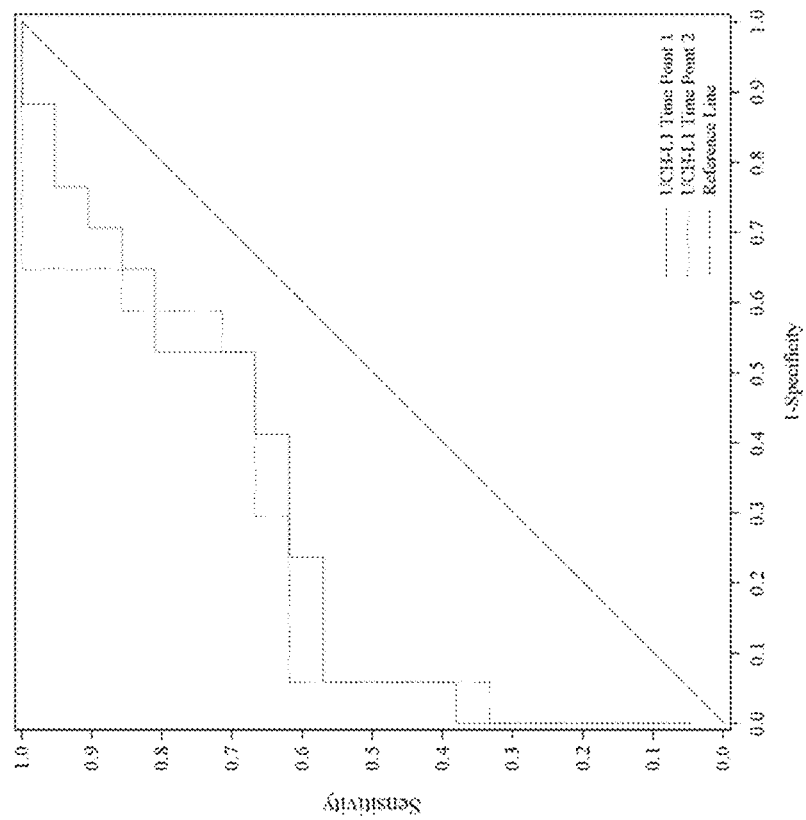
FIG. 8B shows ROC curve of UCH-L1 assay results at Time Point 1 and Time Point 2 correlated with positive vs. negative CT scan results.
Figure 8A:
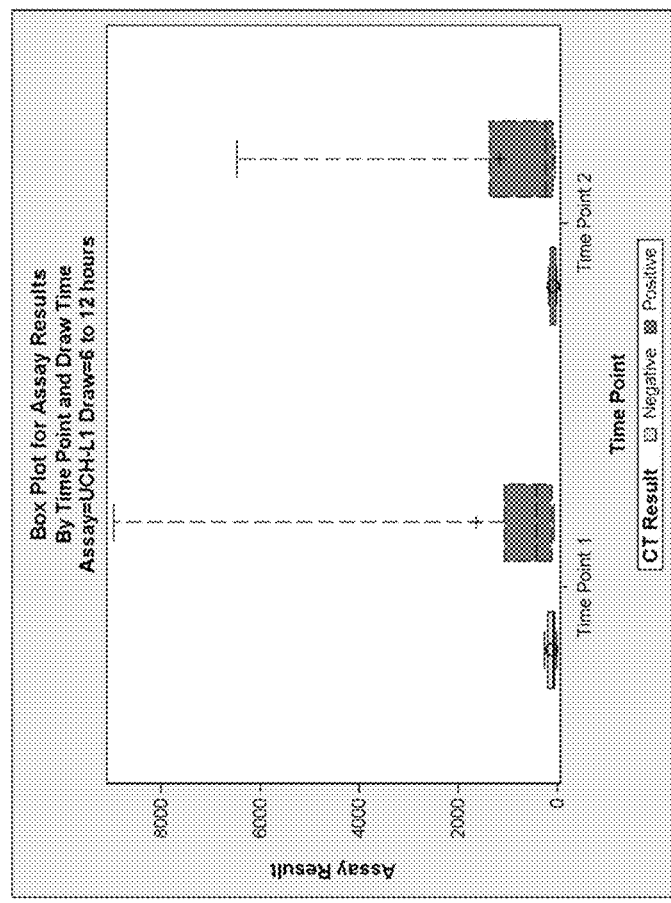
FIG. 8A shows box plot of UCH-L1 assay results at Time Point 1 (taken within 6 to 12 hours after head injury) and Time Point 2 (taken 3 to 6 hours after the sample of Time Point 1) correlated with positive vs. negative CT scan results.

CT Scan. FIGS. 7A and 7B show the UCH-L1 results in the subjects from the 0-6 hour group that had positive or negative head CT scans. FIGS. 8A and 8B show the UCH-L1 results in the subjects from the 6-12 hour group that had positive or negative head CT scans. FIGS. 7A and 8A show the distribution of the UCH-L1 levels at Time Point 1 and Time Point 2 in the subjects that had a positive or negative CT scan. The UCH-L1 levels in the CT positive subjects were higher than the CT negative subjects at both Time Point 1 and Time Point 2 for both the 0-6 hour group and the 6-12 hour group. The UCH-L1 levels in the subjects from the 0-6 hour group having a positive CT scan had a striking decrease from Time Point 1 to Time Point 2. FIGS. 7B and 8B show the ROC curves correlating the UCH-L1 levels at Time Point 1 and Time Point 2 with CT scan result. The sensitivity and specificity of reference levels for 0-6 hour and 6-12 hour groups based on the ROC curves are shown in Table 9.

TABLE 9

| Time Range | Reference Level (pg/mL) | Sensitivity | Specificity |
|---|---|---|---|
| 0-6 | 370 | 100 | 37.5 |
| 0-6 | 509 | 100 | 75 |
| 6-12 | 96 | 96 | 30 |
| 6-12 | 98 | 86 | 35 |

Figure 9B:
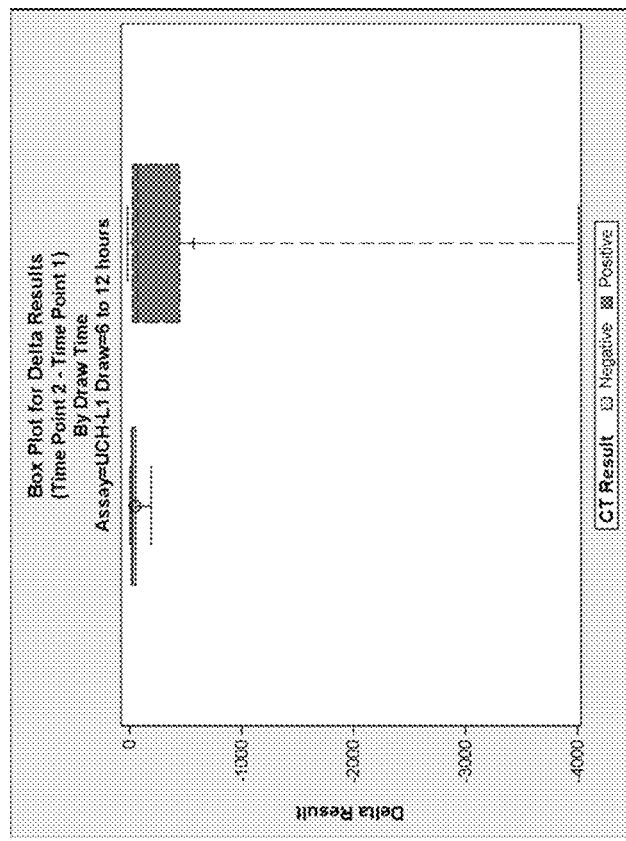
FIGS. 9A and 9B show box plots of the difference or change between Time Point 2 and Time Point 1 ("delta") UCH-L1 assay results correlated with positive vs. negative CT scan results by time range of when the first sample was taken.
Figure 9A:
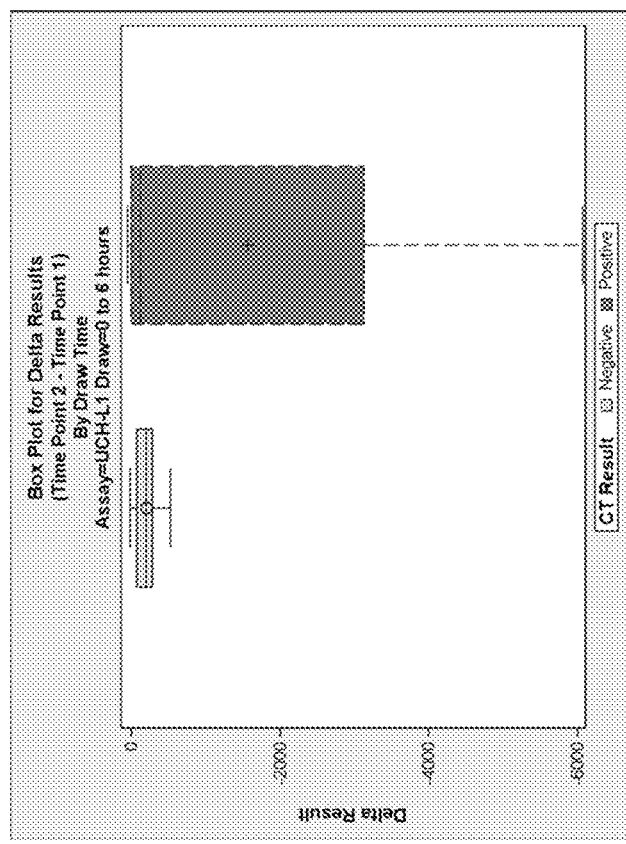
Figure 10B:
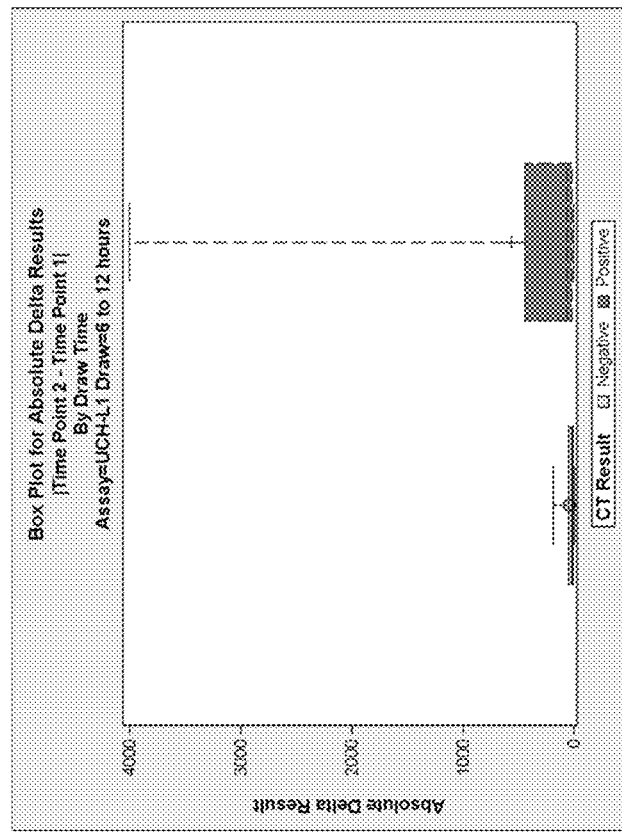
FIGS. 10A and 10B show box plots of absolute amount ("absolute delta") of UCH-L1 results (i.e., the absolute difference between Time Point 2 and Time Point 1) correlated with positive vs. negative CT scan results by time range of when the first sample was taken.
Figure 10A:
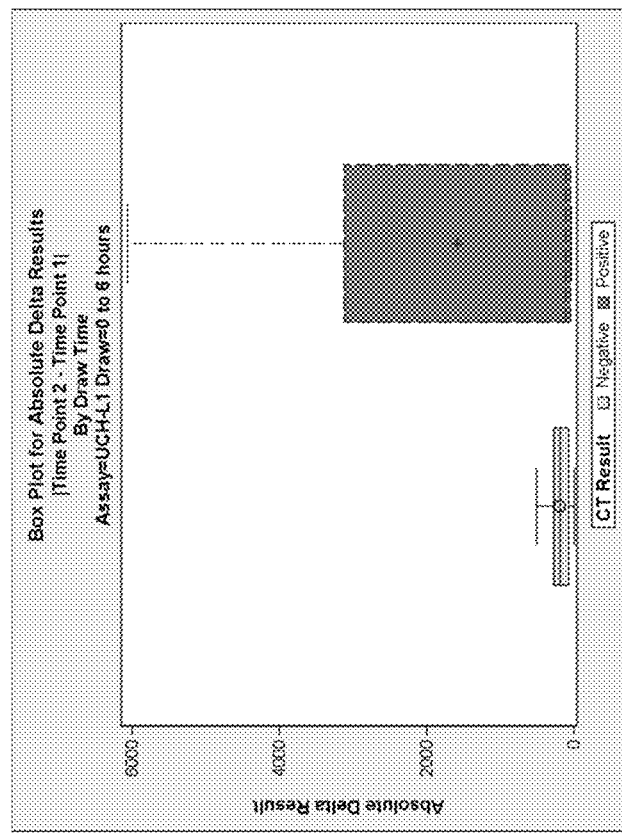
Figure 18:
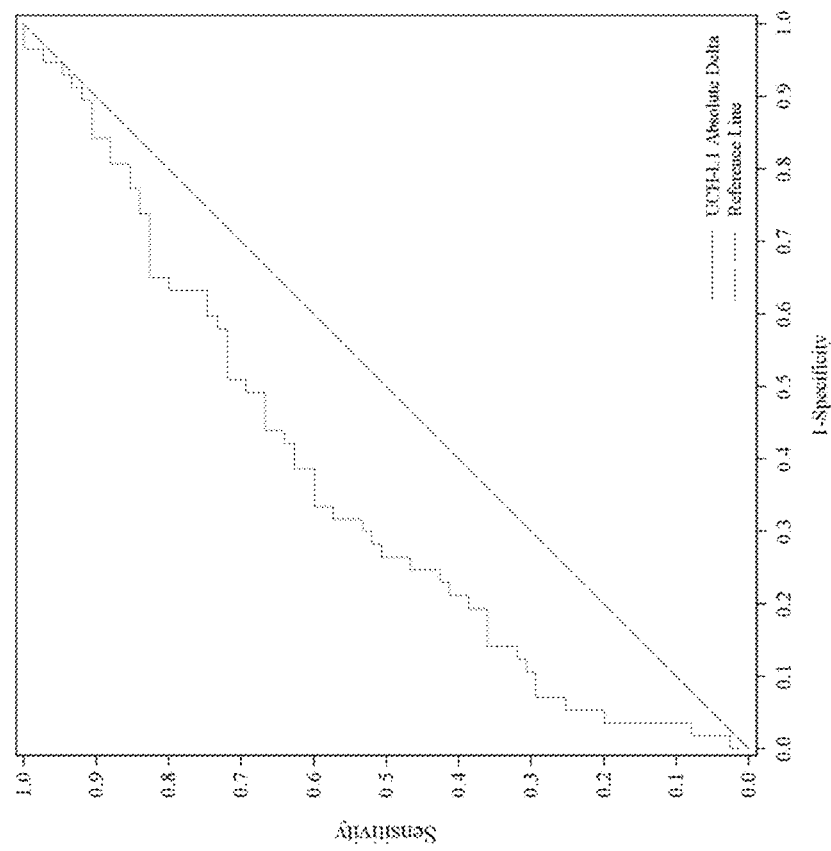
FIG. 18 shows ROC curve of absolute amount ("absolute delta") of UCH-L1 results (i.e., the absolute difference between Time Point 1 (taken more than 10 hours after head injury) and Time Point 2 (taken 3 to 6 hours after the sample of Time Point 1)) correlated with CT scan.
Figure 17:
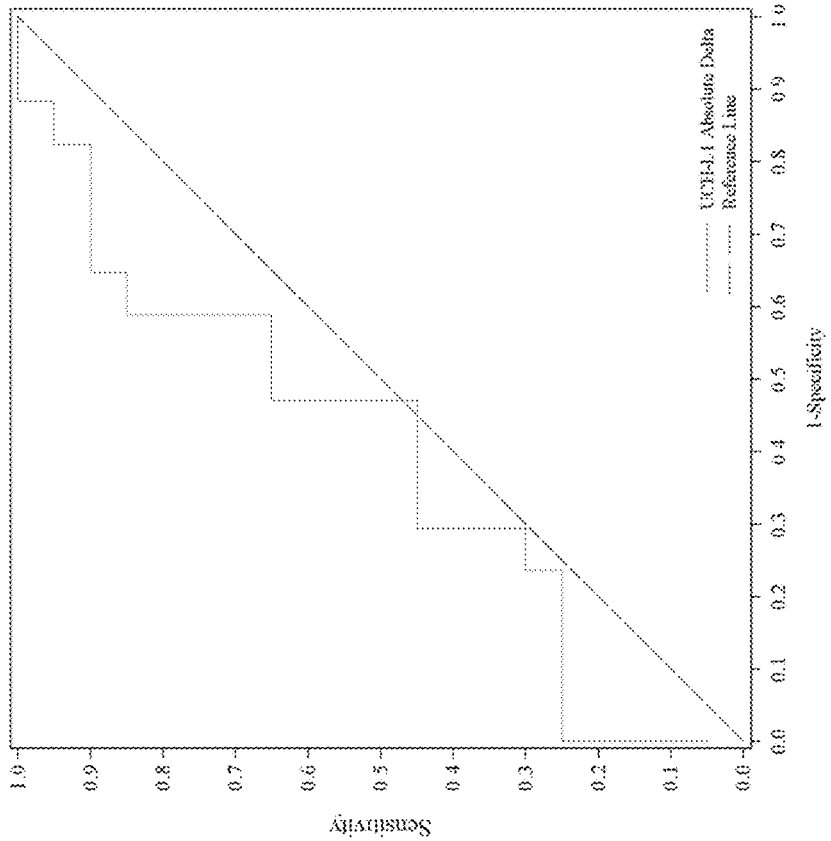
FIG. 17 shows ROC curve of absolute amount ("absolute delta") of UCH-L1 results (i.e., the absolute difference between Time Point 1 (taken within 0 to 10 hours after head injury) and Time Point 2 (taken 3 to 6 hours after the sample of Time Point 1)) correlated with CT scan.

FIG. 9A shows the change ("delta") in UCH-L1 levels of the Time Point 2 sample from the Time Point 1 sample in subjects from the 0-6 hour group that had positive or negative head CT scans, while FIG. 10A shows the absolute amount ("absolute delta") in UCH-L1 levels of this group. FIG. 9B shows the change ("delta") in UCH-L1 levels in the Time Point 2 sample from the Time Point 1 sample in subjects from the 6-12 hour group that had positive or negative head CT scans, while FIG. 10B shows the absolute amount ("absolute delta") in UCH-L1 levels of this group. Subjects having a positive head CT scan had a greater decrease or change in UCH-L1 levels from Time Point 1 to Time Point 2 compared to subjects having a negative head CT scan. The subjects from the 0-6 hour group had a larger change in UCH-L1 levels compared to subjects from the 6-12 hour group. The data was analyzed to examine samples in which the Time Point 1 sample was taken between 0-10 hours after injury ("0-10 hour group") and compared to the respective Time Point 2 samples, as well as samples in which the Time Point 1 sample was taken more than 10 hours after injury (">10 hour group") and compared to the respective Time Point 2 samples. FIGS. 17 and 18 show the ROC curves correlating the absolute amount ("absolute delta") in UCH-L1 levels with the CT scan result for the 0-10 hour group and >10 hour group, respectively. The sensitivity and specificity of absolute amounts (or change between Time Point 1 and Time Point 2) in UCH-L1 levels for the 0-10 hour group based on the ROC curves are shown in Table 10.

TABLE 10

| Time Range | Absolute amount (pg/mL) | Sensitivity (%) | Specificity (%) |
|---|---|---|---|
| 0-10 | 25 | 85 | 41 |
| 0-10 | 23 | 90 | 35 |

Fold Change Analysis for CT Scan.

Figure 16:
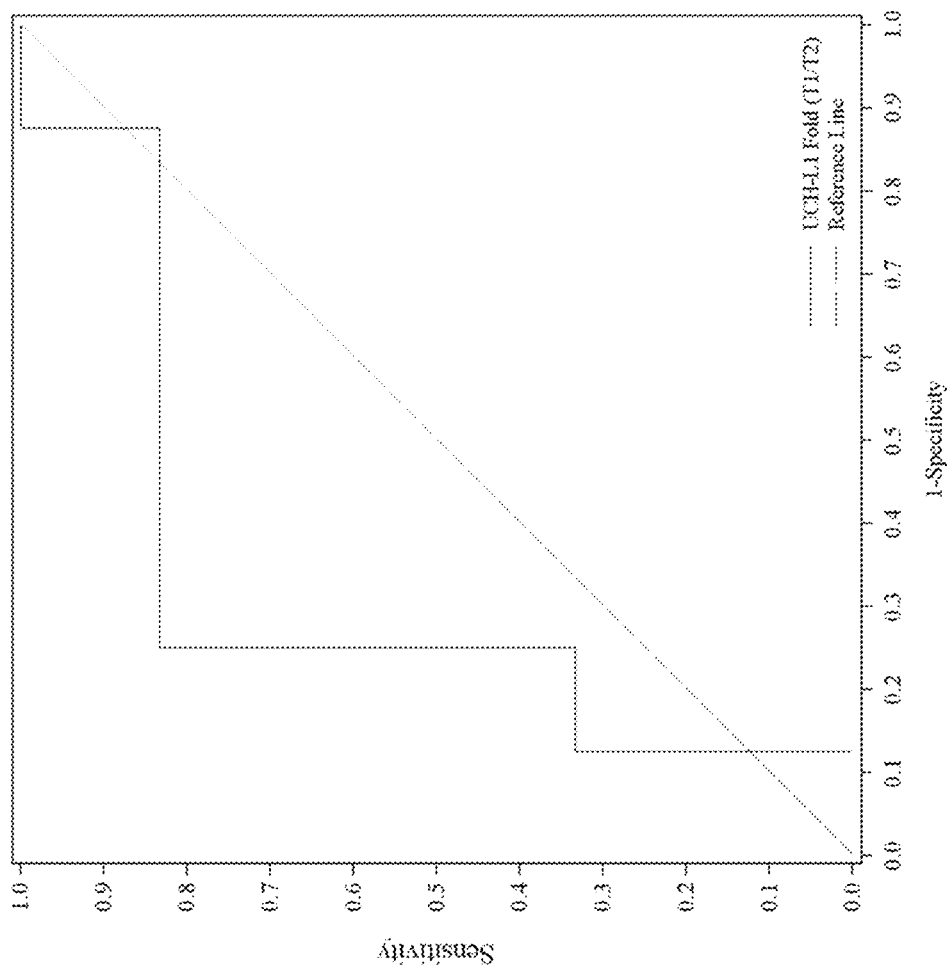
FIG. 16 shows ROC curve of fold change in the UCH-L1 levels between Time Point 1 (taken within 0 to 6 hours after head injury) and Time Point 2 (taken 3 to 6 hours after the sample of Time Point 1) correlated with mild vs. moderate/severe TBI GCS scores.

The fold-change between the levels in Time Point 1 and Time Point 2 was determined in 12-14 subjects of the 0-6 hour group. FIG. 16 shows a ROC curve of the fold-change in the UCH-L1 levels (UCH-L1 levels at Time Point 1/UCH-L1 levels at Time Point 2) correlated with a positive or negative head CT scan. The fold reference level of 1.5 (i.e., Time Point 1 result/Time Point 2 result) had a sensitivity of 83% and specificity of 75% if the Time Point 1 sample is taken within the first 6 hours after injury. This fold reference level does well at predicting a positive CT in a subject, wherein a fold-change less than 1.5 predicted a positive CT scan result in the subject.

The fold-change between the levels in Time Point 1 and Time Point 2 was determined in subjects of the 0-12 hour group. A ROC curve of the fold-change in the UCH-L1 levels (UCH-L1 levels at Time Point 1/UCH-L1 levels at Time Point 2) was correlated with a positive or negative head CT scan (data not shown). The fold reference level of 1.81 (i.e., Time Point 1 result/Time Point 2 result) had a sensitivity of 93% and specificity of 36% if the Time Point 1 sample is taken within the first 12 hours after injury. This fold reference level does well at predicting a positive CT in a subject, wherein a fold-change less than 1.81 predicted a positive CT scan result in the subject and thus classifies the subject as needing a CT scan. A ROC curve of the fold-change in the UCH-L1 levels (UCH-L1 levels at Time Point 2/UCH-L1 levels at Time Point 1) was correlated with a positive or negative head CT scan (data not shown). The fold reference level of 0.55 (i.e., Time Point 2 result/Time Point 1 result) had a sensitivity of 93% and specificity of 36% if the Time Point 1 sample is taken within the first 12 hours after injury. This fold reference level does well at predicting a positive CT in a subject, wherein a fold-change more than 0.55 predicted a positive CT scan result in the subject and thus classifies the subject as needing a CT scan, while a fold-change less than 0.55 classifies the subject as negative for needing a CT scan.

ROC analysis was also performed to show that if the UCH-L1 level at time point 1 is greater than 550 pg/mL or if the fold-change between time point 2 and time point 1 is greater than 0.55, then the subject is classified as positive for needing a CT scan; if the UCH-L1 level at time point 1 is less than 550 pg/mL or if the fold-change between time point 2 and time point 1 is less than 0.55, then the subject is classified as negative for needing a CT scan. These reference levels had a sensitivity of 100% and specificity of 32%.

GCS Scores.

Figure 11B:
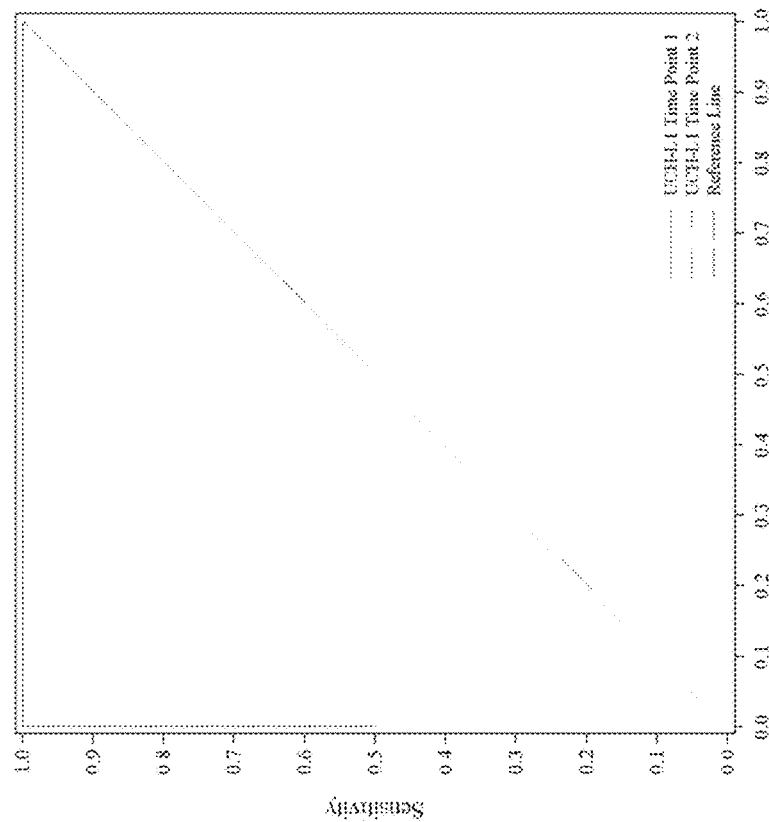
FIG. 11B shows ROC curve of UCH-L1 assay results at Time Point 1 and Time Point 2 correlated with mild vs. moderate/severe TBI GCS scores.
Figure 11A:
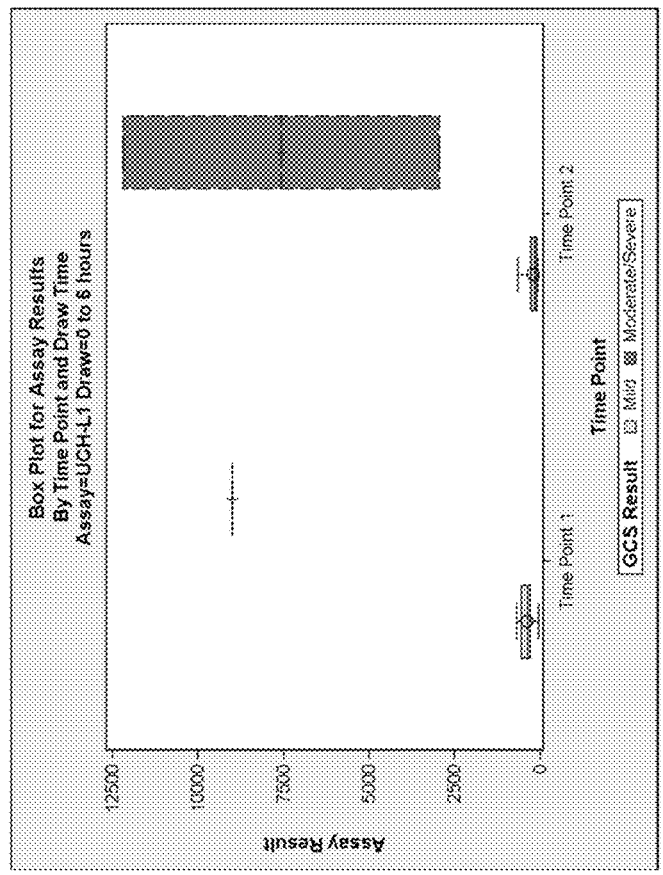
FIG. 11A shows box plot of UCH-L1 assay results at Time Point 1 (taken within 0 to 6 hours after head injury) and Time Point 2 (taken 3 to 6 hours after the sample of Time Point 1) correlated with mild vs. moderate/severe TBI GCS scores.
Figure 12B:
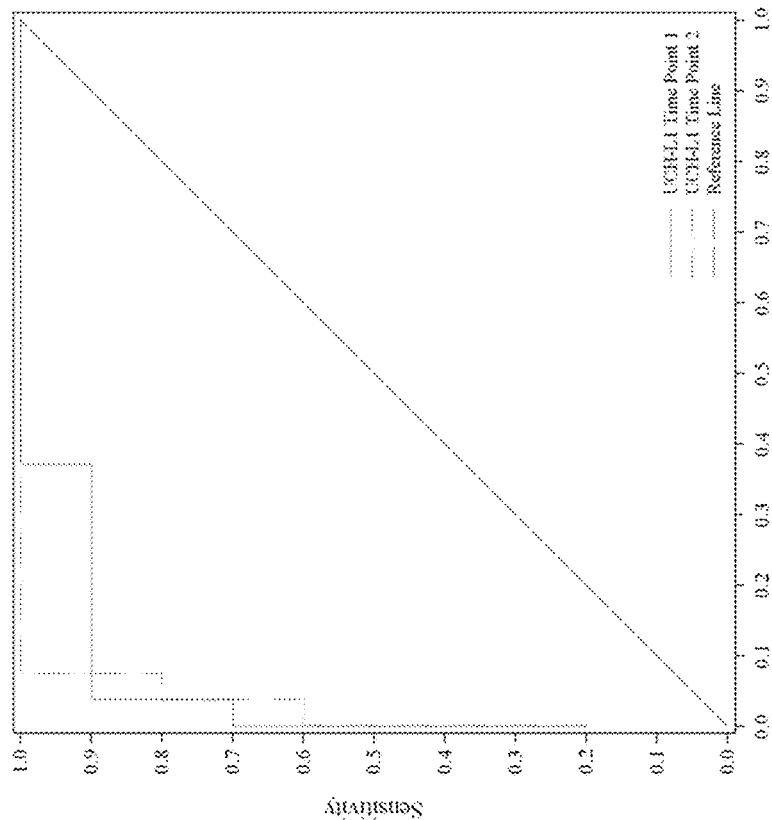
FIG. 12B shows ROC curve of UCH-L1 assay results at Time Point 1 and Time Point 2 correlated with mild vs. moderate/severe TBI GCS scores.
Figure 12A:
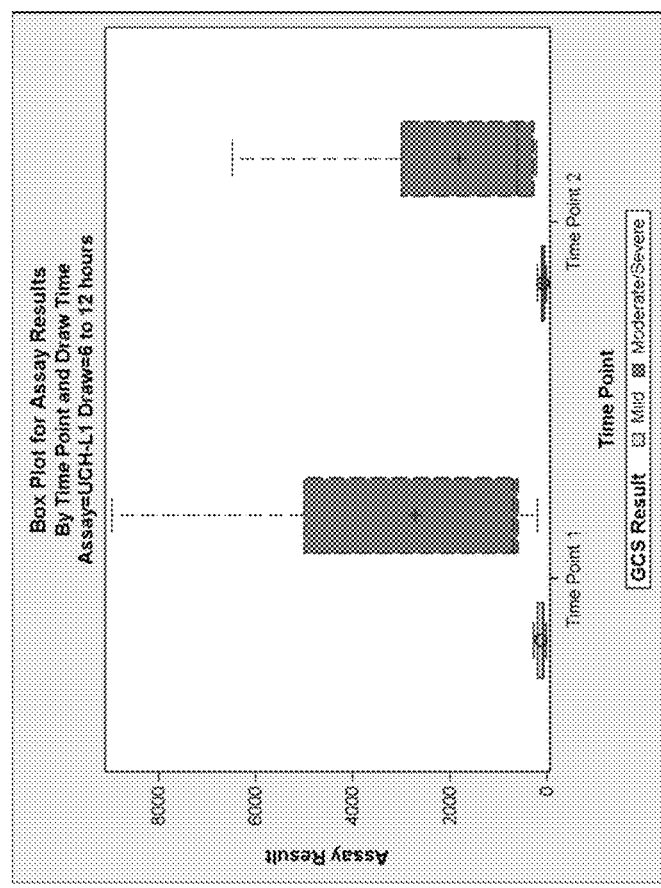
FIG. 12A shows box plot of UCH-L1 assay results at Time Point 1 (taken within 6 to 12 hours after head injury) and Time Point 2 (taken 3 to 6 hours after the sample of Time Point 1) correlated with mild vs. moderate/severe TBI GCS scores.

FIGS. 11A and 11B show the UCH-L1 results in the subjects from the 0-6 hour group that were identified as having mild or moderate to severe ("moderate/severe") TBI based on their GCS score. FIGS. 12A and 12B show the UCH-L1 results in the subjects from the 6-12 hour group that were identified as having mild or moderate to severe ("moderate/severe") TBI based on their GCS score. FIGS. 11A and 12A show the distribution of the UCH-L1 levels at Time Point 1 and Time Point 2 in the subjects determined to have mild or moderate/severe. The UCH-L1 levels in the moderate/severe subjects were significantly higher than the mild subjects at both Time Point 1 and Time Point 2 for both the 0-6 hour group and the 6-12 hour group. The UCH-L1 levels in the 0-6 hour group and 6-12 hour group had a striking decrease from Time Point 1 to Time Point 2. FIGS. 11B and 12B show the ROC curves correlating the UCH-L1 levels at Time Point 1 and Time Point 2 with GCS scores. The sensitivity and specificity of reference levels for 0-6 hour and 6-12 hour groups based on the ROC curves are shown in Table 11.

TABLE 11

| Time Range | Reference Level (pg/mL) | Sensitivity | Specificity |
|---|---|---|---|
| 0-6 | 311 | 100 | 33 |
| 0-6 | 509 | 100 | 66 |
| 0-6 | 710 | 100 | 92 |
| 0-6 | 9019 | 100 | 100 |
| 6-12 | 98 | 100 | 30 |
| 6-12 | 209 | 100 | 63 |
| 6-12 | 238 | 90 | 70 |
| 6-12 | 569 | 90 | 96 |

Figure 13B:
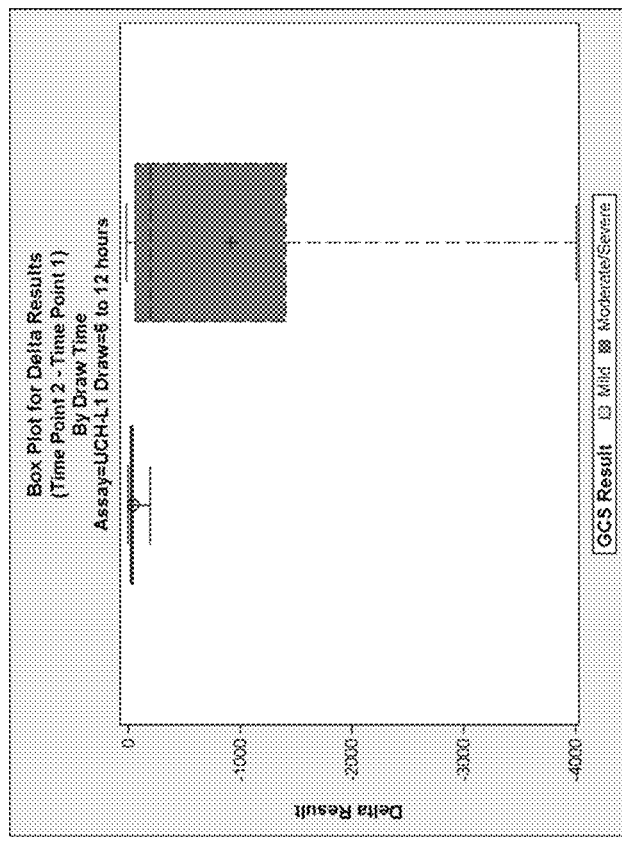
FIGS. 13A and 13B show box plots of the difference or change between Time Point 2 and Time Point 1 ("delta") UCH-L1 assay results correlated with mild vs. moderate/severe TBI GCS scores by time range of when the first sample was taken.
Figure 13A:
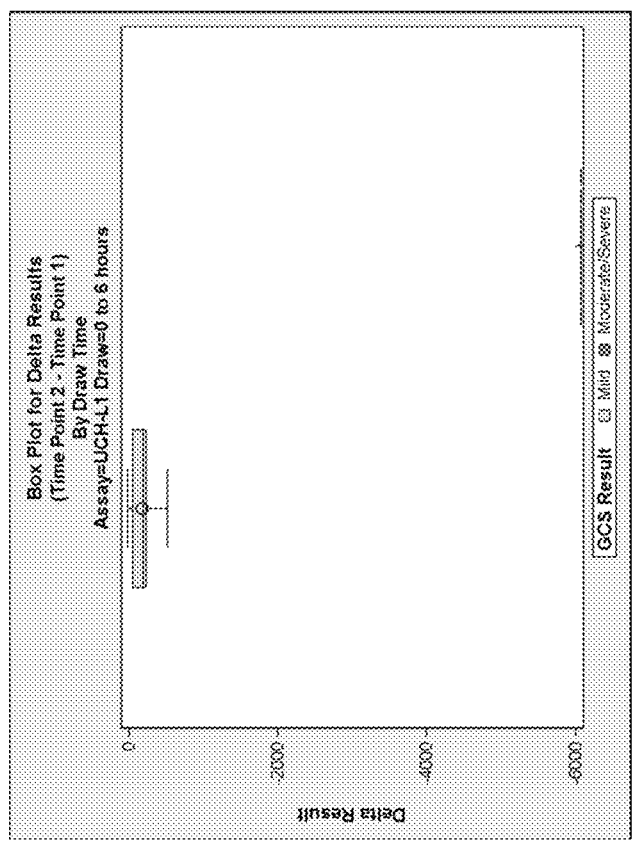

FIG. 13A shows the change ("delta") in UCH-L1 levels of the Time Point 2 sample from the Time Point 1 sample in subjects of the 0-6 hour group. FIG. 13B shows the change ("delta") in UCH-L1 levels in the Time Point 2 sample from the Time Point 1 sample in subjects of the 6-12 hour group.

Figure 14B:
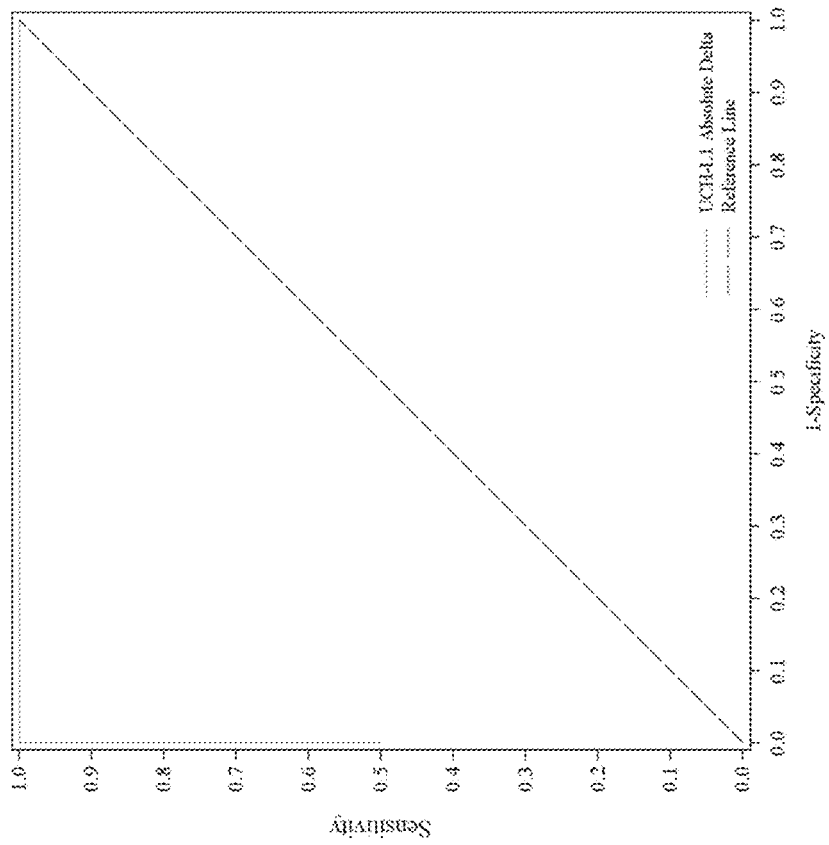
FIG. 14B shows ROC curve of absolute amount ("absolute delta") UCH-L1 assay results correlated with mild vs. moderate/severe TBI GCS scores.
Figure 14A:
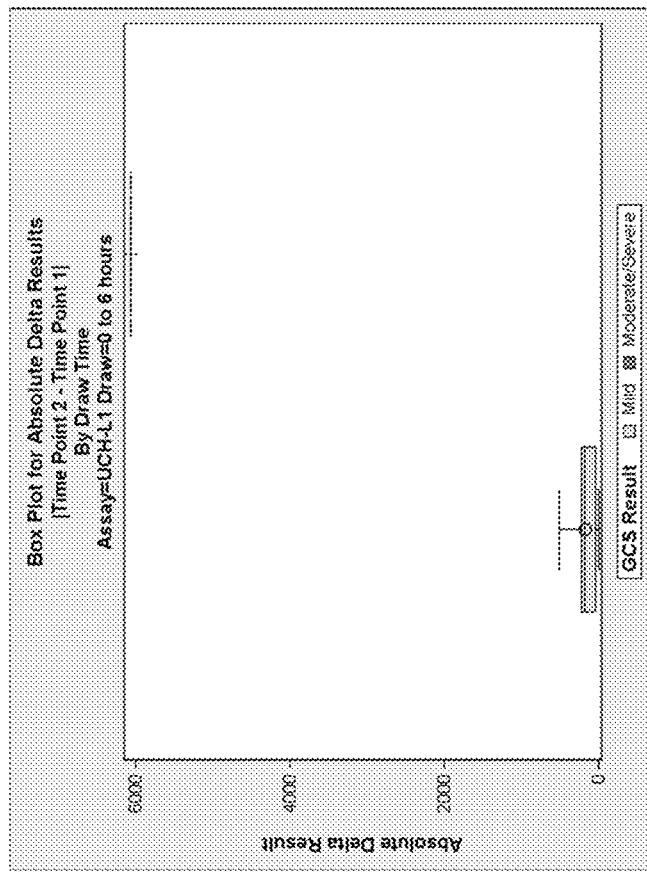
FIG. 14A shows box plot of absolute amount ("absolute delta") UCH-L1 assay results (i.e., the absolute difference between Time Point 1 (taken within 0 to 6 hours after head injury) and Time Point 2 (taken 3 to 6 hours after the sample of Time Point 1)) correlated with mild vs. moderate/severe TBI GCS scores.
Figure 15A:
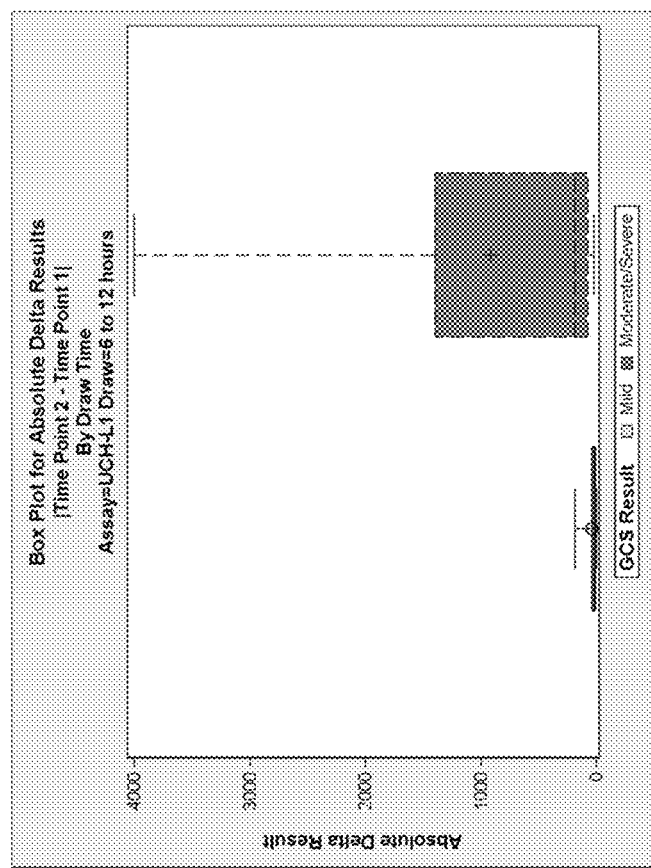
FIG. 15A shows box plot of absolute amount ("absolute delta") of UCH-L1 results (i.e., the absolute difference between Time Point 1 (taken within 6 to 12 hours after head injury) and Time Point 2 (taken 3 to 6 hours after the sample of Time Point 1)) correlated with mild vs. moderate/severe TBI GCS scores.
Figure 15B:
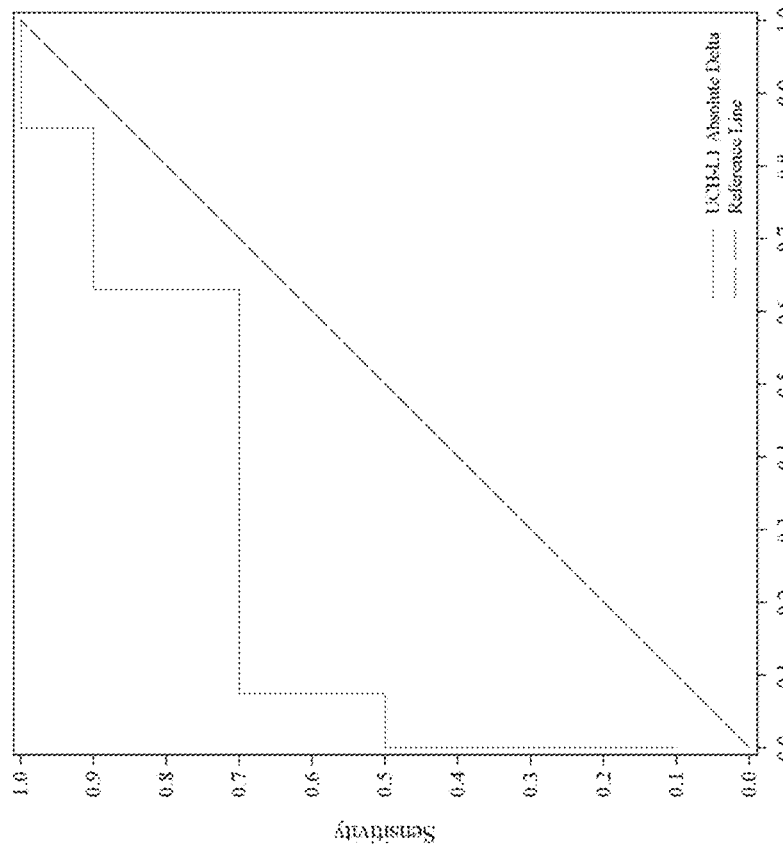
FIG. 15B shows ROC curve of absolute amount ("absolute delta") of UCH-L1 results correlated with mild vs. moderate/severe TBI GCS scores.

FIG. 14A shows the absolute amount (or change between Time Point 1 and Time Point 2; "absolute delta") in UCH-L1 levels of 0-6 hour group and FIG. 14B shows a ROC curve correlating the UCH-L1 levels at Time Point 1 and Time Point 2 with GCS scores (mild vs. moderate/severe). FIG. 15A shows the absolute amount (or change between Time Point 1 and Time Point 2; ("absolute delta") in UCH-L1 levels of 6-12 hour group and FIG. 15B shows a ROC curve correlating the UCH-L1 levels at Time Point 1 and Time Point 2 with GCS scores (mild vs. moderate/severe). Subjects determined to have moderate/severe TBI based on the GCS score had a larger decrease or change in UCH-L1 levels from Time Point 1 to Time Point 2 compared to subjects determined to have mild TBI based on the GCS score. The moderate/severe subjects from the 0-6 hour group had a significantly greater change in UCH-L1 levels compared to subjects from the 6-12 hour group. The sensitivity and specificity of the absolute amounts (or change between Time Point 1 and Time Point 2) in UCH-L1 levels for the 0-6 hour and 6-12 hour groups based on the ROC curves are shown in Table 12.

TABLE 12

| Time Range | Absolute amount (pg/mL) | Sensitivity | Specificity |
|---|---|---|---|
| 0-6 | 2528 | 100 | 100 |
| 6-12 | 129 | 70 | 92 |

Figure 20:
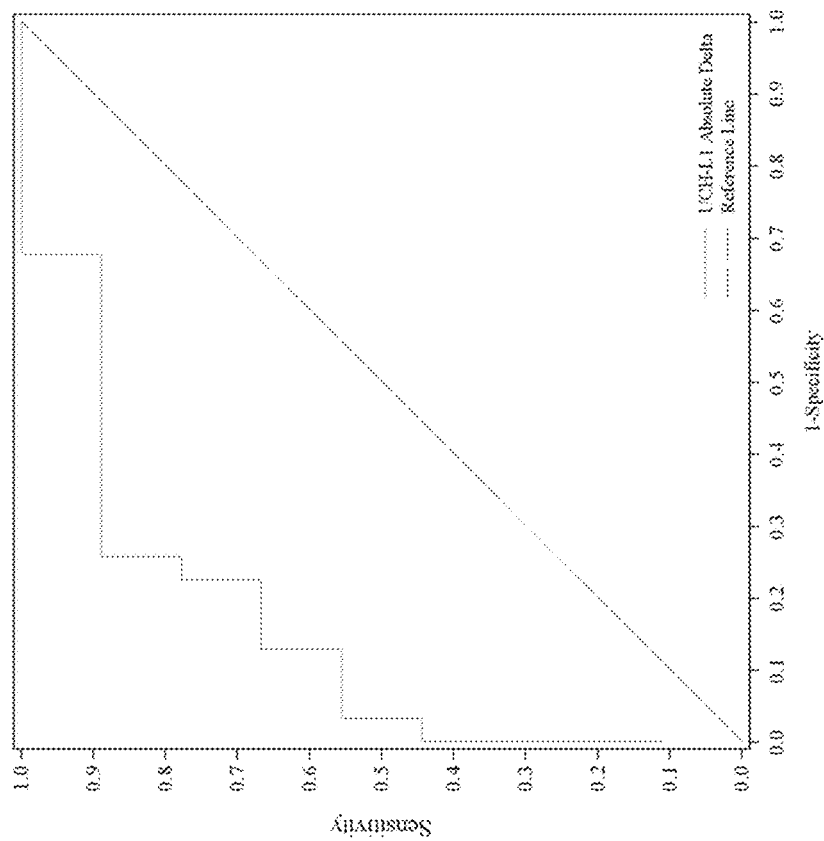
FIG. 20 shows ROC curve of absolute amount ("absolute delta") of UCH-L1 results (i.e., the absolute difference between Time Point 1 (taken more than 11 hours after head injury) and Time Point 2 (taken 3 to 6 hours after the sample of Time Point 1)) correlated with mild vs. moderate/severe TBI GCS scores.
Figure 19:
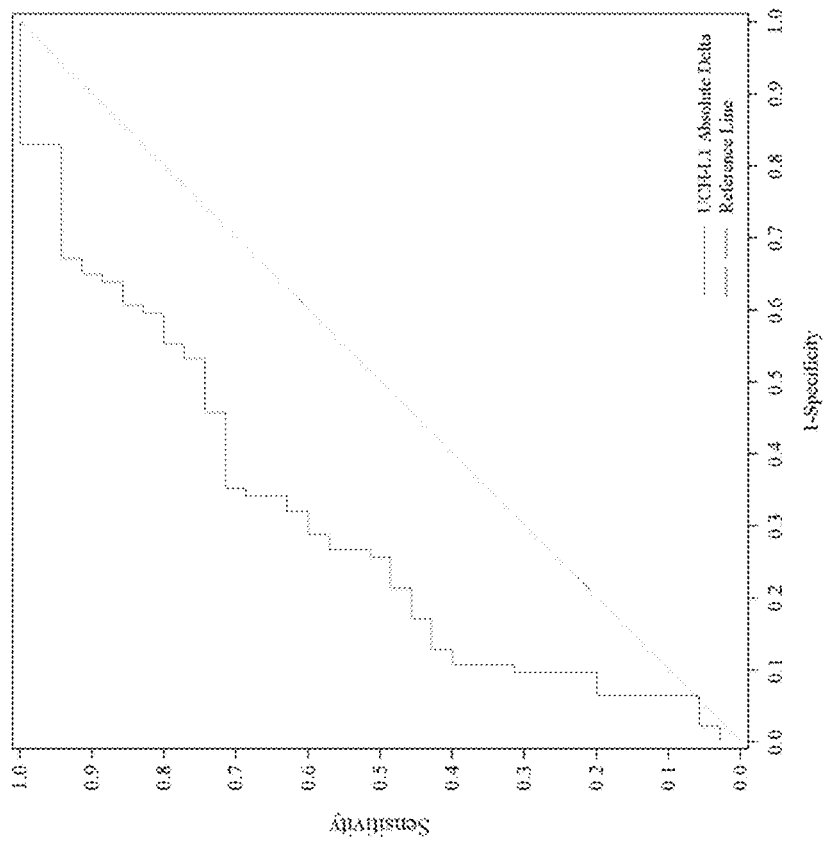
FIG. 19 shows ROC curve of absolute amount ("absolute delta") of UCH-L1 results (i.e., the absolute difference between Time Point 1 (taken within 0 to 11 hours after head injury) and Time Point 2 (taken 3 to 6 hours after the sample of Time Point 1)) correlated with mild vs. moderate/severe TBI GCS scores.
Figure 22:
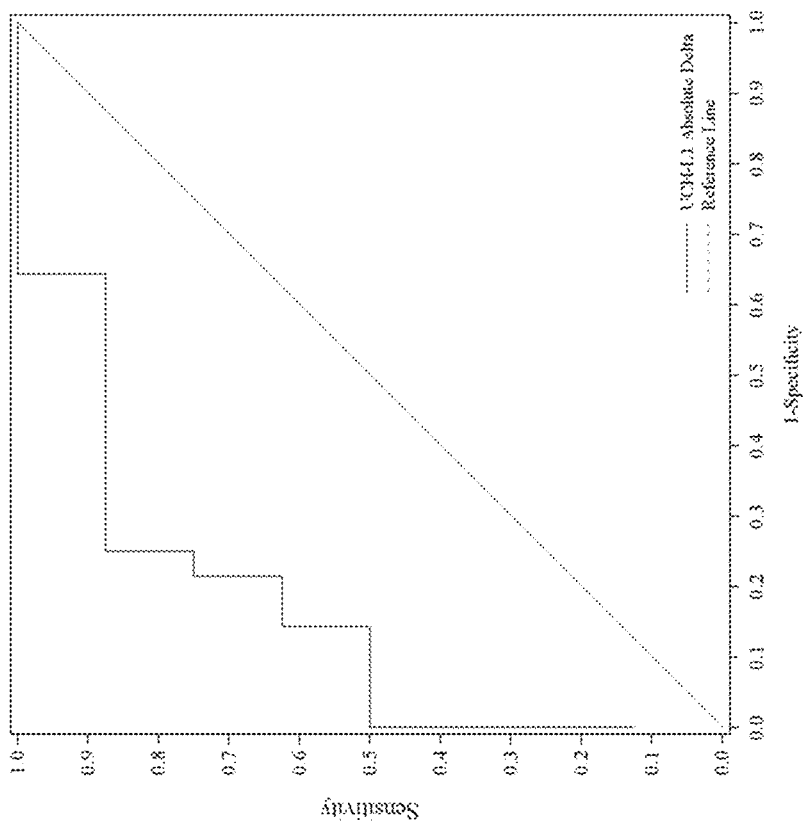
FIG. 22 shows ROC curve of absolute amount ("absolute delta") of UCH-L1 results (i.e., the absolute difference between Time Point 1 (taken more than 12 hours after head injury) and Time Point 2 (taken 3 to 6 hours after the sample of Time Point 1)) correlated with mild vs. moderate/severe TBI GCS scores.
Figure 21:
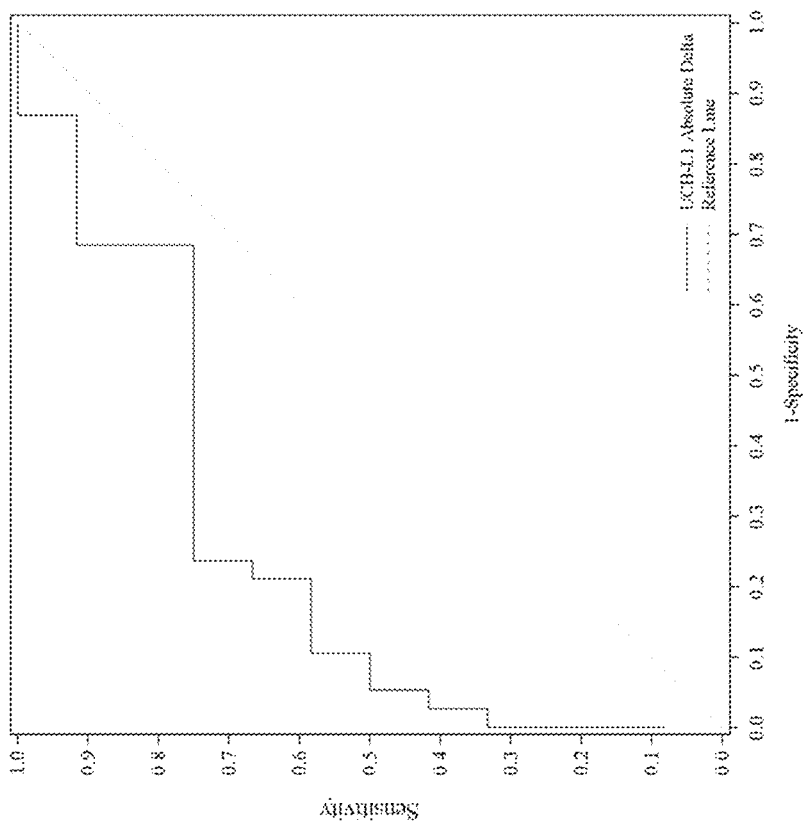
FIG. 21 shows ROC curve of absolute amount ("absolute delta") of UCH-L1 results (i.e., the absolute difference between Time Point 1 (taken within 0 to 10 hours after head injury) and Time Point 2 (taken 3 to 6 hours after the sample of Time Point 1)) correlated with mild vs. moderate/severe TBI GCS scores.

The data was analyzed to examine samples in which the Time Point 1 sample was taken between 0-10 hours after injury ("0-10 hour group"), 0-11 hours after injury ("0-11 hour group"), or 0-12 hours after injury ("0-12 hour group") and compared to the respective Time Point 2 samples. The data was analyzed to examine samples in which the Time Point 1 sample was taken more than 11 hours after injury (">11 hour group") and compared to the respective Time Point 2 samples. FIGS. 19 and 20 show the ROC curves correlating the absolute amount ("absolute delta") in UCH-L1 levels with the CT scan result for the 0-11 hour group and >11 hour group, respectively. FIGS. 21 and 22 show the ROC curves correlating the absolute amount ("absolute delta") in UCH-L1 levels with the CT scan result for the 0-10 hour and 0-12 hour group, respectively. The sensitivity and specificity of absolute amounts (or the change between Time Point 1 and Time Point 2) in UCH-L1 levels for the 0-10 hour, 0-11, and 0-12 groups based on the ROC curves are shown in Table 13.

TABLE 13

| Time Range | Absolute amount (pg/mL) | Sensitivity (%) | Specificity (%) |
|---|---|---|---|
| 0-10 | 25 | 100 | 36 |
| 0-11 | 25 | 100 | 32 |
| 0-12 | 129 | 75 | 76 |

Fold Change Analysis for GCS Score.

The fold-change between the levels in Time Point 2 and Time Point 1 was determined in subjects of the 0-12 hour group. A ROC curve of the fold-change in the UCH-L1 levels (UCH-L1 levels at Time Point 2/UCH-L1 levels at Time Point 1) was correlated with GCS Score (data not shown). The fold reference level of 0.73 (i.e., Time Point 2 result/Time Point 1 result) had a sensitivity of 67% and specificity of 48% if the Time Point 1 sample is taken within the first 12 hours after injury. This fold reference level does well at predicting a moderate to severe TBI in a subject, wherein a fold-change greater than or equal to 0.73 predicted moderate to severe TBI in a subject.

ROC analysis was also performed to show that if the UCH-L1 level at time point 1 is greater than or equal to 550 pg/mL or if the fold-change between time point 2 and time point 1 is greater than 0.73, then the subject is classified as having moderate to severe TBI; if the UCH-L1 level at time point 1 is less than 550 pg/mL or if the fold-change between time point 2 and time point 1 is less than 0.73, then the subject is classified as having mild TBI. These reference levels had a sensitivity of 100% and specificity of 42.5%.

ROC analysis was also performed to show that if the UCH-L1 level at time point 1 is greater than or equal to 450 pg/mL or if the fold-change between time point 2 and time point 1 is greater than 0.73, then the subject is classified as having moderate to severe TBI; if the UCH-L1 level at time point 1 is less than 450 pg/mL or if the fold-change between time point 2 and time point 1 is less than 0.73, then the subject is classified as having mild TBI. These reference levels had a sensitivity of 100% and specificity of 40%.

ROC analysis was also performed to show that if the UCH-L1 level at time point 1 is greater than or equal to 350 pg/mL or if the fold-change between time point 2 and time point 1 is greater than 0.73, then the subject is classified as having moderate to severe TBI; if the UCH-L1 level at time point 1 is less than 350 pg/mL or if the fold-change between time point 2 and time point 1 is less than 0.73, then the subject is classified as having mild TBI. These reference levels had a sensitivity of 100% and specificity of 32.5%.

Taken together, the present disclosure provides specific UCH-L1 reference values and corresponding assay methods that can be used to evaluate a subject for a tramautic brain injury, in addition or as an alternative to, standard clinical assessments.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A method of aiding in the diagnosis and evaluation of a human subject that has sustained or may have sustained an injury to the head, the method comprising: a) performing an assay on a sample taken from the subject within 24 hours after a suspected injury to the head to measure or detect a level of ubiquitin carboxy-terminal hydrolase L1 (UCH-L1) in the sample; and b) determining whether the subject has sustained mild or moderate to severe traumatic brain injury (TBI), wherein the subject is determined as having moderate to severe traumatic brain injury when (i) the level of UCH-L1 in the sample is higher than a reference level of UCH-L1 and the subject is determined as having mild traumatic brain injury when the level of UCH-L1 in the sample is lower than a reference level of UCH-L1; (ii) there is a statistically significant increase or decrease from the level of UCH-L1 in a sample taken at a first time point to the level of UCH-L1 in a sample taken at a second time point and the subject is determined as having mild traumatic brain injury when there is no statistically significant increase or decrease from the level of UCH-L1 in a sample taken at a first time point to the level of UCH-L1 in a sample taken at a second time point; (iii) the level of UCH-L1 decreases or increases by at least an absolute amount from the first sample to the second sample or is determined as having mild traumatic brain injury when there is no decrease or increase by at least an absolute amount in the level of UCH-L1 from the first sample to the second sample; (iv) the level of UCH-L1 decreases or increases by at least a first absolute amount from the first sample to the second sample or is determined as having mild traumatic brain injury when the level of UCH-L1 decreases or increases by at least a second absolute amount from the first sample to the second sample; or (v) the level of UCH-L1 in the sample is higher than a reference level of UCH-L1 or when there is a significant increase or decrease of amount X from the level of UCH-L1 in a sample taken at a first time point to the level of UCH-L1 in a sample taken at a second time point and the subject is determined as having mild traumatic brain injury when the level of UCH-L1 in the sample is lower than a reference level of UCH-L1 or when there is no significant increase or decrease greater than amount X from the level of UCH-L1 in a sample taken at a first time point to the level of UCH-L1 in a sample taken at a second time point.

Clause 2. The method of clause 1, wherein: the first time point is about 0 to about 12 hours after the suspected injury and the statistically significant increase or decrease is more than about 1-fold from the second time point to the first time point; the first time point is about 0 to about 12 hours after the suspected injury and the statistically significant increase or decrease is more than about 0.73-fold from the second time point to the first time point; or the first time point is about 0 to about 12 hours after the suspected injury, the reference level of UCH-L1 is between about 350 pg/mL and about 550 pg/mL, and the statistically significant increase or decrease is more than about 0.73-fold from the second time point to the first time point.

Clause 3. The method of clause 1 or 2, wherein the subject has received a Glasgow Coma Scale score before or after the assay is performed.

Clause 4. The method of clause 3, wherein the subject is suspected as having moderate to severe traumatic brain injury based on the Glasgow Coma Scale score.

Clause 5. The method of clause 4, wherein the reference level is correlated with subjects having moderate and severe traumatic brain injury.

Clause 6. The method of clause 5, wherein the reference level is correlated with a Glasgow Coma Scale score of 3-12.

Clause 7. The method of clause 3, wherein the subject is suspected as having mild traumatic brain injury based on the Glasgow Coma Scale score.

Clause 8. The method of clause 7, wherein the reference level is correlated with subjects having mild traumatic brain injury.

Clause 9. The method of clause 8, wherein the reference level is correlated with a Glasgow Coma Scale score of 13-15.

Clause 10. The method of any one of clauses 1 to 9, wherein the reference level is determined by an assay having a sensitivity of between at least about 85% to 100% and a specificity of between at least about 30% to 100%.

Clause 11. The method of any one of clauses 1 to 10, wherein the reference level is determined by an assay having a sensitivity of at least about 99% and a specificity of at least about 75%.

Clause 12. The method of any one of clauses 1 to 11, wherein the reference level is between at least about 50 pg/mL to about 12000 pg/mL.

Clause 13. The method of any one of clauses 1 to 12, wherein the reference level is between at least about 65 pg/mL to about 9019 pg/mL.

Clause 14. The method of any one of clauses 1 to 13, wherein the sample is taken within 0 to 6 hours after the suspected injury and the reference level is determined by an assay having a sensitivity of about 100% and a specificity of at least about 33%.

Clause 15. The method of clause 14, wherein the sample is taken within 0 to 6 hours after the suspected injury and the reference level is about 311 pg/mL.

Clause 16. The method of any one of clauses 1 to 13, wherein the sample is taken within 0 to 6 hours after the suspected injury and the reference level is determined by an assay having a sensitivity of about 100% and a specificity of about 100%.

Clause 17. The method of clause 16, wherein the sample is taken within 0 to 6 hours after the suspected injury and the reference level is about 9019 pg/mL.

Clause 18. The method of any one of clauses 1 to 13, wherein the sample is taken between about 6 hours to 12 hours after the suspected injury and the reference level is determined by an assay having a sensitivity of about 100% and a specificity of at least about 30%.

Clause 19. The method of clause 18, wherein the sample is taken between about 6 hours to 12 hours after the suspected injury and the reference level is about 98 pg/mL.

Clause 20. The method of any one of clauses 1 to 13, wherein the sample is taken between about 6 hours to 12 hours after the suspected injury and the reference level is determined by an assay having a sensitivity of about 100% and a specificity of at least about 63%.

Clause 21. The method of clause 20, wherein the sample is taken between about 6 hours to 12 hours after the suspected injury and the reference level is about 209 pg/mL.

Clause 22. The method of any one of clauses 1 to 13, wherein the sample is taken between about 6 hours to 12 hours after the suspected injury and the reference level is determined by an assay having a sensitivity of at least about 90% and a specificity of at least about 96%.

Clause 23. The method of clause 22, wherein the sample is taken between about 6 hours to 12 hours after the suspected injury and the reference level is about 569 pg/mL.

Clause 24. The method of clause 4, wherein the absolute amount is correlated with subjects having moderate and severe traumatic brain injury.

Clause 25. The method of clause 24, wherein the absolute amount is correlated with a Glasgow Coma Scale score of 3-12.

Clause 26. The method of clause 7, wherein the absolute amount is correlated with subjects having mild traumatic brain injury.

Clause 27. The method of clause 26, wherein the absolute amount is correlated with a Glasgow Coma Scale score of 13-15.

Clause 28. The method of any one of clauses 1 to 4, 7, or 24 to 27, wherein the absolute amount is determined by an assay having a sensitivity of between at least about 70% to 100% and a specificity of between at least about 30% to 100%.

Clause 29. The method of clause 28, wherein the sample is taken within 0 to 6 hours after the suspected injury and the absolute amount is determined by an assay having a sensitivity of about 100% and a specificity of about 100%.

Clause 30. The method of clause 29, wherein the sample is taken within 0 to 6 hours after the suspected injury and the absolute amount is about 2528 pg/mL.

Clause 31. The method of clause 30, wherein the sample is taken within 6 to 12 hours after the suspected injury and the absolute amount is determined by an assay having a sensitivity of at least about 70% and a specificity of at least about 92%.

Clause 32. The method of clause 31, wherein the sample is taken within 6 to 12 hours after the suspected injury and the absolute amount is about 129 pg/mL.

Clause 33. The method of clause 28, wherein the sample is taken within 0 to 10 hours after the suspected injury and the absolute amount is determined by an assay having a sensitivity of about 100% and a specificity of at least about 36%.

Clause 34. The method of clause 33, wherein the sample is taken within 6 to 12 hours after the suspected injury and the absolute amount is about 25 pg/mL.

Clause 35. The method of clause 28, wherein the sample is taken within 0 to 11 hours after the suspected injury and the absolute amount is determined by an assay having a sensitivity of about 100% and a specificity of at least about 32%.

Clause 36. The method of clause 35, wherein the sample is taken within 0 to 11 hours after the suspected injury and the absolute amount is about 25 pg/mL.

Clause 37. The method of clause 28, wherein the sample is taken within 0 to 12 hours after the suspected injury and the absolute amount is determined by an assay having a sensitivity of at least about 75% and a specificity of at least about 76%.

Clause 38. The method of clause 37, wherein the sample is taken within 0 to 12 hours after the suspected injury and the absolute amount is about 129 pg/mL.

Clause 39. A method of aiding in determining the extent of traumatic brain injury in a human subject who has sustained or may have sustained a suspected injury to the head, the method comprising: a) performing an assay on at least two samples obtained from the subject, the first sample taken from the subject within 24 hours of the suspected injury and the second sample taken from the subject from about 3 to about 6 hours after the first sample is taken; b) detecting in the at least two samples an early biomarker of traumatic brain injury, said early biomarker consisting of ubiquitin carboxy-terminal hydrolase L1 (UCH-L1), wherein the onset of the presence of UCH-L1 appears within about 0 to about 6 hours after the suspected injury; c) determining the level of UCH-L1 in each of the first sample and second sample and determining if the level of UCH-L1 decreases or increases from the first sample to the second sample; and d) determining the extent of the traumatic brain injury in the subject based on whether the level of UCH-L1 decreases, increases, or remains the same from the first sample to the second sample.

Clause 40. The method of clause 39, wherein the first sample is taken within 0 to about 6 hours after the suspected injury.

Clause 41. The method of clauses 39 or 40, wherein the subject is determined to have moderate to severe traumatic brain injury when the level of UCH-L1 increases or decreases between at least about 20 pg/mL to at least about 6100 pg/mL from the first sample to the second sample.

Clause 42. The method of clause 41, wherein the first sample is taken within 0 to about 6 hours after the suspected injury and the level of UCH-L1 increases or decreases by at least about 2528 pg/mL Clause 43. The method of clause 41, wherein the first sample is taken within 6 to about 12 hours after the suspected injury and the level of UCH-L1 increases or decreases by at least about 129 pg/mL Clause 44. The method of clause 41, wherein the first sample is taken within 0 to about 10 or about 11 hours after the suspected injury and the level of UCH-L1 increases or decreases by at least about 25 pg/mL.

Clause 45. The method of clause 41, wherein the first sample is taken within 0 to about 12 hours after the suspected injury and the level of UCH-L1 increases or decreases at least about 129 pg/mL.

Clause 46. The method of any one of clauses 1 to 45, further comprising treating a human subject assessed as having moderate to severe traumatic brain injury with a traumatic brain injury treatment.

Clause 47. The method of any one of clauses 1 to 45, further comprising monitoring a human subject assessed as having mild traumatic brain injury.

Clause 48. A method of aiding in the determination of whether to perform a head computerized tomography (CT) scan on a human subject that has sustained or may have sustained a suspected injury to the head, the method comprising: a) performing an assay on at least two samples obtained from the subject, the first sample taken from the subject within 24 hours of the suspected injury and the second sample taken from the subject from about 3 to about 6 hours after the first sample is taken; b) detecting in the at least two samples an early biomarker of traumatic brain injury, said early biomarker consisting of ubiquitin carboxy-terminal hydrolase L1 (UCH-L1), wherein the onset of the presence of UCH-L1 appears within about 0 to about 6 hours after the suspected injury; c) determining the level of UCH-L1 in each of the first sample and second sample and determining if the level of UCH-L1 decreases or increases from the first sample to the second sample; and d) determining whether to perform a CT scan on the subject based on whether the level of UCH-L1 decreases, increases, or remains the same from the first sample to the second sample.

Clause 49. The method of clause 48, wherein: (i) a CT scan is performed on the subject when the level of UCH-L1 in the first sample is higher than a reference level of UCH-L1 and a CT scan is not performed on the subject when the level of UCH-L1 in the first sample is lower than a reference level of UCH-L1; (ii) a CT scan is performed on the subject when there is a statistically significant increase or decrease from the level of UCH-L1 in the first sample to the level of UCH-L1 in the second sample and a CT scan is not performed on the subject when there is no statistically significant increase or decrease from the level of UCH-L1 in the first sample to the level of UCH-L1 in the second sample; (iii) a CT scan is performed on the subject when the level of UCH-L1 decreases or increases by at least an absolute amount from the first sample to the second sample and a CT scan is not performed on the subject when there is no decrease or increase by at least an absolute amount in the level of UCH-L1 from the first sample to the second sample; or (iv) a CT scan is performed on the subject when the level of UCH-L1 in the first sample is higher than a reference level of UCH-L1 or when there is a statistically significant increase or decrease from the level of UCH-L1 in the first sample to the level of UCH-L1 in the second sample and a CT scan is not performed on the subject when the level of UCH-L1 in the first sample is lower than a reference level of UCH-L1 or when there is no statistically significant increase or decrease from the level of UCH-L1 in the first sample to the level of UCH-L1 in the second sample.

Clause 50. The method of clause 49, wherein: the first time point is about 0 to about 12 hours after the suspected injury and the statistically significant increase or decrease is less than about 2-fold from the first time point to the second time point; the first time point is about 0 to about 12 hours after the suspected injury and the statistically significant increase or decrease is less than about 1.81-fold from the first time point to the second time point; the first time point is about 0 to about 12 hours after the suspected injury and the statistically significant increase is more than about 0.50-fold from the second time point to the first time point; the first time point is about 0 to about 12 hours after the suspected injury and the statistically significant increase is more than about 0.55-fold from the second time point to the first time point; or the first time point is about 0 to about 12 hours after the suspected injury, the reference level of UCH-L1 is about 550 pg/mL, and the statistically significant increase is more than about 0.55-fold from the second time point to the first time point.

Clause 51. The method of any one of clauses 48 to 50, wherein the subject has received a CT scan before or after the assay is performed.

Clause 52. The method of clause 51, wherein the subject is suspected as having a traumatic brain injury based on the CT scan.

Clause 53. The method of any one of clauses 49, 51, or 52, wherein the reference level is correlated with positive head computed tomography.

Clause 54. The method of any one of clauses 49 or 51 to 53, wherein the reference level is determined by an assay having a sensitivity of between at least about 80% to 100% and a specificity of between at least about 30% to 100%.

Clause 55. The method of any one of clauses 49 or 51 to 54, wherein the reference level is between at least about 50 pg/mL to about 1000 pg/mL.

Clause 56. The method of any one of clauses 49 or 51 to 55, wherein the reference level is between at least about 86 pg/mL to about 700 pg/mL.

Clause 57. The method of any one of clauses 49 or 51 to 56, wherein the sample is taken within 0 to 6 hours after the suspected injury and the reference level is determined by an assay having a sensitivity of about 100% and a specificity of at least about 37.5%.

Clause 58. The method of clause 57, wherein the sample is taken within 0 to 6 hours after the suspected injury and the reference level is about 370 pg/mL.

Clause 59. The method of any one of clauses 49 or 51 to 56, wherein the sample is taken within 0 to 6 hours after the suspected injury and the reference level is determined by an assay having a sensitivity of about 100% and a specificity of at least about 75%.

Clause 60. The method of clause 59, wherein the sample is taken within 0 to 6 hours after the suspected injury and the reference level is about 509 pg/mL.

Clause 61. The method of any one of clauses 49 or 51 to 56, wherein the sample is taken between about 6 hours to 12 hours after the suspected injury and the reference level is determined by an assay having a sensitivity of at least about 96% and a specificity of at least about 30%.

Clause 62. The method of clause 61, wherein the sample is taken between about 6 hours to 12 hours after the suspected injury and the reference level is about 96 pg/mL.

Clause 63. The method of any one of clauses 49 or 51 to 56, wherein the sample is taken between about 6 hours to 12 hours after the suspected injury and the reference level is determined by an assay having a sensitivity of at least about 86% and a specificity of at least about 35%.

Clause 64. The method of clause 63, wherein the sample is taken between about 6 hours to 12 hours after the suspected injury and the reference level is about 86 pg/mL.

Clause 65. The method of any one of clauses 49 or 51 to 56, wherein the sample is taken between about 0 hours to 12 hours after the suspected injury and the reference level is determined by an assay having a sensitivity of about 100% and a specificity of at least about 32%.

Clause 66. The method of clause 65, wherein the sample is taken between about 6 hours to 12 hours after the suspected injury and the reference level is about 550 pg/mL.

Clause 67. The method of any one of clauses 49, 51, or 52, wherein the absolute amount is correlated with positive head computed tomography.

Clause 68. The method of clause 67, wherein the absolute amount is determined by an assay having a sensitivity of between at least about 80% to 100% and a specificity of between at least about 30% to 100%.

Clause 69. The method of clause 68, wherein the sample is taken within 0 to 10 hours after the suspected injury and the absolute amount is determined by an assay having a sensitivity of at least about 85% and a specificity of at least about 41%.

Clause 70. The method of clause 69, wherein the sample is taken within 0 to 10 hours after the suspected injury and the absolute amount is about 25 pg/mL.

Clause 71. The method of clause 68, wherein the sample is taken within 0 to 10 hours after the suspected injury and the absolute amount is determined by an assay having a sensitivity of at least about 90% and a specificity of at least about 35%.

Clause 72. The method of clause 71, wherein the sample is taken within 0 to 10 hours after the suspected injury and the absolute amount is about 23 pg/mL.

Clause 73. The method of any one of clauses 1 to 72, wherein the second sample is taken from the human subject between about 5 hours to about 16 hours or about 3 hours to about 6 hours after injury to the head.

Clause 74. The method of any one of clauses 1 to 73, wherein the second sample is taken from the human subject at about 3 hours, at about 4 hours, at about 5 hours, at about 6 hours, at about 7 hours, at about 8 hours, at about 9 hours, at about 10 hours, at about 11 hours, or at about 12 hours after injury to the head.

Clause 75. The method of any one of clauses 1 to 74 further comprising performing an assay on the samples to measure or detect a level of one or more other biomarkers that are not UCH-L1.

Clause 76. The method of clause 75, wherein the assay comprises: I. measuring or detecting a level of one or more other biomarkers in the first sample and the second sample, II. determining a decrease or increase in the level of the one or more other biomarkers from the first sample to the second sample, and III. assessing the human subject as having mild traumatic brain injury if there is a statistically significant decrease or increase in the level of the one or more other biomarkers from the first sample to the level of the one or more other biomarkers in the second sample Clause 77. The method of clause 75 or 76, wherein the one or more other biomarkers is selected from the group consisting of S1000, neuron-specific enolase (NSE), glial fibrillary acidic protein (UCH-L1), Apo lipoprotein 1, Tau, C-reactive protein (CRP), free brain-derived neurotrophic factor (BDNF), p-Tau, total BDNF, troponin I (TnI), and a combination thereof.

Clause 78. The method of clause 77, wherein the one or more other biomarkers is S100β, BDNF, or CRP.

Clause 79. The method of any one of clauses 1 to 78, further comprising treating a human subject assessed as having mild traumatic brain injury with a mild traumatic brain injury treatment.

Clause 80. The method of any one of clauses 1 to 79, further comprising monitoring a human subject assessed as having mild traumatic brain injury.

Clause 81. The method of any one of clauses 1 to 80, wherein measuring the level of UCH-L1 is done by an immunoassay.

Clause 82. The method of any one of clauses 1 to 81, wherein measuring the level of UCH-L1 comprises: A. contacting the sample, either simultaneously or sequentially, in any order with: (1) a capture antibody, which binds to an epitope on UCH-L1 or UCH-L1 fragment to form a capture antibody-UCH-L1 antigen complex, and (2) a detection antibody which includes a detectable label and binds to an epitope on UCH-L1 that is not bound by the capture antibody, to form a UCH-L1 antigen-detection antibody complex, such that a capture antibody-UCH-L1 antigen-detection antibody complex is formed, and B. measuring the amount or concentration of UCH-L1 in the sample based on the signal generated by the detectable label in the capture antibody-UCH-L1 antigen-detection antibody complex.

Clause 83. The method of any one of clauses 1 to 82, wherein the sample is selected from the group consisting of a whole blood sample, a serum sample, a cerebrospinal fluid sample and a plasma sample.

Clause 84. The method of any one of clauses 1 to 83, wherein the sample is obtained after the human subject sustained an injury to the head caused by physical shaking, blunt impact by an external mechanical or other force that results in a closed or open head trauma, one or more falls, explosions or blasts or other types of blunt force trauma.

Clause 85. The method of any one of clauses 1 to 83, wherein the sample is obtained after the human subject has ingested or been exposed to a chemical, toxin or combination of a chemical and toxin.

Clause 86. The method of clause 85, wherein the chemical or toxin is fire, mold, asbestos, a pesticide, an insecticide, an organic solvent, a paint, a glue, a gas, an organic metal, a drug of abuse or one or more combinations thereof.

Clause 87. The method of any one of clauses 1 to 83, wherein the sample is obtained from a human subject that suffers from an autoimmune disease, a metabolic disorder, a brain tumor, hypoxia, a virus, meningitis, hydrocephalus or combinations thereof.

Clause 88. The method of any one of clauses 1 to 83, wherein said method can be carried out on any human subject without regard to factors selected from the group consisting of the human subject's clinical condition, the human subject's laboratory values, the human subject's classification as suffering from mild, moderate to severe traumatic brain injury, the human subject's exhibition of low or high levels of UCH-L1, and the timing of any event wherein said human subject may have sustained an injury to the head.

Clause 89. A method of aiding in the diagnosis and evaluation of a human subject that has sustained or may have sustained a head injury (such as a traumatic brain injury), the method comprising:

a) performing an assay on a sample (such as a biological sample) which has been taken from the subject within 24 hours after a suspected head injury to measure or detect a level of ubiquitin carboxy-terminal hydrolase L1 (UCH-L1) in the sample; and b) determining whether the subject has sustained mild or moderate to severe traumatic brain injury (TBI), wherein the subject is determined as having moderate to severe traumatic brain injury when:

(i) the level of UCH-L1 in the sample is higher than a reference level of UCH-L1 and the subject is determined as having mild traumatic brain injury when the level of UCH-L1 in the sample is lower than a reference level of UCH-L1;

(ii) there is a statistically significant increase or decrease from the level of UCH-L1 in a sample taken at a first time point to the level of UCH-L1 in a sample taken at a second time point and the subject is determined as having mild traumatic brain injury when there is no statistically significant increase or decrease from the level of UCH-L1 in a sample taken at a first time point to the level of UCH-L1 in a sample taken at a second time point;

(iii) the level of UCH-L1 decreases or increases by at least an absolute amount from the first sample to the second sample or is determined as having mild traumatic brain injury when there is no decrease or increase by at least an absolute amount in the level of UCH-L1 from the first sample to the second sample;

(iv) the level of UCH-L1 decreases or increases by at least a first absolute amount from the first sample to the second sample or is determined as having mild traumatic brain injury when the level of UCH-L1 decreases or increases by at least a second absolute amount from the first sample to the second sample; or (v) the level of UCH-L1 in the sample is higher than a reference level of UCH-L1 or when there is a significant increase or decrease of an amount X from the level of UCH-L1 in a sample taken at a first time point to the level of UCH-L1 in a sample taken at a second time point and the subject is determined as having mild traumatic brain injury when the level of UCH-L1 in the sample is lower than a reference level of UCH-L1 or when there is no significant increase or decrease greater than amount X from the level of UCH-L1 in a sample taken at a first time point to the level of UCH-L1 in a sample taken at a second time point.

Clause 90. A method of evaluating a human subject for a head injury (such as a traumatic brain injury), the method comprising:

a) performing an assay on a sample (such as a biological sample) which has been taken from the subject within 24 hours after a suspected head injury to measure a level of ubiquitin carboxy-terminal hydrolase L1 (UCH-L1) in the sample; and b) determining whether the subject has sustained a mild or a moderate to severe traumatic brain injury (TBI), wherein:

(i) the subject has sustained a moderate to severe TBI when the level of UCH-L1 in the sample is higher than a reference level of UCH-L1, and wherein the subject has sustained a mild TBI when the level of UCH-L1 in the sample is lower than a reference level of UCH-L1;

(ii) the subject has sustained a moderate to severe TBI when there is a statistically significant increase or decrease from the level of UCH-L1 in a sample taken at a first time point to the level of UCH-L1 in a sample taken at a second time point, and wherein the subject has sustained a mild TBI when there is no statistically significant increase or decrease from the level of UCH-L1 in a sample taken at a first time point to the level of UCH-L1 in a sample taken at a second time point;

(iii) the subject has sustained a moderate to severe TBI when the level of UCH-L1 decreases or increases by at least an absolute amount from the first sample to the second sample, and wherein the subject has sustained a mild TBI when there is no decrease or increase by at least an absolute amount in the level of UCH-L1 from the first sample to the second sample; or (iv) the subject has sustained a moderate to severe TBI when the level of UCH-L1 decreases or increases by at least a first absolute amount from the first sample to the second sample, and wherein the subject has sustained a mild TBI when the level of UCH-L1 decreases or increases by at least a second absolute amount from the first sample to the second sample.

Clause 91. The method of clause 89 or 90, wherein:
the first time point is about 0 to about 12 hours after the suspected head injury and the statistically significant increase or decrease is selected from the group consisting of:
(a) more than about 1-fold from the second time point to the first time point;
(b) more than about 0.73-fold from the second time point to the first time point; or
(c) more than about 0.73-fold from the second time point to the first time point and the reference level of UCH-L1 is between about 350 pg/mL and about 550 pg/mL.

Clause 92. The method of any of clauses 89 to 91, wherein the subject has received a Glasgow Coma Scale score before or after the assay is performed.

Clause 93. The method of clause 92, wherein the subject is suspected as having moderate to severe TBI based on the Glasgow Coma Scale score.

Clause 94. The method of any of clauses 89 to 93, wherein the reference level is correlated with subjects having moderate to severe TBI.

Clause 95. The method of clause 94, wherein the reference level is correlated with a Glasgow Coma Scale score of 3-12.

Clause 96. The method of clause 92, wherein the subject is suspected as having mild TBI based on the Glasgow Coma Scale score.

Clause 97. The method of any of clauses 89 to 92, wherein the reference level is correlated with subjects having mild TBI.

Clause 98. The method of clause 97, wherein the reference level is correlated with a Glasgow Coma Scale score of 13-15.

Clause 99. The method of any of clauses 89 to 98, wherein the reference level is (a) determined by an assay having a sensitivity of between at least about 85% to about 100% and a specificity of between at least about 30% to about 100%; (b) determined by an assay having a sensitivity of at least about 99% and a specificity of at least about 75%; (c) between at least about 50 pg/mL to about 12000 pg/mL; or (d) between at least about 65 pg/mL to about 9019 pg/mL.

Clause 100. The method of any of clauses 89 to 99, wherein the sample is (a) taken within about 0 to about 6 hours after the suspected head injury and the reference level is determined by an assay having a sensitivity of about 100% and a specificity of at least about 33%; (b) taken within about 0 to about 6 hours after the suspected head injury and the reference level is determined by an assay having a sensitivity of about 100% and a specificity of about 100%; (c) taken between about 6 hours to about 12 hours after the suspected head injury and the reference level is determined by an assay having a sensitivity of about 100% and a specificity of at least about 30%; (d) taken between about 6 hours to about 12 hours after the suspected head injury and the reference level is determined by an assay having a sensitivity of about 100% and a specificity of at least about 63%; or (e) taken between about 6 hours to about 12 hours after the suspected head injury and the reference level is determined by an assay having a sensitivity of at least about 90% and a specificity of at least about 96%.

Clause 101. The method of any of clauses 89 to 100, wherein the sample is (a) taken within 0 to about 6 hours after the suspected head injury and the reference level is about 311 pg/mL; (b) taken within 0 to 6 hours after the suspected head injury and the reference level is about 9019 pg/mL; (c) taken between about 6 hours to about 12 hours after the suspected head injury and the reference level is about 98 pg/mL; (d) taken between about 6 hours to about 12 hours after the suspected head injury and the reference level is about 209 pg/mL; or (e) taken between about 6 hours to about 12 hours after the suspected head injury and the reference level is about 569 pg/mL.

Clause 102. The method of clause 89 or 90, wherein the absolute amount is correlated with subjects having moderate to severe TBI.

Clause 103. The method of clause 102, wherein the absolute amount is correlated with a Glasgow Coma Scale score of 3-12.

Clause 104. The method of clause 89 or 90, wherein the absolute amount is correlated with subjects having mild TBI.

Clause 105. The method of clause 104, wherein the absolute amount is correlated with a Glasgow Coma Scale score of 13-15.

Clause 106. The method of any of clauses 89, 90, and 102 to 105, wherein the absolute amount is determined by an assay having a sensitivity of between at least about 70% to about 100% and a specificity of between at least about 30% to about 100%.

Clause 107. The method of clause 106, wherein the sample is (a) taken within about 0 to about 6 hours after the suspected head injury and the absolute amount is determined by an assay having a sensitivity of about 100% and a specificity of about 100%; (b) taken within about 6 to about 12 hours after the suspected head injury and the absolute amount is determined by an assay having a sensitivity of at least about 70% and a specificity of at least about 92%; (c) taken within about 0 to about 10 hours after the suspected head injury and the absolute amount is determined by an assay having a sensitivity of about 100% and a specificity of at least about 36%; (d) taken within about 0 to about 11 hours after the suspected head injury and the absolute amount is determined by an assay having a sensitivity of about 100% and a specificity of at least about 32%; or (e) taken within about 0 to about 12 hours after the suspected head injury and the absolute amount is determined by an assay having a sensitivity of at least about 75% and a specificity of at least about 76%.

Clause 108. The method of clause 106 or 107, wherein the sample is: (a) taken within about 0 to about 6 hours after the suspected head injury and the absolute amount is about 2528 pg/mL; (b) taken within about 6 to about 12 hours after the suspected head injury and the absolute amount is about 129 pg/mL; (c) taken within about 6 to about 12 hours after the suspected head injury and the absolute amount is about 25 pg/mL; (d) taken within 0 to 11 hours after the suspected head injury and the absolute amount is about 25 pg/mL; or (e) taken within about 0 to about 12 hours after the suspected head injury and the absolute amount is about 129 pg/mL.

Clause 109. A method of aiding in determining the extent of traumatic brain injury in a human subject who has sustained or may have sustained a head injury, the method comprising:
 a) performing an assay on at least two samples (such as biological samples) which has been obtained from the subject, the first sample taken from the subject within 24 hours of the suspected head injury and the second sample taken from the subject from about 3 to about 6 hours after the first sample is taken;
 b) detecting in the at least two samples an early biomarker of traumatic brain injury, said early biomarker consisting of ubiquitin carboxy-terminal hydrolase L1 (UCH-L1), wherein the onset of the presence of UCH-L1 appears within about 0 to about 6 hours after the suspected head injury;
 c) determining the level of UCH-L1 in each of the first sample and second sample and determining if the level of UCH-L1 decreases or increases from the first sample to the second sample; and
 d) determining the extent of the traumatic brain injury in the subject based on whether the level of UCH-L1 decreases, increases, or remains the same from the first sample to the second sample, wherein determining the extent of the traumatic brain injury comprises determining whether the subject has sustained a mild or a moderate to severe traumatic brain injury.

Clause 110. A method of evaluating the extent of traumatic brain injury (TBI) in a human subject, the method comprising:
 a) performing an assay to quantify ubiquitin carboxy-terminal hydrolase L1 (UCH-L1) in at least two samples (such as biological samples) which has been obtained from the subject, the first sample taken from the subject within 24 hours of a suspected head injury and the second sample taken from the subject from about 3 to about 6 hours after the first sample is taken; and
 b) determining the extent of the TBI in the subject based on whether the level of UCH-L1 decreases, increases, or remains the same from the first sample to the second sample, wherein determining the extent of the traumatic brain injury comprises determining whether the subject has sustained a mild or a moderate to severe traumatic brain injury.

Clause 111. The method of clause 109 or 110, wherein the first sample is taken within about 0 to about 6 hours after the suspected head injury.

Clause 112. The method of any of clauses 109 to 111, wherein the subject is determined to have moderate to severe TBI when the level of UCH-L1 increases or decreases between at least about 20 pg/mL to at least about 6100 pg/mL from the first sample to the second sample.

Clause 113. The method of clause 109 or 110, wherein the first sample is (a) taken within about 0 to about 6 hours after the suspected head injury and the level of UCH-L1 increases or decreases by at least about 2528 pg/mL; (b) taken within about 6 to about 12 hours after the suspected head injury and the level of UCH-L1 increases or decreases by at least about 129 pg/mL; (c) taken within about 0 to about 10 hours after the suspected head injury and the level of UCH-L1 increases or decreases by at least about 25 pg/mL; (d) taken within about 0 to about 11 hours after the suspected head injury and the level of UCH-L1 increases or decreases by at least about 25 pg/mL; or (e) taken within about 0 to about 12 hours after the suspected head injury and the level of UCH-L1 increases or decreases at least about 129 pg/mL.

Clause 114. The method of any of clauses 89 to 113, further comprising (a) treating a human subject assessed as having mild or moderate to severe TBI with a treatment for TBI; and optionally, (b) monitoring the human subject after receiving said treatment.

Clause 115. The method of any of clauses 89 to 113, further comprising monitoring a human subject assessed as having mild or moderate to severe TBI.

Clause 116. A method of aiding in the determination of whether to perform a head computerized tomography (CT) scan on a human subject that has sustained or may have sustained a head injury (such as a traumatic brain injury), the method comprising:
 a) performing an assay to detect or measure ubiquitin carboxy-terminal hydrolase L1 (UCH-L1) in at least two samples (such as biological samples) which has been obtained from the subject, the first sample taken from the subject within 24 hours of the suspected head injury and the second sample taken from the subject from about 3 to about 6 hours after the first sample is taken;
 b) determining the level of UCH-L1 in each of the first sample and second sample and determining if the level of UCH-L1 decreases or increases from the first sample to the second sample; and
 c) determining whether to perform a CT scan on the subject based on whether the level of UCH-L1 decreases, increases, or remains the same from the first sample to the second sample, wherein:
  (i) the CT scan is performed when the level of UCH-L1 in the first sample is higher than a reference level of UCH-L1, and wherein the CT scan is not performed when the level of UCH-L1 in the first sample is lower than a reference level of UCH-L1;
  (ii) the CT scan is performed when there is a statistically significant increase or decrease in the level of UCH-L1 in the first sample to the level of UCH-L1 in the second sample, and wherein the CT scan is not performed when there is no statistically significant increase or decrease from the level of UCH-L1 in the first sample to the level of UCH-L1 in the second sample; or
  (iii) the CT scan is performed when the level of UCH-L1 decreases or increases by at least an absolute amount from the first sample to the second sample, and wherein the CT scan is not performed when there is no decrease or increase by at least an absolute amount in the level of UCH-L1 from the first sample to the second sample.

Clause 117. A method of evaluating whether to perform a head computerized tomography (CT) scan on a human subject, the method comprising:
 a) performing an assay to quantify ubiquitin carboxy-terminal hydrolase L1 (UCH-L1) in at least two samples (such as biological samples) which has been obtained from the subject, the first sample taken from the subject within about 24 hours of a suspected head injury and the second sample taken from the subject from about 3 to about 6 hours after the first sample is taken; and b) determining whether to perform a CT scan on the subject based on whether the level of UCH-L1 decreases, increases, or remains the same from the first sample to the second sample, wherein:
  (i) the CT scan is performed when the level of UCH-L1 in the first sample is higher than a reference level of UCH-L1, and wherein the CT scan is not performed when the level of UCH-L1 in the first sample is lower than a reference level of UCH-L1;
  (ii) the CT scan is performed when there is a statistically significant increase or decrease in the level of UCH-L1 in the first sample to the level of UCH-L1 in the second sample, and wherein the CT scan is not performed when there is no statistically significant increase or decrease from the level of UCH-L1 in the first sample to the level of UCH-L1 in the second sample; or
  (iii) the CT scan is performed when the level of UCH-L1 decreases or increases by at least an absolute amount from the first sample to the second sample, and wherein the CT scan is not performed when there is no decrease or increase by at least an absolute amount in the level of UCH-L1 from the first sample to the second sample.

Clause 118. The method of clause 116 or 117, wherein: the first time point is about 0 to about 12 hours after the suspected head injury and the statistically significant increase or decrease is less than about 2-fold from the first time point to the second time point; the first time point is about 0 to about 12 hours after the suspected head injury and the statistically significant increase or decrease is less than about 1.81-fold from the first time point to the second time point; the first time point is about 0 to about 12 hours after the suspected head injury and the statistically significant increase is more than about 0.50-fold from the second time point to the first time point; the first time point is about 0 to about 12 hours after the suspected head injury and the statistically significant increase is more than about 0.55-fold from the second time point to the first time point; or the first time point is about 0 to about 12 hours after the suspected head injury, the reference level of UCH-L1 is about 550 pg/mL, and the statistically significant increase is more than about 0.55-fold from the second time point to the first time point.

Clause 119. The method of any of clauses 116 to 118, wherein the subject has received a CT scan before or after the assay is performed.

Clause 120. The method of clause 119, wherein the subject is suspected as having a traumatic brain injury based on the CT scan.

Clause 121. The method of any of clauses 116 to 120, wherein the reference level is correlated with positive head CT scan.

Clause 122. The method of any of clauses 116 to 121, wherein the reference level is (a) determined by an assay having a sensitivity of between at least about 80% to about 100% and a specificity of between at least about 30% to about 100%; (b) between at least about 50 pg/mL to about 1000 pg/mL; or (c) between at least about 86 pg/mL to about 700 pg/mL.

Clause 123. The method of any of clauses 116 to 122, wherein the sample is (a) taken within about 0 to about 6 hours after the suspected head injury and the reference level is determined by an assay having a sensitivity of about 100% and a specificity of at least about 37.5%; (b) taken within about 0 to about 6 hours after the suspected head injury and the reference level is determined by an assay having a sensitivity of about 100% and a specificity of at least about 75%; (c) taken between about 6 hours to about 12 hours after the suspected head injury and the reference level is determined by an assay having a sensitivity of at least about 96% and a specificity of at least about 30%; (d) taken between about 6 hours to about 12 hours after the suspected head injury and the reference level is determined by an assay having a sensitivity of at least about 86% and a specificity of at least about 35%; or (e) taken between about 0 hours to about 12 hours after the suspected head injury and the reference level is determined by an assay having a sensitivity of about 100% and a specificity of at least about 32%.

Clause 124. The method of any of clauses 116 to 123, wherein the sample is (a) taken within about 0 to about 6 hours after the suspected head injury and the reference level is about 370 pg/mL; (b) taken within about 0 to about 6 hours after the suspected head injury and the reference level is about 509 pg/mL; (c) taken between about 6 hours to about 12 hours after the suspected head injury and the reference level is about 96 pg/mL; (d) taken between about 6 hours to about 12 hours after the suspected head injury and the reference level is about 86 pg/mL; or (e) taken between about 6 hours to about 12 hours after the suspected head injury and the reference level is about 550 pg/mL.

Clause 125. The method of clause 116 or 117, wherein the absolute amount is correlated with positive head CT scan.

Clause 126. The method of clause 116 or 117, wherein the absolute amount is determined by an assay having a sensitivity of between at least about 80% to about 100% and a specificity of between at least about 30% to about 100%.

Clause 127. The method of clause 126, wherein the sample is: (a) taken within about 0 to about 10 hours after the suspected head injury and the absolute amount is determined by an assay having a sensitivity of at least about 85% and a specificity of at least about 41%; or (b) taken within about 0 to about 10 hours after the suspected head injury and the absolute amount is determined by an assay having a sensitivity of at least about 90% and a specificity of at least about 35%.

Clause 128. The method of clause 126, wherein the sample is: (a) taken within about 0 to about 10 hours after the suspected head injury and the absolute amount is about 25 pg/mL; or (b) taken within about 0 to about 10 hours after the suspected head injury and the absolute amount is about 23 pg/mL.

Clause 129. The method of any of clauses 89 to 128, wherein the second sample is taken from the subject between about 5 hours to about 16 hours or about 3 hours to about 6 hours after the suspected head injury.

Clause 130. The method of any of clauses 89 to 128, wherein the second sample is taken from the subject at about 3 hours, at about 4 hours, at about 5 hours, at about 6 hours, at about 7 hours, at about 8 hours, at about 9 hours, at about 10 hours, at about 11 hours, or at about 12 hours after the suspected head injury.

Clause 131. The method of any of clauses 89 to 130, further comprising performing an assay on the samples to measure or detect a level of one or more other biomarkers that are not UCH-L1.

Clause 132. The method of clause 131, wherein the assay comprises:
  (a) measuring or detecting a level of one or more other biomarkers in the first sample and the second sample, (b) determining a decrease or increase in the level of the one or more other biomarkers from the first sample to the second sample, and (c) assessing the subject as having mild TBI if there is a statistically significant decrease or increase in the level of the one or more other biomarkers from the first sample to the level of the one or more other biomarkers in the second sample.

Clause 133. The method of clause 131 or 132, wherein the one or more other biomarkers is selected from the group consisting of S1000, neuron-specific enolase (NSE), glial fibrillary acidic protein (UCH-L1), Apo lipoprotein 1, Tau, C-reactive protein (CRP), free brain-derived neurotrophic factor (BDNF), p-Tau, total BDNF, troponin I (TnI), and a combination thereof.

Clause 134. The method of clause 133, wherein the one or more other biomarkers is S1000, BDNF, or CRP.

Clause 135. The method of any of clauses 89 to 134, wherein the method further comprises (a) treating a human subject assessed as having mild or moderate to severe TBI with a treatment for TBI; and optionally, (b) monitoring the human subject after receiving said treatment.

Clause 136. The method of any of clauses 89 to 135, further comprising monitoring a human subject assessed as having mild or moderate to severe TBI.

Clause 137. The method of any of clauses 89 to 136, wherein measuring the level of UCH-L1 comprises performing an immunoassay.

Clause 138. The method of any of clauses 89 to 137, wherein measuring the level of UCH-L1 comprises:

(a) contacting the sample, either simultaneously or sequentially, in any order with:
 (1) a capture antibody, which binds to an epitope on UCH-L1 or UCH-L1 fragment to form a capture antibody-UCH-L1 antigen complex, and
 (2) a detection antibody which includes a detectable label and binds to an epitope on UCH-L1 that is not bound by the capture antibody, to form a UCH-L1 antigen-detection antibody complex, such that a capture antibody-UCH-L1 antigen-detection antibody complex is formed, and (b) measuring the amount or concentration of UCH-L1 in the sample based on the signal generated by the detectable label in the capture antibody-UCH-L1 antigen-detection antibody complex.

Clause 139. The method of any of clauses 89 to 138, wherein the sample is selected from the group consisting of a whole blood sample, a serum sample, a cerebrospinal fluid sample and a plasma sample.

Clause 140. The method of any of clauses 89 to 139, wherein the sample is obtained after the subject sustained a head injury caused by physical shaking, blunt impact by an external mechanical or other force that results in a closed or open head trauma, one or more falls, explosions or blasts or other types of blunt force trauma.

Clause 141. The method of any of clauses 89 to 139, wherein the sample is obtained after the subject has ingested or been exposed to a chemical, toxin or combination of a chemical and toxin.

Clause 142. The method of clause 141, wherein the chemical or toxin is fire, mold, asbestos, a pesticide, an insecticide, an organic solvent, a paint, a glue, a gas, an organic metal, a drug of abuse or one or more combinations thereof.

Clause 143. The method of any of clauses 89 to 139, wherein the sample is obtained from a subject that suffers from an autoimmune disease, a metabolic disorder, a brain tumor, hypoxia, a virus, meningitis, hydrocephalus or combinations thereof.

Clause 144. The method of any of clauses 89 to 139, wherein the method can be carried out on any human subject without regard to factors selected from the group consisting of the human subject's clinical condition, the human subject's laboratory values, the human subject's classification as suffering from mild or moderate to severe TBI, the human subject's exhibition of low or high levels of UCH-L1, and the timing of any event wherein the human subject may have sustained head injury.

Clause 145. The method of any of clauses 89 to 144, wherein the sample is a biological sample.

Clause 146. The method of any of clauses 89 to 145, wherein the sample is a whole blood sample.

Clause 147. The method of any of clauses 89 to 145, wherein the sample is a serum sample.

Clause 148. The method of any of clauses 89 to 145, wherein the sample is a plasma sample.

What is claimed is:

1. A method comprising:
performing an assay for ubiquitin carboxy-terminal hydrolase L1 (UCH-L1) in at least a first sample taken at a first time point and a second sample taken at a second time point and obtained from a human subject after a head injury or suspected head injury; and
treating the subject for a moderate to severe traumatic brain injury (TBI) when the level of UCH-L1 in the second sample exhibits a fold-change greater than or equal to about 0.73 as compared to the level of UCH-L1 in the first sample, or for a mild TBI when the level of UCH-L1 in the second sample exhibits a fold-change less than about 0.73 as compared to the level of UCH-L1 in the first sample;
wherein the sample is whole blood, serum, or plasma obtained
wherein the first time point is within about 24 hours after the head injury or suspected head injury and the second time point is within about 3 to about 6 hours after the first sample is taken.

2. The method of claim 1, wherein the first time point is within about 0 to about 12 hours of the head injury or suspected head injury.

3. The method of claim 1, wherein the assay is selected from the group consisting of an immunoassay and a clinical chemistry assay.

4. The method of claim 1, wherein the assay is performed using single molecule detection or a point-of-care assay.

5. The method of claim 1, wherein the subject has received a Glasgow Coma Scale score before or after the assay is performed, and the subject is suspected as having moderate to severe TBI or mild TBI based on the Glasgow Coma Scale score.

6. The method of claim 1, further comprising monitoring a subject determined to have a mild TBI or moderate to severe TBI.

7. A method comprising:
performing an assay for ubiquitin carboxy-terminal hydrolase L1 (UCH-L1) in a sample obtained from a human subject after a head injury or suspected head injury; and
treating the subject for a moderate to severe TBI when the level of UCH-L1 in the sample is greater than or equal to about 550 pg/mL, or for a mild TBI when the level of UCH-L1 in the sample is less than about 550 pg/mL;
wherein the sample is whole blood, serum, or plasma obtained within about 24 hours after the head injury or suspected head injury.

8. The method of claim 7, wherein the first sample is obtained within about 0 to about 12 hours of the head injury or suspected head injury.

9. The method of claim 7, wherein the assay is selected from the group consisting of an immunoassay and a clinical chemistry assay.

10. The method of claim 7, wherein the assay is performed using single molecule detection or a point-of-care assay.

11. The method of claim 7, further wherein for the assay has a sensitivity of about 100% and a specificity of about 42.5%.

12. The method of claim 7, wherein the subject has received a Glasgow Coma Scale score before or after assay is performed, and the subject is suspected as having moderate to severe TBI or mild TBI based on the Glasgow Coma Scale score.

13. The method of claim 7, further comprising monitoring a subject determined to have a mild TBI or moderate to severe TBI.

14. A method comprising:
performing an assay for ubiquitin carboxy-terminal hydrolase L1 (UCH-L1) in at least a first sample taken at a first time point and a second sample taken at a second time point and obtained from a human subject after a head injury or suspected head injury; and
performing a head computed tomography (CT) scan on the subject when the level of UCH-L1 in the second sample exhibits a fold-change of less than about 1.81 as compared to the level of UCH-L1 in the first sample; and
wherein the sample is whole blood, serum, or plasma obtained wherein the first time point is within about 24 hours after the head injury or suspected head injury and the second time point is within about 3 to about 6 hours after the first sample is taken.

15. The method of claim 14, wherein the first time point is within about 0 to about 6 hours or about 0 to about 12 hours of the head injury or suspected head injury.

16. The method of claim 14, wherein the assay is selected from the group consisting of an immunoassay and a clinical chemistry assay.

17. The method of claim 14, wherein the assay is performed using single molecule detection or a point-of-care assay.

18. The method of claim 14, further wherein the assay has a sensitivity of about 93% and a specificity of about 36%.

19. The method of claim 18, further comprising monitoring the subject who has received the head CT scan.

* * * * *

SEQUENCE LISTING

```
<160> NUMBER OF SEQ ID NOS: 4

<210> SEQ ID NO 1
<211> LENGTH: 223
<212> TYPE: PRT
<213> ORGANISM: Homo sapiens

<400> SEQUENCE: 1

Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
        35                  40                  45

Leu Leu Leu Leu Phe Pro Leu Thr Ala Gln His Glu Asn Phe Arg Lys
    50                  55                  60

Lys Gln Ile Glu Glu Leu Lys Gly Gln Glu Val Ser Pro Lys Val Tyr
65                  70                  75                  80
```

```
Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
            100                 105                 110

Val Leu Lys Gln Phe Leu Ser Glu Thr Glu Lys Met Ser Pro Glu Asp
        115                 120                 125

Arg Ala Lys Cys Phe Glu Lys Asn Glu Ala Ile Gln Ala Ala His Asp
    130                 135                 140

Ala Val Ala Gln Glu Gly Gln Cys Arg Val Asp Asp Lys Val Asn Phe
145                 150                 155                 160

His Phe Ile Leu Phe Asn Asn Val Asp Gly His Leu Tyr Glu Leu Asp
                165                 170                 175

Gly Arg Met Pro Phe Pro Val Asn His Gly Ala Ser Ser Glu Asp Thr
            180                 185                 190

Leu Leu Lys Asp Ala Ala Lys Val Cys Arg Glu Phe Thr Glu Arg Glu
        195                 200                 205

Gln Gly Glu Val Arg Phe Ser Ala Val Ala Leu Cys Lys Ala Ala
    210                 215                 220

<210> SEQ ID NO 2
<211> LENGTH: 6
<212> TYPE: PRT
<213> ORGANISM: Artificial sequence
<220> FEATURE:
<223> OTHER INFORMATION: Synthetic

<400> SEQUENCE: 2

His His His His His His
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic

<400> SEQUENCE: 3

Asp Asp Asp Asp Lys
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic

<400> SEQUENCE: 4

Ala Asp Asp Asp Asp Lys
1               5
```